(12) United States Patent
Abovitz et al.

(10) Patent No.: US 11,060,858 B2
(45) Date of Patent: Jul. 13, 2021

(54) METHOD AND SYSTEM FOR GENERATING A VIRTUAL USER INTERFACE RELATED TO A TOTEM

(71) Applicant: MAGIC LEAP, INC., Plantation, FL (US)

(72) Inventors: Rony Abovitz, Weston, FL (US); Brian T. Schowengerdt, Seattle, WA (US); Mathew D. Watson, Bellevue, WA (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 16/410,617

(22) Filed: May 13, 2019

(65) Prior Publication Data

US 2019/0368868 A1 Dec. 5, 2019

Related U.S. Application Data

(63) Continuation of application No. 14/707,253, filed on May 8, 2015, now Pat. No. 10,288,419, which is a (Continued)

(51) Int. Cl.
*G01B 11/30* (2006.01)
*G06F 3/01* (2006.01)
(Continued)

(52) U.S. Cl.
CPC ............ *G01B 11/303* (2013.01); *A61B 34/10* (2016.02); *A63F 13/00* (2013.01); *A63F 13/213* (2014.09);
(Continued)

(58) Field of Classification Search
CPC combination set(s) only.
See application file for complete search history.

(56) References Cited

U.S. PATENT DOCUMENTS 5,463,696 A  10/1995  Beernink et al.
5,495,576 A   2/1996  Ritchey
(Continued)

FOREIGN PATENT DOCUMENTS

WO   WO 2013188464   12/2013

OTHER PUBLICATIONS

Notice of Allowance for U.S. Appl. No. 14/704,800 dated Aug. 21, 2019.

(Continued)

*Primary Examiner* — Motilewa Good Johnson
(74) *Attorney, Agent, or Firm* — Vista IP Law Group, LLP

(57) ABSTRACT

A waveguide apparatus includes a planar waveguide and at least one optical diffraction element (DOE) that provides a plurality of optical paths between an exterior and interior of the planar waveguide. A phase profile of the DOE may combine a linear diffraction grating with a circular lens, to shape a wave front and produce beams with desired focus. Waveguide apparati may be assembled to create multiple focal planes. The DOE may have a low diffraction efficiency, and planar waveguides may be transparent when viewed normally, allowing passage of light from an ambient environment (e.g., real world) useful in AR systems. Light may be returned for temporally sequentially passes through the planar waveguide. The DOE(s) may be fixed or may have dynamically adjustable characteristics. An optical coupler system may couple images to the waveguide apparatus from a projector, for instance a biaxially scanning cantilevered optical fiber tip.

16 Claims, 109 Drawing Sheets

Related U.S. Application Data continuation-in-part of application No. 14/641,376, filed on Mar. 7, 2015, now Pat. No. 9,874,749, and a continuation of application No. 14/696,347, filed on Apr. 24, 2015, now Pat. No. 9,612,403, which is a continuation of application No. 14/331,218, filed on Jul. 14, 2014, now Pat. No. 9,671,566.

(60) Provisional application No. 62/012,273, filed on Jun. 14, 2014, provisional application No. 61/950,001, filed on Mar. 7, 2014, provisional application No. 61/845,907, filed on Jul. 12, 2013.

(51) Int. Cl.

| | |
|---|---|
| *G06F 3/00* | (2006.01) |
| *G06F 3/0488* | (2013.01) |
| *G02B 27/42* | (2006.01) |
| *G02B 6/10* | (2006.01) |
| *G06F 16/783* | (2019.01) |
| *G06K 9/00* | (2006.01) |
| *G06F 3/0484* | (2013.01) |
| *A61B 34/10* | (2016.01) |
| *A63F 13/428* | (2014.01) |
| *A63F 13/213* | (2014.01) |
| *G16H 40/67* | (2018.01) |
| *H04B 10/25* | (2013.01) |
| *G06T 19/00* | (2011.01) |
| *G06K 9/62* | (2006.01) |
| *G02B 27/01* | (2006.01) |
| *G02B 6/34* | (2006.01) |
| *G06Q 30/06* | (2012.01) |
| *G06F 3/03* | (2006.01) |
| *G06F 3/0487* | (2013.01) |
| *G06F 3/0481* | (2013.01) |
| *G06F 3/0485* | (2013.01) |
| *A63F 13/00* | (2014.01) |
| *G06T 7/60* | (2017.01) |
| *G16H 40/20* | (2018.01) |
| *G16H 40/00* | (2018.01) |

(52) U.S. Cl.
CPC .............. *A63F 13/428* (2014.09); *G02B 6/10* (2013.01); *G02B 6/34* (2013.01); *G02B 27/0101* (2013.01); *G02B 27/017* (2013.01); *G02B 27/0172* (2013.01); *G02B 27/42* (2013.01); *G02B 27/4205* (2013.01); *G02B 27/4227* (2013.01); *G06F 3/005* (2013.01); *G06F 3/011* (2013.01); *G06F 3/013* (2013.01); *G06F 3/017* (2013.01); *G06F 3/0304* (2013.01); *G06F 3/0485* (2013.01); *G06F 3/0487* (2013.01); *G06F 3/04815* (2013.01); *G06F 3/04842* (2013.01); *G06F 3/04845* (2013.01); *G06F 3/04883* (2013.01); *G06F 16/7837* (2019.01); *G06K 9/00214* (2013.01); *G06K 9/00355* (2013.01); *G06K 9/00664* (2013.01); *G06K 9/00671* (2013.01); *G06K 9/00711* (2013.01); *G06K 9/6201* (2013.01); *G06K 9/6212* (2013.01); *G06K 9/6215* (2013.01); *G06Q 30/0643* (2013.01); *G06T 7/60* (2013.01); *G06T 19/006* (2013.01); *G16H 40/00* (2018.01); *G16H 40/20* (2018.01); *G16H 40/67* (2018.01); *H04B 10/25891* (2020.05); *A61B 2034/101* (2016.02); *G02B 2027/014* (2013.01); *G02B 2027/0105* (2013.01); *G02B 2027/0127* (2013.01); *G02B 2027/0178* (2013.01); *G02B 2027/0185* (2013.01); *G02B 2027/0187* (2013.01); *G06K 9/00389* (2013.01); *G06T 2200/04* (2013.01); *G06T 2200/24* (2013.01); *G06T 2207/10004* (2013.01); *G06T 2207/30196* (2013.01); *G06T 2210/41* (2013.01); *G06T 2219/024* (2013.01)

(56) References Cited

U.S. PATENT DOCUMENTS

| | | |
|---|---|---|
| 5,563,988 A | 10/1996 | Maes et al. |
| 5,577,188 A | 11/1996 | Zhu |
| 5,594,469 A | 1/1997 | Freeman et al. |
| 5,659,691 A | 8/1997 | Durward et al. |
| 5,758,122 A | 5/1998 | Corda et al. |
| 5,886,822 A | 3/1999 | Spitzer |
| 5,999,185 A | 12/1999 | Kato |
| 6,088,017 A | 7/2000 | Tremblay et al. |
| 6,244,987 B1 | 6/2001 | Ohsuga |
| 6,417,969 B1 | 7/2002 | Deluca et al. |
| 6,549,288 B1 | 4/2003 | Migdal |
| 6,608,628 B1 | 8/2003 | Ross |
| 6,614,422 B1 | 9/2003 | Rafii et al. |
| 6,726,567 B1 | 4/2004 | Khosla |
| 6,771,294 B1 | 8/2004 | Pulli |
| 6,842,175 B1 | 1/2005 | Schmalstieg et al. |
| 7,084,884 B1 | 8/2006 | Nelson et al. |
| 7,181,690 B1 | 2/2007 | Leahy et al. |
| 7,193,633 B1 | 3/2007 | Reinhardt et al. |
| 7,257,249 B2 | 8/2007 | Farsaie |
| 7,353,481 B2 | 4/2008 | Kinoshita |
| 7,412,125 B2 | 8/2008 | Papakos |
| 7,685,023 B1 | 3/2010 | Abraham |
| 7,702,130 B2 | 4/2010 | Im |
| 7,834,847 B2 | 11/2010 | Boillot |
| 8,000,328 B1 | 8/2011 | Kandekar et al. |
| 8,016,416 B1 | 9/2011 | Straus |
| 8,018,579 B1 | 9/2011 | Krah |
| 8,072,470 B2 | 12/2011 | Marks |
| 8,086,971 B2 | 12/2011 | Radivojevic |
| 8,135,018 B1 | 3/2012 | Kandekar et al. |
| 8,149,265 B2 | 4/2012 | Smalley et al. |
| 8,179,604 B1 | 5/2012 | Prada Gomez |
| 8,196,066 B1 | 6/2012 | Ouyang |
| 8,228,315 B1 | 7/2012 | Starner |
| 8,230,367 B2 | 7/2012 | Bell et al. |
| 8,254,699 B1 | 8/2012 | Zhao et al. |
| 8,334,841 B2 | 12/2012 | Boillot et al. |
| 8,384,710 B2 | 2/2013 | Schlottmann et al. |
| 8,386,918 B2 | 2/2013 | Do et al. |
| 8,448,190 B2 | 5/2013 | Lineberger |
| 8,503,086 B2 | 8/2013 | French et al. |
| 8,514,251 B2 | 8/2013 | Hildreth et al. |
| 8,578,282 B2 | 11/2013 | Boillot |
| 8,600,166 B2 | 12/2013 | Adhikari |
| 8,639,072 B2 | 1/2014 | Popovich et al. |
| 8,693,724 B2 | 4/2014 | Ahmed |
| 8,743,052 B1 | 6/2014 | Keller |
| 8,777,735 B1 | 7/2014 | Fine et al. |
| 8,818,795 B1 | 8/2014 | Cassimatis et al. |
| 8,819,812 B1 | 8/2014 | Weber et al. |
| 8,836,768 B1 | 9/2014 | Rafii et al. |
| 8,848,203 B2 | 9/2014 | Bridges |
| 8,854,433 B1 | 10/2014 | Rafii |
| 8,866,740 B2 * | 10/2014 | Underkoffler ........... G06F 3/011 345/158 |
| 8,866,781 B2 | 10/2014 | Li |
| 8,884,984 B2 | 11/2014 | Flaks et al. |
| 8,923,562 B2 | 12/2014 | Lin et al. |
| 8,930,227 B2 | 1/2015 | Nepomuceno |
| 8,965,152 B2 | 2/2015 | Simmonds et al. |
| 9,013,396 B2 | 4/2015 | Lewis et al. |
| 9,047,698 B2 | 6/2015 | Maciocci et al. |
| 9,052,744 B2 | 6/2015 | Ma et al. |
| 9,069,164 B2 | 6/2015 | Starner |
| 9,128,520 B2 | 9/2015 | Geisner et al. |
| 9,131,163 B2 | 9/2015 | Pau et al. |

(56) References Cited

U.S. PATENT DOCUMENTS

| | | |
|---|---|---|
| 9,165,405 B2 | 10/2015 | Meier et al. |
| 9,208,615 B2 | 12/2015 | Kashitani |
| 9,215,293 B2 | 12/2015 | Miller |
| 9,229,230 B2 | 1/2016 | Scales et al. |
| 9,241,141 B1 | 1/2016 | Chang et al. |
| 9,261,262 B1 | 2/2016 | Baloga |
| 9,310,559 B2 | 4/2016 | Macnamara |
| 9,317,124 B2 | 4/2016 | Kongqiao |
| 9,329,469 B2 | 5/2016 | Benko et al. |
| 9,330,477 B2 | 5/2016 | Rappel |
| 9,330,499 B2 | 5/2016 | Perez et al. |
| 9,366,862 B2 | 6/2016 | Haddick et al. |
| 9,367,142 B2 | 6/2016 | Lee |
| 9,383,895 B1 | 7/2016 | Vinayak et al. |
| 9,384,469 B2 | 7/2016 | Alkov et al. |
| 9,448,620 B2 | 9/2016 | Kim |
| 9,520,002 B1 | 12/2016 | Gavriliuc et al. |
| 9,552,049 B1 | 1/2017 | Butler et al. |
| 9,606,668 B2 | 3/2017 | Hotelling et al. |
| 9,679,215 B2 | 6/2017 | Holz |
| 9,696,808 B2 | 7/2017 | Nishihara |
| 9,772,683 B2 | 9/2017 | Matsuda |
| 9,785,241 B2 | 10/2017 | Mason |
| 9,857,868 B2 | 1/2018 | Plagemann et al. |
| 9,857,971 B2 | 1/2018 | Chang |
| 9,965,038 B2 | 5/2018 | Walline et al. |
| 10,013,083 B2 | 7/2018 | Amariutei et al. |
| 10,068,374 B2 | 9/2018 | Miller |
| 10,173,129 B2 | 1/2019 | Mikhailov et al. |
| 10,175,483 B2 | 1/2019 | Salter |
| 10,203,761 B2 | 2/2019 | Seo et al. |
| 10,216,996 B2 | 2/2019 | Black |
| 10,349,036 B2 * | 7/2019 | Holz ................. H04N 5/332 |
| 10,614,468 B2 | 4/2020 | Vedula |
| 2001/0044858 A1 | 11/2001 | Rekimoto |
| 2002/0133264 A1 | 9/2002 | Maiteh et al. |
| 2003/0063042 A1 | 4/2003 | Friesem et al. |
| 2003/0108802 A1 | 6/2003 | Bablumyan |
| 2003/0210228 A1 | 11/2003 | Ebersole et al. |
| 2003/0214533 A1 | 11/2003 | Cull |
| 2004/0113885 A1 | 6/2004 | Genc et al. |
| 2004/0193413 A1 | 9/2004 | Wilson |
| 2004/0208466 A1 | 10/2004 | Mossberg |
| 2004/0246391 A1 | 12/2004 | Travis |
| 2005/0018209 A1 | 1/2005 | Lemelin |
| 2005/0162402 A1 | 7/2005 | Watanachote |
| 2005/0226471 A1 | 10/2005 | Singh et al. |
| 2006/0036946 A1 | 2/2006 | Radtke et al. |
| 2006/0181482 A1 | 8/2006 | Iaquinto |
| 2006/0227283 A1 | 10/2006 | Ooi |
| 2007/0080967 A1 | 4/2007 | Miller |
| 2007/0130547 A1 | 6/2007 | Boillot |
| 2007/0210155 A1 | 9/2007 | Swartz et al. |
| 2007/0220437 A1 | 9/2007 | Boillot |
| 2008/0005703 A1 | 1/2008 | Radivojevic |
| 2008/0055194 A1 | 3/2008 | Baudino |
| 2008/0071559 A1 | 3/2008 | Arrasvuori |
| 2008/0136775 A1 | 6/2008 | Conant |
| 2008/0155478 A1 | 6/2008 | Stross |
| 2008/0192794 A1 | 8/2008 | Hammer |
| 2008/0229194 A1 | 9/2008 | Boler et al. |
| 2008/0231926 A1 * | 9/2008 | Klug ................. H04N 13/327 359/23 |
| 2008/0254417 A1 | 10/2008 | Mohamed |
| 2008/0266323 A1 | 10/2008 | Biocca |
| 2008/0280684 A1 | 11/2008 | McBride et al. |
| 2009/0024614 A1 | 1/2009 | Pousti et al. |
| 2009/0040175 A1 | 2/2009 | Xu |
| 2009/0040215 A1 | 2/2009 | Afzulpurkar |
| 2009/0066690 A1 | 3/2009 | Harrison |
| 2009/0129116 A1 | 5/2009 | Kim |
| 2009/0228841 A1 | 9/2009 | Hildreth |
| 2009/0254843 A1 | 10/2009 | Van Wie |
| 2010/0045701 A1 | 2/2010 | Scott et al. |
| 2010/0045705 A1 | 2/2010 | Vertegaal et al. |
| 2010/0074532 A1 | 3/2010 | Gordon |
| 2010/0079369 A1 | 4/2010 | Hartmann et al. |
| 2010/0121697 A1 | 5/2010 | Lin |
| 2010/0134869 A1 | 6/2010 | Bernet |
| 2010/0141868 A1 | 6/2010 | St. Hilaire |
| 2010/0153313 A1 | 6/2010 | Baldwin |
| 2010/0199229 A1 | 8/2010 | Kipman |
| 2010/0199232 A1 | 8/2010 | Mistry |
| 2010/0208038 A1 | 8/2010 | Kutliroff |
| 2010/0217837 A1 | 8/2010 | Ansari et al. |
| 2010/0241947 A1 | 9/2010 | Dahn et al. |
| 2010/0257252 A1 | 10/2010 | Dougherty |
| 2011/0026781 A1 | 2/2011 | Osadchy |
| 2011/0050575 A1 | 3/2011 | Krahenbuhl et al. |
| 2011/0057929 A1 | 3/2011 | Chen et al. |
| 2011/0096072 A1 | 4/2011 | Kim et al. |
| 2011/0098056 A1 | 4/2011 | Rhoads et al. |
| 2011/0107239 A1 | 5/2011 | Adoni et al. |
| 2011/0125735 A1 | 5/2011 | Petrou |
| 2011/0128555 A1 | 6/2011 | Rotschild et al. |
| 2011/0151974 A1 | 6/2011 | Deaguero |
| 2011/0164032 A1 | 7/2011 | Shadmi |
| 2011/0187746 A1 | 8/2011 | Suto et al. |
| 2011/0193939 A1 | 8/2011 | Vassigh et al. |
| 2011/0194772 A1 | 8/2011 | SanJuan et al. |
| 2011/0216002 A1 | 9/2011 | Weising et al. |
| 2011/0219419 A1 | 9/2011 | Reisman |
| 2011/0246329 A1 | 10/2011 | Geisner et al. |
| 2011/0298704 A1 | 12/2011 | Krah |
| 2011/0301760 A1 | 12/2011 | Shuster et al. |
| 2012/0016641 A1 | 1/2012 | Raffa |
| 2012/0038549 A1 | 2/2012 | Mandella et al. |
| 2012/0069131 A1 | 3/2012 | Abelow |
| 2012/0075168 A1 | 3/2012 | Osterhout et al. |
| 2012/0078643 A1 | 3/2012 | Nagpal et al. |
| 2012/0113223 A1 | 5/2012 | Hilliges et al. |
| 2012/0127284 A1 | 5/2012 | Bar-Zeev et al. |
| 2012/0127751 A1 | 5/2012 | Kimmel |
| 2012/0154296 A1 | 6/2012 | Hinckley |
| 2012/0155774 A1 | 6/2012 | Li |
| 2012/0183137 A1 | 7/2012 | Laughlin |
| 2012/0194418 A1 | 8/2012 | Osterhout |
| 2012/0194419 A1 | 8/2012 | Osterhout et al. |
| 2012/0209514 A1 | 8/2012 | Chrysanthakopoulos |
| 2012/0214594 A1 | 8/2012 | Kirovski |
| 2012/0229377 A1 | 9/2012 | Kim |
| 2012/0229446 A1 | 9/2012 | Hyndman et al. |
| 2012/0229509 A1 | 9/2012 | Liu |
| 2012/0242942 A1 | 9/2012 | Jeon |
| 2012/0249741 A1 | 10/2012 | Maciocci et al. |
| 2012/0300979 A1 | 11/2012 | Pircheim |
| 2012/0306847 A1 | 12/2012 | Lim et al. |
| 2012/0306850 A1 | 12/2012 | Balan |
| 2012/0311564 A1 | 12/2012 | Khalid |
| 2012/0314902 A1 | 12/2012 | Kimura |
| 2012/0316421 A1 | 12/2012 | Kumar et al. |
| 2012/0317108 A1 | 12/2012 | Okazaki |
| 2012/0327125 A1 | 12/2012 | Kutliroff et al. |
| 2013/0006064 A1 | 1/2013 | Reiner |
| 2013/0009994 A1 | 1/2013 | Hill |
| 2013/0016070 A1 | 1/2013 | Starner et al. |
| 2013/0016908 A1 | 1/2013 | Xin et al. |
| 2013/0030552 A1 | 1/2013 | Beckley |
| 2013/0038601 A1 | 2/2013 | Han et al. |
| 2013/0044129 A1 | 2/2013 | Latta |
| 2013/0044912 A1 | 2/2013 | Kulkarni |
| 2013/0050069 A1 | 2/2013 | Ota |
| 2013/0073504 A1 | 3/2013 | Mohindra |
| 2013/0083009 A1 | 4/2013 | Geisner et al. |
| 2013/0083063 A1 | 4/2013 | Geisner et al. |
| 2013/0083064 A1 | 4/2013 | Geisner et al. |
| 2013/0095924 A1 | 4/2013 | Geisner et al. |
| 2013/0097534 A1 | 4/2013 | Lewin et al. |
| 2013/0106692 A1 | 5/2013 | Maizels et al. |
| 2013/0117377 A1 | 5/2013 | Miller |
| 2013/0121600 A1 | 5/2013 | Lin |
| 2013/0128230 A1 | 5/2013 | Macnamara |
| 2013/0166137 A1 | 6/2013 | Ahn |
| 2013/0173445 A1 | 7/2013 | Johnson et al. |

(56) References Cited

U.S. PATENT DOCUMENTS

| | | |
|---|---|---|
| 2013/0211843 A1 | 8/2013 | Clarkson |
| 2013/0215239 A1 | 8/2013 | Wang |
| 2013/0216098 A1 | 8/2013 | Hasegawa |
| 2013/0218721 A1 | 8/2013 | Borhan |
| 2013/0222367 A1 | 8/2013 | Mariappan |
| 2013/0222369 A1* | 8/2013 | Huston .................. G06T 19/20 345/419 |
| 2013/0222371 A1 | 8/2013 | Reitan |
| 2013/0265220 A1 | 10/2013 | Fleischmann et al. |
| 2013/0267318 A1 | 10/2013 | Pryor et al. |
| 2013/0282792 A1 | 10/2013 | Graham |
| 2013/0283213 A1 | 10/2013 | Guendelman et al. |
| 2013/0294651 A1 | 11/2013 | Zhou et al. |
| 2013/0300637 A1 | 11/2013 | Smits et al. |
| 2013/0321261 A1 | 12/2013 | Nakasu et al. |
| 2013/0342570 A1 | 12/2013 | Kinnebrew et al. |
| 2013/0342572 A1* | 12/2013 | Poulos ................... G06F 3/012 345/633 |
| 2014/0002351 A1 | 1/2014 | Nakayama |
| 2014/0007022 A1 | 1/2014 | Tocino Diaz et al. |
| 2014/0015831 A1 | 1/2014 | Kim et al. |
| 2014/0028714 A1 | 1/2014 | Keating |
| 2014/0028850 A1 | 1/2014 | Keating et al. |
| 2014/0055343 A1 | 2/2014 | Kim |
| 2014/0055352 A1 | 2/2014 | Davis et al. |
| 2014/0063055 A1 | 3/2014 | Osterhout et al. |
| 2014/0063060 A1* | 3/2014 | Maciocci ............. G06T 19/006 345/633 |
| 2014/0068526 A1 | 3/2014 | Figelman et al. |
| 2014/0081659 A1 | 3/2014 | Nawana |
| 2014/0089326 A1 | 3/2014 | Lin |
| 2014/0101195 A1 | 4/2014 | Li et al. |
| 2014/0104168 A1 | 4/2014 | Hegde |
| 2014/0118270 A1 | 5/2014 | Moses et al. |
| 2014/0123077 A1 | 5/2014 | Kutliroff et al. |
| 2014/0125584 A1 | 5/2014 | Xun et al. |
| 2014/0125598 A1 | 5/2014 | Cheng et al. |
| 2014/0162220 A1 | 6/2014 | Rao et al. |
| 2014/0176530 A1 | 6/2014 | Pathre |
| 2014/0176603 A1 | 6/2014 | Kumar |
| 2014/0184644 A1 | 7/2014 | Sharma |
| 2014/0192087 A1 | 7/2014 | Frost |
| 2014/0195988 A1* | 7/2014 | Kramer .................. G06F 3/017 715/863 |
| 2014/0198954 A1 | 7/2014 | Bulzacki |
| 2014/0201666 A1 | 7/2014 | Bedikian et al. |
| 2014/0214547 A1 | 7/2014 | Signorelli |
| 2014/0223327 A1 | 8/2014 | Mantripragada et al. |
| 2014/0247279 A1 | 9/2014 | Nicholas |
| 2014/0267407 A1 | 9/2014 | Mullins |
| 2014/0267417 A1 | 9/2014 | Bare |
| 2014/0272812 A1 | 9/2014 | Hing |
| 2014/0274283 A1 | 9/2014 | Helava |
| 2014/0279860 A1 | 9/2014 | Pan |
| 2014/0282273 A1 | 9/2014 | Anderson |
| 2014/0287389 A1 | 9/2014 | Kallmann et al. |
| 2014/0289323 A1 | 9/2014 | Kutaragi et al. |
| 2014/0300632 A1 | 10/2014 | Laor |
| 2014/0306993 A1 | 10/2014 | Poulos |
| 2014/0310595 A1 | 10/2014 | Acharya |
| 2014/0314322 A1 | 10/2014 | Snavely |
| 2014/0333666 A1 | 11/2014 | Poulos et al. |
| 2014/0347392 A1 | 11/2014 | Odessky |
| 2014/0361988 A1 | 12/2014 | Katz |
| 2014/0364209 A1 | 12/2014 | Perry |
| 2015/0002475 A1 | 1/2015 | Tiao |
| 2015/0007114 A1 | 1/2015 | Poulos et al. |
| 2015/0009124 A1 | 1/2015 | Antoniac |
| 2015/0016712 A1 | 1/2015 | Rhoads et al. |
| 2015/0016777 A1 | 1/2015 | Abovitz |
| 2015/0023557 A1 | 1/2015 | Yoo et al. |
| 2015/0023602 A1 | 1/2015 | Wnuk |
| 2015/0040074 A1 | 2/2015 | Hofmann |
| 2015/0046296 A1 | 2/2015 | Hart |
| 2015/0054748 A1 | 2/2015 | Mason |
| 2015/0078613 A1 | 3/2015 | Forutanpour |
| 2015/0079560 A1 | 3/2015 | Cowan |
| 2015/0084859 A1 | 3/2015 | Itzhaik |
| 2015/0091780 A1 | 4/2015 | Lyren |
| 2015/0130836 A1 | 5/2015 | Anderson |
| 2015/0145985 A1 | 5/2015 | Gourlay et al. |
| 2015/0153833 A1 | 6/2015 | Pinault |
| 2015/0169176 A1 | 6/2015 | Cohen et al. |
| 2015/0169746 A1 | 6/2015 | Hatami-Hanza |
| 2015/0172626 A1 | 6/2015 | Martini |
| 2015/0185825 A1 | 7/2015 | Mullins |
| 2015/0186708 A1 | 7/2015 | Katz |
| 2015/0187137 A1 | 7/2015 | Mullins |
| 2015/0234475 A1 | 8/2015 | Latta |
| 2015/0235441 A1 | 8/2015 | Abovitz et al. |
| 2015/0241705 A1 | 8/2015 | Abovitz |
| 2015/0241984 A1 | 8/2015 | Itzhaik |
| 2015/0242575 A1 | 8/2015 | Abovitz et al. |
| 2015/0243106 A1 | 8/2015 | Abovitz et al. |
| 2015/0247975 A1 | 9/2015 | Abovitz |
| 2015/0247976 A1 | 9/2015 | Abovitz |
| 2015/0262208 A1 | 9/2015 | Bjontegard |
| 2015/0268730 A1 | 9/2015 | Walline et al. |
| 2015/0268731 A1 | 9/2015 | Sanaullah et al. |
| 2015/0268773 A1 | 9/2015 | Sanaullah et al. |
| 2015/0268812 A1* | 9/2015 | Walline ................. G06F 1/1686 715/773 |
| 2015/0269783 A1 | 9/2015 | Yun |
| 2015/0278691 A1 | 10/2015 | Xia |
| 2015/0309263 A2 | 10/2015 | Abovitz |
| 2015/0309264 A1 | 10/2015 | Abovitz |
| 2015/0324001 A1 | 11/2015 | Yanai et al. |
| 2016/0011896 A1 | 1/2016 | Khalid |
| 2016/0012643 A1 | 1/2016 | Kezele et al. |
| 2016/0026253 A1 | 1/2016 | Bradski et al. |
| 2016/0048024 A1 | 2/2016 | Yang et al. |
| 2016/0055674 A1 | 2/2016 | Mullins |
| 2016/0178906 A1 | 6/2016 | Rider |
| 2016/0217614 A1 | 7/2016 | Kraver |
| 2016/0257000 A1 | 9/2016 | Guerin |
| 2016/0259409 A1 | 9/2016 | Lee |
| 2016/0283014 A1 | 9/2016 | Rider |
| 2016/0313816 A1 | 10/2016 | Krishnakumar et al. |
| 2017/0185156 A1* | 6/2017 | Shotton .................. G06F 3/017 |
| 2017/0255648 A1 | 9/2017 | Dube et al. |
| 2017/0262045 A1* | 9/2017 | Rouvinez ............... G06F 3/011 |
| 2019/0178638 A1 | 6/2019 | Abovitz et al. |

OTHER PUBLICATIONS

Non-final office action for U.S. Appl. No. 14/707,271, dated Sep. 10, 2019.

Notice of Allowance for U.S. Appl. No. 14/706,889 dated Sep. 13, 2019.

Response to Non-Final Office Action filed Sep. 19, 2019 for U.S. Appl. No. 14/707,310.

Response to Non-Final Office Action filed Sep. 26, 2019 for U.S. Appl. No. 16/276,511.

Notice of Allowance for U.S. Appl. No. 14/707,310 dated Oct. 16, 2019.

Non-Final Office Action for U.S. Appl. No. 14/707,266 dated Oct. 23, 2019.

Notice of Allowance for U.S. Appl. No. 14/707,385 dated Oct. 30, 2019.

RCE and Response to Final Office Action filed Jun. 3, 2019 for U.S. Appl. No. 14/707,310.

Advisory Action dated Jun. 3, 2019 for U.S. Appl. No. 14/707,338.

Advisory Action dated Jun. 7, 2019 for U.S. Appl. No. 14/707,3266.

Notice of Allowance dated Jun. 10, 2019 for U.S. Appl. No. 14/704,800.

RCE and Response to Final Office Action filed Jun. 18, 2019 for U.S. Appl. No. 14/707,271.

RCE and Response to Final Office Action filed Jun. 19, 2019 for U.S. Appl. No. 14/707,338.

Non-Final Office Action dated Jun. 24, 2019 for U.S. Appl. No. 14/707,310.

(56) References Cited

OTHER PUBLICATIONS

Non-Final Office Action dated Jun. 28, 2019 for U.S. Appl. No. 16/276,511.
Notice of Allowance dated Jul. 11, 2019 for U.S. Appl. No. 14/704,765.
Appeal Brief filed Jul. 15, 2018 for U.S. Appl. No. 14/707,385.
Reply Brief filed Jul. 29, 2019 for U.S. Appl. No. 14/707,513.
Non final office action dated Nov. 13, 2019 for U.S. Appl. No. 14/707,338.
Notice of Allowance for U.S. Appl. No. 16/276,511 dated Jan. 9, 2020.
Amendment Response for U.S. Appl. No. 14/707,271 dated Jan. 10, 2020.
Notice of Allowance for U.S. Appl. No. 14/707,385 dated Jan. 13, 2020.
Response to Non-final Office Action filed Jan. 23, 2020 for U.S. Appl. No. 14/707,266.
Amendment After Non-Final Office Action filed Feb. 13, 2020 for U.S. Appl. No. 14/707,338.
Notice of Allowance for U.S. Appl. No. 14/707,271 dated Mar. 18, 2020.
Bonnani et al., "Attention-based design of augmented reality interfaces," CHI extended abstracts of human factors in computing systems, ACM, Apr. 2005, pp. 1228-1231 (4 pages).
Fadil et al., "Mixed reality cooling support system using content-free recipe selection," Dec. 2006, IEEE International Symposium, Multimedia, pp. 845-850 (6 pages).
Miyawaki et al., "A virtual agent for a cooking navigation system using augmented reality," 2008, Intelligent Virtual Agents vol. 5208 for the series Lecture Notes in Computer Science, pp. 97-103 (7 pages).
Nakamoto et al., "Cooking up an interactive olfactory game display," Jan.-Feb. 2008, IEEE Computer Graphics and Applications, vol. 28, pp. 75-78 (4 pages).
Non-Final Office Action for U.S. Appl. No. 14/331,218 dated Jul. 22, 2015 (18 pages).
Amendment Response to Non-Final Office Action for U.S. Appl. No. 14/331,218 dated Jul. 22, 2015, response filed Jan. 22, 2016 (7 pages).
Final Office Action for U.S. Appl. No. 14/331,218 dated Jun. 3, 2016 (19 pages).
Non-Final Office Action for U.S. Appl. No. 14/696,347 dated Jun. 17, 2016 (15 pages).
Non-Final Office Action for U.S. Appl. No. 14/704,765 dated May 16, 2016 (46 pages).
Non-Final Office Action for U.S. Appl. No. 14/704,800 dated Jun. 3, 2016 (25 pages).
Non-Final Office Action for U.S. Appl. No. 14/704,826 dated May 16, 2016 (30 pages).
Non-Final Office Action for U.S. Appl. No. 14/704,844 dated May 18, 2016 (23 pages).
Non-Final Office Action for U.S. Appl. No. 14/707,241 dated May 13, 2016 (10 pages).
Non-Final Office Action for U.S. Appl. No. 14/707,266 dated Jun. 2, 2016 (10 pages).
Non-Final Office Action for U.S. Appl. No. 14/707,290 dated May 12, 2016 (10 pages).
Non-Final Office Action for U.S. Appl. No. 14/707,271 dated Jun. 3, 2016 (11 pages).
Non-Final Office Action for U.S. Appl. No. 14/707,616 dated Jun. 16, 2016 (10 pages).
Non-Final Office Action for U.S. Appl. No. 14/707,338 dated May 12, 2016 (8 pages).
http:wvvw.youtube.com/watch?v=t0H1NNa6zXc, dated Jun. 4, 2015.
http:www.yankodesign.com/20110802/going-beyond-augemented-reality, dated Jun. 4, 2015.
http:www.yankodesign.com/20110914/virtualarchitecture, dated Jun. 4, 2015.
http:www.fastcodesign.com/1670420/watch-what-happens-if-googles-glasses-are-evil, dated Jun. 4, 2015.
https:www.youtube.com/watch?v=rOOyk8ro6, dated Jun. 4, 2015.
http:www.ted.com/talks/anand_agarawala_demos_his_bumptop_desktop.html, dated Jun. 4, 2015.
https:www.youtube.com/watch?v=QBAnr2gQTH0, dated Jun. 4, 2015.
http:www.youtube.com/watch?v=MytC7rnnJM8, dated Jun. 4, 2015.
http:imgur.com/gallery/0COOH, dated Jun. 4, 2015.
http:www.ted.com/talksjohn_underkoffler_drive_3d_data_with_a_gesture?language=en, dated Jun. 4, 2015.
https:www.behance.net/gallery/4170939/Ringo-Holographic-Interface-2008, dated Jun. 4, 2015.
https:vimeo.com/24860709, dated Jun. 4, 2015.
https:vimeo.com/46304267, dated Jun. 4, 2015.
https:www.youtube.com/watch?v=6QHaUAnecuM, dated Jun. 4, 2015.
https:www.youtube.com/watch?v=o8fNdDkfw_w, dated Jun. 4, 2015.
International Search Report and Written Opinion dated Jan. 12, 2015 for PCT/US2014/046572, Applicant Magic Leap, Inc., filed Jul. 14, 2014 13 pages.
Notice of Allowance for U.S. Appl. No. 14/707,354, dated Jun. 22, 2016 (12 pages).
Non-Final Office Action for U.S. Appl. No. 14/706,889, dated Jun. 27, 2016 (17 pages.).
Non-Final Office Action for U.S. Appl. No. 14/707,253, dated Jun. 29, 2016 (10 pages).
Non-Final Office Action for U.S. Appl. No. 14/707,513, dated Aug. 2, 2016 (17 pages).
Response filed Aug. 8, 2016 to Non-Final Office Action dated May 13, 2016, for U.S. Appl. No. 14/707,241, (9 pages).
Response filed Aug. 10, 2016 to Non-Final Office Action dated May 12, 2016, for U.S. Appl. No. 14/707,338, (10 pages).
Non-Final Office Action for U.S. Appl. No. 14/707,581 dated Aug. 12, 2016 (18 pages).
Non-Final Office Action for U.S. Appl. No. 14/707,640 dated Aug. 10, 2016 (21 pages).
Response filed Aug. 12, 2016 to Non-Final Office Action dated May 12, 2016, for U.S. Appl. No. 14/707,290, (8 pages).
Shute et al. "Monitoring and Fostering Learning Through Games and Embedded Assessments;" ETS RR-08-69; Educational Testing Service, Princeton, NJ; Dec. 2008; (39 pages).
Non-Final Office Action for U.S. Appl. No. 14/707,608 dated Aug. 11, 2016 (18 pages).
Response filed Aug. 16, 2016 to Non-Final Office Action for U.S. Appl. No. 14/704,765 (11 pages).
Non-Final Office Action for U.S. Appl. No. 14/707,425 dated Aug. 23, 2016 (18 pages).
Response filed Sep. 15, 2016 to Non-Final Office Action for U.S. Appl. No. 14/696,347 (6 pages).
Non-Final Office Action for U.S. Appl. No. 14/707,745 dated Sep. 16, 2016 (20 pages).
Response filed Sep. 15, 2016 to Non-Final Office Action for U.S. Appl. No. 14/704,826 (23 pages).
Response filed Sep. 14, 2016 to Non-Final Office Action for U.S. Appl. No. 14/707,616 (5 pages).
Non-Final Office Action for U.S. Appl. No. 14/707,311 dated Sep. 9, 2016 (17 pages).
Response filed Aug. 30, 2016 Non-Final Office Action for U.S. Appl. No. 14/707,271 dated (13 pages).
Response filed Sep. 6, 2016 Non-Final Office Action for U.S. Appl. No. 14/704,800 (22 pages).
Response filed Sep. 6, 2016 to Final Office Action for U.S. Appl. No. 14/331,218 (5 pages).
Response Non-Final Office Action filed Sep. 27, 2016 for U.S. Appl. No. 14/706,889 (12 pages).
Response submitted Sep. 28, 2016 to Non-final office action for U.S. Appl. No. 14/707,253 (11 pages).
Non-Final Office Action dated Oct. 5, 2016 for U.S. Appl. No. 14/331,218 (15 pages).
Final Office Action dated Oct. 11, 2016, for U.S. Appl. No. 14/707,290, (15 pages.
Notice of Allowance dated Oct. 11, 2016, for U.S. Appl. No. 14/707,616 (8 pages).

(56) References Cited

OTHER PUBLICATIONS

Final Office Action for U.S. Appl. No. 14/707,338 dated Oct. 13, 2016 (14 pages).
Final Office Action for U.S. Appl. No. 14/707,241 dated Oct. 13, 2016 (15 pages).
Response filed Oct. 31, 2016 to Non-Final Office Action for U.S. Appl. No. 14/707,513, (17 pages).
Final Office Action for U.S. Appl. No. 14/706,889, dated Oct. 28, 2016 (36 pages).
Response filed Oct. 3, 2016 to Non-Final Office Action for U.S. Appl. No. 14/707,266 (18 pages).
Non-final Office Action dated Sep. 21, 2016 for U.S. Appl. No. 14/707,385 (18 pages).
Da-Peng Yang et al. An Anthropomorphic Robot Hand Developed Based on Underactuated Mechanism and Controlled by EMG Signals, Journal of Bionic Engineering 6, Issue 3, Sep. 2009) 255-263, (9 pages).
Response filed Nov. 9, 2016 to Non-Final office action for U.S. Appl. No. 14/707,640 (14 pages).
Response filed Nov. 10, 2016 to Non-Final office action for U.S. Appl. No. 14/707,608 (18 pages).
Response filed Nov. 11, 2016 to Non-Final office action for U.S. Appl. No. 14/707,581 (21 pages).
Response filed Nov. 17, 2016 to Non-Final office action for U.S. Appl. No. 14/707,844 (21 pages).
Response filed Nov. 22, 2016 to Non-final office action for U.S. Appl. No. 14/707,425 (21 pages).
Final office action for U.S. Appl. No. 14/704,765 dated Nov. 22, 2016 (100 pages).
Non-final office action for U.S. Appl. No. 14/704,858 dated Nov. 29, 2016 (43 pages).
Final office action for U.S. Appl. No. 14/704,844 dated Dec. 1, 2016 (30 pages).
Final office action for U.S. Appl. No. 14/707,266 dated Dec. 8, 2016 (13 pages).
Final office action for U.S. Appl. No. 14/704,826 dated Dec. 8, 2016 (31 pages).
Notice of Allowance for U.S. Appl. No. 14/696,347 dated Dec. 28, 2016 (25 pages).
Final Rejection for U.S. Appl. No. 14/707,271 dated Nov. 16, 2016 (18 pages).
Final Rejection for U.S. Appl. No. 14/704,800 dated Dec. 13, 2016 (66 pages).
Final Office Action for U.S. Appl. No. 14/707,253 dated Dec. 16, 2016 (12 pages).
Final Office Action for U.S. Appl. No. 14/707,513, dated Dec. 20, 2016 (20 pages).
Final Office Action for U.S. Appl. No. 14/707,581, dated Dec. 14, 2016 (15 pages).
Final Office Action for U.S. Appl. No. 14/707,425, dated Jan. 9, 2017 (18 pages).
Final Office Action for U.S. Appl. No. 14/707,608, dated Jan. 6, 2017 (19 pages).
Response filed Jan. 12, 2017 to Final Office Action for U.S. Appl. No. 14/707,338 (15 pages).
Final Office Action for U.S. Appl. No. 14/707,640, dated Jan. 12, 2017 (16 pages).
Amendment Response to Final office action filed Jan. 30, 2017 for U.S. Appl. No. 14/706,889 (14 pages).
Amendment Response to Non-Final Office Action filed Feb. 9, 2017 for U.S. Appl. No. 14/707,311.
Amendment Response to Final Office Action filed Feb. 13, 2017 for U.S. Appl. No. 14/707,241.
Response filed Feb. 15, 2017 to Final office action for U.S. Appl. No. 14/707,271.
Response filed Feb. 15, 2017 to Non-Final office action for U.S. Appl. No. 14/707,745.
Response filed Feb. 21, 2017 to Final office action for U.S. Appl. No. 14/704,765.
Response filed Feb. 21, 2017 to Non-Final office action for U.S. Appl. No. 14/707,385.
Response filed Feb. 28, 2017 to Non-Final office action for U.S. Appl. No. 14/704,858.
Response filed Mar. 3, 2017 to Non-Final office action for U.S. Appl. No. 14/331,218.
Response filed Mar. 10, 2017 to Final Office Action for U.S. Appl. No. 14/707,290.
Response filed Mar. 13, 2017 to Final Office Action for U.S. Appl. No. 14/704,800.
Response filed Mar. 16, 2017 to Final Office Action for U.S. Appl. No. 14/707,513.
Response filed Apr. 3, 2017 to Final Office Action for U.S. Appl. No. 14/707,266.
Response filed Apr. 3, 2017 to Final Office Action for U.S. Appl. No. 14/707,425.
Response filed Apr. 3, 2017 to Final Office Action for U.S. Appl. No. 14/707,608.
Notice of Allowance dated Feb. 24, 2017, for U.S. Appl. No. 14/707,616 (22 pages).
Notice of Allowance dated Apr. 4, 2017 for U.S. Appl. No. 14/331,218 (21 pages).
Response filed Apr. 10, 2017 to Final Office Action for U.S. Appl. No. 14/704,826.
Non Final Rejection for U.S. Appl. No. 14/704,800 dated Apr. 7,2017 (74 pages).
Response filed Apr. 10, 2017 to Final Office Action for U.S. Appl. No. 14/707,581.
Response filed Apr. 11, 2017 to Final Office Action for U.S. Appl. No. 14/707,253.
Response filed Apr. 27, 2017 to Final Office Action for U.S. Appl. No. 14/707,844.
Non Final Rejection for U.S. Appl. No. 14/706,889 dated Apr. 21, 2017 (36 pages).
Final Office Action for U.S. Appl. No. 14/707,385, dated May 3, 2017 (44 pages).
Non-Final Office Action for U.S. Appl. No. 14/707,425 dated May 22, 2017 (13 pages).
Final Office Action for U.S. Appl. No. 14/704,858 dated May 26, 2017 (65 pages).
Final Office Action for U.S. Appl. No. 14/707,745 dated May 31, 2017 (24 pages).
Non-Final Office Action for U.S. Appl. No. 14/707,513 dated May 19, 2017 (20 pages).
Non-Final Office Action for U.S. Appl. No. 14/707,581 dated May 19, 2017 (13 pages).
Non-Final Office Action for U.S. Appl. No. 14/707,640 dated Jun. 5, 2017 (18 pages).
Non-Final Office Action for U.S. Appl. No. 14/704,826 dated May 18, 2017 (52 pages).
Final Office Action for U.S. Appl. No. 14/707,311 dated May 11, 2017 (33 pages).
Non-Final Office Action for U.S. Appl. No. 14/707,608 dated May 8, 2017 (52 pages).
Response filed Jul. 3, 2017 to Final Office Action for U.S. Appl. No. 14/707,385.
Response filed Jul. 7, 2017 to Office Action for U.S. Appl. No. 14/704,800.
Response filed Jul. 11, 2017 to Final Office Action for U.S. Appl. No. 14/707,311.
Non final office action for U.S. Appl. No. 14/707,310, dated Jul. 11, 2017.
Non final office action for U.S. Appl. No. 14/707,241 dated Jun. 26, 2017.
Non final office action for U.S. Appl. No. 14/707,338 dated Jun. 22, 2017.
Response to Non Final Rejection filed Jul. 19, 2017 for U.S. Appl. No. 14/706,889 (18 pages).
Notice of Allowance, Interview Summary and AFCP decision dated Jul. 24, 2017 for U.S. Appl. No. 14/707,311.
Advisory Action dated Jul. 28, 2017 for U.S. Appl. No. 14/707,385, 13 pages.

(56) References Cited

OTHER PUBLICATIONS

Response to Final Office Action filed Jul. 27, 2017 for U.S. Appl. No. 14/707,745, 16 pages.
Non Final Office Action for U.S. Appl. No. 14/707,271 dated Jul. 27, 2017.
Non-Final Office Action for U.S. Appl. No. 14/704,765 dated Jul. 26, 2017.
Response to Final Office Action filed Aug. 3, 2017 for U.S. Appl. No. 14/707,385, 21 pages.
Response to Non Final Rejection filed Aug. 8, 2017 for U.S. Appl. No. 14/707,608 (14 pages).
Wikipedia Entry for "Wii Remote", https://en.wikipedia.org/wiki/Wii_Remote, PDF copy created on Aug. 8, 2017, page last edited on Aug. 3, 2017; 19 pages.
Non-Final Office Action for U.S. Appl. No. 14/707,266, dated Aug. 7, 2017 (12 pages).
Non-Final Office Action for U.S. Appl. No. 14/707,290, dated Aug. 7, 2017 (15 pages).
Response to Non Final Rejection filed Aug. 18, 2017 for U.S. Appl. No. 14/704,826 (11 pages).
Response to Non Final Rejection filed Aug. 21, 2017 for U.S. Appl. No. 14/707,581 (9 pages).
Response to Non Final Rejection filed Aug. 21, 2017 for U.S. Appl. No. 14/707,531 (11 pages).
Response to Non Final Rejection filed Aug. 22, 2017 for U.S. Appl. No. 14/707,425 (7 pages).
Response to Final Office Action filed Aug. 28, 2017 for U.S. Appl. No. 14/704,858, 23 pages.
RCE Response to Final Office Action filed Aug. 31, 2017 for U.S. Appl. No. 14/707,745, 19 pages.
Response to Non Final Rejection filed Sep. 5, 2017, for U.S. Appl. No. 14/707,640 (10 pages).
Response to Non Final Rejection filed Sep. 22, 2017, for U.S. Appl. No. 14/707,338 (16 pages).
Final Office Action for U.S. Appl. No. 14/704,800, dated Sep. 7, 2017 (89 pages).
Final Office Action for U.S. Appl. No. 14/704,826, dated Sep. 15, 2017 (52 pages).
Non-Final Office Action for U.S. Appl. No. 14/707,253, dated Sep. 8, 2017 (33 pages).
Advisory Action dated Aug. 17, 2017 for U.S. Appl. No. 14/707,745, 3 pages.
Final office action for U.S. Appl. No. 14/707,640, dated Oct. 10, 2017.
Response to Non Final Rejection filed Oct. 11, 2017, for U.S. Appl. No. 14/707,310.
Non-Final Office Action for U.S. Appl. No. 14/707,745, dated Oct. 4, 2017.
Non-Final Office Action for U.S. Appl. No. 14/707,385, dated Oct. 4, 2017.
Response to Non Final Rejection dated Oct. 27, 2017 for U.S. Appl. No. 14/707,271.
Response to Non-Final Office Action filed Oct. 26, 2017 for U.S. Appl. No. 14/704,765.
Non-Final Office Action for U.S. Appl. No. 14/704,844 dated Oct. 30, 2017 (30 pages).
Final Office Action dated Oct. 31, 2017 for U.S. Appl. No. 14/707,608 (21 pages).
Notice of Allowance for U.S. Appl. No. 14/707,311, dated Nov. 2, 2017.
Final Office Action for U.S. Appl. No. 14/706,889 dated Nov. 6, 2017.
Final Office Action for U.S. Appl. No. 14/707,310 dated Nov. 6, 2017.
Response to Final Office Action filed Nov. 7, 2017 for U.S. Appl. No. 14/704,800.
Response to Non-Final Office Action filed Nov. 7, 2017 for U.S. Appl. No. 14/707,266.
Response to Non-Final Office Action filed Nov. 7, 2017 for U.S. Appl. No. 14/707,290.
Response to Final Office Action filed Dec. 11, 2017 for U.S. Appl. No. 14/707,640.
Advisory Action dated Nov. 28, 2017 for U.S. Appl. No. 14/704,800.
Final Office Action for U.S. Appl. No. 14/707,425 dated Nov. 27, 2017.
Final Office Action for U.S. Appl. No. 14/707,513 dated Nov. 28, 2017.
Non-Final Office Action for U.S. Appl. No. 14/707,581, dated Nov. 27, 2017.
Final Office Action for U.S. Appl. No. 14/707,241 dated Dec. 6, 2017.
Final Office Action for U.S. Appl. No. 14/707,338 dated Dec. 6, 2017.
Final Office Action for U.S. Appl. No. 14/704,765 dated Dec. 11, 2017.
Amendment and Response filed Dec. 8, 2017 for U.S. Appl. No. 14/707,253.
Amendment and Response filed Dec. 15, 2017 for U.S. Appl. No. 14/704,826.
Notice of Allowance dated Dec. 28, 2017 for U.S. Appl. No. 14/704,858.
Amendment and Response to Final Office Action for U.S. Appl. No. 14/707,608, filed Dec. 29, 2017.
Amendment and Response to Final Office Action for U.S. Appl. No. 14/707,745, filed Jan. 4, 2018.
Amendment and Response to Final Office Action for U.S. Appl. No. 14/707,385, filed Jan. 4, 2018.
Amendment and Response to Final Office Action for U.S. Appl. No. 14/706,889, filed Jan. 8, 2018.
Response to Final Office Action and RCE filed Jan. 8, 2018 for U.S. Appl. No. 14/704,800.
Advisory Action dated Jan. 12, 2018 for U.S. Appl. No. 14/707,608.
Advisory Action dated Jan. 16, 2018 for U.S. Appl. No. 14/707,640.
Advisory Action dated Jan. 22, 2018 for U.S. Appl. No. 14/706,889.
Notice of Allowance dated Jan. 30, 2018 for U.S. Appl. No. 14/704,826.
Amendment and Response to Non-Final Office Action for U.S. Appl. No. 14/704,844, filed Jan. 30, 2018.
Response to Final Office Action and RCE filed Jan. 31, 2018 for U.S. Appl. No. 14/707,608.
Amendment and Response to Final Office Action for U.S. Appl. No. 14/707,241, filed Feb. 2, 2018.
Response to Final Office Action and RCE filed Feb. 5, 2018 for U.S. Appl. No. 14/706,889.
Response to Final Office Action and RCE filed Feb. 5, 2018 for U.S. Appl. No. 14/707,310.
Final office action dated Feb. 5, 2018 for U.S. Appl. No. 14/707,290.
Final office action dated Feb. 5, 2018 for U.S. Appl. No. 14/707,271.
Funkhouser, RING: a client-server system for multi-user virtual environments, Apr. 9-12, 1995, ACM Proceedings of the 1995 symposium on Interactive 3D graphics, pp. 85-92, 209.
Final office action dated Feb. 5, 2018 for U.S. Appl. No. 14/707,266.
Response to Final Office Action filed Feb. 15, 2018 for U.S. Appl. No. 14/707,338.
Amendment and Response to Final Office Action filed Feb. 15, 2018 for U.S. Appl. No. 14/707,640.
Non-Final Office Action dated Feb. 20, 2018 for U.S. Appl. No. 14/707,310.
Response to Final Office Action and RCE filed Feb. 28, 2018 for U.S. Appl. No. 14/707,513.
Amendment and Response to Final Office Action filed Mar. 6, 2018 for U.S. Appl. No. 14/707,241.
Final Office Action dated Mar. 2, 2018 for U.S. Appl. No. 14/707,385.
Advisory Action dated Mar. 1, 2018 for U.S. Appl. No. 14/707,241.
Non-Final Office Action dated Mar. 2, 2018 for U.S. Appl. No. 14/704,800.
Advisory Action dated Mar. 15, 2018 for U.S. Appl. No. 14/707,338.
Response to Non Final Office Action filed Mar. 26, 2018 for U.S. Appl. No. 14/707,581.
Final office action dated Mar. 26, 2018 for U.S. Appl. No. 14/707,745.
Final office action dated Mar. 28, 2018 for U.S. Appl. No. 14/707,253.
Non final Office Action dated Apr. 2, 2018 for U.S. Appl. No. 14/707,608.

(56) References Cited

OTHER PUBLICATIONS

Non final Office Action dated Apr. 4, 2018 for U.S. Appl. No. 14/707,640.
Non final Office Action dated Apr. 4, 2018 for U.S. Appl. No. 14/707,513.
RCE and Response to Final Office Action filed Apr. 6, 2018 for U.S. Appl. No. 14/707,338.
Amendment RCE and Response to Final Office Action filed Apr. 11, 2018 for U.S. Appl. No. 14/704,765.
Final office action dated Apr. 25, 2018 for U.S. Appl. No. 14/707,581.
Response to Final Office Action filed May 2, 2018 for U.S. Appl. No. 14/707,385.
Response to Final Office Action filed May 4, 2018 for U.S. Appl. No. 14/707,271.
Response to Final Office Action filed May 4, 2018 for U.S. Appl. No. 14/707,266.
Response to Final Office Action filed May 7, 2018 for U.S. Appl. No. 14/707,290.
Response to Non Final Office Action filed May 21, 2018 for U.S. Appl. No. 14/707,310.
Non Final office action dated May 22, 2018 for U.S. Appl. No. 14/706,889.
Timotheüs van der Niet, Christoph P.E. Zollikofer, Marcia S. Ponce de León, Steven D. Johnson, H. Peter Linder, "Three-dimensional geometric morphometrics for studying floral shape variation", Trends in Plant Science, vol. 15, No. 8, pp. 423-426 (4 pages), Aug. 2010.
Response to Final Office Action filed Jun. 4, 2018 for U.S. Appl. No. 14/704,800.
Advisory Action dated Jun. 8, 2018 for U.S. Appl. No. 14/707,385.
Response to Final Office Action filed Jun. 25, 2018 for U.S. Appl. No. 14/707,581.
Pre Appeal brief filed Jun. 5, 2018 for U.S. Appl. No. 14/707,290.
Final Office Action dated Jun. 15, 2018 for U.S. Appl. No. 14/704,844.
Response to Final Office Action filed Jun. 28, 2018 for U.S. Appl. No. 14/707,253.
Response to Non-final Office Action filed Jul. 5, 2018 for U.S. Appl. No. 14/707,513.
Response to Final Office Action filed Jul. 9, 2018 for U.S. Appl. No. 14/707,385.
Non-Final Office Action filed Jul. 9, 2018 for U.S. Appl. No. 14/707,241.
Response to Final Office Action and RCE filed Jul. 26, 2018 for U.S. Appl. No. 14/707,745.
Advisory Action dated Jul. 23, 2018 for U.S. Appl. No. 14/707,581.
Advisory Action dated Aug. 7, 2018 for U.S. Appl. No. 14/707,290.
Appeal Brief filed Aug. 6, 2018 for U.S. Appl. No. 14/707,290.
Final office action dated Jul. 31, 2018 for U.S. Appl. No. 14/707,310.
Amendment After Non-Final Rejection dated Aug. 22, 2018 for U.S. Appl. No. 14/706,889.
Non-Final Office Action dated Sep. 5, 2018 for U.S. Appl. No. 14/707,385.
Final office action dated Sep. 6, 2018 for U.S. Appl. No. 14/707,608.
Final office action dated Sep. 12, 2018 for U.S. Appl. No. 14/707,513.
Response to Final Office Action and RCE filed Sep. 17, 2018 for U.S. Appl. No. 14/704,844.
Non Final Office Action dated Sep. 18, 2018 for U.S. Appl. No. 14/707,266.
Non Final Office Action dated Sep. 18, 2018 for U.S. Appl. No. 14/707,338.
Final office action dated Sep. 19, 2018 for U.S. Appl. No. 14/704,800.
Non Final Office Action dated Sep. 27, 2018 for U.S. Appl. No. 14/707,271.
Non Final Office Action dated Oct. 1, 2018 for U.S. Appl. No. 14/707,745.
Response to Non-final Office Action filed Oct. 3, 2018 for U.S. Appl. No. 14/707,640.
Response to Non-final Office Action filed Oct. 5, 2018 for U.S. Appl. No. 14/707,241.
Examiner's Answer to Appeal Brief dated Oct. 11, 2018 for U.S. Appl. No. 14/707,290.
Appeal Brief filed Oct. 29, 2018 for U.S. Appl. No. 14/707,581.
Amendment After Final Rejection filed Oct. 31, 2018 for U.S. Appl. No. 14/707,310.
Non Final Office Action dated Nov. 8, 2018 for U.S. Appl. No. 14/707,310.
Final Office Action dated Nov. 27, 2018 for U.S. Appl. No. 14/707,640.
Amendment After Non-Final Rejection dated Dec. 6, 2018 for U.S. Appl. No. 14/707,385.
Non Final Office Action dated Dec. 10, 2018 for U.S. Appl. No. 14/704,765.
PABR with Appeal Brief filed Dec. 12, 2018 for U.S. Appl. No. 14/707,513.
Response to Non-final Office Action filed Dec. 18, 2018 for U.S. Appl. No. 14/707,266.
Response to Non-final Office Action filed Dec. 18, 2018 for U.S. Appl. No. 14/707,338.
Response to Non-final Office Action filed Dec. 19, 2018 for U.S. Appl. No. 14/707,271.
Notice of Allowance dated Dec. 28, 2018 for U.S. Appl. No. 14/707,253.
Examiner's Answer to Appeal Brief dated Dec. 28, 2018 for U.S. Appl. No. 14/707,581.
Response to Non-final Office Action filed Jan. 2, 2019 for U.S. Appl. No. 14/707,745.
Notice of Allowance dated Dec. 31, 2018 for U.S. Appl. No. 14/704,858.
Final Office Action dated Jan. 7, 2019 for U.S. Appl. No. 14/706,889.
Wii Motion Plus, Nintendo, Jun. 8, 2009 (Year: 2009).
Three-dimensional geometric morphometrics for studying floral shape variation, year 2010 (Year: 2010).
Final Office Action dated Jan. 17, 2019 for U.S. Appl. No. 14/707,241.
Amendment After Non-Final filed Feb. 8, 2019 for U.S. Appl. No. 14/707,310.
Appeal Brief filed on Feb. 12, 2019 for U.S. Appl. No. 14/707,513.
Final Office Action dated Feb. 15, 2019 for U.S. Appl. No. 14/707,385.
Appeal Brief filed on Feb. 19, 2019 for U.S. Appl. No. 14/704,800.
Response to Final Office Action and AFCP filed Feb. 26, 2019 for U.S. Appl. No. 14/707,640.
Reply Brief filed on Feb. 28, 2019 for U.S. Appl. No. 14/707,581.
Notice of Allowance dated Mar. 4, 2019 for U.S. Appl. No. 14/704,844.
Final office action dated Mar. 4, 2019 for U.S. Appl. No. 14/707,310.
Final office action dated Mar. 18, 2019 for U.S. Appl. No. 14/707,266.
Final office action dated Mar. 18, 2019 for U.S. Appl. No. 14/707,271.
Final office action dated Mar. 19, 2019 for U.S. Appl. No. 14/707,2338.
Chen et al., Extending a mobile device's interaction space through body-centric interaction. In Proceedings of the 14th international conference on Human-computer interaction with mobile devices and services (MobileHCI '12). Sep. 21-24, 2012, ACM, pp. 151-160, (Year: 2012).
Shoemaker et al., Body-Centric Interaction Techniques for Very Large Wall Displays, ACM, NordiCH12010, Oct. 16-20, 2010, pp. 463-472 (Year: 2010).
Response to Final Office Action and AFCP filed Apr. 8, 2019 for U.S. Appl. No. 14/707,889.
Response to Non-final Office Action filed Apr. 10, 2019 for U.S. Appl. No. 14/707,765.
Notice of Allowance dated Apr. 17, 2019 for U.S. Appl. No. 14/707,745.
Response to Final Office Action and AFCP filed May 6, 2019 for U.S. Appl. No. 14/707,310.
Response to Final Office Action and AFCP filed May 20, 2019 for U.S. Appl. No. 14/707,271.
Response to Final Office Action and AFCP filed May 20, 2019 for U.S. Appl. No. 14/707,338.
Notice of Allowance dated May 20, 2019 for U.S. Appl. No. 14/706,889.
Examiner's Answer dated May 29, 2019 for U.S. Appl. No. 14/707,513.
Advisory Action dated May 23, 2019 for U.S. Appl. No. 14/707,310.
Final Office Action for U.S. Appl. No. 14/707,266 dated Apr. 15, 2020.

(56) References Cited

OTHER PUBLICATIONS

Notice of Allowance for U.S. Appl. No. 14/707,338 dated May 13, 2020.
Amendment After Final for U.S. Appl. No. 14/707,266 dated Jul. 15, 2020.
Notice of Allowance for U.S. Appl. No. 14/707,266 dated Sep. 22, 2020.

* cited by examiner

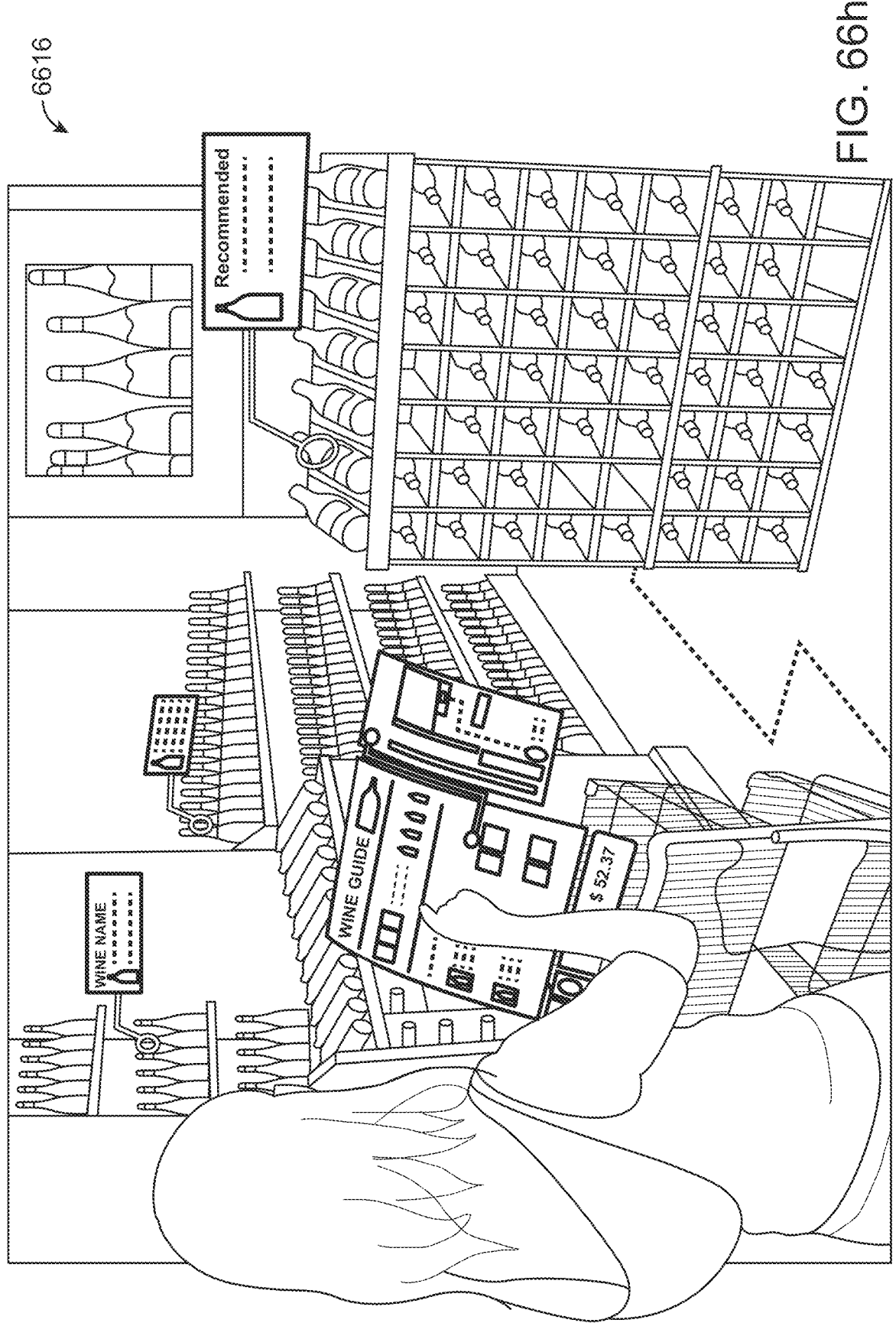

US 11,060,858 B2

METHOD AND SYSTEM FOR GENERATING A VIRTUAL USER INTERFACE RELATED TO A TOTEM

CROSS-REFERENCE TO RELATED APPLICATION(S)

This application is a continuation of U.S. patent application Ser. No. 14/707,253 entitled "METHOD AND SYSTEM FOR GENERATING A VIRTUAL USER INTERFACE RELATED TO A TOTEM", filed May 8, 2015, which is a continuation of U.S. patent application Ser. No. 14/696,347, entitled "PLANAR WAVEGUIDE APPARATUS WITH DIFFRACTION ELEMENT(S) AND SYSTEM EMPLOYING SAME", filed Apr. 24, 2015, which is a continuation of U.S. patent application Ser. No. 14/331,218, entitled "PLANAR WAVEGUIDE APPARATUS WITH DIFFRACTION ELEMENT(S) AND SYSTEM EMPLOYING SAME", filed Jul. 14, 2014, which claims priority to U.S. Provisional Application Ser. No. 61/845,907, entitled "PLANAR WAVEGUIDE APPARATUS WITH DIFFRACTION ELEMENT(S) AND SYSTEM EMPLOYING SAME", filed Jul. 12, 2013, and also claims priority to U.S. Provisional Application Ser. No. 62/012,273, entitled "METHODS AND SYSTEMS FOR CREATING VIRTUAL AND AUGMENTED REALITY", filed on Jun. 14, 2014. This application is also a continuation-in-part of U.S. patent application Ser. No. 14/641,376, entitled "VIRTUAL AND AUGMENTED REALITY SYSTEMS AND METHODS", filed Mar. 7, 2015, which claims priority to U.S. Provisional Application Ser. No. 61/950,001 filed Mar. 7, 2014. This application is cross-related to U.S. patent application Ser. No. 14/690,401, entitled "SYSTEMS AND METHOD FOR AUGMENTED REALITY", filed Apr. 18, 2015 and to U.S. patent application Ser. No. 14/641,376, entitled "VIRTUAL AND AUGMENTED REALITY SYSTEMS AND METHODS," filed Mar. 7, 2015, and U.S. patent application Ser. No. 13/915,530, entitled "MULTIPLE DEPTH PLANE THREE-DIMENSIONAL DISPLAY USING A WAVE GUIDE REFLECTOR ARRAY PROJECTOR", filed Jun. 11, 2013. This application is also cross-related to U.S. patent application Ser. No. 14/205,126, entitled "SYSTEM AND METHOD FOR AUGMENTED AND VIRTUAL REALITY", filed Mar. 11, 2014. The contents of the aforementioned patent applications are hereby expressly incorporated by reference in their entireties.

FIELD OF THE INVENTION

The present invention generally relates to systems and methods configured to facilitate interactive virtual or augmented reality environments for one or more users.

BACKGROUND

A light field encompasses all the light rays at every point in space traveling in every direction. Light fields are considered four dimensional because every point in a three-dimensional space also has an associated direction, which is the fourth dimension.

Wearable three-dimensional displays may include a substrate guided optical device, also known as the light-guide optical element (LOE) system. Such devices are manufactured by, for example Lumus Ltd. However, these LOE systems only project a single depth plane, focused at infinity, with a spherical wave front curvature of zero.

One prior art system (Lumus) comprises multiple angle-dependent reflectors embedded in a waveguide to outcouple light from the face of the waveguide. Another prior art system (BAE) embeds a linear diffraction grating within the waveguide to change the angle of incident light propagating along the waveguide. By changing the angle of light beyond the threshold of TIR, the light escapes from one or more lateral faces of the waveguide. The linear diffraction grating has a low diffraction efficiency, so only a fraction of the light energy is directed out of the waveguide, each time the light encounters the linear diffraction grating. By outcoupling the light at multiple locations along the grating, the exit pupil of the display system is effectively increased.

A primary limitation of the prior art systems is that they only relay collimated images to the eyes (i.e., images at optical infinity). Collimated displays are adequate for many applications in avionics, where pilots are frequently focused upon very distant objects (e.g., distant terrain or other aircraft). However, for many other head-up or augmented reality applications, it is desirable to allow users to focus their eyes upon (i.e., "accommodate" to) objects closer than optical infinity.

The wearable 3D displays may be used for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user.

The U.S. patent applications listed above present systems and techniques to work with the visual configuration of a typical human to address various challenges in virtual reality and augmented reality applications. The design of these virtual reality and/or augmented reality systems (AR systems) presents numerous challenges, including the speed of the system in delivering virtual content, quality of virtual content, eye relief of the user, size and portability of the system, and other system and optical challenges.

The systems and techniques described herein are configured to work with the visual configuration of the typical human to address these challenges.

SUMMARY

Embodiments of the present invention are directed to devices, systems and methods for facilitating virtual reality and/or augmented reality interaction for one or more users.

Light that is coupled into a planar waveguide (e.g., pane of glass, pane of fused silica, pane of polycarbonate), will propagate along the waveguide by total internal reflection (TIR). Planar waveguides may also be referred to as "substrate-guided optical elements," or "light guides."

If that light encounters one or more diffraction optical elements (DOE) in or adjacent to the planar waveguide, the characteristics of that light (e.g., angle of incidence, wavefront shape, wavelength, etc.) can be altered such that a portion of the light escapes TIR and emerges from one or more faces of the waveguide.

If the light coupled into the planar waveguide is varied spatially and/or temporally to contain or encode image data that image data can propagate along the planar waveguide by TIR. Examples of elements that spatially vary light include LCDs, LCoS panels, OLEDs, DLPs, and other image arrays. Typically, these spatial light modulators may update image data for different cells or sub-elements at different points in time, and thus may produce sub-frame temporal variation, in addition to changing image data on a frame-by-frame basis to produce moving video. Examples of elements that temporally vary light include acousto-optical modulators, interferometric modulators, optical choppers, and directly modulated emissive light sources such as LEDs and laser diodes. These temporally varying elements may be coupled to one or more elements to vary the light spatially, such as scanning optical fibers, scanning mirrors, scanning prisms, and scanning cantilevers with reflective elements—or these temporally varying elements may be actuated directly to move them through space. Such scanning systems may utilize one or more scanned beams of light that are modulated over time and scanned across space to display image data.

If image data contained in spatially and/or temporally varying light that propagates along a planar waveguide by TIR encounters one or more DOEs in or adjacent to the planar waveguide, the characteristics of that light can be altered such that the image data encoded in light will escape TIR and emerge from one or more faces of the planar waveguide. Inclusion of one or more DOEs which combine a linear diffraction grating function or phase pattern with a radially symmetric or circular lens function or phase pattern, may advantageously allow steering of beams emanating from the face of the planar waveguide and control over focus or focal depth.

By incorporating such a planar waveguide system into a display system, the waveguide apparatus (e.g., planar waveguide and associated DOE) can be used to present images to one or more eyes. Where the planar waveguide is constructed of a partially or wholly transparent material, a human may view real physical objects through the waveguide. The waveguide display system can, thus, comprise an optically see-through mixed reality (or "augmented reality") display system, in which artificial or remote image data can be superimposed, overlaid, or juxtaposed with real scenes.

The structures and approaches described herein may advantageously produce a relatively large eye box, readily accommodating viewer's eye movements.

In another aspect, a method of rendering virtual content to a user is disclosed. The method comprises detecting a location of a user, retrieving a set of data associated with a part of a virtual world model that corresponds to the detected location of the user, wherein the virtual world model comprises data associated with a set of map points of the real world, and rendering, based on the set of retrieved data, virtual content to a user device of the user, such that the virtual content, when viewed by the user, appears to be placed in relation to a set of physical objects in a physical environment of the user.

In another aspect, a method of recognizing objects is disclosed. The method comprises capturing an image of a field of view of a user, extracting a set of map points based on the captured image, recognizing an object based on the extracted set of map points, retrieving semantic data associated with the recognized objects and attaching the semantic data to data associated with the recognized object and inserting the recognized object data attached with the semantic data to a virtual world model such that virtual content is placed in relation to the recognized object.

In another aspect, a method comprises capturing an image of a field of view of a user, extracting a set of map points based on the captured image, identifying a set of sparse points and dense points based on the extraction, performing point normalization on the set of sparse points and dense points, generating point descriptors for the set of sparse points and dense points, and combining the sparse point descriptors and dense point descriptors to store as map data.

In another aspect, a method of determining user input is disclosed. In one embodiment, the method comprises capturing an image of a field of view of a user, the image comprising a gesture created by the user, analyzing the captured image to identify a set of points associated with the gesture, comparing the set of identified points to a set of points associated with a database of predetermined gestures, generating a scoring value for the set of identified points based on the comparison, recognizing the gesture when the scoring value exceeds a threshold value, and determining a user input based on the recognized gesture.

In another aspect, a method of determining user input is disclosed. The method comprises detecting a movement of a totem in relation to a reference frame, recognizing a pattern based on the detected movement, comparing the recognizing pattern to a set of predetermined patterns, generating a scoring value for the recognized pattern based on the comparison, recognizing the movement of the totem when the scoring value exceeds a threshold value, and determining a user input based on the recognized movement of the totem.

In another aspect, a method of generating a virtual user interface is disclosed. The method comprises identifying a virtual user interface to be displayed to a user, generating a set of data associated with the virtual user interface, tethering the virtual user interface to a set of map points associated with at least one physical entity at the user's location, and displaying the virtual user interface to the user, such that the virtual user interface, when viewed by the user, moves in relation to a movement of the at least one physical entity.

In another aspect, a method comprises detecting a movement of a user's fingers or a totem, recognizing, based on the detected movement, a command to create a virtual user interface, determining, from a virtual world model, a set of map points associated with a position of the user's fingers or the totem, and rendering, in real-time, a virtual user interface at the determined map points associated with the position of the user's fingers or the totem such that the user views the virtual user interface being created simultaneously as the user's fingers or totem move to define a location or outline of the virtual user interface.

In another aspect, a method comprises identifying a real-world activity of a user; retrieving a knowledge base associated with the real-world activity, creating a virtual user interface in a field of view of the user, and displaying, on the virtual user interface, a set of information associated with the real-world activity based on the retrieved knowledge base.

In yet another aspect, a method comprises uploading a set of data associated with a physical environment of a first user to a virtual world model residing in a cloud server, updating the virtual world model based on the uploaded data, transmitting a piece of the virtual world model associated with the physical environment of the first user to a second user located at a different location than the first user, and displaying, at a user device of the second user, a virtual copy of the physical environment of the first user based on the transmitted piece of the virtual world model.

Additional and other objects, features, and advantages of the invention are described in the detail description, figures and claims.

BRIEF DESCRIPTION OF THE DRAWINGS

FIGS. 66A-66J illustrate a user scenario of a mother and daughter on a shopping trip and interacting with the AR system, according to one illustrated embodiment.

DETAILED DESCRIPTION

Figure 1:
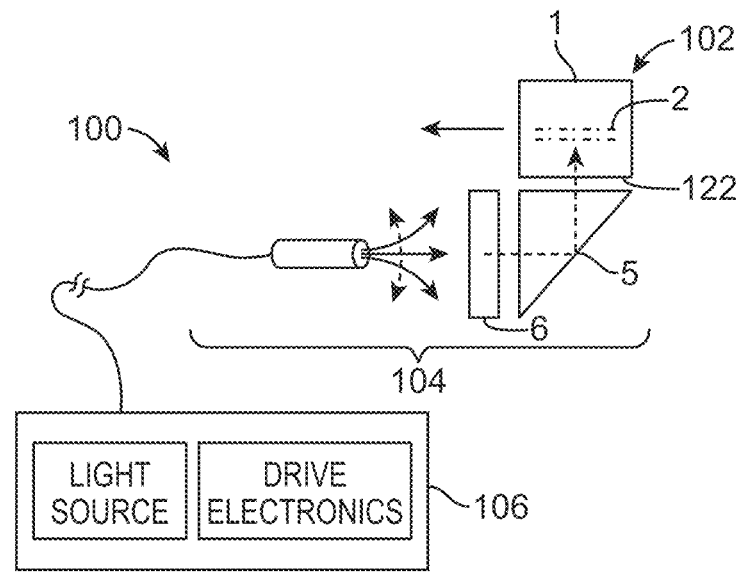
FIG. 1 is a schematic diagram showing an optical system including a waveguide apparatus, a subsystem to couple light to or from the waveguide apparatus, and a control subsystem, according to one illustrated embodiment.

Various embodiments will now be described in detail with reference to the drawings, which are provided as illustrative examples of the invention so as to enable those skilled in the art to practice the invention. Notably, the figures and the examples below are not meant to limit the scope of the present invention. Where certain elements of the present invention may be partially or fully implemented using known components (or methods or processes), only those portions of such known components (or methods or processes) that are necessary for an understanding of the present invention will be described, and the detailed descriptions of other portions of such known components (or methods or processes) will be omitted so as not to obscure the invention. Further, various embodiments encompass present and future known equivalents to the components referred to herein by way of illustration. Disclosed are methods and systems for generating virtual and/or augmented reality.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computer systems, server computers, and/or communications networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Numerous implementations are shown and described. To facilitate understanding, identical or similar structures are identified with the same reference numbers between the various drawings, even though in some instances these structures may not be identical.

The headings and Abstract of the Disclosure provided herein are for convenience only and do not interpret the scope or meaning of the embodiments.

In contrast to the conventional approaches, at least some of the devices and/or systems described herein enable: (1) a waveguide-based display that produces images at single optical viewing distance closer than infinity (e.g., arm's length); (2) a waveguide-based display that produces images at multiple, discrete optical viewing distances; and/or (3) a waveguide-based display that produces image layers stacked at multiple viewing distances to represent volumetric 3D objects. These layers in the light field may be stacked closely enough together to appear continuous to the human visual system (i.e., one layer is within the cone of confusion of an adjacent layer). Additionally or alternatively, picture elements may be blended across two or more layers to increase perceived continuity of transition between layers in the light field, even if those layers are more sparsely stacked (i.e., one layer is outside the cone of confusion of an adjacent layer). The display system may be monocular or binocular.

Embodiments of the described volumetric 3D displays may advantageously allow digital content superimposed over the user's view of the real world to be placed at appropriate viewing distances that do not require the user to draw his or her focus away from relevant real world objects. For example, a digital label or "call-out" for a real object can be placed at the same viewing distance as that object, so both label and object are in clear focus at the same time.

Embodiments of the described volumetric 3D displays may advantageously result in stereoscopic volumetric 3D displays that mitigate or entirely resolve the accommodation-vergence conflict produced in the human visual system by conventional stereoscopic displays. A binocular stereoscopic embodiment can produce 3D volumetric scenes in which the optical viewing distance (i.e., the focal distance) matches the fixation distance created by the stereoscopic imagery—i.e., the stimulation to ocular vergence and ocular accommodation are matching, allowing users to point their eyes and focus their eyes at the same distance.

FIG. 1 showing an optical system 100 including a primary waveguide apparatus 102, an optical coupler subsystem 104, and a control subsystem 106, according to one illustrated embodiment.

The primary waveguide apparatus 102 includes one or more primary planar waveguides 1 (only one show in FIG. 1), and one or more diffractive optical elements (DOEs) 2 associated with each of at least some of the primary planar waveguides 1.

Figure 2:
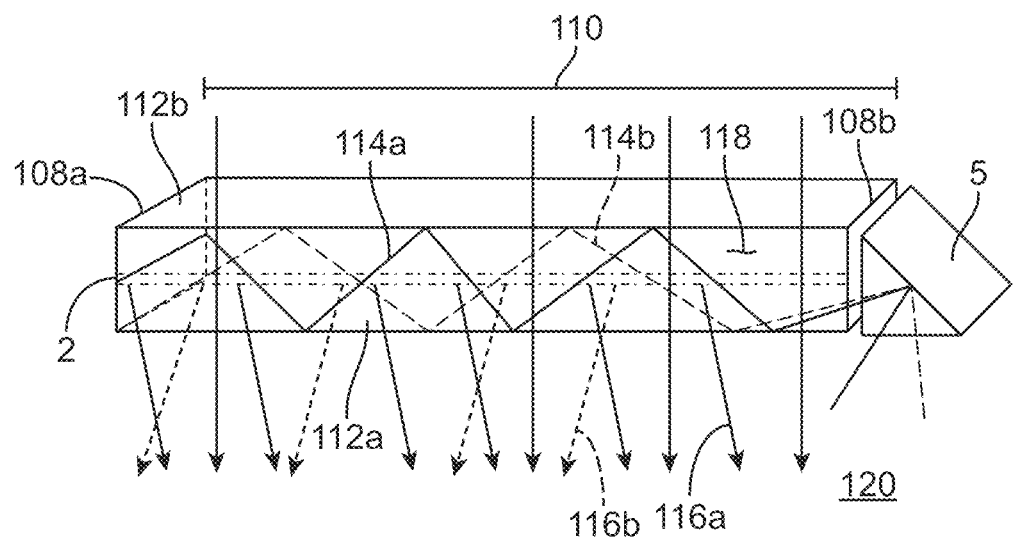
FIG. 2 an elevational view showing a waveguide apparatus including a planar waveguide and at least one diffractive optical element positioned within the planar waveguide, illustrating a number of optical paths including totally internally reflective optical paths and optical paths between an exterior and an interior of the planar waveguide, according to one illustrated embodiment.

As best illustrated in FIG. 2, the primary planar waveguides 1 each have at least a first end 108a and a second end 108b, the second end 108b opposed to the first end 108a along a length 110 of the primary planar waveguide 1. The primary planar waveguides 1 each have a first face 112a and a second face 112b, at least the first and the second faces 112a, 112b (collectively 112) forming an at least partially internally reflective optical path (illustrated by arrow 114a and broken line arrow 114b, collectively 114) along at least a portion of the length 110 of the primary planar waveguide 1. The primary planar waveguide(s) 1 may take a variety of forms which provides for substantially total internal reflection (TIR) for light striking the faces 112 at less than a defined critical angle. The planar waveguides 1 may, for example, take the form of a pane or plane of glass, fused silica, acrylic, or polycarbonate.

The DOEs 4 (illustrated in FIGS. 1 and 2 by dash-dot double line) may take a large variety of forms which interrupt the TIR optical path 114, providing a plurality of optical paths (illustrated by arrows 116a and broken line arrows 116b, collectively 116) between an interior 118 and an exterior 120 of the planar waveguide 1 extending along at least a portion of the length 110 of the planar waveguide 1. As explained below in reference to FIGS. 3A-3C, the DOEs 4 may advantageously combine the phase functions of a linear diffraction grating with that of a circular or radial symmetric lens, allowing positioning of apparent objects and focus plane for apparent objects. Such may be achieved on a frame-by-frame, subframe-by-subframe, or even pixel-by-pixel basis.

With reference to FIG. 1, the optical coupler subsystem 104 optically couples light to, or from, the waveguide apparatus 102. As illustrated in FIG. 1, the optical coupler subsystem may include an optical element 5, for instance a reflective surface, mirror, dichroic mirror or prism to optically couple light to, or from, an edge 122 of the primary planar waveguide 1. The optical coupler subsystem 104 may additionally or alternatively include a collimation element 6 that collimates light.

The control subsystem 106 includes one or more light sources 11 and drive electronics 12 that generate image data that is encoded in the form of light that is spatially and/or temporally varying. As noted above, a collimation element 6 may collimate the light, and the collimated light optically s coupled into one or more primary planar waveguides 1 (only one illustrated in FIGS. 1 and 2).

As illustrated in FIG. 2, the light propagates along the primary planar waveguide with at least some reflections or "bounces" resulting from the TIR propagation. It is noted that some implementations may employ one or more reflectors in the internal optical path, for instance thin-films, dielectric coatings, metalized coatings, etc., which may facilitate reflection. Light propagates along the length 110 of the waveguide 1 intersects with one or more DOEs 4 at various positions along the length 110.

As explained below in reference to FIGS. 4A-4C, the DOE(s) 4 may be incorporated within the primary planar waveguide 1 or abutting or adjacent one or more of the faces 112 of the primary planar waveguide 1. The DOE(s) 4 accomplishes at least two functions. The DOE(s) 4 shift an angle of the light, causing a portion of the light to escape TIR, and emerge from the interior 118 to the exterior 120 via one or more faces 112 of the primary planar waveguide 1. The DOE(s) 4 focus the out-coupled light at one or more viewing distances. Thus, someone looking through a face 112a of the primary planar waveguide 1 can see digital imagery at one or more viewing distances.

Figure 3A:
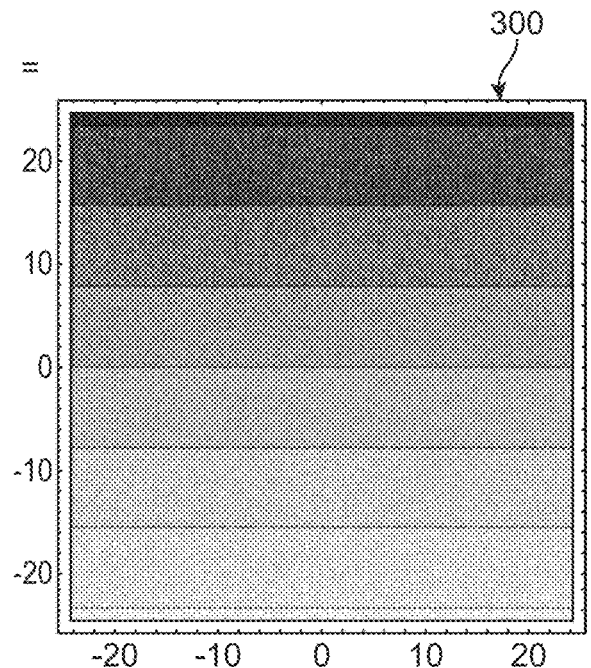
FIG. 3A a schematic diagram showing a linear diffraction or diffractive phase function, according to one illustrated embodiment.

FIG. 3A shows a linear diffraction or diffractive phase function 300, according to one illustrated embodiment. The linear diffraction or diffractive function 300 may be that of a linear diffractive grating, for example a Bragg grating.

Figure 3B:
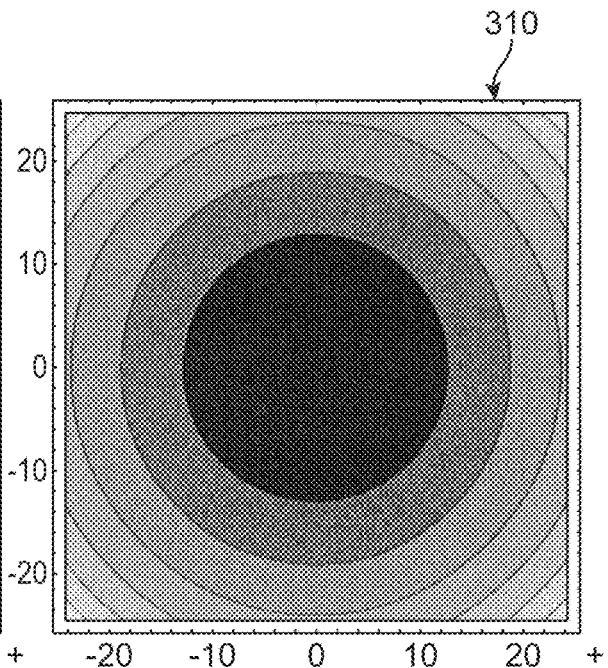
FIG. 3B a schematic diagram showing a radially circular lens phase function, according to one illustrated embodiment.

FIG. 3B showings a radially circular or radially symmetric lens phase function 310, according to one illustrated embodiment.

FIG. 3B shows a phase pattern 320 for at least one diffractive optical element that combines the linear diffraction and the radially circular lens functions 300, 310, according to one illustrated embodiment, at least one diffractive optical element associated with at least one planar waveguide. Notably, each band has a curved wavefront.

Figure 4A:
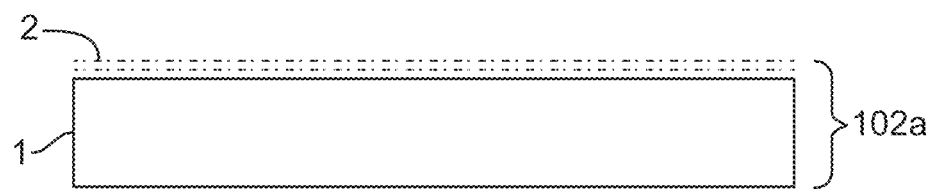
FIG. 4A an elevational view showing a waveguide apparatus including a planar waveguide and at least one diffractive optical element carried on an outer surface of the planar waveguide, according to one illustrated embodiment.
Figure 4B:
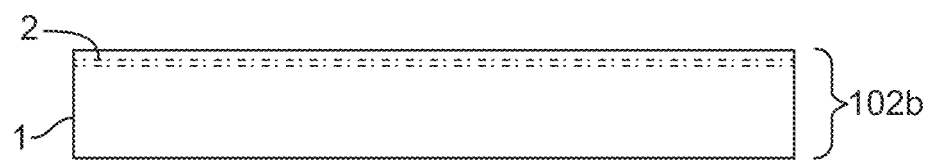
FIG. 4B an elevational view showing a waveguide apparatus including a planar waveguide and at least one diffractive optical element positioned internally immediately adjacent an outer surface of the planar waveguide, according to one illustrated embodiment.
Figure 4C:
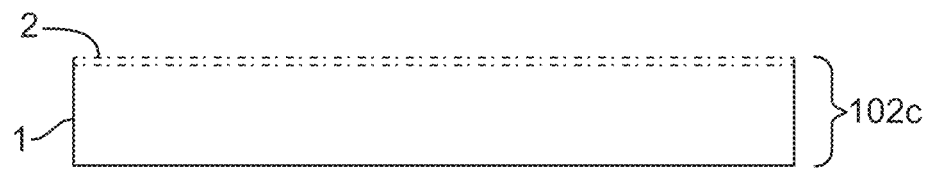
FIG. 4C an elevational view showing a waveguide apparatus including a planar waveguide and at least one diffractive optical element formed in an outer surface of the planar waveguide, according to one illustrated embodiment.

While FIGS. 1 and 2 show the DOE 2 positioned in the interior 118 of the primary planar waveguide 1, spaced from the faces 112, the DOE 2 may be positioned at other locations in other implementations, for example as illustrated in FIGS. 4A-4C.

FIG. 4A shows a waveguide apparatus 102a including a primary planar waveguide 1 and at least one DOE 2 carried on an outer surface or face 112 of the primary planar waveguide 1, according to one illustrated embodiment. For example, the DOE 2 may be deposited on the outer surface or face 112 of the primary planar waveguide 1, for instance as a patterned metal layer.

FIG. 4B shows a waveguide apparatus 102b including a primary planar waveguide 1 and at least one DOE 2 positioned internally immediately adjacent an outer surface or face 112 of the primary planar waveguide 1, according to one illustrated embodiment. For example, the DOE 2 may be formed in the interior 118 via selective or masked curing of material of the primary planar waveguide 1. Alternatively, the DOE 2 may be a distinct physical structure incorporated into the primary planar waveguide 1.

FIG. 4C shows a waveguide apparatus 102c including a primary planar waveguide 1 and at least one DOE 2 formed in an outer surface of the primary planar waveguide 1, according to one illustrated embodiment. The DOE 2 may, for example be etched, patterned, or otherwise formed in the outer surface or face 112 of the primary planar waveguide 1, for instances as grooves. For example, the DOE 2 may take the form of linear or saw tooth ridges and valleys which may be spaced at one or more defined pitches (i.e., space between individual elements or features extending along the length 110). The pitch may be a linear function or may be a non-linear function.

The primary planar waveguide 1 is preferably at least partially transparent. Such allows one or more viewers to view the physical objects (i.e., the real world) on a far side of the primary planar waveguide 1 relative to a vantage of the viewer. This may advantageously allow viewers to view the real world through the waveguide and simultaneously view digital imagery that is relayed to the eye(s) by the waveguide.

In some implementations a plurality of waveguides systems may be incorporated into a near-to-eye display. For example, a plurality of waveguides systems may be incorporated into a head-worn, head-mounted, or helmet-mounted display—or other wearable display.

In some implementations, a plurality of waveguides systems may be incorporated into a head-up display (HUD), that is not worn (e.g., an automotive HUD, avionics HUD). In such implementations, multiple viewers may look at a shared waveguide system or resulting image field. Multiple viewers may, for example see or optically perceive a digital or virtual object from different viewing perspectives that match each viewer's respective locations relative to the waveguide system.

The optical system 100 is not limited to use of visible light, but may also employ light in other portions of the electromagnetic spectrum (e.g., infrared, ultraviolet) and/or may employ electromagnetic radiation that is outside the band of "light" (i.e., visible, UV, or IR), for example employing electromagnetic radiation or energy in the microwave or X-ray portions of the electromagnetic spectrum.

In some implementations, a scanning light display is used to couple light into a plurality of primary planar waveguides. The scanning light display can comprise a single light source that forms a single beam that is scanned over time to form an image. This scanned beam of light may be intensity-modulated to form pixels of different brightness levels. Alternatively, multiple light sources may be used to generate multiple beams of light, which are scanned either with a shared scanning element or with separate scanning elements to form imagery.

These light sources may comprise different wavelengths, visible and/or non-visible, they may comprise different geometric points of origin (X, Y, or Z), they may enter the scanner(s) at different angles of incidence, and may create light that corresponds to different portions of one or more images (flat or volumetric, moving or static).

The light may, for example, be scanned to form an image with a vibrating optical fiber, for example as discussed in U.S. patent application Ser. No. 13/915,530, International Patent Application Serial No. PCT/US2013/045267, and U.S. provisional patent application Ser. No. 61/658,355. The optical fiber may be scanned biaxially by a piezoelectric actuator. Alternatively, the optical fiber may be scanned uniaxially or triaxially. As a further alternative, one or more optically components (e.g., rotating polygonal reflector or mirror, oscillating reflector or mirror) may be employed to scan an output of the optical fiber.

The optical system 100 is not limited to use in producing images or as an image projector or light field generation. For example, the optical system 100 or variations thereof may optical, be employed as an image capture device, such as a digital still or digital moving image capture or camera system.

Figure 5A:
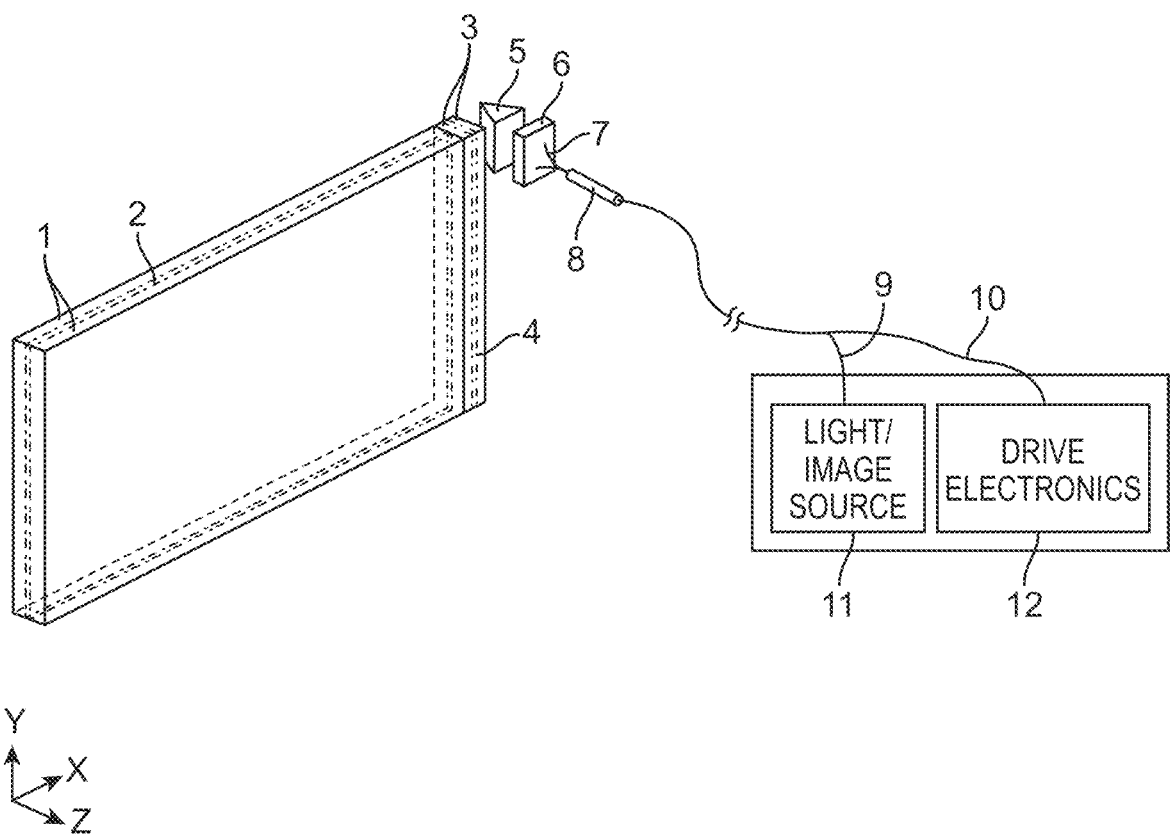
FIG. 5A is a schematic diagram showing an optical system including a waveguide apparatus, an optical coupler subsystem to optically couple light to or from the waveguide apparatus, and a control subsystem, according to one illustrated embodiment.

FIG. 5A shows an optical system 500 including a waveguide apparatus, an optical coupler subsystem to optically couple light to or from the waveguide apparatus, and a control subsystem, according to one illustrated embodiment.

Many of the structures of the optical system 500 of FIG. 5A are similar or even identical to those of the optical system 100 of FIG. 1. In the interest of conciseness, in many instances only significant differences are discussed below.

The optical system 500 may employ a distribution waveguide apparatus, to relay light along a first axis (vertical or Y-axis in view of FIG. 5A), and expand the light's effective exit pupil along the first axis (e.g., Y-axis). The distribution waveguide apparatus, may, for example include a distribution planar waveguide 3 and at least one DOE 4 (illustrated by double dash-dot line) associated with the distribution planar waveguide 3. The distribution planar waveguide 3 may be similar or identical in at least some respects to the primary planar waveguide 1, having a different orientation therefrom. Likewise, the at least one DOE 4 may be similar or identical in at least some respects to the DOE 2. For example, the distribution planar waveguide 3 and/or DOE 4 may be comprised of the same materials as the primary planar waveguide 1 and/or DOE 2, respectively The relayed and exit-pupil expanded light is optically coupled from the distribution waveguide apparatus into one or more primary planar waveguide 1. The primary planar waveguide 1 relays light along a second axis, preferably orthogonal to first axis, (e.g., horizontal or X-axis in view of FIG. 5A). Notably, the second axis can be a non-orthogonal axis to the first axis. The primary planar waveguide 1 expands the light's effective exit pupil along that second axis (e.g. X-axis). For example, a distribution planar waveguide 3 can relay and expand light along the vertical or Y-axis, and pass that light to the primary planar waveguide 1 which relays and expands light along the horizontal or X-axis.

Figure 5B:
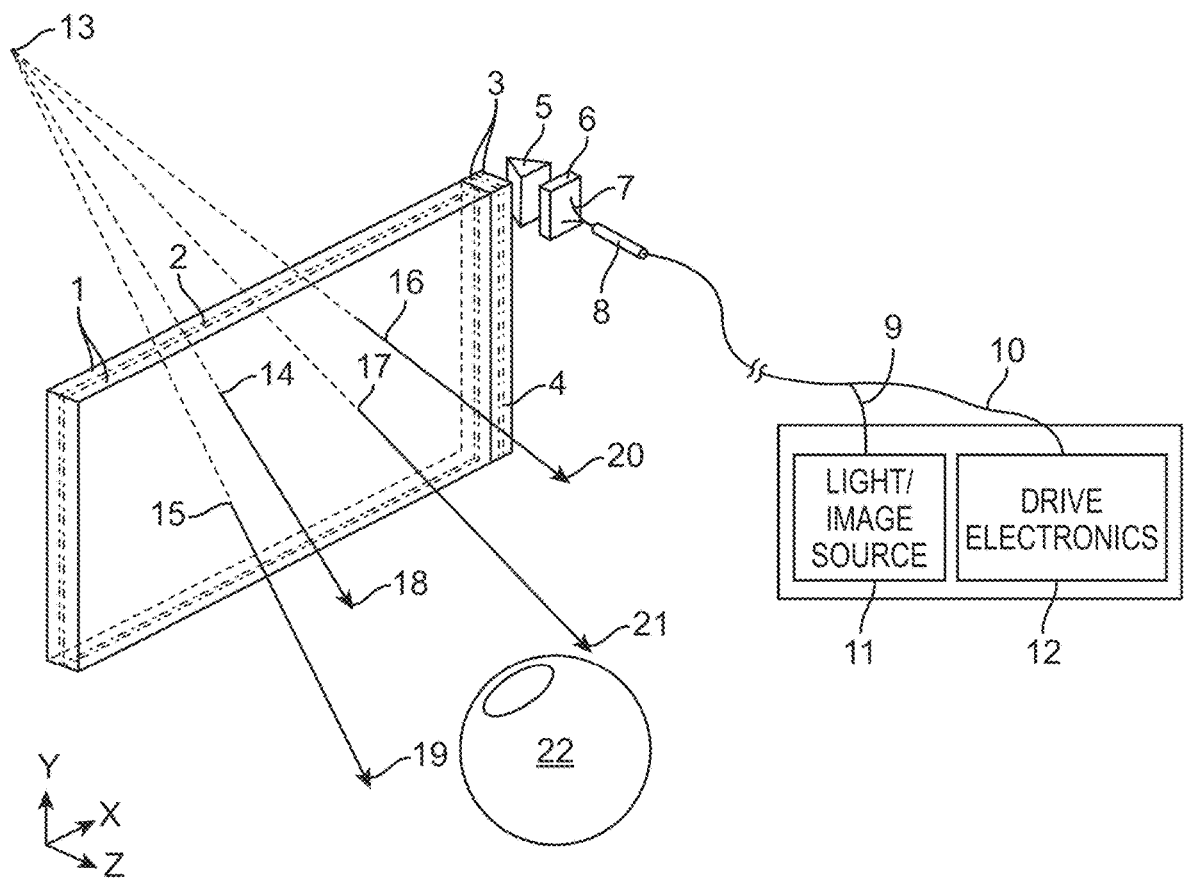
FIG. 5B is a schematic diagram of the optical system of FIG. 5A illustrating generation of a single focus plane that is capable of being positioned closer than optical infinity, according to one illustrated embodiment.

FIG. 5B shows the optical system 500, illustrating generation thereby of a single focus plane that is capable of being positioned closer than optical infinity.

The optical system 500 may include one or more sources of red, green, and blue laser light 11, which may be optically coupled into a proximal end of a single mode optical fiber 9. A distal end of the optical fiber 9 may be threaded or received through a hollow tube 8 of piezoelectric material. The distal end protrudes from the tube 8 as fixed-free flexible cantilever 7. The piezoelectric tube 8 is associated with 4 quadrant electrodes (not illustrated). The electrodes may, for example, be plated on the outside, outer surface or outer periphery or diameter of the tube 8. A core electrode (not illustrated) is also located in a core, center, inner periphery or inner diameter of the tube 8.

Drive electronics 12, for example electrically coupled via wires 11, drive opposing pairs of electrodes to bend the piezoelectric tube 8 in two axes independently. The protruding distal tip of the optical fiber 7 has mechanical modes of resonance. The frequencies of resonance which depend upon a diameter, length, and material properties of the optical fiber 7. By vibrating the piezoelectric tube 8 near a first mode of mechanical resonance of the fiber cantilever 7, the fiber cantilever 7 is caused to vibrate, and can sweep through large deflections.

By stimulating resonant vibration in two axes, the tip of the fiber cantilever 7 is scanned biaxially in an area filling 2D scan. By modulating an intensity of light source(s) 11 in synchrony with the scan of the fiber cantilever 7, light emerging from the fiber cantilever 7 forms an image. Descriptions of such a set up are provide in U.S. patent application Ser. No. 13/915,530, International Patent Application Serial No. PCT/US2013/045267, and U.S. provisional patent application Ser. No. 61/658,355, all of which are incorporated by reference herein in their entireties.

A component of an optical coupler subsystem 104 collimates the light emerging from the scanning fiber cantilever 7. The collimated light is reflected by mirrored surface 5 into a narrow distribution planar waveguide 3 which contains at least one diffractive optical element (DOE) 4. The collimated light propagates vertically (i.e., relative to view of FIG. 5B) along the distribution planar waveguide 3 by total internal reflection, and in doing so repeatedly intersects with the DOE 4. The DOE 4 preferably has a low diffraction efficiency. This causes a fraction (e.g., 10%) of the light to be diffracted toward an edge of the larger primary planar waveguide 1 at each point of intersection with the DOE 4, and a fraction of the light to continue on its original trajectory down the length of the distribution planar waveguide 3 via TIR.

At each point of intersection with the DOE 4, additional light is diffracted toward the entrance of the primary waveguide 1. By dividing the incoming light into multiple outcoupled sets, the exit pupil of the light is expanded vertically by the DOE 4 in the distribution planar waveguide 3. This vertically expanded light coupled out of distribution planar waveguide 3 enters the edge of the primary planar waveguide 1.

Light entering primary waveguide 1 propagates horizontally (i.e., relative to view of FIG. 5B) along the primary waveguide 1 via TIR. As the light intersects with DOE 2 at multiple points as it propagates horizontally along at least a portion of the length of the primary waveguide 1 via TIR. The DOE 2 may advantageously be designed or configured to have a phase profile that is a summation of a linear diffraction grating and a radially symmetric diffractive lens. The DOE 2 may advantageously have a low diffraction efficiency.

At each point of intersection between the propagating light and the DOE 2, a fraction of the light is diffracted toward the adjacent face of the primary waveguide 1 allowing the light to escape the TIR, and emerge from the face of the primary waveguide 1. The radially symmetric lens aspect of the DOE 2 additionally imparts a focus level to the diffracted light, both shaping the light wavefront (e.g., imparting a curvature) of the individual beam as well as steering the beam at an angle that matches the designed focus level. FIG. 5B illustrates four beams 18, 19, 20, 21 extending geometrically to a focus point 13, and each beam is advantageously imparted with a convex wavefront profile with a center of radius at focus point 13 to produce an image or virtual object 22 at a given focal plane.

Figure 5C:
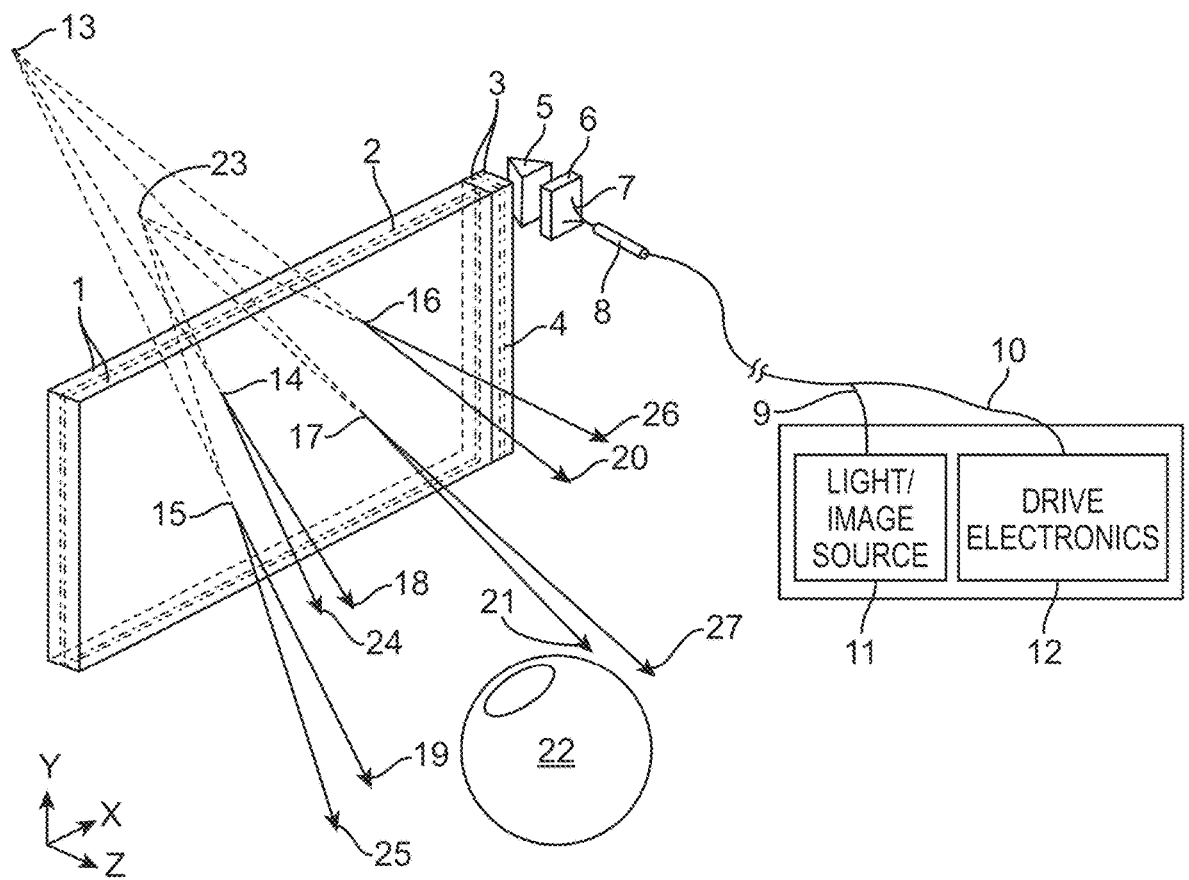
FIG. 5C is a schematic diagram of the optical system of FIG. 5A illustrating generation of a multi-focal volumetric display, image or light field, according to one illustrated embodiment.

FIG. 5C shows the optical system 500 illustrating generation thereby of a multi-focal volumetric display, image or light field. The optical system 500 may include one or more sources of red, green, and blue laser light 11, optically coupled into a proximal end of a single mode optical fiber 9. A distal end of the optical fiber 9 may be threaded or received through a hollow tube 8 of piezoelectric material. The distal end protrudes from the tube 8 as fixed-free flexible cantilever 7. The piezoelectric tube 8 is associated with 4 quadrant electrodes (not illustrated). The electrodes may, for example, be plated on the outside or outer surface or periphery of the tube 8. A core electrode (not illustrated) is positioned in a core, center, inner surface, inner periphery or inner diameter of the tube 8.

Drive electronics 12, for example coupled via wires 11, drive opposing pairs of electrodes to bend the piezoelectric tube 8 in two axes independently. The protruding distal tip of the optical fiber 7 has mechanical modes of resonance. The frequencies of resonance of which depend upon the a diameter, length, and material properties of the fiber cantilever 7. By vibrating the piezoelectric tube 8 near a first mode of mechanical resonance of the fiber cantilever 7, the fiber cantilever 7 is caused to vibrate, and can sweep through large deflections.

By stimulating resonant vibration in two axes, the tip of the fiber cantilever 7 is scanned biaxially in an area filling 2D scan. By modulating the intensity of light source(s) 11 in synchrony with the scan of the fiber cantilever 7, the light emerging from the fiber cantilever 7 forms an image. Descriptions of such a set up are provide in U.S. patent application Ser. No. 13/915,530, International Patent Application Serial No. PCT/US2013/045267, and U.S. provisional patent application Ser. No. 61/658,355, all of which are incorporated by reference herein in their entireties.

A component of an optical coupler subsystem 104 collimates the light emerging from the scanning fiber cantilever 7. The collimated light is reflected by mirrored surface 5 into a narrow distribution planar waveguide 3, which contains diffractive optical element (DOE) 4. The collimated light propagates along the distribution planar waveguide by total internal reflection (TIR), and in doing so repeatedly intersects with the DOE 4. The DOE has a low diffraction efficiency.

This causes a fraction (e.g., 10%) of the light to be diffracted toward an edge of a larger primary planar waveguide 1 at each point of intersection with the DOE 4, and a fraction of the light to continue on its original trajectory down the distribution planar waveguide 3 via TIR. At each point of intersection with the DOE 4, additional light is diffracted toward the entrance of the primary planar waveguide 1. By dividing the incoming light into multiple out-coupled sets, the exit pupil of the light is expanded vertically by DOE 4 in distribution planar waveguide 3. This vertically expanded light coupled out of the distribution planar waveguide 3 enters the edge of the primary planar waveguide 1.

Light entering primary waveguide 1 propagates horizontally (i.e., relative to view of FIG. 5C) along the primary waveguide 1 via TIR. As the light intersects with DOE 2 at multiple points as it propagates horizontally along at least a portion of the length of the primary waveguide 1 via TIR. The DOE 2 may advantageously be designed or configured to have a phase profile that is a summation of a linear diffraction grating and a radially symmetric diffractive lens. The DOE 2 may advantageously have a low diffraction efficiency. At each point of intersection between the propagating light and the DOE 2, a fraction of the light is diffracted toward the adjacent face of the primary waveguide 1 allowing the light to escape the TIR, and emerge from the face of the primary waveguide 1.

The radially symmetric lens aspect of the DOE 2 additionally imparts a focus level to the diffracted light, both shaping the light wavefront (e.g., imparting a curvature) of the individual beam as well as steering the beam at an angle that matches the designed focus level. FIG. 5C illustrates a first set of four beams 18, 19, 20, 21 extending geometrically to a focus point 13, and each beam 18, 19, 20, 21 is advantageously imparted with a convex wavefront profile with a center of radius at focus point 13 to produce another portion of the image or virtual object 22 at a respective focal plane. FIG. 5C illustrates a second set of four beams 24, 25, 26, 27 extending geometrically to a focus point 23, and each beam 24, 25, 26, 27 is advantageously imparted with a convex wavefront profile with a center of radius at focus point 23 to produce another portion of the image or virtual object 22 at a respective focal plane.

Figure 6:
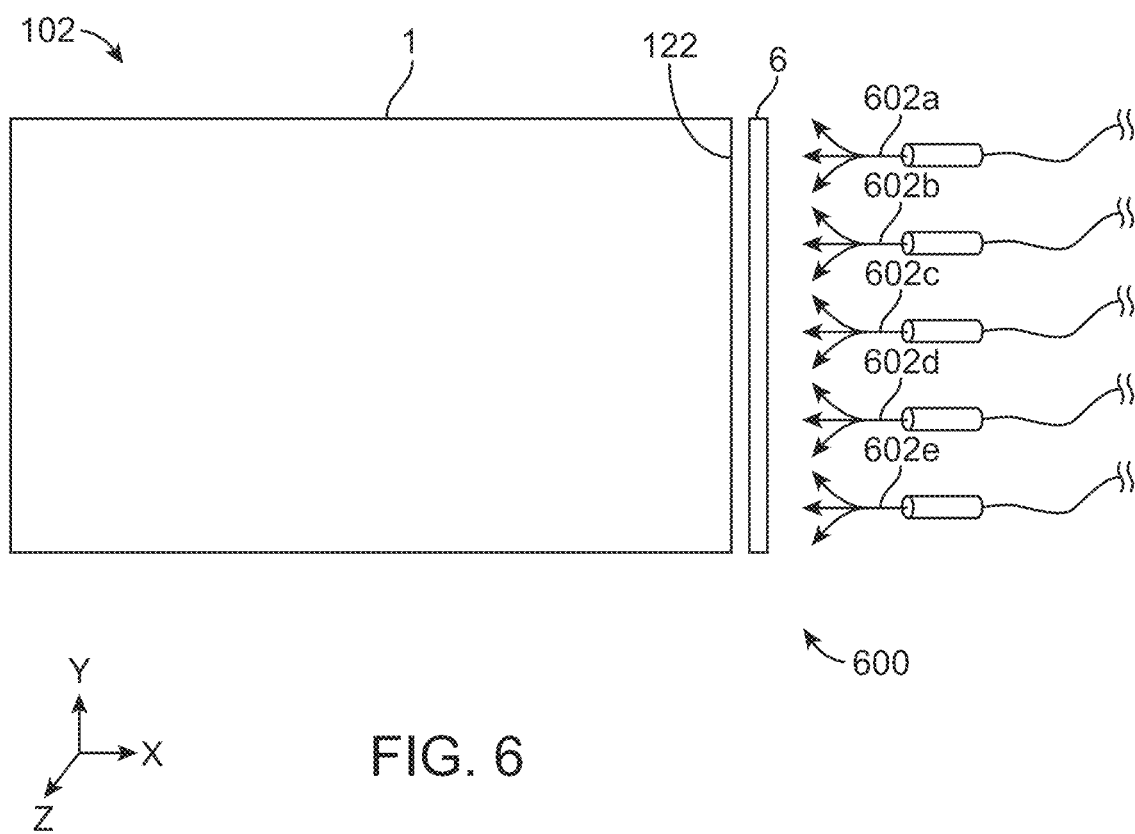
FIG. 6 is a schematic diagram showing an optical system including a waveguide apparatus, an optical coupler subsystem including a plurality of projectors to optically couple light to a primary planar waveguide, according to one illustrated embodiment.

FIG. 6 shows an optical system 600, according to one illustrated embodiment. The optical system 600 is similar in some respects to the optical systems 100, 500. In the interest of conciseness, only some of the difference are discussed.

The optical system 600 includes a waveguide apparatus 102, which as described above may comprise one or more primary planar waveguides 1 and associated DOE(s) 2 (not illustrated in FIG. 6). In contrast to the optical system 500 of FIGS. 5A-5C, the optical system 600 employs a plurality of microdisplays or projectors 602a-602e (only five shown, collectively 602) to provide respective image data to the primary planar waveguide(s) 1. The microdisplays or projectors 602 are generally arrayed or arranged along are disposed along an edge 122 of the primary planar waveguide 1.

There may, for example, be a one to one (1:1) ratio or correlation between the number of planar waveguides 1 and the number of microdisplays or projectors 602. The microdisplays or projectors 602 may take any of a variety of forms capable of providing images to the primary planar waveguide 1. For example, the microdisplays or projectors 602 may take the form of light scanners or other display elements, for instance the cantilevered fiber 7 previously described. The optical system 600 may additionally or alternatively include a collimation element 6 that collimates light provided from microdisplay or projectors 602 prior to entering the primary planar waveguide(s) 1.

The optical system 600 can enable the use of a single primary planar waveguide 1, rather using two or more primary planar waveguides 1 (e.g., arranged in a stacked configuration along the Z-axis of FIG. 6). The multiple microdisplays or projectors 602 can be disposed, for example, in a linear array along the edge 122 of a primary planar waveguide that is closest to a temple of a viewer's head. Each microdisplay or projector 602 injects modulated light encoding sub-image data into the primary planar waveguide 1 from a different respective position, thus generating different pathways of light.

These different pathways can cause the light to be coupled out of the primary planar waveguide 1 by a multiplicity of DOEs 2 at different angles, focus levels, and/or yielding different fill patterns at the exit pupil. Different fill patterns at the exit pupil can be beneficially used to create a light field display. Each layer in the stack or in a set of layers (e.g., 3 layers) in the stack may be employed to generate a respective color (e.g., red, blue, green). Thus, for example, a first set of three adjacent layers may be employed to respectively produce red, blue and green light at a first focal depth. A second set of three adjacent layers may be employed to respectively produce red, blue and green light at a second focal depth. Multiple sets may be employed to generate a full 3D or 4D color image field with various focal depths.

Figure 7:
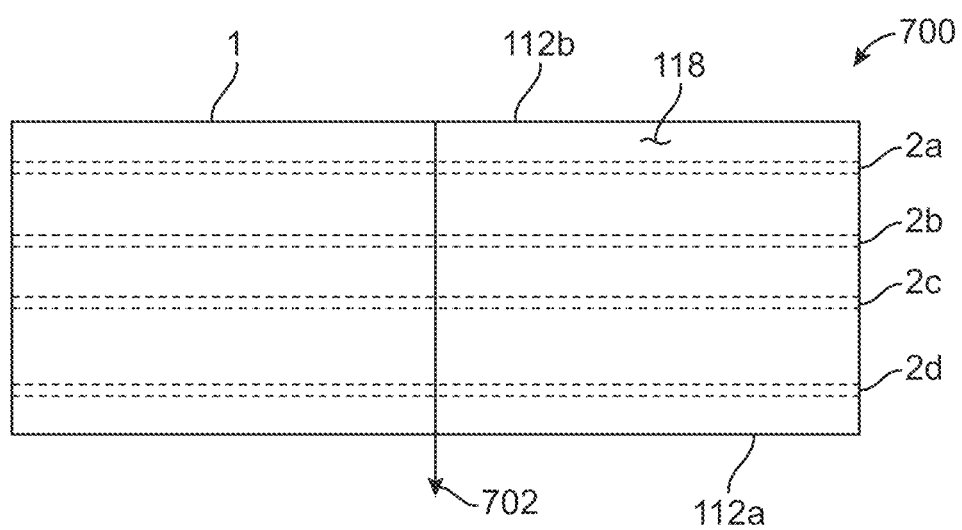
FIG. 7 is an elevational view of a planar waveguide apparatus including a planar waveguide with a plurality of DOEs, according to one illustrated embodiment.

FIG. 7 shows a planar waveguide apparatus 700 including a planar waveguide 1 with a plurality of DOEs 2a-2d (four illustrated, each as a double dash-dot line, collectively 2), according to one illustrated embodiment.

The DOEs 2 are stacked along an axis 702 that is generally parallel to the field-of-view of the planar waveguide 700. While illustrated as all being in the interior 118, in some implementations one, more or even all of the DOEs may be on an exterior of the planar waveguide 1.

In some implementations, each DOE 2 may be capable of being independently switched ON and OFF. That is each DOE 2 can be made active such that the respective DOE 2 diffracts a significant fraction of light that intersects with the respective DOE 2, or it can be rendered inactive such that the respective DOE 2 either does not diffract light intersecting with the respective DOE 2 at all, or only diffracts an insignificant fraction of light. "Significant" in this context means enough light to be perceived by the human visual system when coupled out of the planar waveguide 1, and "insignificant" means not enough light to be perceived by the human visual system, or a low enough level to be ignored by a viewer.

The switchable DOEs 2 may be switched on one at a time, such that only one DOE 2 in the primary planar waveguide 1 is actively diffracting the light in the primary planar waveguide 1, to emerge from one or more faces 112 of the primary planar waveguide 1 in a perceptible amount. Alternatively, two or more DOEs 2 may be switched ON simultaneously, such that their diffractive effects are combined.

The phase profile of each DOE 2 is advantageously a summation of a linear diffraction grating and a radially symmetric diffractive lens. Each DOE 2 preferably has a low (e.g., less than 50%) diffraction efficiency.

The light intersects with the DOEs at multiple points along the length of the planar waveguide 1 as the light propagates horizontally in the planar waveguide 1 via TIR. At each point of intersection between the propagating light and a respective one of the DOEs 2, a fraction of the light is diffracted toward the adjacent face 112 of the planar waveguide 1, allowing the light to escape TIR and emerge from the face 112 of the planar waveguide 1.

The radially symmetric lens aspect of the DOE 2 additionally imparts a focus level to the diffracted light, both shaping the light wavefront (e.g., imparting a curvature) of the individual beam, as well as steering the beam at an angle that matches the designed focus level. Such is best illustrated in FIG. 5B where the four beams 18, 19, 20, 21, if geometrically extended from the far face 112b of the planar waveguide 1, intersect at a focus point 13, and are imparted with a convex wavefront profile with a center of radius at focus point 13.

Each DOE 2 in the set of DOEs can have a different phase map. For example, each DOE 2 can have a respective phase map such that each DOE 2, when switched ON, directs light to a different position in X, Y, or Z. The DOEs 2 may, for example, vary from one another in their linear grating aspect and/or their radially symmetric diffractive lens aspect. If the DOEs 2 vary from one another in their diffractive lens aspect, different DOEs 2 (or combinations of DOEs 2) will produce sub-images at different optical viewing distances—i.e., different focus distances.

If the DOEs 2 vary from one another in their linear grating aspect, different DOEs 2 will produce sub-images that are shifted laterally relative to one another. Such lateral shifts can be beneficially used to create a foveated display, to steer a display image with non-homogenous resolution or other non-homogenous display parameters (e.g., luminance, peak wavelength, polarization, etc.) to different lateral positions, to increase the size of the scanned image, to produce a variation in the characteristics of the exit pupil, and/or to generate a light field display. Lateral shifts may be advantageously employed to preform tiling or realize a tiling effect in generated images.

For example, a first DOE 2 in the set, when switched ON, may produce an image at an optical viewing distance of 1 meter (e.g., focal point 23 in FIG. 5C) for a viewer looking into the primary or emission face 112a of the planar waveguide 1. A second DOE 2 in the set, when switched ON, may produce an image at an optical viewing distance of 1.25 meters (e.g., focal point 13 in FIG. 5C) for a viewer looking into the primary or emission face 112a of the planar waveguide 1.

By switching exemplary DOEs 2 ON and OFF in rapid temporal sequence (e.g., on a frame-by-frame basis, a sub-frame basis, a line-by-line basis, a sub-line basis, pixel-by-pixel basis, or sub-pixel-by-sub-pixel basis) and synchronously modulating the image data being injected into the planar waveguide 1, for instance by a scanning fiber display sub-system, a composite multi-focal volumetric image is formed that is perceived to a be a single scene to the viewer. By rendering different objects or portions of objects to sub-images relayed to the eye of the viewer (at location 22 in FIG. 5C) by the different DOEs 2, virtual objects or images are placed at different optical viewing distances, or a virtual object or image can be represented as a 3D volume that extends through multiple planes of focus.

Figure 8:
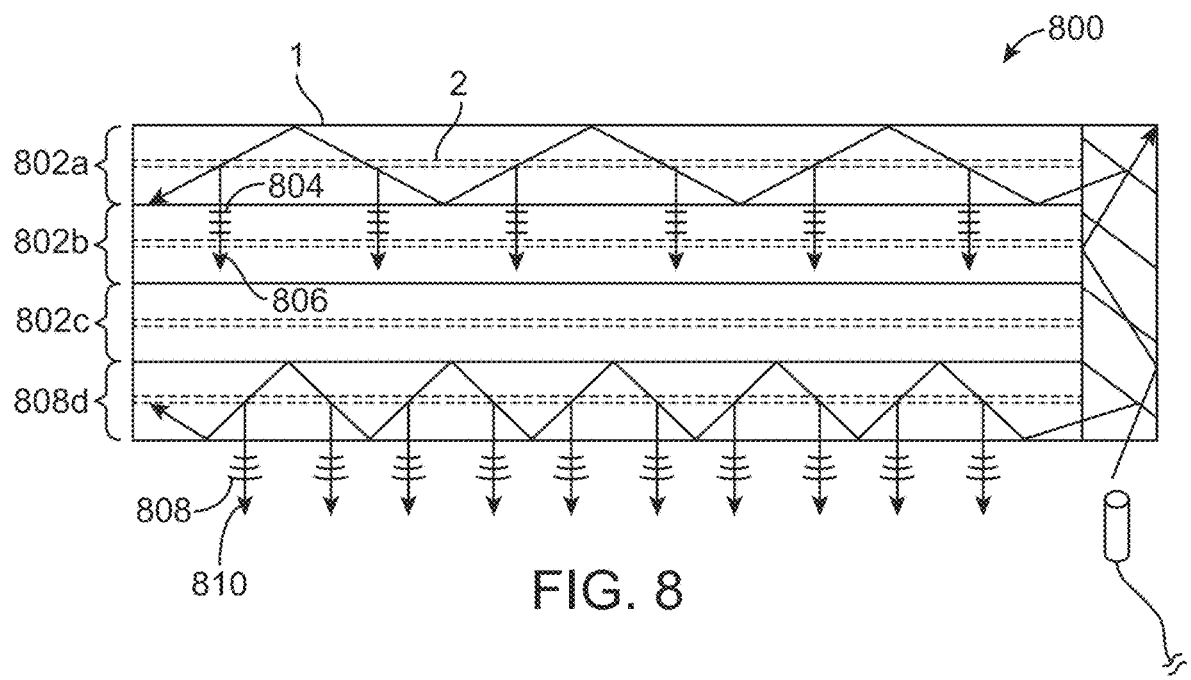
FIG. 8 is an elevational view showing a portion of an optical system including a plurality of planar waveguide apparati in a stacked array, configuration or arrangement, according to one illustrated embodiment.

FIG. 8 shows a portion of an optical system 800 including a plurality of planar waveguide apparati 802a-802d (four shown, collectively 802), according to one illustrated embodiment.

The planar waveguide apparati 802 are stacked, arrayed, or arranged along an axis 804 that is generally parallel to the field-of-view of the portion of the optical system 800. Each of the planar waveguide apparati 802 includes at least one planar waveguide 1 (only one called out in FIG. 8) and at least one associated DOE 2 (illustrated by dash-dot double line, only one called out in FIG. 8). While illustrated as all being in the interior 118, in some implementations one, more or even all of the DOEs 2 may be on an exterior of the planar waveguide 1. Additionally or alternatively, while illustrated with a single linear array of DOEs 2 per planar waveguide 1, one or more of the planar waveguides 1 may include two or more stacked, arrayed or arranged DOEs 2, similar to the implementation described with respect to FIG. 7.

Each of the planar waveguide apparati 802a-802d may function analogously to the operation of the DOEs 2 of the optical system 7 (FIG. 7), That is the DOEs 2 of the respective planar waveguide apparati 802 may each have a respective phase map, the phase maps of the various DOEs 2 being different from one another. While dynamic switching (e.g., ON/OFF) of the DOEs 2 was employed in the optical system 700 (FIG. 7), such can be avoided in the optical system 800. Instead of, or in additional to dynamic switching, the optical system 800 may selectively route light to the planar waveguide apparati 802a-802d based on the respective phase maps. Thus, rather than turning ON a specific DOE 2 having a desired phase map, the optical system 800 may route light to a specific planar waveguide 802 that has or is associated with a DOE 2 with the desired phase mapping. Again, the may be in lieu of, or in addition to, dynamic switching of the DOEs 2.

In one example, the microdisplays or projectors may be selectively operated to selectively route light to the planar waveguide apparati 802a-802d based on the respective phase maps. In another example, each DOE 4 may be capable of being independently switched ON and OFF, similar to as explained with reference to switching DOEs 2 ON and OFF. The DOEs 4 may be switched ON and OFF to selectively route light to the planar waveguide apparati 802a-802d based on the respective phase maps.

FIG. 8 also illustrated outward emanating rays from two of the planar waveguide apparati 802a, 802d. For sake of illustration, a first one of the planar waveguide apparatus 802a produces a plane or flat wavefront (illustrated by flat lines 804 about rays 806, only one instance of each called out for sake of drawing clarity) at an infinite focal distance. In contrast, another one of the planar waveguide apparatus 802d produces a convex wavefront (illustrated by arc 808 about rays 810, only one instance of each called out for sake of drawing clarity) at a defined focal distance less than infinite (e.g., 1 meter).

Figure 9:
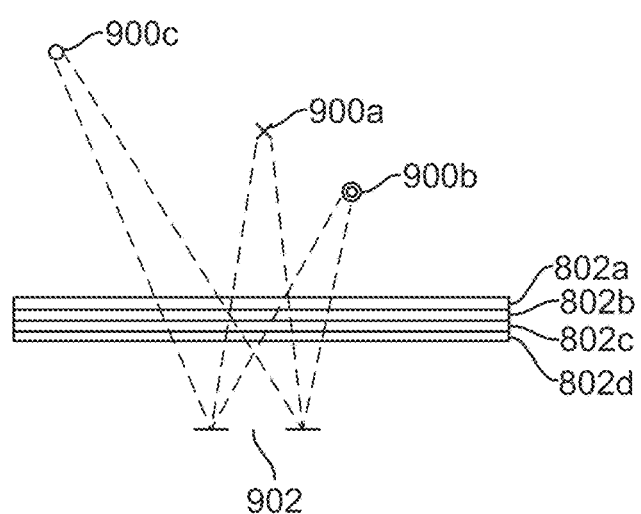
FIG. 9 is a top plan view showing a portion of the optical system of FIG. 8, illustrating a lateral shifting and change in focal distance in an image of a virtual object, according to one illustrated embodiment.

As illustrated in FIG. 9, the planar waveguide apparati 802a-802d may laterally shift the appearance and/or optical viewing distances—i.e., different focus distances of a virtual object 900a-900c with respect to an exit pupil 902.

Figure 10:
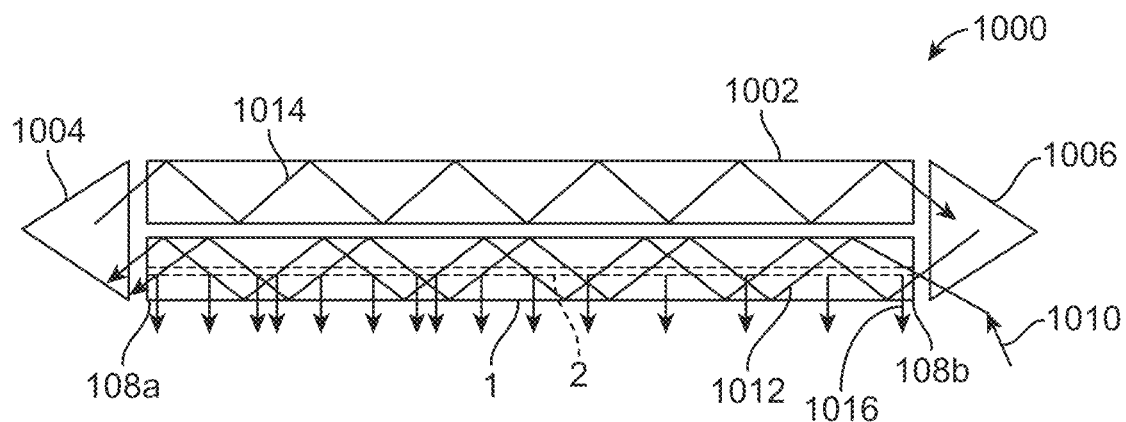
FIG. 10 is an elevational view showing a portion of an optical system including a planar waveguide apparatus with a return planar waveguide, according to one illustrated embodiment.

FIG. 10 shows a portion of an optical system 1000 including a planar waveguide apparatus 102 with a return planar waveguide 1002, according to one illustrated embodiment.

The planar waveguide apparatus 102 may be similar to those described herein, for example including one or more planar waveguides 1 and one or more associated DOEs 2.

In contrast to previously described implementations, the optical system 1000 includes the return planar waveguide 1002, which provides a TIR optical path for light to return from one end 108b of the planar waveguide 1 to the other end 108a of the planar waveguide 1 for recirculation. The optical system 1000 also include is a first mirror or reflector 1004, located at a distal end 108a (i.e., end opposed to end at which light first enters). The mirror or reflector 1004 at the distal end 108a may be completely reflecting. The optical system 1000 optionally includes is a second mirror or reflector 1006, located at a proximate end 108b (i.e., end at which light first enters as indicated by arrow 1010). The second mirror or reflector 1006 may be a dichroic mirror or prism, allowing light to initially enter the optical system, and then reflecting light returned from the distal end 108a.

Thus, light may enter at the proximate end 108b as indicated by arrow 1010. The light may traverse or propagate along the planar waveguide 1 in a first pass, as illustrated by arrow 1012, exiting at the distal end 112b. The first mirror or reflector 1004 may reflect the light to propagate via the return planar waveguide 1002, as illustrated by arrow 1014. The second mirror or reflector 1006 may reflect the remaining light back to the planar waveguide 1 for a second pass, as illustrated by arrow 1016. This may repeat until there is no appreciable light left to recirculate. This recirculation of light may advantageously increase luminosity or reduce system luminosity requirements.

Figure 11:
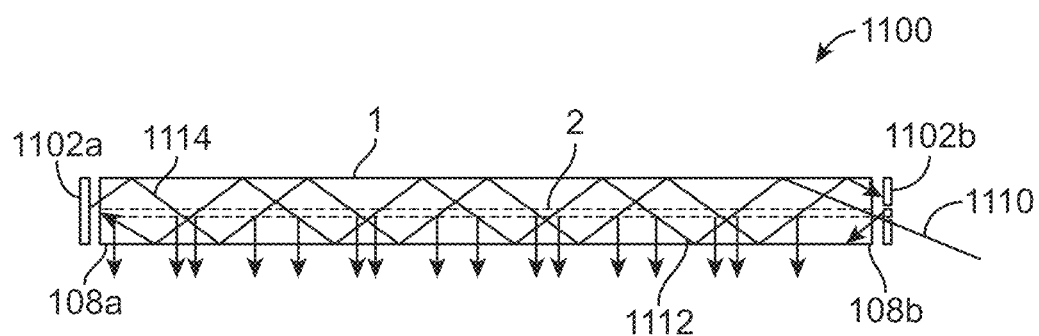
FIG. 11 is an elevational view showing a portion of an optical system including a planar waveguide apparatus with at least partially reflective mirrors or reflectors at opposed ends thereof to return light through a planar waveguide, according to one illustrated embodiment.

FIG. 11 shows a portion of an optical system 1100 including a planar waveguide apparatus 102 with at least partially reflective mirrors or reflectors 1102a, 1102b at opposed ends 112a, 112b thereof to return light through a planar waveguide 1, according to one illustrated embodiment.

Light may enter at the proximate end 108b as indicated by arrow 1110. The light may traverse or propagate along the planar waveguide 1 in a first pass, as illustrated by arrow 1112, exiting at the distal end 112b. The first mirror or reflector 1102a may reflect the light to propagate the planar waveguide 1, as illustrated by arrow 1114. The second mirror or reflector 1006 may optionally reflect the remaining light back to the planar waveguide 1 for a second pass (not illustrated). This may repeat until there is no appreciable light left to recirculate. This recirculation of light may advantageously increase luminosity or reduce system luminosity requirements.

In some implementations, an optical coupling system collimates the light emerging from a multiplicity of displays or projectors, prior to optically coupling the light to a planar waveguide. This optical coupling system may include, but is not limited to, a multiplicity of DOEs, refractive lenses, curved mirrors, and/or freeform optical elements. The optical coupling subsystem may serve multiple purposes, such as collimating the light from the multiplicity of displays and coupling the light into a waveguide. The optical coupling subsystem may include a mirrored surface or prism to reflect or deflect the collimated light into a planar waveguide.

In some implementations the collimated light propagates along a narrow planar waveguide via TIR, and in doing so repeatedly intersects with a multiplicity of DOEs 2. As described above, the DOEs 2 may comprise or implement respective different phase maps, such that the DOEs 2 steer the light in the waveguide along respective different paths. For example, if the multiple DOEs 2 contain linear grating elements with different pitches, the light is steered at different angles, which may beneficially be used to create a foveated display, steer a non-homogenous display laterally, increase the lateral dimensions of the out-coupled image, increase effective display resolution by interlacing, generate different fill patterns at the exit pupil, and/or generate a light field display.

As previously described, a multiplicity of DOEs 2 may be arrayed or arranged or configured in a stack within or on a respective planar waveguide 1, 3.

The DOEs 2 in the distribution planar waveguide 3 may have a low diffraction efficiency, causing a fraction of the light to be diffracted toward the edge of the larger primary planar waveguide 1, at each point of intersection, and a fraction of the light to continue on its original trajectory down the distribution planar waveguide 3 via TIR. At each point of intersection, additional light is diffracted toward an edge or entrance of the primary planar waveguide 1. By dividing the incoming light into multiple out-coupled sets, the exit pupil of the light is expanded vertically by multiplicity of DOEs 4 in distribution planar waveguide 3.

As described above, vertically expanded light coupled out of the distribution planar waveguide 3 enters an edge of larger primary planar waveguide 1, and propagates horizontally along the length of the primary planar waveguide 1 via TIR.

The multiplicity of DOEs 4 in the narrow distribution planar waveguide 3 can have a low diffraction efficiency, causing a fraction of the light to be diffracted toward the edge of the larger primary planar waveguide 1 at each point of intersection, and a fraction of the light to continue on its original trajectory down the distribution planar waveguide 3 by TIR. At each point of intersection, additional light is diffracted toward the entrance of larger primary planar waveguide 1. By dividing the incoming light into multiple out-coupled sets, the exit pupil of the light is expanded vertically by the multiplicity of DOEs 4 in distribution planar waveguide 3. A low diffraction efficiency in the multiplicity of DOEs in the primary planar waveguide 1 enables viewers to see through the primary planar waveguide 1 to view real objects, with a minimum of attenuation or distortion.

In at least one implementation, the diffraction efficiency of the multiplicity of DOEs 2 is low enough to ensure that any distortion of real world is not perceptible to a human looking through the waveguide at the real world.

Since a portion or percentage of light is diverted from the internal optical path as the light transits the length of the planar waveguide(s) 1, 3, less light may be diverted from one end to the other end of the planar waveguide 1, 3 if the diffraction efficiency is constant along the length of the planar waveguide 1,3. This change or variation in luminosity or output across the planar waveguide 1, 3 is typically undesirable. The diffraction efficiency may be varied along the length to accommodate for this undesired optical effect. The diffraction efficiency may be varied in a fixed fashion, for example by fixedly varying a pitch of the DOEs 2, 4 along the length when the DOEs 2, 4 and/or planar waveguide 1, 3 is manufactured or formed. Intensity of light output may be advantageously be increased or varied as a function of lateral offset of pixels in the display or image.

Alternatively, the diffraction efficiency may be varied dynamically, for example by fixedly varying a pitch of the DOEs 2, 4 along the length when the DOEs 2, 4 and/or planar waveguide 1,3 is in use. Such may employ a variety of techniques, for instance varying an electrical potential or voltage applied to a material (e.g., liquid crystal). For example, voltage changes could be applied, for instance via electrodes, to liquid crystals dispersed in a polymer host or carrier medium.

The voltage may be used to change the molecular orientation of the liquid crystals to either match or not match a refractive index of the host or carrier medium. As explained herein, a structure which employs a stack or layered array of switchable layers (e.g., DOEs 2, planer waveguides 1), each independently controllable may be employed to advantageous affect.

In at least one implementation, the summed diffraction efficiency of a subset of simultaneously switched on DOEs 2 of the multiplicity of DOEs 2 is low enough to enable viewers to see through the waveguide to view real objects, with a minimum of attenuation or distortion.

It may be preferred if the summed diffraction efficiency of a subset of simultaneously switched on DOEs 2 of the multiplicity of DOEs 2 is low enough to ensure that any distortion of real world is not perceptible to a human looking through the waveguide at the real world.

As described above, each DOE 2 in the multiplicity or set of DOEs 2 may be capable of being switched ON and OFF—i.e., it can be made active such that the respective DOE 2 diffracts a significant fraction of light that intersects with the respective DOE 2, or can be rendered inactive such that the respective DOE 2 either does not diffract light intersecting with it at all, or only diffracts an insignificant fraction of light. "Significant" in this context means enough light to be perceived by the human visual system when coupled out of the waveguide, and "insignificant" means not enough light to be perceived by the human visual system, or a low enough level to be ignored by a viewer.

The switchable multiplicity of DOEs 2 may be switched ON one at a time, such that only one DOE 2 associated with the large primary planar waveguide 1 is actively diffracting the light in the primary planar waveguide 1 to emerge from one or more faces 112 of the primary planar waveguide 1 in a perceptible amount. Alternatively, two or more DOEs 2 in the multiplicity of DOEs 2 may be switched ON simultaneously, such that their diffractive effects are advantageously combined. It may thus be possible to realize 2N combinations, where N is the number of DOEs 2 in associated with a respective planar waveguide 1, 3.

Figure 3C:
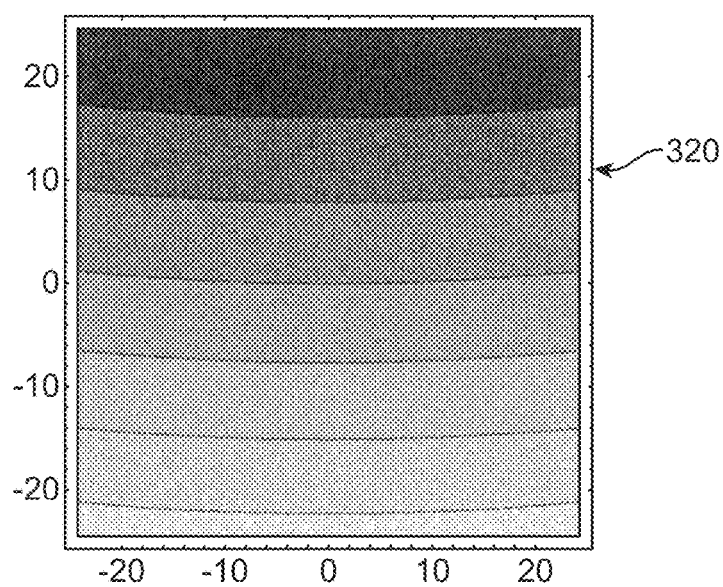
FIG. 3C a schematic diagram showing a linear diffraction or diffractive phase function of a diffractive optical element that combines the linear diffraction and the radially circular lens phase functions, the diffractive optical element associated with a planar waveguide.

In at least some implementations, the phase profile or map of each DOE 2 in at least the large or primary planar waveguide 1 is or reflects a summation of a linear diffraction grating and a radially symmetric diffractive lens, and has a low (less than 50%) diffraction efficiency. Such is illustrated in FIGS. 3A-3C. In particular, the hologram phase function comprises a linear function substantially responsible for coupling the light out of the waveguide, and a lens function substantially responsible for creating a virtual image $$p(x, y) = p1(x, y) + p2(x, y),$$

where $$p1(x, y) = \frac{x0y1y}{nr},$$

and $$p2(x, y) = x2y0\left(\frac{x}{nr}\right)^2 + x2y2\left(\frac{x}{nr}\right)^2\left(\frac{y}{nr}\right)^2 + x2y4\left(\frac{x}{nr}\right)^2\left(\frac{y}{nr}\right)^4 + x4y0\left(\frac{x}{nr}\right)^4 +$$
$$x4y2\left(\frac{x}{nr}\right)^4\left(\frac{y}{nr}\right)^2 + x6y0\left(\frac{x}{nr}\right)^6 + x0y2\left(\frac{y}{nr}\right)^2 + x0y4\left(\frac{y}{nr}\right)^4 + x0y6\left(\frac{y}{nr}\right)^6$$

In this example, the coefficients of p2 are constrained to produce a radially symmetric phase function.

An example EDGE element was designed for a 40 degree diagonal field of view having a 16×9 aspect ratio. The virtual object distance is 500 mm (2 diopters). The design wavelength is 532 nanometers. The substrate material is fused silica, and the y angles of incidence in the substrate lie between 45 and 72 degrees. The y angle of incidence required to generate an on axis object at is 56 degrees. The phase function defining the example element is:

$$\Phi g = \frac{12.4113 x^2}{mm^2} - \frac{0.00419117 x^4}{mm^4} - \frac{14315. y}{mm} - \frac{12.4113 y^2}{mm^2} - \frac{0.00838233 x^2 y^2}{mm^4} - \frac{0.00419117 y^4}{mm^4}$$

Figure 12:
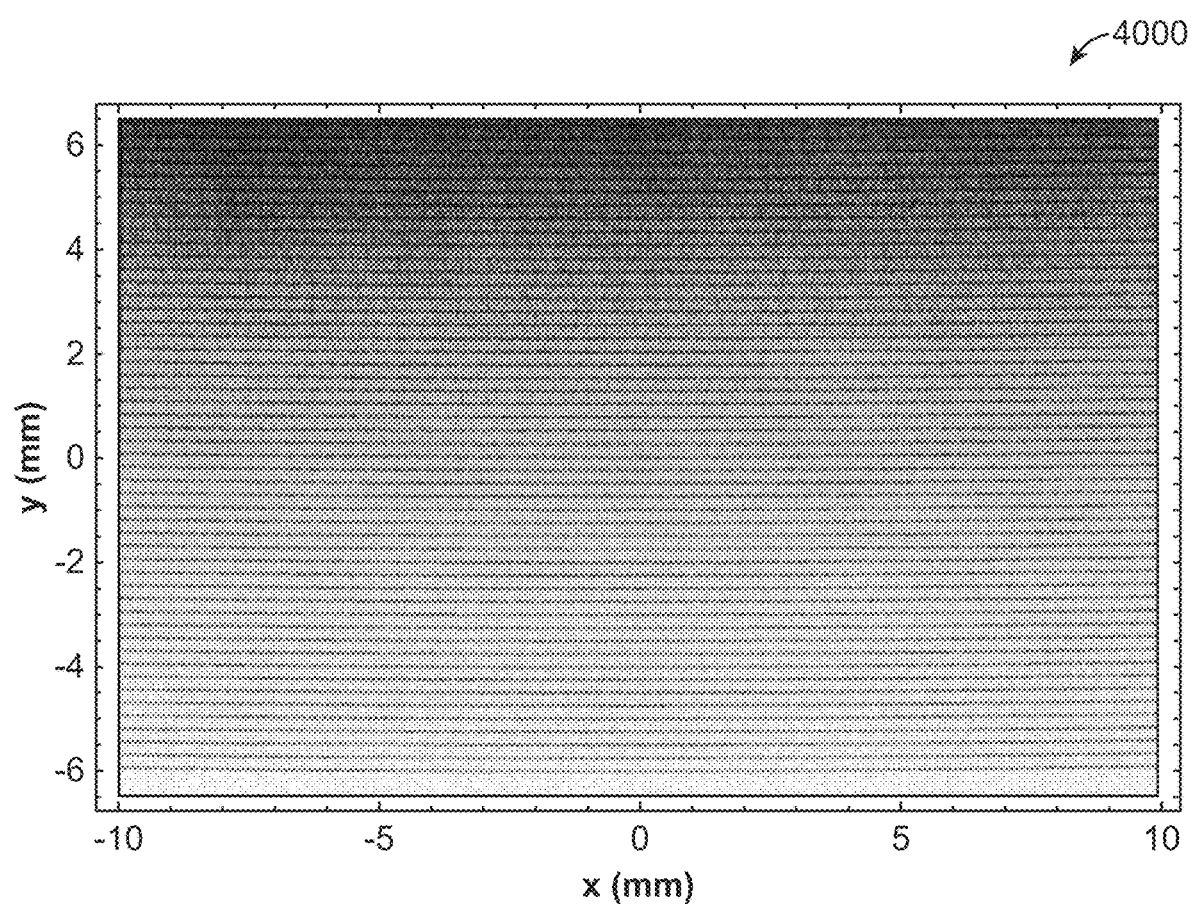
FIG. 12 is a contour plot of a function for an exemplary diffractive element pattern, according to one illustrated embodiment.

The diffractive element pattern is generated by evaluating the 2 pi phase contours. FIG. 12 shows a contour plot 4000 illustrating the function evaluated over a 20×14 mm element area (required to provide a 4 mm eye box at a 25 mm eye relief. The contour interval was chosen to make the groove pattern visible. The actual groove spacing in this design is approximately 0.5 microns.

The relationship between substrate index and field of view is described in FIGS. 13A-13E. The relationship is nontrivial, but a higher substrate index always allows for a large field of view. One should always prefer higher index of refraction materials if all other considerations are equal.

Figure 13A:
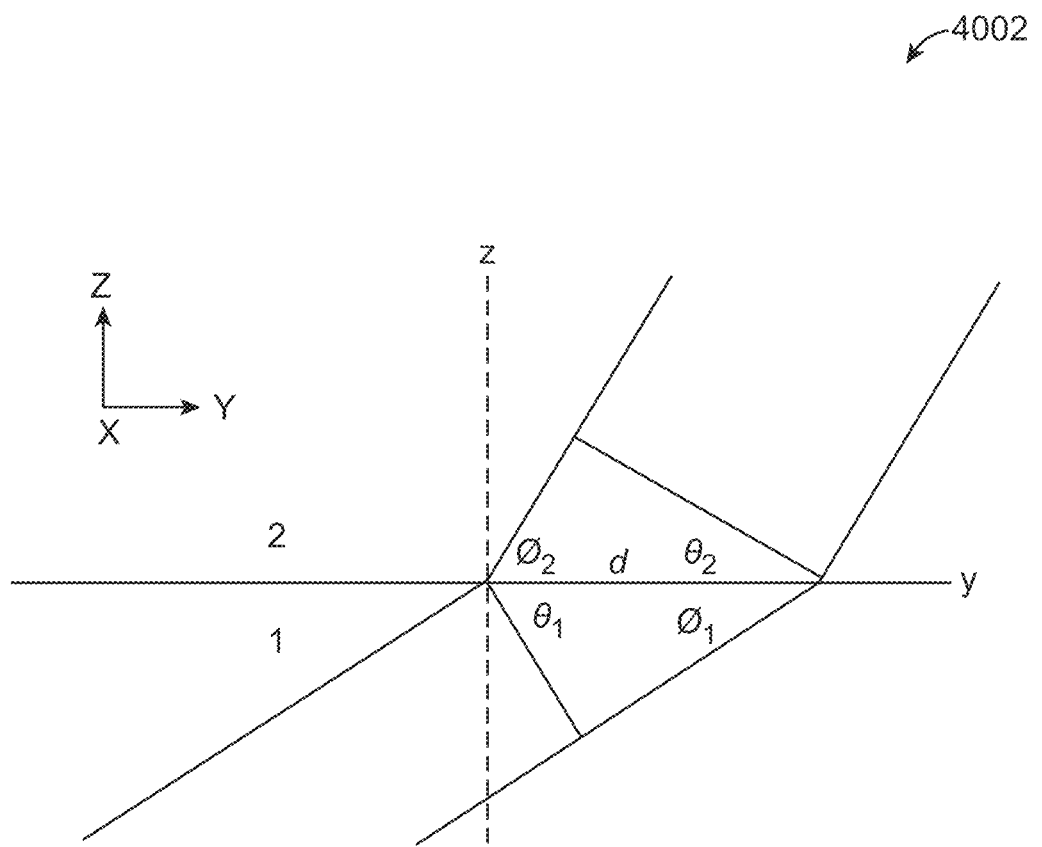
FIGS. 13A-13E illustrate a relationship between a substrate index and a field of view, according to one illustrated embodiment.
Figure 13B:
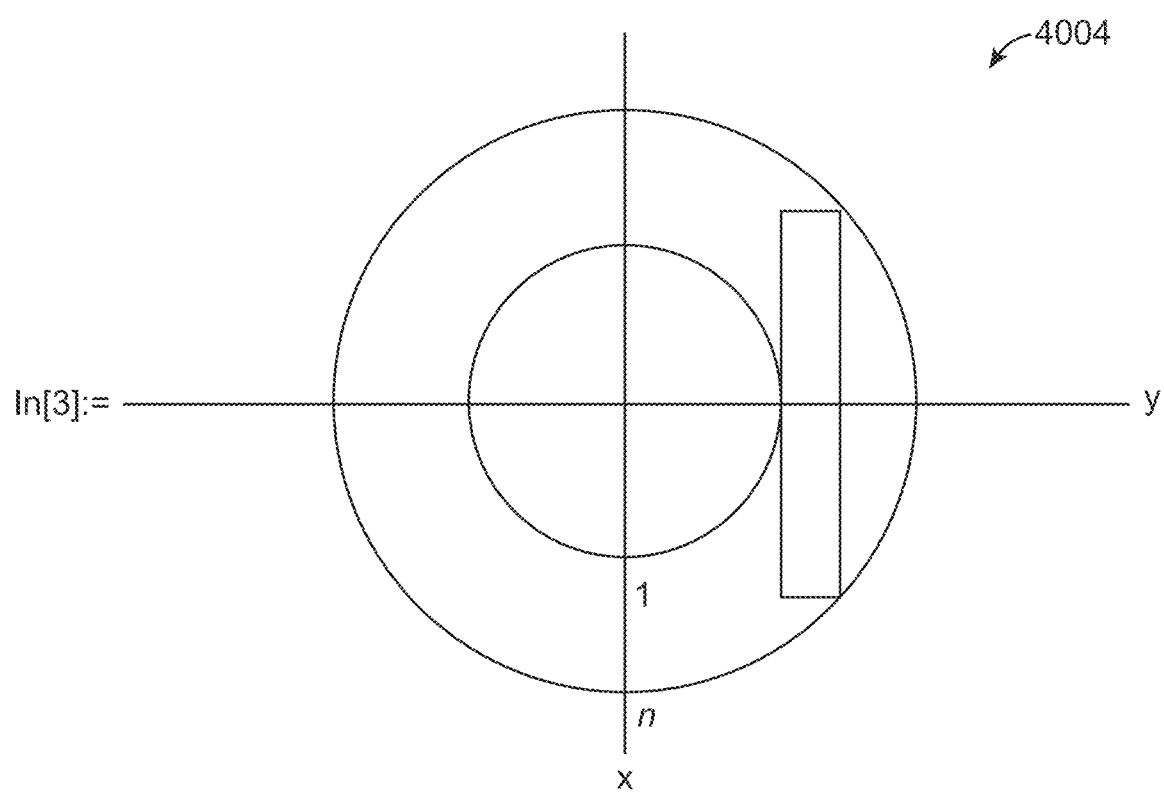

Referring to FIG. 13A, plot 4002 describes a relationship between the substrate index and field of view according to one embodiment. Referring to the following equation, $$k_j = \frac{2\pi}{\lambda_j}$$

where j is the region index. The index 0 is used to indicate free space (air).

$$k_2 d\sin(\theta_2) - k_1 d\sin(\theta_1) = m2\pi$$
$$\frac{2\pi}{\lambda_1}\sin(\theta_2) - \frac{2\pi}{\lambda_2}\sin(\theta_1) = m\frac{2\pi}{d}$$
$$\frac{2\pi}{\lambda_2}\sin(\theta_2) = m\frac{2\pi}{d} + \frac{2\pi}{\lambda_1}\sin(\theta_1)$$
$$k_2\sin(\theta_2) = m\frac{2\pi}{d} + k_1\sin(\theta_1)$$
$$k_{2y} = m\frac{2\pi}{d} + k_{1y}$$
$$k_{2y} = mk_g + k_{1y}$$

Alternative formulation normalized using the free space wavelength may be the following:

$$\vec{h}_j = \frac{\vec{k}_j}{k_0}$$
$$h_j = \frac{k_j}{k_0} = n_j$$
$$hg = \frac{k_g}{k_0} = \frac{\lambda_0}{d}$$
$$h_{2y} = mh_g + h_{1y}$$

where $$h_{jy} = h_j\sin(\theta_j)$$

If $|h_{2,y}| \le h_2$ then the wave associated with $\vec{h}_2$ (vector h2) is not evanescent.

For the substrate guided wave, the rectangle in the following diagram indicates the region of allowed projections of $\vec{h}$ (vector h) into the X Y plane. The outer circle has radius n, and indicates a wave vector parallel to the X Y plane. The inner circle has radius 1 and indicates the TIR (total internal reflection) boundary.

Referring now to FIG. 13 B (plot 4004) in the normalized representation, $\vec{h}$ (vector h) is a vector of magnitude n independent of free space wavelength. When the index is 1, the components are the direction of cosines of $\vec{k}$ (vector k).

$$k_x^2 + k_y^2 + k_z^2 = k_0^2$$

$$h_x^2 + h_y^2 + h_z^2 = n_0^2$$

The wavelengths used to design an earlier fiber scanner lens (ref. sfe-06aa.zmx) were 443, 532, and 635 nm. The red and blue wavelengths are used in the following calculation.

Figure 13C:
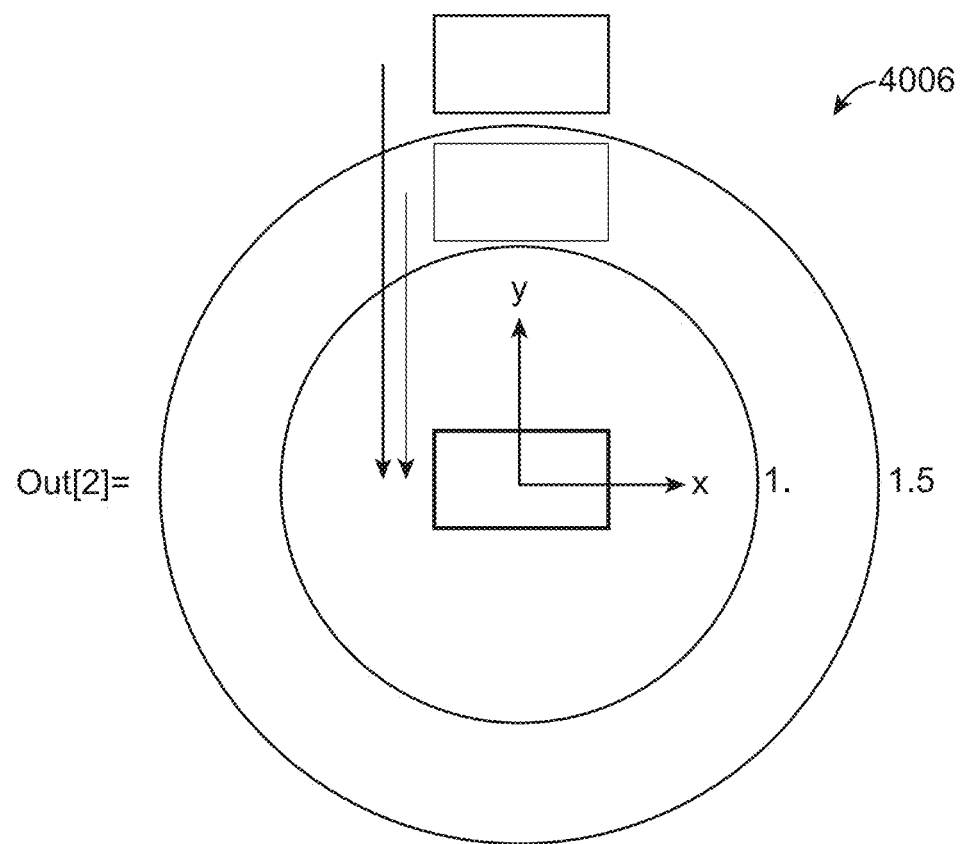
Figure 13D:
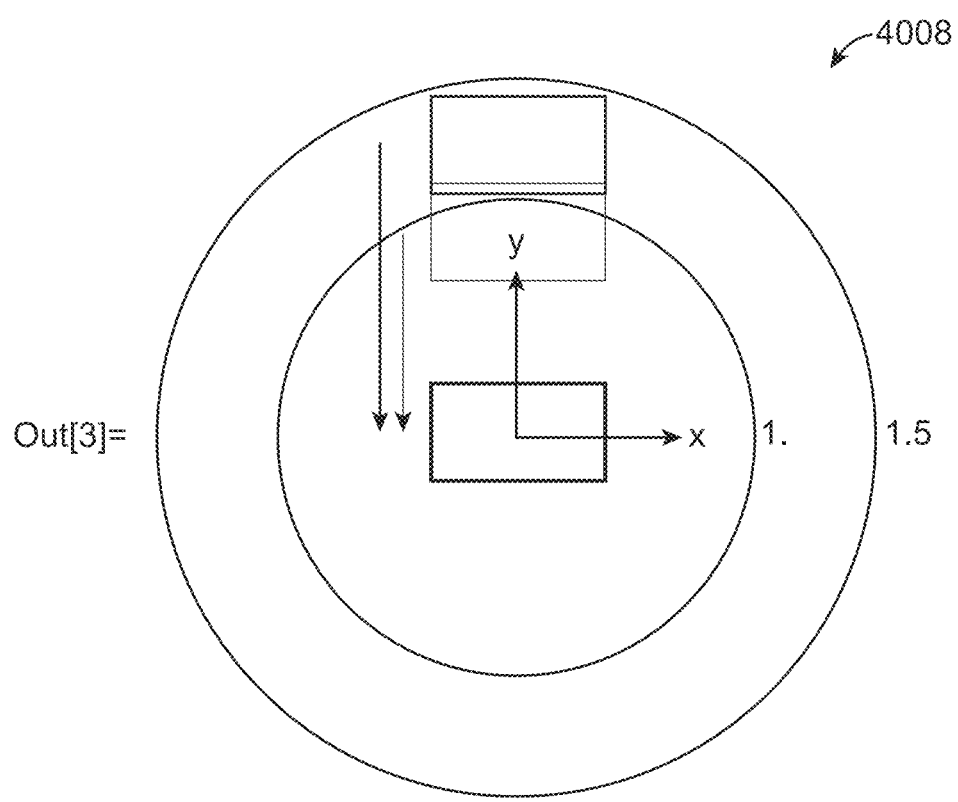
Figure 13E:
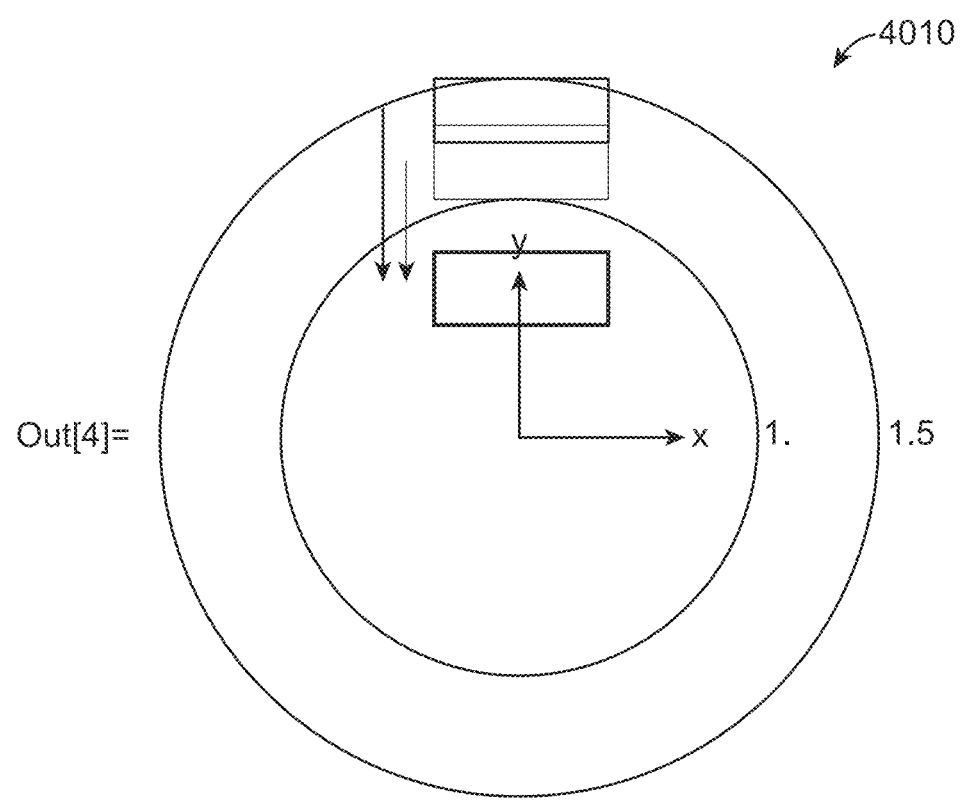

Referring now to FIG. 13C-13E, FIGS. 13C-13E show plots (4006-4010) of normalized wave vector regions projected into the x y plane (i.e. parallel to the substrate). The rectangle in the middle represents the eye field of view. The top two rectangles represent the waveguide vector projections required to produce the eye field of view. The arrows indicate the deflection provided by the grating.

The unit radius circle represents the TIR (total internal reflection) constraint for a guided wave in the substrate, and the 1.5 radius circle represents a wave propagating parallel to the substrate when the index n=1.5. Wave vectors propagating between the two circles are allowed. This plot is for the substrate oriented vertically, a 50° diagonal (16×9 format) eye field of view, and a 0.36 micron grating line spacing. Note that the rectangle in the concentric circle lies inside the region of allowed region, whereas the topmost rectangle lies in the evanescent region.

By increasing the groove spacing to 5.2 microns, the vector from the outer circle (red) can be brought inside the allowed region, but then a majority of the vectors in the concentric circle (blue) do not totally internally reflect (FIG. 13 D)

Tilting the substrate with respect to the eye is equivalent to biasing the eye field of view with respect to the substrate. This plot shows the effect of tilting the waveguide 45° and increasing the groove width to 0.85 mm. Note that the difference between the grating arrows is less, and that both the vectors fall substantially within the allowed region (FIG. 13E).

First order diffraction efficiencies should be in the neighborhood of 0.01 to 0.20. Lower values require higher input energy to create specified image brightness, while larger values lead to increased pupil non-uniformity. The particular value chosen depends on the particular application requirements.

It may be advantageous to vary one or more characteristics of the DOEs 2, for example along a longitudinal or axial dimension thereof. For instance, a pitch may be varied, or a height of a groove or angle (e.g., 90 degree, 60 degree) of a structure forming the DOE 2 or portion thereof. Such may advantageously address higher order aberrations.

Two beams of mutually coherent light may be employed to dynamically vary the properties of the DOEs 2. The beams of mutually coherent light may, for example, be generated via a single laser and a beam splitter. The beams may interact with a liquid crystal film to create a high interference pattern on or in the liquid crystal film to dynamically generate at least one diffraction element, e.g., a grating such as a Bragg grating. The DOEs 2 may be addressable on a pixel-by-pixel basis. Thus, for example, a pitch of the elements of the DOEs 2 may be varied dynamically. The interference patterns are typically temporary, but may be held sufficiently long to affect the diffraction of light.

Further, diffraction gratings may be employed to split lateral chromatic aberrations. For example, a relative difference in angle can be expected for light of different colors when passed through a DOE 2. Where a pixel is being generated via three different colors, the colors may not be perceived as being in the same positions due to the difference in bending of the respective colors of light. This may be addressed by introducing a very slight delay between the signals used to generate each color for any given pixel. One way of addressing this is via software, where image data is "pre-misaligned" or pre-wrapped, to accommodate the differences in location of the various colors making up each respective pixel. Thus, the image data for generating a blue component of a pixel in the image may be offset spatially and/or temporally with respect to a red component of the pixel to accommodate a known or expected shift due to diffraction. Likewise, a green component may be offset spatially and/or temporally with respect to a red and blue components of the pixel.

The image field may be generated to have a higher concentration of light or image information proximal to the viewer in contrast to portions that are relatively distal to the viewer. Such may advantageously take into account the typically higher sensitivity of the vision system for relative close objects or images as compared to more distal objects of images. Thus, virtual objects in the foreground of an image field may be rendered at a higher resolution (e.g., higher density of focal planes) than objects in the background of the image field. The various structures and approaches described herein advantageously allow such non-uniform operation and generation of the image field.

In at least some implementations, the light intersects with the multiplicity of DOEs 2 at multiple points as it propagates horizontally via TIR. At each point of intersection between the propagating light and the multiplicity of DOEs 2, a fraction of the light is diffracted toward the adjacent face of the planar waveguide 1, 3 allowing the light to escape TIR and emerge from the face 112 of the planar waveguide 1, 3.

In at least some implementations, the radially symmetric lens aspect of the DOE 2 additionally imparts a focus level to the diffracted light, both shaping the light wavefront (e.g., imparting a curvature) of the individual beam as well as steering the beam at an angle that matches the designed focus level. In FIG. 5B, the four beams 18, 19, 20, 21, if geometrically extended from the far face of the primary planar waveguide 1, intersect at a focus point 13, and are imparted with a convex wavefront profile with a center of radius at focus point 13.

In at least some implementations, each DOE 2 in the multiplicity or set of DOEs 2 can have a different phase map, such that each DOE 2, when switched ON or when fed light, directs light to a different position in X, Y, or Z. The DOEs 2 may vary from one another in their linear grating aspect and/or their radially symmetric diffractive lens aspect. If the DOEs 2 vary in their diffractive lens aspect, different DOEs 2 (or combinations of DOEs) will produce sub-images at different optical viewing distances—i.e., different focus distances. If the DOEs 2 vary in their linear grating aspect, different DOEs 2 will produce sub-images that are shifted laterally relative to one another.

In at least some implementations, lateral shifts generated by the multiplicity of DOEs can be beneficially used to create a foveated display. In at least some implementations, lateral shifts generated by the multiplicity of DOEs 2 can be beneficially used to steer a display image with non-homogenous resolution or other non-homogenous display parameters (e.g., luminance, peak wavelength, polarization, etc.) to different lateral positions. In at least some implementations, lateral shifts generated by the multiplicity of DOEs can be beneficially used to increase the size of the scanned image.

In at least some implementations, lateral shifts generated by the multiplicity of DOEs can be beneficially used to produce a variation in the characteristics of the exit pupil. In at least some implementations, lateral shifts generated by the multiplicity of DOEs can be beneficially used, to produce a variation in the characteristics of the exit pupil and generate a light field display.

In at least some implementations, a first DOE 2, when switched ON, may produce an image at a first optical viewing distance 23 (FIG. 5C) for a viewer looking into the face of the primary planar waveguide 1. A second DOE 2 in the multiplicity, when switched ON, may produce an image at a second optical viewing distance 13 (FIG. 5C) for a viewer looking into the face of the waveguide.

In at least some implementations, DOEs 2 are switched ON and OFF in rapid temporal sequence. In at least some implementations, DOEs 2 are switched ON and OFF in rapid temporal sequence on a frame-by-frame basis. In at least some implementations, DOEs 2 are switched ON and OFF in rapid temporal sequence on a sub-frame basis. In at least some implementations, DOEs 2 are switched ON and OFF in rapid temporal sequence on a line-by-line basis. In at least some implementations, DOEs 2 are switched ON and OFF in rapid temporal sequence on a sub-line basis. In at least some implementations, DOEs 2 are switched ON and OFF in rapid temporal sequence on a pixel-by-pixel basis. In at least some implementations, DOEs 2 are switched ON and OFF in rapid temporal sequence on a sub-pixel-by-sub-pixel basis. In at least some implementations, DOEs 2 are switched ON and OFF in rapid temporal sequence on some combination of a frame-by-frame basis, a sub-frame basis, a line-by-line basis, a sub-line basis, pixel-by-pixel basis, and/or sub-pixel-by-sub-pixel basis.

In at least some implementations, while DOEs 2 are switched ON and OFF the image data being injected into the waveguide by the multiplicity of microdisplays is simultaneously modulated. In at least some implementations, while DOEs 2 are switched ON and OFF the image data being injected into the waveguide by the multiplicity of microdisplays is simultaneously modulated to form a composite multi-focal volumetric image that is perceived to a be a single scene to the viewer.

In at least some implementations, by rendering different objects or portions of objects to sub-images relayed to the eye (position 22 in FIG. 5C) by the different DOEs 2, objects are placed at different optical viewing distances, or an object can be represented as a 3D volume that extends through multiple planes of focus.

In at least some implementations, the multiplicity of switchable DOEs 2 is switched at a fast enough rate to generate a multi-focal display that is perceived as a single scene.

In at least some implementations, the multiplicity of switchable DOEs 2 is switched at a slow rate to position a single image plane at a focal distance. The accommodation state of the eye is measured and/or estimated either directly or indirectly. The focal distance of the single image plane is modulated by the multiplicity of switchable DOEs in accordance with the accommodative state of the eye. For example, if the estimated accommodative state of the eye suggests that the viewer is focused at a 1 meter viewing distance, the multiplicity of DOEs is switched to shift the displayed image to approximate at 1 meter focus distance. If the eye's accommodative state is estimated to have shifted to focus at, e.g., a 2 meter viewing distance, the multiplicity of DOEs 2 is switched to shift the displayed image to approximate at 2 meter focus distance.

In at least some implementations, the multiplicity of switchable DOEs 2 is switched at a slow rate to position a single image plane at a focal distance. The accommodation state of the eye is measured and/or estimated either directly or indirectly. The focal distance of the single image plane is modulated by the multiplicity of switchable DOEs in accordance with the accommodative state of the eye, and the image data presented by the multiplicity of display elements is switched synchronously.

For example, if the estimated accommodative state of the eye suggests that the viewer is focused at a 1 meter viewing distance, the multiplicity of DOEs 2 is switched to shift the displayed image to approximate at 1 meter focus distance, and the image data is updated to render the virtual objects at a virtual distance of 1 meter in sharp focus and to render virtual objects at a virtual distance other than 1 meter with some degree of blur, with greater blur for objects farther from the 1 meter plane.

If the eye's accommodative state is estimated to have shifted to focus at, e.g., a 2 meter viewing distance, the multiplicity of DOEs is switched to shift the displayed image to approximate at 2 meter focus distance and the image data is updated to render the virtual objects at a virtual distance of 2 meters in sharp focus and to render virtual objects at a virtual distance other than 2 meters with some degree of blur, with greater blur for objects farther from the 2 meter plane.

In at least some implementations, the DOEs 2 may be used to bias rays outwardly to create a large field of view, at least up to a limit at which light leaks from the planar waveguide(s) 1. For example, varying a pitch of a grating may achieve a desired change in angle sufficient to modify the angles associated with or indicative of a field of view. In some implements, pitch may be tuned to achieve a lateral or side-to-side movement or scanning motion along at least one lateral (e.g., Y-axis). Such may be done in two dimensions to achieve a lateral or side-to-side movement or scanning motion along both the Y-axis and X-axis. One or more acousto-optic modulators may be employed, changing frequency, period, or angle of deflection.

Various standing surface wave techniques (e.g., standing plane wave field) may be employed, for example to dynamically adjust the characteristics of the DOEs 2. For instance standing waves may be generated in a liquid crystal medium trapped between two layers, creating an interference pattern with desired frequency, wavelength and/or amplitude characteristics.

The DOEs 2 may be arranged to create a toe in effect, creating an eye box that tapers from larger to smaller as the light approaches the viewer from the planar waveguide 1. The light box may taper in one or two dimensions (e.g., Y-axis, X-axis, as function of position along the Z-axis). Concentrating light may advantageously reduce luminosity requires or increase brightness. The light box should still be maintain sufficiently large to accommodate expected eye movement.

While various embodiments have located the DOEs 2 in or on the primary planar waveguide 1, other implementations may located one or more DOEs 2 spaced from the primary planar waveguide 1. For example, a first set of DOEs 2 may be positioned between the primary planar waveguide 1 and the viewer, spaced from the primary planar waveguide 1. Additionally, a second set of DOEs 2 may be positioned between the primary planar waveguide 1 and background or real world, spaced from the primary planar waveguide 1. Such may be used to cancel light from the planar waveguides with respect to light from the background or real world, in some respects similar to noise canceling headphones.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. patent application Ser. No. 13/915,530, International Patent Application Serial No. PCT/US2013/045267, and U.S. provisional patent application Ser. No. 61/658,355, are incorporated herein by reference, in their entirety. Aspects of the embodiments can be modified, if necessary, to employ systems, circuits and concepts of the various patents, applications and publications to provide yet further embodiments.

System Components

The DOEs described above may be incorporated into an augmented reality (AR) system. The DOE elements or volumetric 3D displays allow for the creation of multiple focal planes based on which numerous virtual reality or augmented virtual reality applications may be realized. Methods and systems of the overall AR system will be described. Various applications of the AR system will also be described further below. It should be appreciated that the systems below may use the volumetric 3D displays in their optical components, or any other suitable optical components (e.g., birdbath optics, free form optics, etc.) may be similarly used. The AR system may be a stationary system or a portable system that may have a body or head worn component. For illustrative purposes, the following discussion will focus on portable AR systems, but it should be appreciated that stationary systems may also be used.

Figure 14:
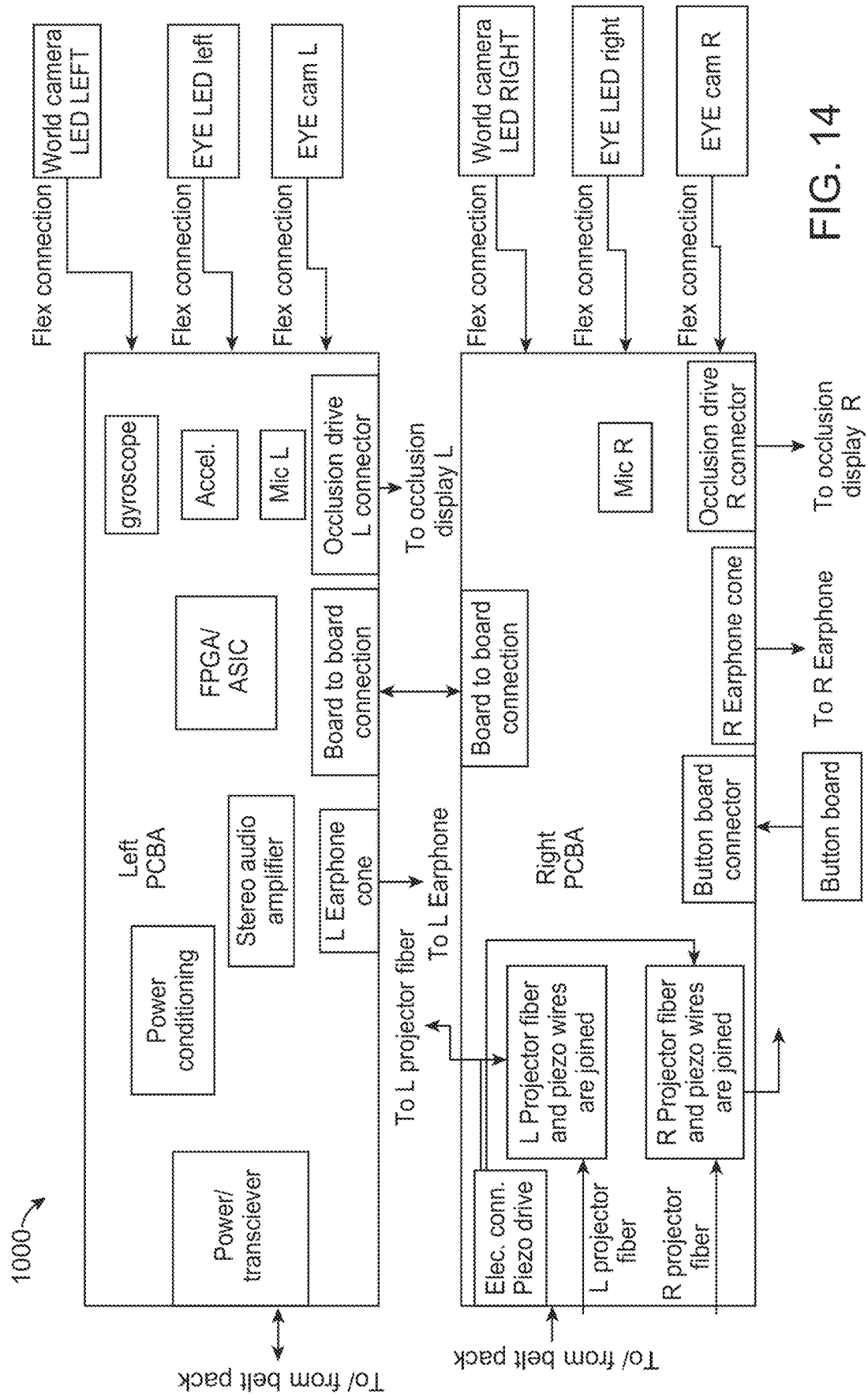
FIG. 14 illustrates an internal circuitry of an exemplary AR system, according to one illustrated embodiment.

FIG. 14 shows an architecture 1000 for the electronics for a body or head worn component, according to one illustrated embodiment. It should be appreciated that the following system architecture may be used for optical elements apart from volumetric 3D displays.

The body or head worn component may include one or more printed circuit board components, for instance left and right printed circuit board assemblies (PCBA). As illustrated, the left PCBA includes most of the active electronics, while the right PCBA supports principally supports the display or projector elements.

The right PCBAs may include a number of projector driver structures which provide image information and control signals to image generation components. For example, the right PCBA may carry a first or left projector driver structure and a second or right projector driver structure. The first or left projector driver structure join a first or left projector fiber and a set of signal lines (e.g., piezo driver wires).

The second or right projector driver structure join a second or right projector fiber and a set of signal lines (e.g., piezo driver wires). The first or left projector driver structure is communicatively coupled to a first or left image projector, while the second or right projector drive structure is communicatively coupled to the second or right image projector.

In operation, the image projectors render virtual content to the left and right eyes (e.g., retina) of the user via respective optical components (e.g., the volumetric 3D display described above, for example), for instance waveguides and/or compensation lenses. The image projectors may, for example, include left and right projector assemblies. The projector assemblies may use a variety of different image forming or production technologies, for example, fiber scan projectors, liquid crystal displays (LCD), digital light processing (DLP) displays.

Where a fiber scan projector is employed, images may be delivered along an optical fiber, to be projected therefrom via a tip of the optical fiber (e.g., as shown in FIG. 1). The tip may be oriented to feed into the waveguide. An end of the optical fiber with the tip from which images project may be supported to flex or oscillate. A number of piezoelectric actuators may control an oscillation (e.g, frequency, amplitude) of the tip. The projector driver structures provide images to respective optical fiber and control signals to control the piezoelectric actuators, to project images to the user's eyes.

Continuing with the right PCBA, a button board connector may provide communicative and physical coupling a button board which carries various user accessible buttons, keys, switches or other input devices. The right PCBA may include a right earphone or speaker connector, to communicatively couple audio signals to a right earphone or speaker of the head worn component. The right PCBA may also include a right microphone connector to communicatively couple audio signals from a microphone of the head worn component. The right PCBA may further include a right occlusion driver connector to communicatively couple occlusion information to a right occlusion display of the head worn component. The right PCBA may also include a board-to-board connector to provide communications with the left PCBA via a board-to-board connector thereof.

The right PCBA may be communicatively coupled to one or more right outward facing or world view cameras which are body or head worn, and optionally a right cameras visual indicator (e.g., LED) which illuminates to indicate to others when images are being captured. The right PCBA may be communicatively coupled to one or more right eye cameras, carried by the head worn component, positioned and orientated to capture images of the right eye to allow tracking, detection, or monitoring of orientation and/or movement of the right eye. The right PCBA may optionally be communicatively coupled to one or more right eye illuminating sources (e.g., LEDs), which as explained herein, illuminates the right eye with a pattern (e.g., temporal, spatial) of illumination to facilitate tracking, detection or monitoring of orientation and/or movement of the right eye.

The left PCBA may include a control subsystem, which may include one or more controllers (e.g., microcontroller, microprocessor, digital signal processor, graphical processing unit, central processing unit, application specific integrated circuit (ASIC), field programmable gate array (FPGA), and/or programmable logic unit (PLU)). The control system may include one or more non-transitory computer- or processor readable medium that stores executable logic or instructions and/or data or information. The non-transitory computer- or processor readable medium may take a variety of forms, for example volatile and nonvolatile forms, for instance read only memory (ROM), random access memory (RAM, DRAM, SD-RAM), flash memory, etc. The non-transitory computer- or processor readable medium may be formed as one or more registers, for example of a microprocessor, FPGA or ASIC.

The left PCBA may include a left earphone or speaker connector, to communicatively couple audio signals to a left earphone or speaker of the head worn component. The left PCBA may include an audio signal amplifier (e.g., stereo amplifier), which is communicative coupled to the drive earphones or speakers The left PCBA may also include a left microphone connector to communicatively couple audio signals from a microphone of the head worn component. The left PCBA may further include a left occlusion driver connector to communicatively couple occlusion information to a left occlusion display of the head worn component.

The left PCBA may also include one or more sensors or transducers which detect, measure, capture or otherwise sense information about an ambient environment and/or about the user. For example, an acceleration transducer (e.g., three axis accelerometer) may detect acceleration in three axis, thereby detecting movement. A gyroscopic sensor may detect orientation and/or magnetic or compass heading or orientation. Other sensors or transducers may be employed, The left PCBA may be communicatively coupled to one or more left outward facing or world view cameras which are body or head worn, and optionally a left cameras visual indicator (e.g., LED) which illuminates to indicate to others when images are being captured. The left PCBA may be communicatively coupled to one or more left eye cameras, carried by the head worn component, positioned and orientated to capture images of the left eye to allow tracking, detection, or monitoring of orientation and/or movement of the left eye. The left PCBA may optionally be communicatively coupled to one or more left eye illuminating sources (e.g., LEDs), which as explained herein, illuminates the left eye with a pattern (e.g., temporal, spatial) of illumination to facilitate tracking, detection or monitoring of orientation and/or movement of the left eye.

The PCBAs are communicatively coupled with the distinct computation component (e.g., belt pack) via one or more ports, connectors and/or paths. For example, the left PCBA may include one or more communications ports or connectors to provide communications (e.g., bi-directional communications) with the belt pack. The one or more communications ports or connectors may also provide power from the belt pack to the left PCBA The left PCBA may include power conditioning circuitry (e.g., DC/DC power converter, input filter), electrically coupled to the communications port or connector and operable to condition (e.g., step up voltage, step down voltage, smooth current, reduce transients).

The communications port or connector may, for example, take the form of a data and power connector or transceiver (e.g., Thunderbolt® port, USB® port). The right PCBA may include a port or connector to receive power from the belt pack. The image generation elements may receive power from a portable power source (e.g., chemical battery cells, primary or secondary battery cells, ultra-capacitor cells, fuel cells), which may, for example be located in the belt pack.

As illustrated, the left PCBA includes most of the active electronics, while the right PCBA supports principally supports the display or projectors, and the associated piezo drive signals. Electrical and/or fiber optic connections are employed across a front, rear or top of the body or head worn component.

Both PCBAs may be communicatively (e.g., electrically, optically) coupled to a belt pack. It should be appreciated that other embodiments of the AR system may not include a belt back, and the associated circuitry of the belt pack may simply be incorporated in a compact form into the electronics of the head worn component of the AR system.

The left PCBA includes the power subsystem and a high speed communications subsystem. The right PCBA handles the fiber display piezo drive signals. In the illustrated embodiment, only the right PCBA needs to be optically connected to the belt pack.

While illustrated as employing two PCBAs, the electronics of the body or head worn component may employ other architectures. For example, some implementations may use a fewer or greater number of PCBAs. Also for example, various components or subsystems may be arranged differently than illustrated in FIG. 14. For example, in some alternative embodiments some of the components illustrated in FIG. 14 as residing on one PCBA, may be located on the other PCBA, without loss of generality.

As illustrated, each individual may use their own respective AR system. In some implementations, the respective AR systems may communicate between one another. For example, two or more proximately located AR systems may communicate between one another. As described further herein, communications may occur after performance of a handshaking protocol. The AR systems may communicate wirelessly via one or more radios. As discussed above, such radios may be capable of short range direct communications, or may be capable of longer range direct communications (i.e., without a repeater, extender, etc.). Additionally or alternatively, indirect longer range communications may be achieved via one or more intermediary devices (e.g., wireless access points, repeaters, extenders).

The head-worn component, some of whose components, including circuitry, have been described above, has many components, including optical components, camera systems etc. that enable a user of the system to enjoy 3D vision.

Figure 15:
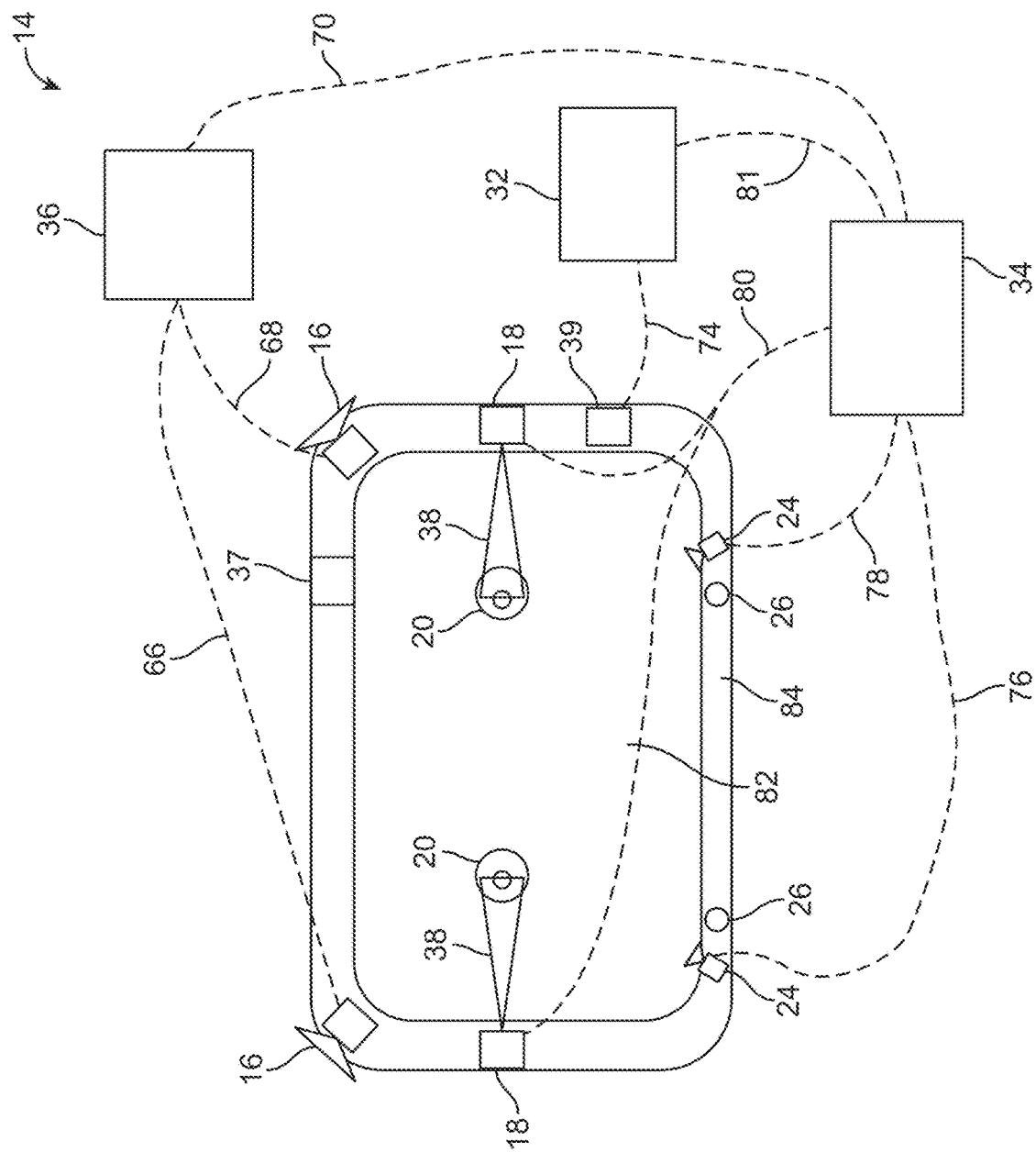
FIG. 15 illustrates hardware components of a head mounted AR system, according to one illustrated embodiment.

Referring to FIG. 15, one embodiment of the head-worn AR system has a suitable user display device (14) as shown in FIG. 15. The user display device may comprise a display lens (82) which may be mounted to a user's head or eyes by a housing or frame (84). The display lens (82) may comprise one or more transparent mirrors positioned by the housing (84) in front of the user's eyes (20) and configured to bounce projected light (38) into the eyes (20) and facilitate beam shaping, while also allowing for transmission of at least some light from the local environment in an augmented reality configuration (in a virtual reality configuration, it may be desirable for the display system to be capable of blocking substantially all light from the local environment, such as by a darkened visor, blocking curtain, all black LCD panel mode, or the like).

It should be appreciated that various optical systems may be used as a suitable display lens. In one embodiment, the volumetric 3D display, discussed above, may be used as the display lens in this exemplary system.

In the depicted embodiment, two wide-field-of-view machine vision cameras (16) are coupled to the housing (84) to image the environment around the user; in one embodiment these cameras (16) are dual capture visible light/infrared light cameras. The depicted embodiment also comprises a pair of scanned-laser shaped-wavefront (i.e., for depth) light projector modules with display mirrors and optics configured to project light (38) into the eyes (20) as shown. The depicted embodiment also comprises two miniature infrared cameras (24) paired with infrared light sources (26, such as light emitting diodes "LED"s), which are configured to be able to track the eyes (20) of the user to support rendering and user input.

The system (14) further features a sensor assembly (39), which may comprise X, Y, and Z axis accelerometer capability as well as a magnetic compass and X, Y, and Z axis gyro capability, preferably providing data at a relatively high frequency, such as 200 Hz. The depicted system (14) also comprises a head pose processor (36), such as an ASIC (application specific integrated circuit), FPGA (field programmable gate array), and/or ARM processor (advanced reduced-instruction-set machine), which may be configured to calculate real or near-real time user head pose from wide field of view image information output from the capture devices (16). Also shown is another processor (32) configured to execute digital and/or analog processing to derive pose from the gyro, compass, and/or accelerometer data from the sensor assembly (39).

The depicted embodiment also features a GPS (37, global positioning satellite) subsystem to assist with pose and positioning. Finally, the depicted embodiment comprises a rendering engine (34) which may feature hardware running a software program configured to provide rendering information local to the user to facilitate operation of the scanners and imaging into the eyes of the user, for the user's view of the world. The rendering engine (34) is operatively coupled (81, 70, 76/78, 80; i.e., via wired or wireless connectivity) to the sensor pose processor (32), the image pose processor (36), the eye tracking cameras (24), and the projecting subsystem (18) such that light of rendered augmented and/or virtual reality objects is projected using a scanned laser arrangement (18) in a manner similar to a retinal scanning display. The wavefront of the projected light beam (38) may be bent or focused to coincide with a desired focal distance of the augmented and/or virtual reality object.

The mini infrared cameras (24) may be utilized to track the eyes to support rendering and user input (i.e., where the user is looking, what depth he is focusing; as discussed below, eye verge may be utilized to estimate depth of focus). The GPS (37), gyros, compass, and accelerometers (39) may be utilized to provide course and/or fast pose estimates. The camera (16) images and pose, in conjunction with data from an associated cloud computing resource, may be utilized to map the local world and share user views with a virtual or augmented reality community. While much of the hardware in the display system (14) featured in FIG. 14 is depicted directly coupled to the housing (84) which is adjacent the display (82) and eyes (20) of the user, the hardware components depicted may be mounted to or housed within other components, such as a belt-mounted component, as discussed above.

In one embodiment, all of the components of the system (14) featured in FIG. 15 are directly coupled to the display housing (84) except for the image pose processor (36), sensor pose processor (32), and rendering engine (34), and communication between the latter three and the remaining components of the system (14) may be by wireless communication, such as ultra wideband, or wired communication. The depicted housing (84) preferably is head-mounted and wearable by the user. It may also feature speakers, such as those which may be inserted into the ears of a user and utilized to provide sound to the user which may be pertinent to an augmented or virtual reality experience, and microphones, which may be utilized to capture sounds local to the user.

Regarding the projection of light (38) into the eyes (20) of the user, in one optional embodiment the mini cameras (24) may be utilized to measure where the centers of a user's eyes (20) are geometrically verged to, which, in general, coincides with a position of focus, or "depth of focus", of the eyes (20). A 3-dimensional surface of all points the eyes verge to is called the "horopter". The focal distance may take on a finite number of depths, or may be infinitely varying. Light projected from the vergence distance appears to be focused to the subject eye (20), while light in front of or behind the vergence distance is blurred.

Further, it has been discovered that spatially coherent light with a beam diameter of less than about 0.7 millimeters is correctly resolved by the human eye regardless of where the eye focuses; given this understanding, to create an illusion of proper focal depth, the eye vergence may be tracked with the mini cameras (24), and the rendering engine (34) and projection subsystem (18) may be utilized to render all objects on or close to the horopter in focus, and all other objects at varying degrees of defocus (i.e., using intentionally-created blurring). A see-through light guide optical element configured to project coherent light into the eye may be provided by suppliers such as Lumus, Inc.

Preferably the system renders to the user at a frame rate of about 60 frames per second or greater. As described above, preferably the mini cameras (24) may be utilized for eye tracking, and software may be configured to pick up not only vergence geometry but also focus location cues to serve as user inputs. Preferably such system is configured with brightness and contrast suitable for day or night use. In one embodiment such system preferably has latency of less than about 20 milliseconds for visual object alignment, less than about 0.1 degree of angular alignment, and about 1 arc minute of resolution, which is approximately the limit of the human eye. The display system (14) may be integrated with a localization system, which may involve the GPS element, optical tracking, compass, accelerometer, and/or other data sources, to assist with position and pose determination; localization information may be utilized to facilitate accurate rendering in the user's view of the pertinent world (i.e., such information would facilitate the glasses to know where they are with respect to the real world).

Other suitable display device include but are not limited to desktop and mobile computers, smartphones, smartphones which may be enhanced additional with software and hardware features to facilitate or simulate 3-D perspective viewing (for example, in one embodiment a frame may be removably coupled to a smartphone, the frame featuring a 200 Hz gyro and accelerometer sensor subset, two small machine vision cameras with wide field of view lenses, and an ARM processor—to simulate some of the functionality of the configuration featured in FIG. 15), tablet computers, tablet computers which may be enhanced as described above for smartphones, tablet computers enhanced with additional processing and sensing hardware, head-mounted systems that use smartphones and/or tablets to display augmented and virtual viewpoints (visual accommodation via magnifying optics, mirrors, contact lenses, or light structuring elements), non-see-through displays of light emitting elements (LCDs, OLEDs, vertical-cavity-surface-emitting lasers, steered laser beams, etc.), see-through displays that simultaneously allow humans to see the natural world and artificially generated images (for example, light-guide optical elements, transparent and polarized OLEDs shining into close-focus contact lenses, steered laser beams, etc.), contact lenses with light-emitting elements (such as those available from Innovega, Inc., of Bellevue, Wash., under the tradename Loptik®; they may be combined with specialized complimentary eyeglasses components), implantable devices with light-emitting elements, and implantable devices that stimulate the optical receptors of the human brain.

Now that the circuitry and the basic components of the AR system, and specifically the user display portion of the system has been described, various physical forms of the head worn component of the AR system will be described briefly.

Figure 16:
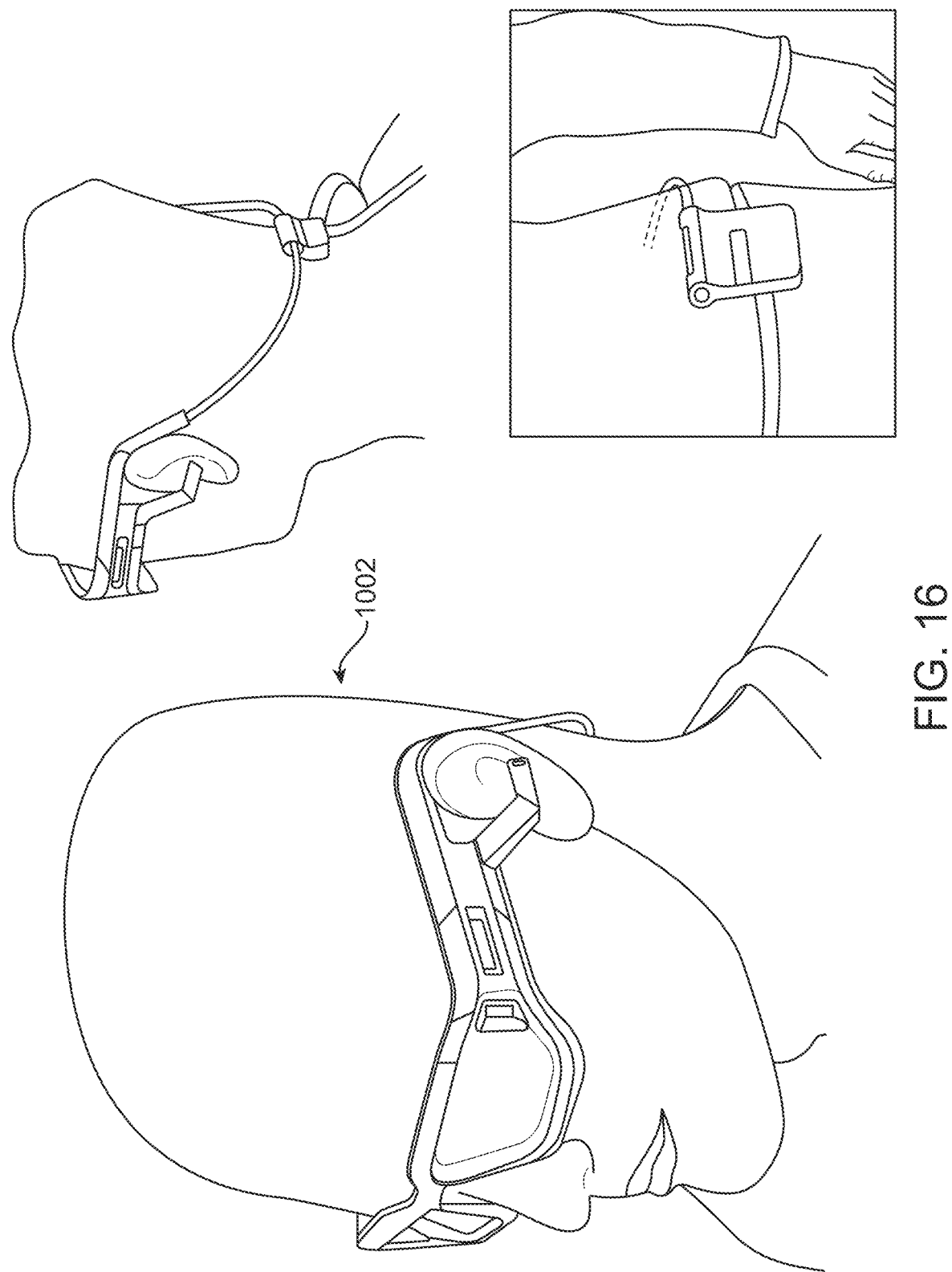
FIG. 16 illustrates an exemplary physical form of the head mounted AR system of FIG. 15.

Referring now to FIG. 16, an exemplary embodiment of a physical form of the head worn component of the AR system will be briefly described in relation to the overall AR system. As shown in FIG. 16, the head worn component comprises optics coupled with a user display system that allows the user to view virtual or augmented reality content. The light associated with the virtual content, when projected to the user display system of the head worn component, may appear to be coming from various focal depths, giving the user a sense of 3D perception.

It should be appreciated, as will be described in further detail below, that the head worn component of the AR system or the belt pack of the AR system, also shown in FIG. 16, are connectively coupled to one or more networks such that the AR system is constantly retrieving and uploading information to the cloud. For example, the virtual content being projected to the user through the display system may be associated with virtual content downloaded from the cloud. Or, in other embodiment, images captured through the user's FOV cameras may be processed and uploaded to the cloud, such that another user may be able to experience the physical surroundings of the first user, as if the other user were physically present along with the first user. More user scenarios such as the above will be described further below.

As shown in FIG. 16, the head worn component 1002 may simply resemble a pair of reading glasses or goggles, or in other embodiments, may take the form of a helmet display, or any other form factor. The belt pack is typically communicatively coupled to one or both sides of the head worn component, as explained above.

Cloud Servers

Figure 17:
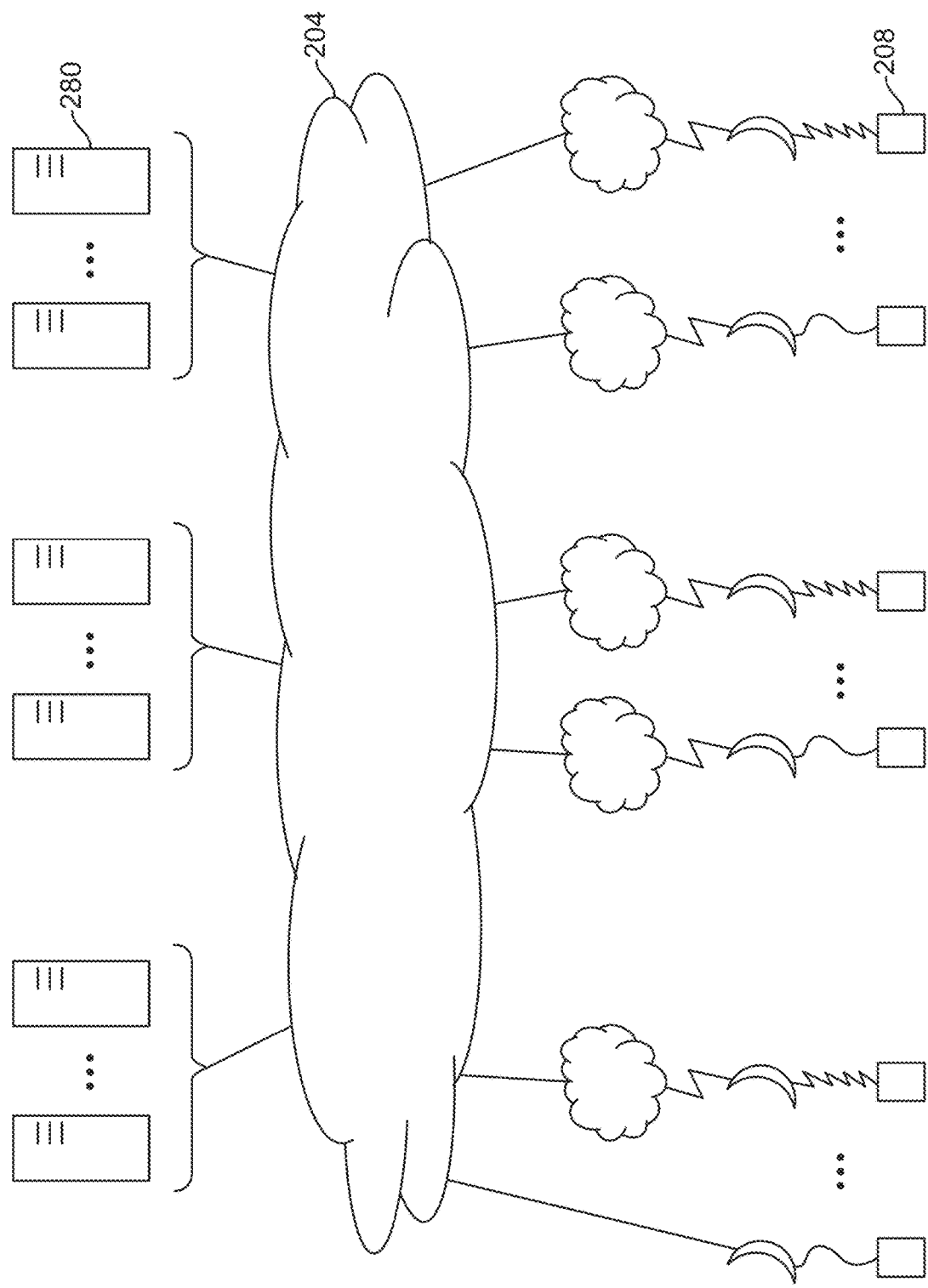
FIG. 17 illustrates multiple user devices connected to each other through a cloud server of the AR system.

FIG. 17 illustrates a communications architecture which employs one or more hub, central, or distributed, server computer systems 280 and one or more individual AR systems 208 communicatively coupled by one or more wired or wireless networks 204, according to one illustrated embodiment.

The server computer systems 280 may, for example, be clustered. For instance, clusters of server computer systems may be located at various geographically dispersed locations. Such may facilitate communications, shortening transit paths and/or provide for redundancy.

Specific instances of personal AR systems 208 may be communicatively coupled to the server computer system(s). The server computer system(s) may maintain information about a specific user's own physical and/or virtual worlds. The server computer system(s) 280 may allow a given user to share information about the specific user's own physical and/or virtual worlds with other users. Additionally or alternatively, the server computer system(s) 280 may allow other users to share information about their own physical and/or virtual worlds with the given or specific user. As described herein, server computer system(s) 280 may allow mapping and/or characterizations of large portions of the physical worlds.

Information may be collected via the personal AR system of one or more users. The models of the physical world may be developed over time, and by collection via a large number of users. This may allow a given user to enter a new portion or location of the physical world, yet benefit by information collected by others who either previously or are currently in the particular location. Models of virtual worlds may be created over time via user by a respective user.

The personal AR system(s) 208 may be communicatively coupled to the server computer system(s). For example, the personal AR system(s) may be wirelessly communicatively coupled to the server computer system(s) via one or more radios. The radios may take the form of short range radios, as discussed above, or relatively long range radios, for example cellular chip sets and antennas. The personal AR system(s) will typically be communicatively coupled to the server computer system(s) indirectly, via some intermediary communications network or component. For instance, the personal AR system(s) will typically be communicatively coupled to the server computer system(s) 280 via one or more telecommunications provider systems, for example one or more cellular communications provider networks.

Other Components

In many implementations, the AR system may include other components. The AR system or Sensorywear™ augmented reality devices may, for example, include one or more haptic devices or components. The haptic device(s) or component(s) may be operable to provide a tactile sensation to a user. For example, the haptic device(s) or component(s) may provide a tactile sensation of pressure and/or texture when touching virtual content (e.g., virtual objects, virtual tools, other virtual constructs). The tactile sensation may replicate a feel of a physical object which a virtual object represents, or may replicate a feel of an imagined object or character (e.g., a dragon) which the virtual content represents.

In some implementations, haptic devices or components may be worn by the user. An example of a haptic device in the form of a user wearable glove is described herein. In some implementations, haptic devices or components may be held the user. An example of a haptic device in the form of a user wearable glove and as is described herein. Other examples of haptic devices in the form of various haptic totems are described herein. The AR system may additionally or alternatively employ other types of haptic devices or components.

The AR system may, for example, include one or more physical objects which are manipulable by the user to allow input or interaction with the AR system. These physical objects are referred to herein as totems. Some totems may take the form of inanimate objects, for example a piece of metal or plastic, a wall, a surface of table. Alternatively, some totems may take the form of animate objects, for example a hand of the user. As described herein, the totems may not actually have any physical input structures (e.g., keys, triggers, joystick, trackball, rocker switch).

Instead, the totem may simply provide a physical surface, and the AR system may render a user interface so as to appear to a user to be on one or more surfaces of the totem. For example, and as discussed in more detail further herein, the AR system may render an image of a computer keyboard and trackpad to appear to reside on one or more surfaces of a totem. For instance, the AR system may render a virtual computer keyboard and virtual trackpad to appear on a surface of a thin rectangular plate of aluminum which serves as a totem. The rectangular plate does not itself have any physical keys or trackpad or sensors. However, the AR system may detect user manipulation or interaction or touches with the rectangular plate as selections or inputs made via the virtual keyboard and/or virtual trackpad. Many of these components are described in detail elsewhere herein.

Capturing 3D Points and Creating Passable Worlds

With a system such as that depicted in FIG. 17 and other figures above, 3-D points may be captured from the environment, and the pose (i.e., vector and/or origin position information relative to the world) of the cameras that capture those images or points may be determined, so that these points or images may be "tagged", or associated, with this pose information. Then points captured by a second camera may be utilized to determine the pose of the second camera. In other words, one can orient and/or localize a second camera based upon comparisons with tagged images from a first camera.

Then this knowledge may be utilized to extract textures, make maps, and create a virtual copy of the real world (because then there are two cameras around that are registered). So at the base level, in one embodiment you have a person-worn system that can be utilized to capture both 3-D points and the 2-D images that produced the points, and these points and images may be sent out to a cloud storage and processing resource. They may also be cached locally with embedded pose information (i.e., cache the tagged images); so the cloud may have on the ready (i.e., in available cache) tagged 2-D images (i.e., tagged with a 3-D pose), along with 3-D points. If a user is observing something dynamic, he may also send additional information up to the cloud pertinent to the motion (for example, if looking at another person's face, the user can take a texture map of the face and push that up at an optimized frequency even though the surrounding world is otherwise basically static).

The cloud system may be configured to save some points as fiducials for pose only, to reduce overall pose tracking calculation. Generally it may be desirable to have some outline features to be able to track major items in a user's environment, such as walls, a table, etc., as the user moves around the room, and the user may want to be able to "share" the world and have some other user walk into that room and also see those points. Such useful and key points may be termed "fiducials" because they are fairly useful as anchoring points—they are related to features that may be recognized with machine vision, and that can be extracted from the world consistently and repeatedly on different pieces of user hardware. Thus these fiducials preferably may be saved to the cloud for further use.

In one embodiment it is preferable to have a relatively even distribution of fiducials throughout the pertinent world, because they are the kinds of items that cameras can easily use to recognize a location.

In one embodiment, the pertinent cloud computing configuration may be configured to groom the database of 3-D points and any associated meta data periodically to use the best data from various users for both fiducial refinement and world creation. In other words, the system may be configured to get the best dataset by using inputs from various users looking and functioning within the pertinent world. In one embodiment the database is intrinsically fractal—as users move closer to objects, the cloud passes higher resolution information to such users. As a user maps an object more closely, that data is sent to the cloud, and the cloud can add new 3-D points and image-based texture maps to the database if they are better than what has been previously stored in the database. All of this may be configured to happen from many users simultaneously.

As described above, an augmented or virtual reality experience may be based upon recognizing certain types of objects. For example, it may be important to understand that a particular object has a depth in order to recognize and understand such object. Recognizer software objects ("recognizers") may be deployed on cloud or local resources to specifically assist with recognition of various objects on either or both platforms as a user is navigating data in a world. For example, if a system has data for a world model comprising 3-D point clouds and pose-tagged images, and there is a desk with a bunch of points on it as well as an image of the desk, there may not be a determination that what is being observed is, indeed, a desk as humans would know it. In other words, some 3-D points in space and an image from someplace off in space that shows most of the desk may not be enough to instantly recognize that a desk is being observed.

To assist with this identification, a specific object recognizer may be created that will go into the raw 3-D point cloud, segment out a set of points, and, for example, extract the plane of the top surface of the desk. Similarly, a recognizer may be created to segment out a wall from 3-D points, so that a user could change wallpaper or remove part of the wall in virtual or augmented reality and have a portal to another room that is not actually there in the real world. Such recognizers operate within the data of a world model and may be thought of as software "robots" that crawl a world model and imbue that world model with semantic information, or an ontology about what is believed to exist amongst the points in space. Such recognizers or software robots may be configured such that their entire existence is about going around the pertinent world of data and finding things that it believes are walls, or chairs, or other items. They may be configured to tag a set of points with the functional equivalent of, "this set of points belongs to a wall", and may comprise a combination of point-based algorithm and pose-tagged image analysis for mutually informing the system regarding what is in the points.

Object recognizers may be created for many purposes of varied utility, depending upon the perspective. For example, in one embodiment, a purveyor of coffee such as Starbucks may invest in creating an accurate recognizer of Starbucks coffee cups within pertinent worlds of data. Such a recognizer may be configured to crawl worlds of data large and small searching for Starbucks coffee cups, so they may be segmented out and identified to a user when operating in the pertinent nearby space (i.e., perhaps to offer the user a coffee in the Starbucks outlet right around the corner when the user looks at his Starbucks cup for a certain period of time).

With the cup segmented out, it may be recognized quickly when the user moves it on his desk. Such recognizers may be configured to run or operate not only on cloud computing resources and data, but also on local resources and data, or both cloud and local, depending upon computational resources available. In one embodiment, there is a global copy of the world model on the cloud with millions of users contributing to that global model, but for smaller worlds or sub-worlds like an office of a particular individual in a particular town, most of the global world will not care what that office looks like, so the system may be configured to groom data and move to local cache information that is believed to be most locally pertinent to a given user.

In one embodiment, for example, when a user walks up to a desk, related information (such as the segmentation of a particular cup on his table) may be configured to reside only upon his local computing resources and not on the cloud, because objects that are identified as ones that move often, such as cups on tables, need not burden the cloud model and transmission burden between the cloud and local resources.

Thus the cloud computing resource may be configured to segment 3-D points and images, thus factoring permanent (i.e., generally not moving) objects from movable ones, and this may affect where the associated data is to remain, where it is to be processed, remove processing burden from the wearable/local system for certain data that is pertinent to more permanent objects, allow one-time processing of a location which then may be shared with limitless other users, allow multiple sources of data to simultaneously build a database of fixed and movable objects in a particular physical location, and segment objects from the background to create object-specific fiducials and texture maps.

In one embodiment, the system may be configured to query a user for input about the identity of certain objects (for example, the system may present the user with a question such as, "is that a Starbucks coffee cup?"), so that the user may train the system and allow the system to associate semantic information with objects in the real world. An ontology may provide guidance regarding what objects segmented from the world can do, how they behave, etc. In one embodiment the system may feature a virtual or actual keypad, such as a wirelessly connected keypad, connectivity to a keypad of a smartphone, or the like, to facilitate certain user input to the system.

The system may be configured to share basic elements (walls, windows, desk geometry, etc.) with any user who walks into the room in virtual or augmented reality, and in one embodiment that person's system will be configured to take images from his particular perspective and upload those to the cloud. Then the cloud becomes populated with old and new sets of data and can run optimization routines and establish fiducials that exist on individual objects.

GPS and other localization information may be utilized as inputs to such processing. Further, other computing systems and data, such as one's online calendar or Facebook® account information, may be utilized as inputs (for example, in one embodiment, a cloud and/or local system may be configured to analyze the content of a user's calendar for airline tickets, dates, and destinations, so that over time, information may be moved from the cloud to the user's local systems to be ready for the user's arrival time in a given destination).

In one embodiment, tags such as QR codes and the like may be inserted into a world for use with non-statistical pose calculation, security/access control, communication of special information, spatial messaging, non-statistical object recognition, etc.

In one embodiment, cloud resources may be configured to pass digital models of real and virtual worlds between users, as described above in reference to "passable worlds", with the models being rendered by the individual users based upon parameters and textures. This reduces bandwidth relative to the passage of realtime video, allows rendering of virtual viewpoints of a scene, and allows millions or more users to participate in one virtual gathering without sending each of them data that they need to see (such as video), because their views are rendered by their local computing resources.

The virtual reality system ("VRS") may be configured to register the user location and field of view (together known as the "pose") through one or more of the following: realtime metric computer vision using the cameras, simultaneous localization and mapping techniques, maps, and data from sensors such as gyros, accelerometers, compass, barometer, GPS, radio signal strength triangulation, signal time of flight analysis, LIDAR ranging, RADAR ranging, odometry, and sonar ranging. The wearable device system may be configured to simultaneously map and orient. For example, in unknown environments, the VRS may be configured to collect information about the environment, ascertaining fiducial points suitable for user pose calculations, other points for world modeling, images for providing texture maps of the world. Fiducial points may be used to optically calculate pose.

As the world is mapped with greater detail, more objects may be segmented out and given their own texture maps, but the world still preferably is representable at low spatial resolution in simple polygons with low resolution texture maps. Other sensors, such as those discussed above, may be utilized to support this modeling effort. The world may be intrinsically fractal in that moving or otherwise seeking a better view (through viewpoints, "supervision" modes, zooming, etc.) request high-resolution information from the cloud resources. Moving closer to objects captures higher resolution data, and this may be sent to the cloud, which may calculate and/or insert the new data at interstitial sites in the world model.

Figure 18:
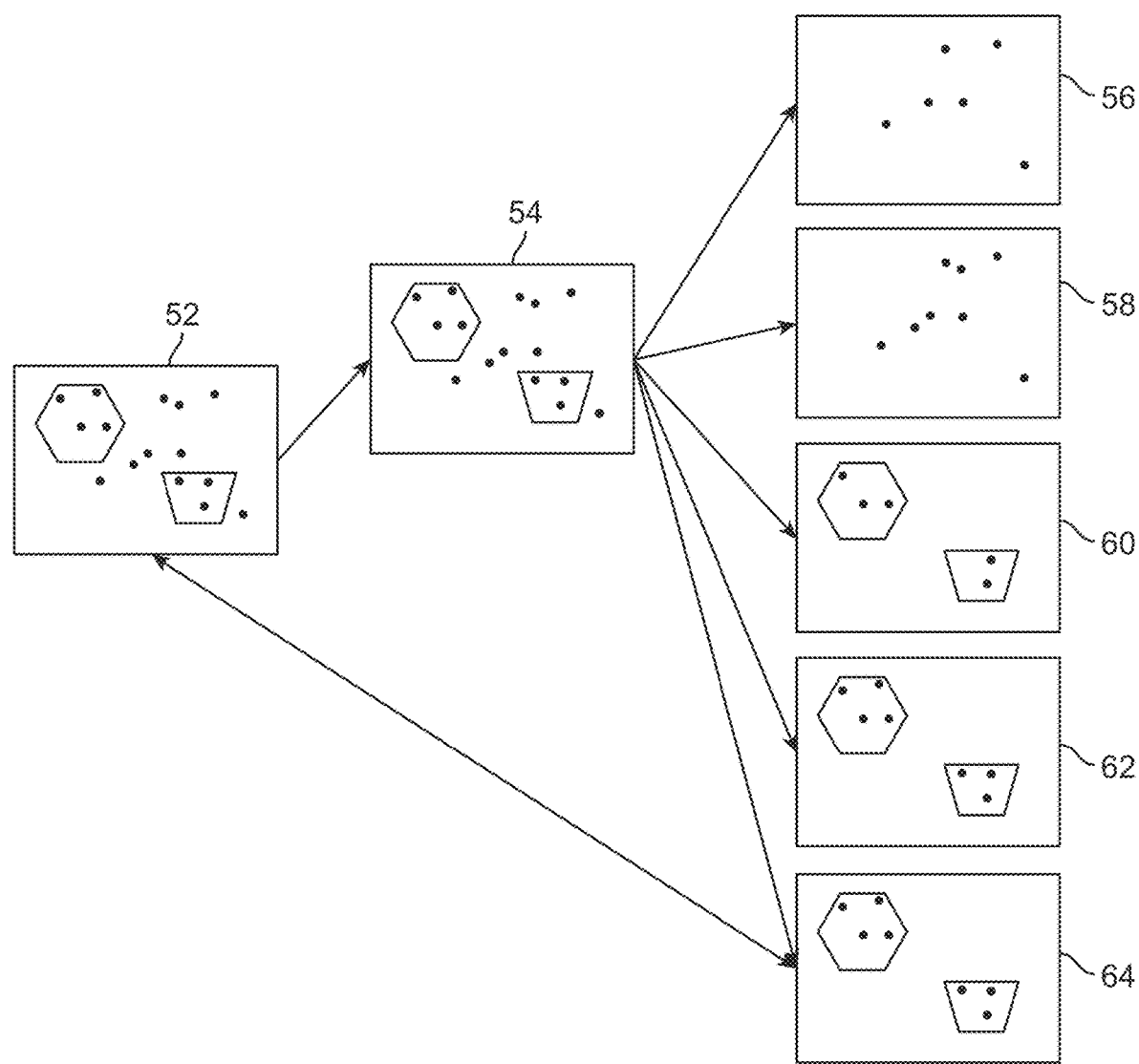
FIG. 18 illustrates capturing 2D and 3D points in an environment of the user, according to one illustrated embodiment.

Referring to FIG. 18, the wearable AR system may be configured to capture image information and extract fiducials and recognized points (52). The wearable local system may calculate pose using one of the pose calculation techniques discussed below. The cloud (54) may be configured to use images and fiducials to segment 3-D objects from more static 3-D background; images provide textures maps for objects and the world (textures may be realtime videos). The cloud resources (56) may be configured to store and make available static fiducials and textures for world registration. The cloud resources may be configured to groom the point cloud for optimal point density for registration.

The cloud resources (60) may store and make available object fiducials and textures for object registration and manipulation; the cloud may groom point clouds for optimal density for registration. The could resource may be configured (62) to use all valid points and textures to generate fractal solid models of objects; the cloud may groom point cloud information for optimal fiducial density. The cloud resource (64) may be configured to query users for training on identity of segmented objects and the world; an ontology database may use the answers to imbue objects and the world with actionable properties.

The passable world model essentially allows a user to effectively pass over a piece of the user's world (i.e., ambient surroundings, interactions, etc.) to another user. Each user's respective individual AR system (e.g., Sensorywear™ augmented reality devices) captures information as the user passes through or inhabits an environment, which the AR system processes to produce a passable world model. The individual AR system may communicate or pass the passable world model to a common or shared collection of data, referred to as the cloud. The individual AR system may communicate or pass the passable world model to other users, either directly or via the cloud. The passable world model provides the ability to efficiently communicate or pass information that essentially encompasses at least a field of view of a user. In one embodiment, the system uses the pose and orientation information, as well as collected 3D points described above in order to create the passable world.

Figure 19:
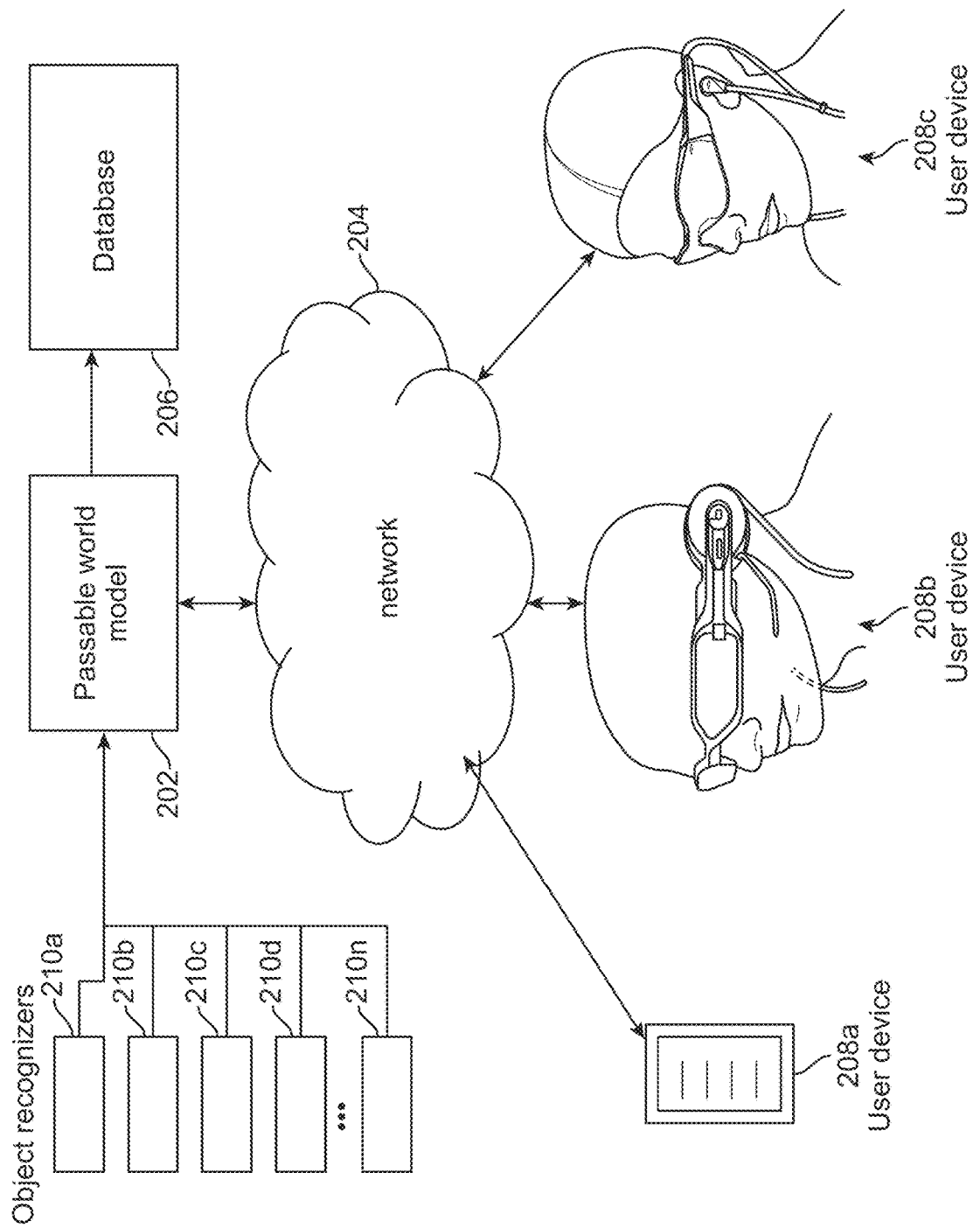
FIG. 19 illustrates an overall system view depicting multiple AR systems interacting with a passable world model, according to one illustrated embodiment.

Referring now to FIG. 19, similar to the system described in FIG. 17, the passable world system comprises one or more user AR systems or user devices 208 (e.g., 208*a*, 208*b*, 208*c*) that are able to connect to the cloud network 204, a passable world model 202, a set of object recognizers 210, and a database 206. The cloud server may be a LAN, a WAN or any other network.

As shown in FIG. 19, the passable world model is configured to receive information from the user devices 208 and also transmit data to them through the network. For example, based on the input from a user, a piece of the passable world may be passed on from one user to the other. The passable world model may be thought of collection of images, points and other information based on which the AR system is able to construct, update and build the virtual world on the cloud, and effectively pass pieces of the virtual world to various users.

For example, a set of points collects from user device 208 may be collected in the passable world model 202. Various object recognizers 210 may crawl through the passable world model 202 to recognize objects, tag images, etc., and attach semantic information to the objects, as will be described in further detail below. The passable world model 202 may use the database 206 to build its knowledge of the world, attach semantic information, and store data associated with the passable world.

Figure 20:
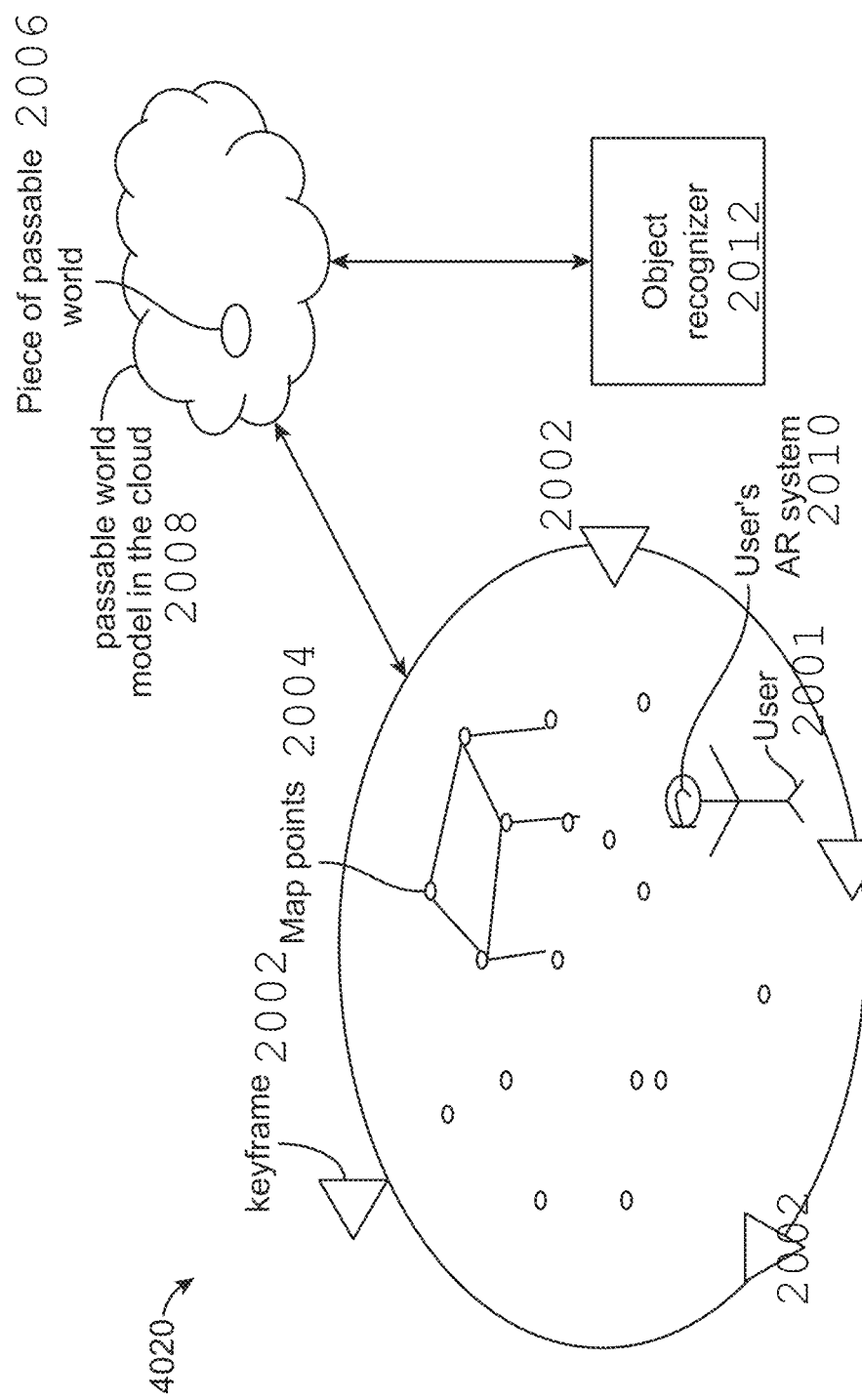
FIG. 20 is a schematic diagram showing multiple keyframes that capture and transmit data to the passable world model, according to one illustrated embodiment.

FIG. 20 illustrates aspects of a passable world model 4020 according to one illustrated embodiment. As a user walks through an environment, the user's individual AR system captures information (e.g., images) and saves the information posed tagged images, which form the core of the passable world model, as shown by multiple keyframes (cameras) that have captured information about the environment. The passable world model is a combination of raster imagery, point+descriptors clouds, and polygonal/geometric definitions (referred to herein as parametric geometry).

All this information is uploaded to and retrieved from the cloud, a section of which corresponds to this particular space that the user has walked into. As shown in FIG. 19, the passable world model also contains many object recognizers that work on the cloud (or on the user's individual system) to recognize objects in the environment based on points and pose-tagged images captured through the various keyframes of multiple users.

Asynchronous communications is established between the user's respective individual AR system and the cloud based computers (e.g., server computers). In other words, the user's individual AR system (e.g., user's sensorywear) is constantly updating information about the user's surroundings to the cloud, and also receiving information from the cloud about the passable world. Thus, rather than each user having to capture images, recognize objects of the images etc., having an asynchronous system allows the system to be more efficient. Information that already exists about that part of the world is automatically communicated to the individual AR system while new information is updated to the cloud. It should be appreciated that the passable world model lives both on the cloud or other form of networking computing or peer to peer system, and also may live on the user's individual system.

The AR system may employ different levels of resolutions for the local components (e.g., computational component such as belt pack) and remote components (e.g., cloud based computers) which are typically more computationally powerful than local components. The cloud based computers may pick data collected by the many different individual AR systems, and optionally from one or more space or room based sensor systems. The cloud based computers may aggregate only the best (i.e., most useful) information into a persistent world model.

Figure 21:
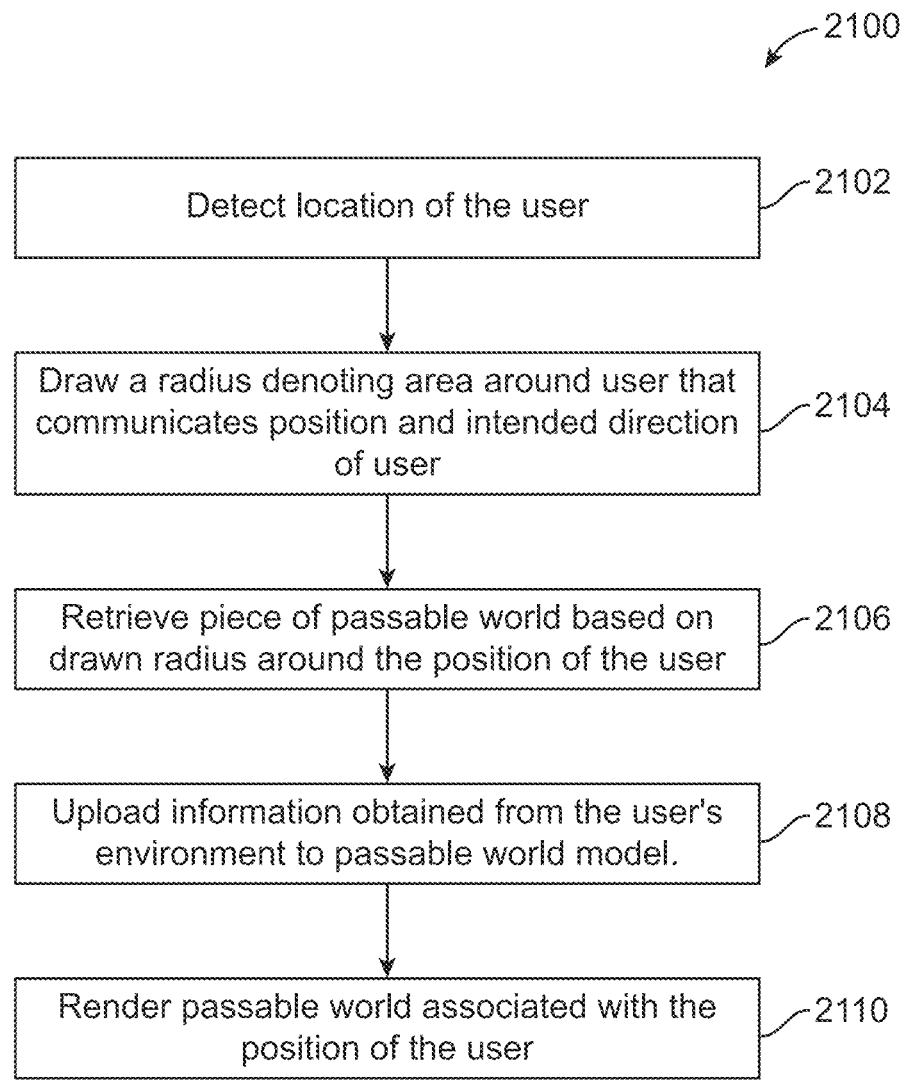
FIG. 21 is a process flow diagram illustrating an interaction between a user device and the passable world model, according to one illustrated embodiment.

FIG. 21 illustrates an exemplary method 2100 of interacting with the passable world model. First, the user's individual AR system may detect a location of the user (step 2102). The location may be derived by the topological map of the system, as will be described in further detail below. The location may be derived by GPS or any other localization tool. It should be appreciated that the passable world is constantly accessed by the individual system.

In another embodiment (not shown), the user may request access to another user's space, prompting the system to access the section of the passable world, and associated parametric information corresponding to the other user. Thus, there may be many triggers for the passable world. At the simplest level, however, it should be appreciated that the passable world is constantly being updated and accessed by multiple user systems, thereby constantly adding and receiving information from the cloud.

Following the above example, based on the known location of the user, the system may draw a radius denoting a physical area around the user that communicates both the position and intended direction of the user (step 2104). Next, the system may retrieve the piece of the passable world based on the anticipated position of the user (step 2106) Next, the system may upload information obtained from the user's environment to the passable world mode (step 2108) and render the passable world model associated with the position of the user (step 2110).

The piece of the passable world may contain information from the geometric map of the space acquired through previous keyframes and captured images and data that is stored in the cloud. Having this information enables virtual content to meaningfully interact with the user's real surroundings in a coherent manner. For example, the user may want to leave a virtual object for a friend in a real space such that the friend, when he/she enters the real space finds the virtual object. Thus, it is important for the system to constantly access the passable world to retrieve and upload information. It should be appreciated that the passable world contains a persistent digital representations of real spaces that is important in rendering virtual or digital content in relation to real coordinates of a physical space.

It should be appreciated that the passable world model does not itself render content that is displayed to the user. Rather it is a high level concept of dynamically retrieving and updating a persistent digital representation of the real world in the cloud. The derived geometric information is loaded onto a game engine, which actually does the rendering of the content associated with the passable world.

Thus, regardless of whether the user is in a particular space or not, that particular space has a digital representation in the cloud that can be accessed by any user. This piece of the passable world may contain information about the physical geometry of the space and imagery of the space, information about various avatars that are occupying the space, information about virtual objects and other miscellaneous information.

As described in detail further herein, object recognizers, examine or "crawl" the passable world models, tagging points that belong to parametric geometry. Parametric geometry and points+descriptors are packaged as passable world models, to allow low latency passing or communicating of information which defines a portion of a physical world or environment. The AR system can implement a two tier structure, in which the passable world model allow fast pose in a first tier, but then inside that framework a second tier (e.g., FAST® features) can increase resolution by performing a frame-to-frame based three-dimensional (3D) feature mapping, than tracking.

Figure 22:
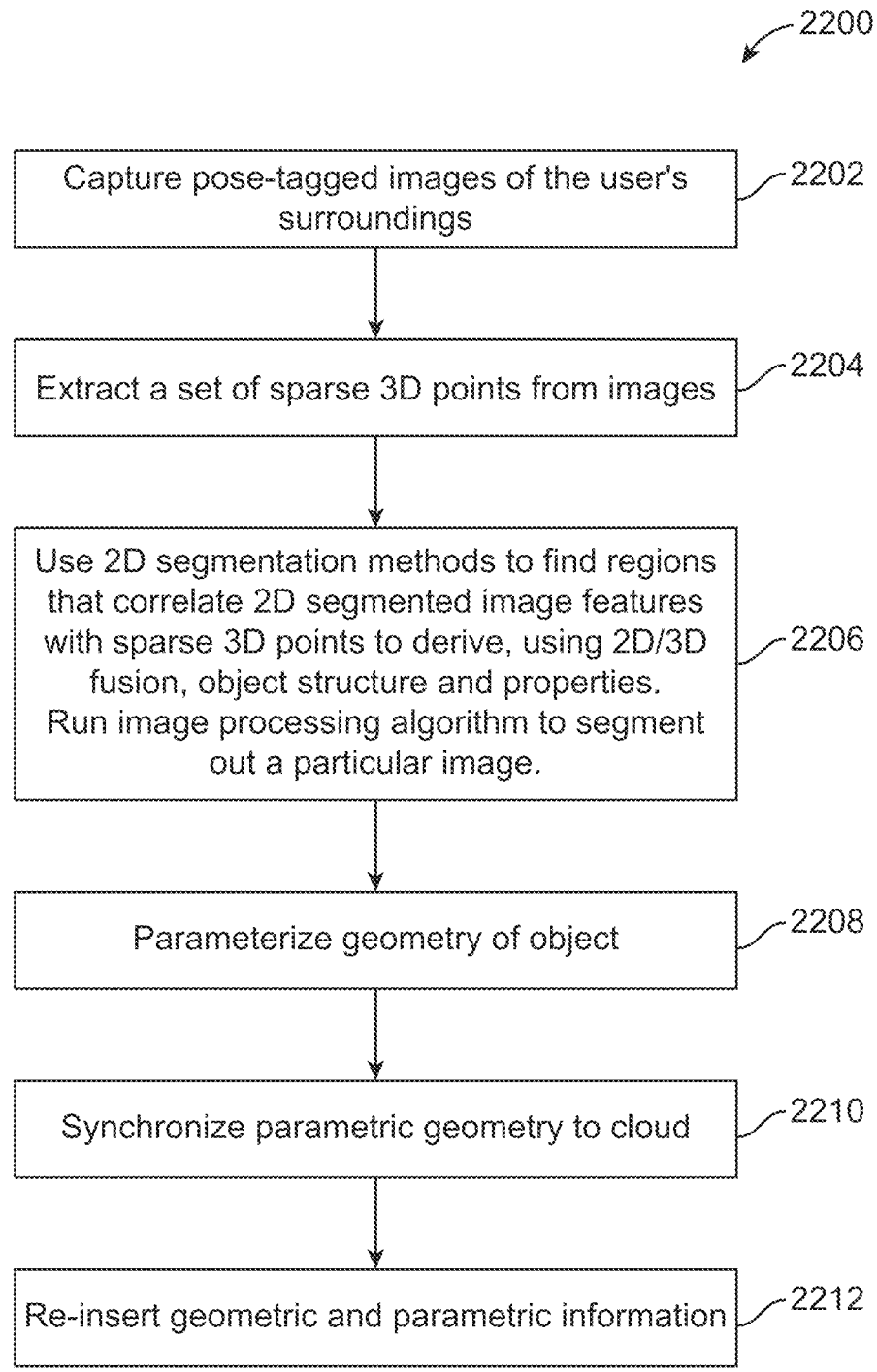
FIG. 22 is a process flow diagram illustrating recognition of objects by object recognizers, according to one illustrated embodiment.

FIG. 22 illustrates an exemplary method 2200 of recognizing objects through object recognizers. When a user walks into a room, the user's sensorywear captures information (e.g., pose tagged images) about the user's surroundings from multiple points of view (step 2202). For example, by the time the user walks into a section of a room, the user's individual AR system has already captured numerous keyframes and pose tagged images about the surroundings. It should be appreciated that each keyframe may include information about the depth and color of the objects in the surroundings. Next, the object recognizer extracts a set of sparse 3D points from the images (step 2204).

Next, the object recognizer (either locally or in the cloud) uses image segmentation to find a particular object in the keyframe (step 2206). It should be appreciated that different objects have different object recognizers that have been written and programmed to recognize that particular object. For illustrative purposes, the following example, will assume that the object recognizer recognizes doors.

The object recognizer may be an autonomous and atomic software object "robot" that takes pose tagged images of the space, key frames, 2D or 3D feature points, and geometry of the space to recognize the door. It should be appreciated that multiple object recognizers may run simultaneously on a set of data, and they can run independent of each other. It should be appreciated that the object recognizer takes 2D images of the object (2D color information, etc.), 3D images (depth information) and also takes 3D sparse points to recognize the object in a geometric coordinate frame of the world.

Next, the object recognizer may correlate the 2D segmented image features with the sparse 3D points to derive, using 2D/3D data fusion, object structure and properties. For example, the object recognizer may identify specific geometry of the door with respect the key frames. Next, based on this, the object recognizer parameterizes the geometry of the object (step 2208). For example, the object recognizer may attach semantic information to the geometric primitive (e.g., the door has a hinge, the door can rotate 90 degrees, etc.). Or, the object recognizer may reduce the size of the door, etc. Next, the object recognizer may synchronize the parametric geometry to the cloud (step 2210).

Next, after recognition, the object recognizer re-inserts the geometric and parametric information into the passable world model (step 2212). For example, the object recognizer may dynamically estimate the angle of the door, and insert it into the world. Thus, it can be appreciated that using the object recognizer allows the system to save computational power because rather than constant real-time capture of information about the angle of the door or movement of the door, the object recognizer uses the stored parametric information to estimate the movement or angle of the door. This information may be updated to the cloud so that other users can see the angle of the door in various representations of the passable world.

As briefly discussed above, object recognizers are atomic autonomous software and/or hardware modules which ingest sparse points (i.e., not necessarily a dense point cloud), pose-tagged images, and geometry, and produce parametric geometry that has semantics attached. The semantics may take the form of taxonomical descriptor, for example "wall," "chair," "Aeron® chair," and properties or characteristics associated with the taxonomical descriptor.

For example, a taxonomical descriptor such as a table may have associated descriptions such as "has a flat horizontal surface which can support other objects." Given an ontology, an object recognizer turns images, points, and optionally other geometry, into geometry that has meaning (i.e., semantics).

Since the individual AR systems are intended to operate in the real world environment, the points represent sparse, statistically relevant, natural features. Natural features are those that are inherent to the object (e.g., edges, holes), in contrast to artificial features added (e.g., printed, inscribed or labeled) to objects for the purpose of machine-vision recognition. The points do not necessarily need to be visible to humans. The points are not limited to point features, e.g., line features and high dimensional features.

Object recognizers may be categorized into two types, Type 1—Basic Objects (e.g., walls, cups, chairs, etc.), Type 2—Detailed Objects (e.g., Aeron® chair, my wall). In some implementations, the Type 1 recognizers run across the entire cloud, while the Type 2 recognizers run against previously found Type 1 data (e.g., search all chairs for Aeron® chairs). The object recognizers may use inherent properties of an object to facilitate in object identification. Or, the object recognizers may use ontological relationship between objects to facilitate implementation. For example, an object recognizer may use the fact that window must be in a wall to facilitate recognition of instances of windows.

Object recognizers will typically be bundled, partnered or logically associated with one or more applications. For example, a cup finder object recognizer may be associated with one, two or more applications in which identifying a presence of a cup in a physical space would be useful. Applications can be logically connected tor associated with defined recognizable visual data or models. For example, in response to a detection of any Aeron® chairs in an image, the AR system calls or executes an application from the Herman Miller Company, the manufacturer and/or seller of Aeron® chairs. Similarly, in response to detection of a Starbucks® signs or logo in an image, the AR system calls or executes a Starbucks® application.

As an example, the AR system may employ an instance of a generic wall finder object recognizer. The generic wall finder object recognizer identifies instances of walls in image information, without regard to specifics about a wall. Thus, the generic wall finder object recognizer identifies vertically oriented surfaces that constitute walls in the image data. The AR system may also employ an instance of a specific wall finder object recognizer, which is separate and distinct from the generic wall finder. The specific wall finder object recognizer identifies vertically oriented surfaces that constitute walls in the image data and which have one or more specific characteristics beyond those of generic wall.

For example, a given specific wall may have one or more windows in defined positions, one or more doors in defined positions, may have a defined paint color, may have artwork hung from the wall, etc., which visually distinguishes the specific wall from other walls. Such allows the specific wall finder object recognizer to identify particular walls. For example, one instance of a specific wall finder object recognizer may identify a wall of a user's office. Other instances of specific wall finder object recognizers may identify respective walls of a user's living room or bedroom.

A specific object recognizer may stand independently from a generic object recognizer. For example, a specific wall finder object recognizer may run completely independently from a generic wall finder object recognizer, not employing any information produced by the generic wall finder object recognizer. Alternatively, a specific (i.e., more refined) object recognizer may be run nested against objects previously found by a more generic object recognizer. For example, a generic and/or a specific door finder object recognizer may run against a wall found by a generic and/or specific wall finder object recognizer, since a door must be in a wall. Likewise, a generic and/or a specific window finder object recognizer may run against a wall found by a generic and/or specific wall finder object recognizer, since a window must be in a wall.

An object recognizer may not only identify the existence or presences of an object, but may identify other characteristics associated with the object. For example, a generic or specific door finder object recognizer may identify a type of door, whether the door is hinged or sliding, where the hinge or slide is located, whether the door is currently in an open or a closed position, and/or whether the door is transparent or opaque, etc.

As noted above, each object recognizer is atomic, that is they are autonomic, autonomous, asynchronous, essentially a black box software object. This allows object recognizers to be community built. The building of object recognizers may be incentivized with various incentives. For example, an online marketplace or collection point for object recognizers may be established. Object recognizer developers may be allowed of post object recognizers for linking or associating with applications developed by other object recognizer or application developers.

Various incentives may be provided. For example, an incentive may be provided for posting of an object recognizer. Also for example, an incentive may be provided to an object recognizer developer or author based on the number of times an object recognizer is logically associated with an application and/or based on the total number of distributions of an application to which the object recognizer is logically associated. As a further example, an incentive may be provided to an object recognizer developer or author based on the number of times an object recognizer is used by applications that are logically associated with the object recognizer. The incentives may be monetary incentives, may provide access to services or media behind a pay wall, and/or credits for acquiring services, media, or goods.

It would, for example, be possible to instantiate 10,000 or more distinct generic and/or specific object recognizers. These generic and/or specific object recognizers can all be run against the same data. As noted above, some object recognizers can be nested, essentially layered on top of each other.

A control program may control the selection, use or operation of the various object recognizers, for example arbitrating the use or operation thereof. Some object recognizers may be placed in different regions, to ensure that the object recognizers do not overlap each other. One, more or even all of the object recognizers can run locally at the user, for example on the computation component (e.g., belt pack). One, more or even all of the object recognizers can run remotely from the user, for example on the cloud server computers.

Object recognizers are related to Apps in the ecosystem. Each application has an associated list of object recognizers it requires. Extensible, can write own apps and recognizers. Could run locally on belt pack, or submit to app store. Monetize apps and object recognizers, e.g., small royalty to author for each download and/or each successful use of object recognizer.

In some implementations, a user may train an AR system, for example moving through a desired set of movements. In response, the AR system may generate an avatar sequence in which an avatar replicates the movements, for example animating the avatar. Thus, the AR system captures or receives images of a user, and generates animation of an avatar based on movements of the user in the captured images. The user may be instrumented, for example wearing one or more sensors. The AR system knows where the pose of the user's head, eyes, and/or hands. The user can, for example, simply act out some motions they want to train.

The AR system preforms a reverse kinematics analysis of the rest of user's body, and makes an animation based on the reverse kinematics analysis.

Avatars in the Passable World

The passable world also contains information about various avatars inhabiting a space. It should be appreciated that every user may be rendered as an avatar in one embodiment. Or, a user operating sensorywear from a remote location can create an avatar and digitally occupy a particular space as well.

In either case, since the passable world is not a static data structure, but rather constantly receives information, avatar rendering and remote presence of users into a space may be based on the user's interaction with the user's individual AR system. Thus, rather than constantly updating an avatar's movement based on captured keyframes, as captured by cameras, avatars may be rendered based on a user's interaction with his/her sensorywear device.

More particularly, the user's individual AR system contains information about the user's head pose and orientation in a space, information about hand movement etc. of the user, information about the user's eyes and eye gaze, information about any totems that are being used by the user. Thus, the user's individual AR system already holds a lot of information about the user's interaction within a particular space that is transmitted to the passable world model. This information may then be reliably used to create avatars for the user and help the avatar communicate with other avatars or users of that space. It should be appreciated that no third party cameras are needed to animate the avatar, rather, the avatar is animated based on the user's individual AR system.

For example, if the user is not in currently at a conference room, but wants to insert an avatar into that space to participate in a meeting at the conference room, the AR system takes information about the user's interaction with his/her own system and uses those inputs to render the avatar into the conference room through the passable world model.

The avatar may be rendered such that the avatar takes the form of the user's own image such that it looks like the user himself/herself is participating in the conference. Or, based on the user's preference, the avatar may be any image chosen by the user. For example, the user may render himself/herself as a bird that flies around the space of the conference room.

At the same time, information about the conference room (e.g., key frames, points, pose-tagged images, avatar information of people in the conference room, recognized objects, etc.) are rendered to the user who is not currently in the conference room. In the physical space, the system may have captured keyframes that are geometrically registered and derives points from the keyframes.

As discussed above, based on these points, the system calculates pose and runs object recognizers, and reinserts parametric geometry into the keyframes, such that the points of the keyframes also have semantic information attached to them. Thus, with all this geometric and semantic information, the conference room may now be shared with other users. For example, the conference room scene may be rendered on the user's table. Thus, even if there is no camera at the conference room, the passable world model, using information collected through prior key frames etc., is able to transmit information about the conference room to other users and recreate the geometry of the room for other users in other spaces.

Topological Map

It should be appreciated that the AR system may use topological maps for localization purposes rather than using geometric maps created from extracted points and pose tagged images. The topological map is a simplified representation of physical spaces in the real world that is easily accessible from the cloud and only presents a fingerprint of a space, and the relationship between various spaces.

The AR system may layer topological maps on the passable world model, for example to localize nodes. The topological map can layer various types of information on the passable world model, for instance: point cloud, images, objects in space, global positioning system (GPS) data, Wi-Fi data, histograms (e.g., color histograms of a room), received signal strength (RSS) data, etc.

In order to create a complete virtual world that maybe reliably passed between various users, the AR system captures information (e.g., map points, features, pose tagged images, objects in a scene, etc.) that is stored in the cloud, and then retrieved as needed. As discussed previously, the passable world model is a combination of raster imagery, point+descriptors clouds, and polygonal/geometric definitions (referred to herein as parametric geometry). Thus, it should be appreciated that the sheer amount of information captured through the users' individual AR system allows for high quality and accuracy in creating the virtual world. However, for localization purposes, sorting through much information to find the piece of passable world most relevant to the user is highly inefficient and costs bandwidth.

To this end, the AR system creates a topological map that essentially provides less granular information about a particular scene or a particular place. The topological map may be derived through global positioning system (GPS) data, Wi-Fi data, histograms (e.g., color histograms of a room), received signal strength (RSS) data, etc. For example, the topological map may use a color histogram of a particular room, and use it as a node in the topological map. In doing so, the room has a distinct signature that is different from any other room or place.

Thus, although the histogram will not contain particular information about all the features and points that have been captured by various cameras (keyframes), the system may immediately detect, based on the histogram, where the user is, and then retrieve all the more particular geometric information associated with that particular room or place. Thus, rather than sorting through the vast amount of geometric and parametric information that encompasses the passable world model, the topological map allows for a quick and efficient way to localize, and then only retrieve the keyframes and points most relevant to that location.

For example, after the system has determined that the user is in a conference room of a building, the system may then retrieve all the keyframes and points associated with the conference room rather than searching through all the geometric information stored in the cloud.

For example, the AR system can represent two images captured by respective cameras of a part of the same scene in a graph theoretic context as first and second pose tagged images. It should be appreciated that the cameras in this context may refer to a single camera taking images of different scenes, or it may be two cameras. There is some strength of connection between the pose tagged images, which could for example be the points that are in the field of views of both of the cameras. The cloud based computer constructs such as a graph (i.e., a topological representation of a geometric world). The total number of nodes and edges in the graph is much smaller than the total number of points in the images.

At a higher level of abstraction higher, other information monitored by the AR system can be hashed together. For example, the cloud based computer(s) may hash together one or more of global positioning system (GPS) location information, Wi-Fi location information (e.g., signal strengths), color histograms of a physical space, and/or information about physical objects around a user. The more points of data, the more likely that the computer will statistically have a unique identifier for that space. In this case, space is a statistically defined concept. For example, in a graph each node may have a histogram profile.

As an example, an office may be a space that is represented as, for example 500 points and two dozen pose tagged images. The same space may be represented topologically as a graph having only 25 nodes, and which can be easily hashed against. Graph theory allows representation of connectedness, for example as a shortest path algorithmically between two spaces.

Thus, the system abstracts away from the specific geometry by turning the geometry into pose tagged images having implicit topology. The system takes the abstraction a level higher by adding other pieces of information, for example color histogram profiles, and the Wi-Fi signal strengths. This makes it easier for the system to identify an actual real world location of a user without having to understand or process all of the geometry associated with the location.

Figure 23:
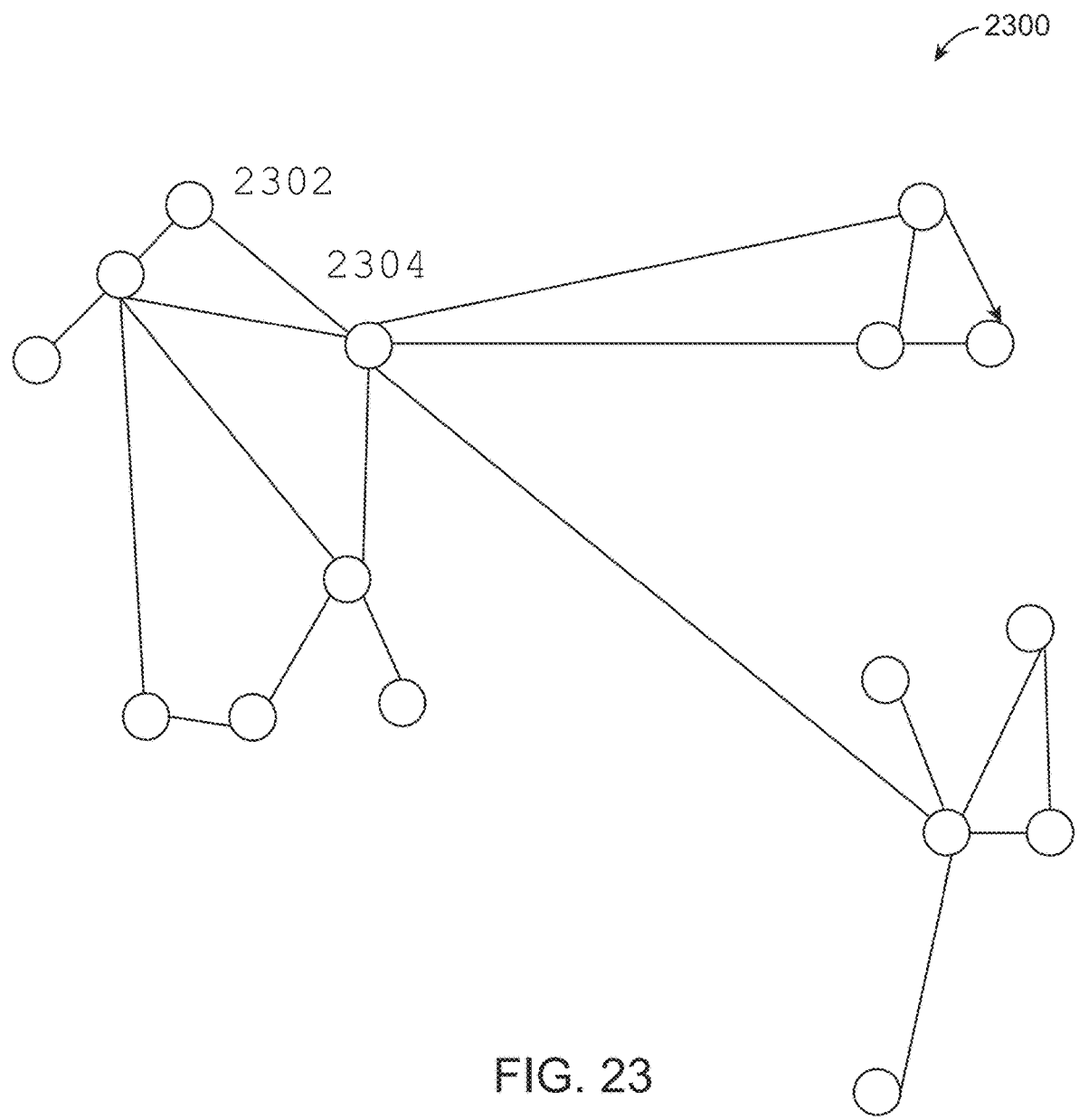
FIG. 23 is a schematic diagram illustrating a topological map, according to one illustrated embodiment.

Referring now to FIG. 23, the topological map 2300, in one embodiment, may simply be a collection of nodes and lines. Each node may represent a particular localized location (e.g., the conference room of an office building) having a distinct signature (e.g., GPS information, histogram, Wi-Fi data, RSS data etc.) and the lines may represent the connectivity between them. It should be appreciated that the connectivity may not have anything to do with geographical connectivity, but rather may be a shared device or a shared user. Thus, layering the topological map on the geometric map is especially helpful for localization and efficiently retrieving only relevant information from the cloud.

Figure 24:
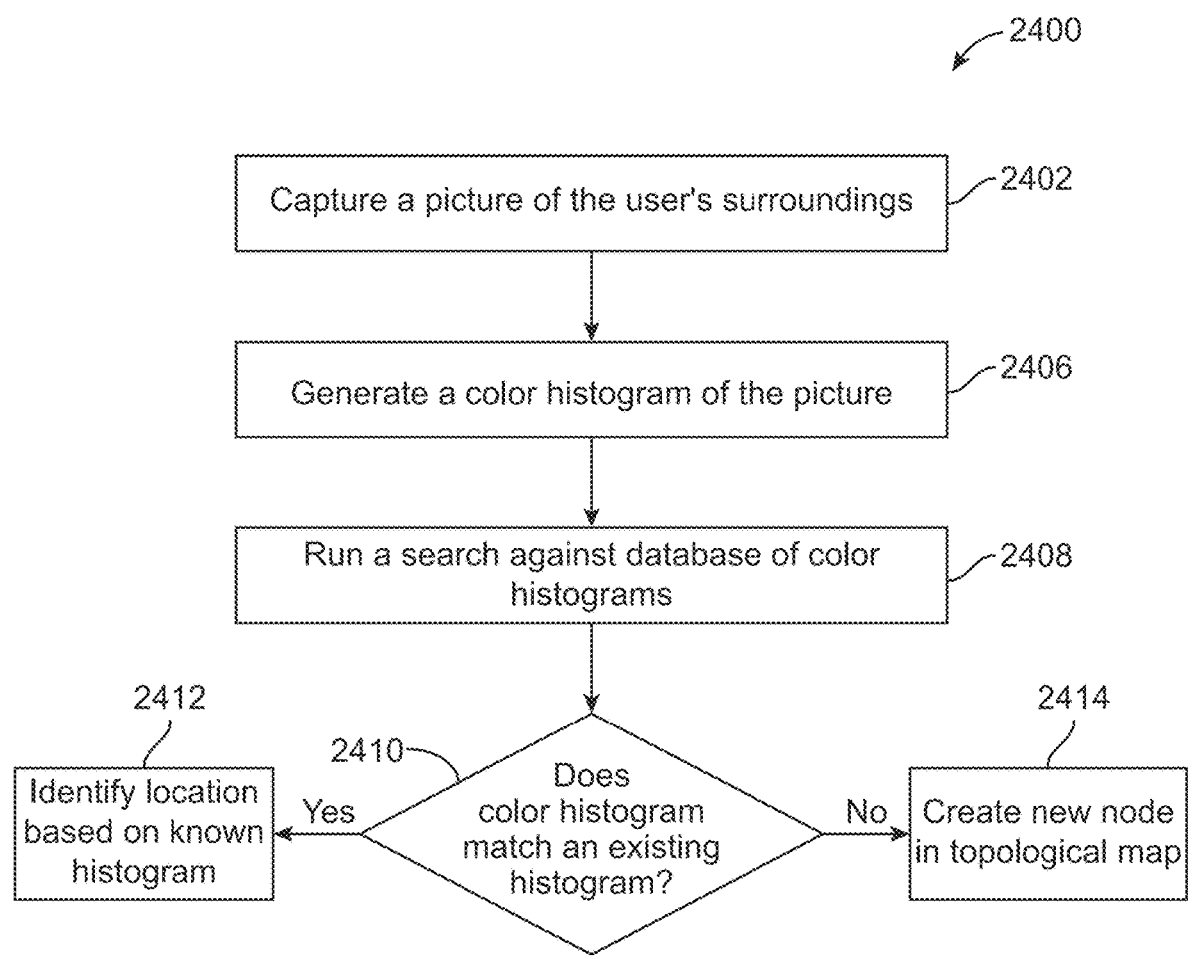
FIG. 24 is a process flow diagram illustrating an identification of a location of a user through the topological map of FIG. 23, according to one illustrated embodiment.

FIG. 24 illustrates an exemplary method 2400 of constructing a topological map. First, the user's individual AR system may take a wide angle camera picture of a particular location (step 2402), and automatically generate a color histogram of the particular location (step 2406). As discussed above, the system may use any other type of identifying information, (Wi-Fi data, RSS information, GPS data, number of windows, etc.) but the color histogram is used in this example for illustrative purposes.

Next, the system runs a search to identify the location of the user by comparing the color histogram to a database of color histograms stored in the cloud. (step 2408) Next, the system determines if the color histogram matches an existing histogram (step 2410). If the color histogram does not match any color histogram of the database of color histograms, it may then be stored in the cloud. Next, the particular location having the distinct color histogram is stored as a node in the topological map (step 2414).

Next, the user may walk into another location, where the user's individual AR system takes another picture and generates another color histogram of the other location. If the color histogram is the same as the previous color histogram or any other color histogram, the AR system identifies the location of the user (step 2412). Here, since the first node and second node were taken by the same user (or same camera/same individual user system), the two nodes are connected in the topological map.

In addition to localization, the topological map may also be used to find loop-closure stresses in geometric maps or geometric configurations of a particular place. It should be appreciated that for any given space, images taken by the user's individual AR system (multiple field of view images captured by one user's individual AR system or multiple users' AR systems) give rise a large number of map points of the particular space.

For example, a single room may have a thousand map points captured through multiple points of views of various cameras (or one camera moving to various positions). Thus, if a camera (or cameras) associated with the users' individual AR system captures multiple images, a large number of points are collected and transmitted to the cloud. These points not only help the system recognize objects, as discussed above, and create a more complete virtual world that may be retrieved as part of the passable world model, they also enable refinement of calculation of the position of the camera based on the position of the points. In other words, the collected points may be used to estimate the pose (e.g., position and orientation) of the keyframe (e.g. camera) capturing the image.

It should be appreciated, however, that given the large number of map points and keyframes, there are bound to be some errors (i.e., stresses) in this calculation of keyframe position based on the map points. To account for these stresses, the AR system may perform a bundle adjust. A bundle adjust allows for the refinement, or optimization of the map points and keyframes to minimize the stresses in the geometric map.

Figure 25:
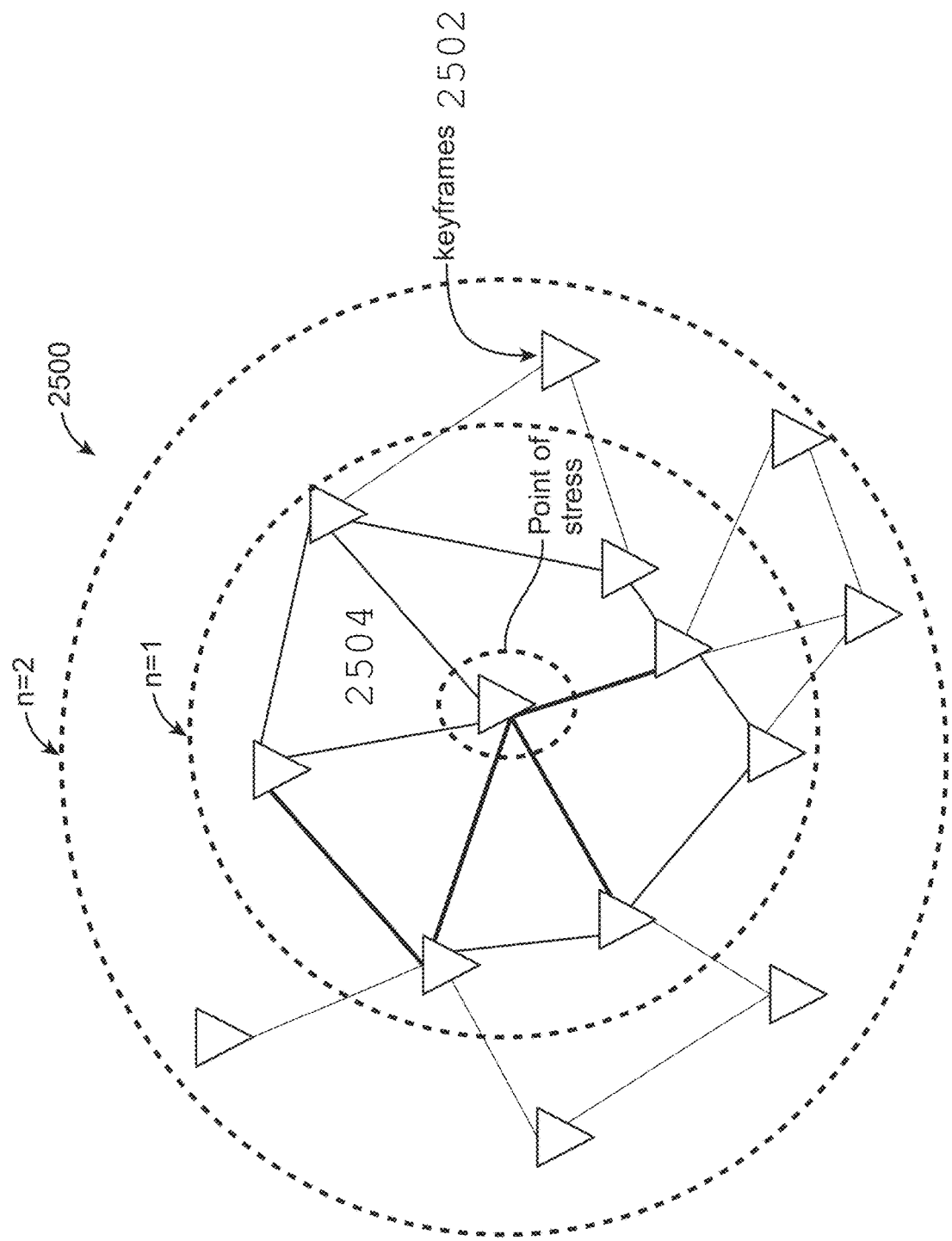
FIG. 25 is a schematic diagram illustrating a network of keyframes and a point of stress on which to perform a bundle adjust, according to one illustrated embodiment.

For example, as illustrated in FIG. 25, the geometric map 2500 may be a collection of keyframes that are all connected to each other. For example, each node of the geometric map may represent a keyframe. The strength of lines between the keyframes may represent the number of features or map points shared between them. For example, if a first keyframe and a second keyframe are close together, they may share a large number of map points, and may thus be represented with a thicker connecting line.

It should be appreciated that other ways of representing geometric maps may be similarly used. For example, the strength of the line may be based on a geographical proximity, in another embodiment. Thus, as shown in FIG. 25, each geometric map may represent a large number of keyframes and their connection to each other. Now, assuming that a stress is identified in a particular point of the geometric map, by performing a bundle adjust, the stress may be alleviated by radially pushing the stress out from the particular point in waves propagating from the particular point of stress.

The following paragraph illustrates an exemplary method of performing a wave propagation bundle adjust. It should be appreciated that all the examples below refer solely to wave propagation bundle adjusts. First, a particular point of stress is identified. For example, the system may determine that the stress at a particular point of the geometric map is especially high (e.g., residual errors, etc.).

The stress may be identified based on one of two reasons. One, a maximum residual error may be defined for the geometric map. If a residual error at a particular point is greater than the predefined maximum residual error, a bundle adjust may be initiation. Second, a bundle adjust may be initiated in the case of loop closures, as will be described further below (when a topological map indicates that misalignments of map points)

Next, the system distributes the error evenly starting with the point of stress and propagating it radially through a network of nodes that surround the particular point of stress. For example, referring back to FIG. 25, the bundle adjust may distribute the error to n=1 around the identified point of stress.

Next, the system may propagate the stress even further, and push out the stress to n=2, or n=3 such that the stress is radially pushed out further and further until the stress is distributed evenly. Thus, performing the bundle adjust is an important way of reducing stress in the geometric maps, and helps optimize the points and keyframes. Ideally, the stress is pushed out to n=2 or n=3 for better results.

It should be appreciated, that the waves may be propagated in smaller increments. For example, after the wave has been pushed out to n=2 around the point of stress, a bundle adjust can be performed in the area between n=3 and n=2, and propagated radially. Thus, this iterative wave propagating bundle adjust process can be run on massive data.

In an optional embodiment, because each wave is unique, the nodes that have been touched by the wave (i.e., bundle adjusted) may be colored so that the wave does not re-propagate on an adjusted section of the geometric map. In another embodiment, nodes may be colored so that simultaneous waves may propagate/originate from different points in the geometric map.

As discussed previously, layering the topological map on the geometric map of keyframes and map points may be especially crucial in finding loop-closure stresses. A loop-closure stress refers to discrepancies between map points captured at different times that should be aligned but are mis-aligned. For example, if a user walks around the block and returns to the same place, map points derived from the position of the first keyframe and the map points derived from the position of the last keyframe as extrapolated from the collected map points should ideally be identical.

However, given stresses inherent in the calculation of pose (position of keyframes) based on the map points, there are often errors and the system does not recognize that the user has come back to the same position because estimated key points from the first key frame are not geometrically aligned with map points derived from the last keyframe. This may be an example of a loop-closure stress.

Figure 26:
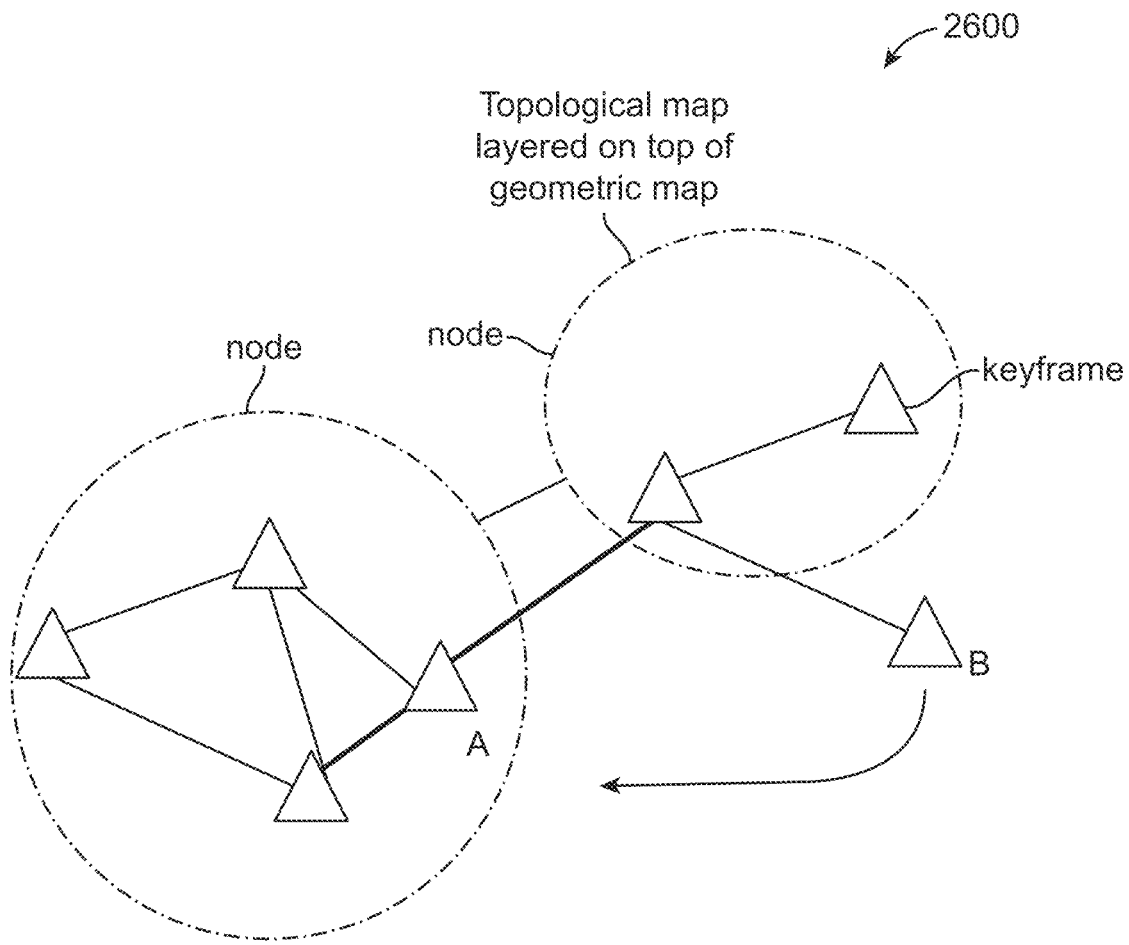
FIG. 26 is a schematic diagram that illustrates performing a bundle adjust on a set of keyframes, according to one illustrated embodiment.

To this end, the topological map may be used to find the loop-closure stresses. Referring back to the previous example, using the topological map along with the geometric map allows the system to recognize the loop-closure stress in the geometric map because the topological map may indicate that the user is back to the starting point (based on the color histogram, for example). For, example, referring to FIG. 26, plot 2600 shows that the color histogram of keyframe B, based on the topological map may be the same as keyframe A. Based on this, the system detects that A and B should be closer together in the same node, and the system may then perform a bundle adjust.

Thus, having identified the loop-closure stress, the system may then perform a bundle adjust on the keyframes and map points derived from them that share a common topological map node. However, doing this using the topological map ensures that the system only retrieves the keyframes on which the bundle adjust needs to be performed instead of retrieving all the keyframes in the system. For example, if the system identifies, based on the topological map that there is a loop closure stress, the system may simply retrieve the keyframes associated with that particular node of the topological map, and perform the bundle adjust on only those set of keyframes rather than all the keyframes of the geometric map.

Figure 27:
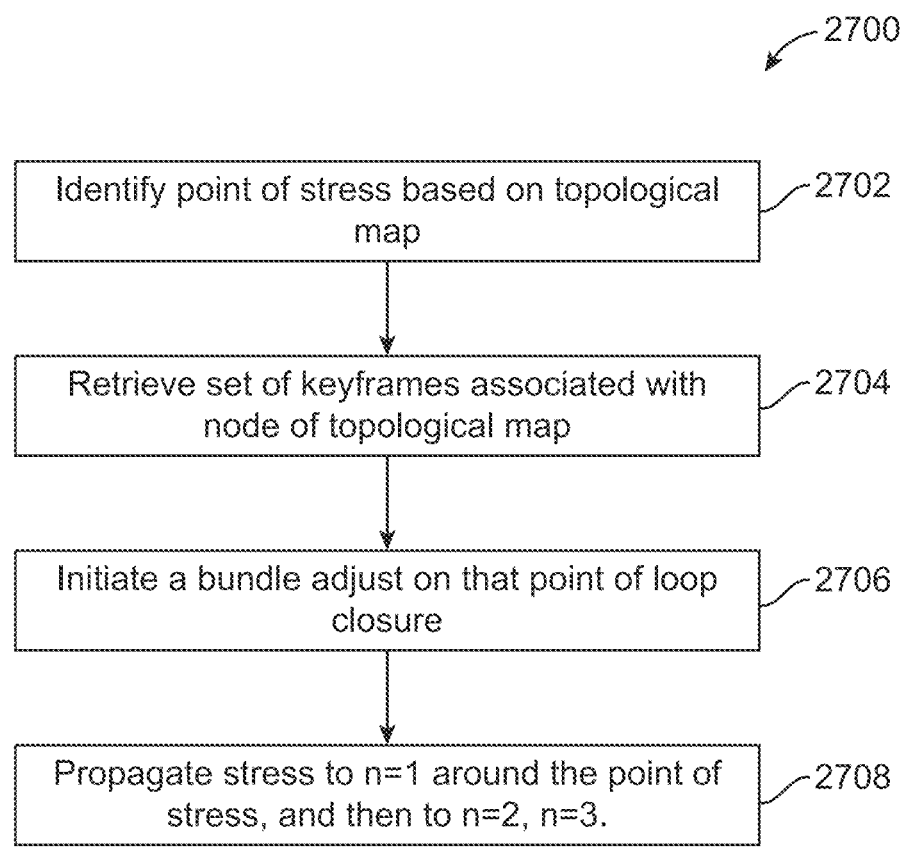
FIG. 27 is a process flow diagram of an exemplary method of performing a bundle adjust, according to one illustrated embodiment.

FIG. 27 illustrates an exemplary algorithm 2700 for correcting loop closure stresses based on the topological map. First, the system may identify a loop closure stress based on the topological map that is layered on top of the geometric map (step 2702). Once the loop closure stress has been identified, the system may retrieve the set of key frames associated with the node of the topological map at which the loop closure stress has occurred (step 2704). After having retrieved the key frames of that node of the topological map, the system may initiate a bundle adjust (step 2706) on that point in the geometric map, and resolves look closure stress in waves, thus propagating the error radially away from the point of stress (step 2708).

Mapping

The AR system may employ various mapping related techniques in order to achieve high depth of field in the rendered light fields. In mapping out the virtual world, it is important to know all the features and points in the real world to accurately portray virtual objects in relation to the real world. To this end, as discussed previously, field of view images captured from users of the AR system are constantly adding to the passable world model by adding in new pictures that convey information about various points and features of the real world.

Based on the points and features, as discussed before, one can also extrapolate the pose and position of the keyframe (e.g., camera, etc.). While this allows the AR system to collect a set of features (2D points) and map points (3D points), it may also be important to find new features and map points to render a more accurate version of the passable world.

One way of finding new map points and/or features may be to compare features of one image against another. Each feature may have a label or feature descriptor attached to it (e.g., color, identifier, etc.). Comparing the labels of features in one picture to another picture may be one way of uniquely identifying natural features in the environment. For example, if there are two keyframes, each of which captures about 500 features, comparing the features of one keyframe with another may help determine if there are new points. However, while this might be a feasible solution when there are just two keyframes, it becomes a very large search problem that takes up a lot of processing power when there are multiple keyframes, each having many points. In other words, if there are M keyframes, each having N unmatched features, searching for new features involves an operation of MN2 (O(MN2)), which is a huge search operation.

Figure 28:
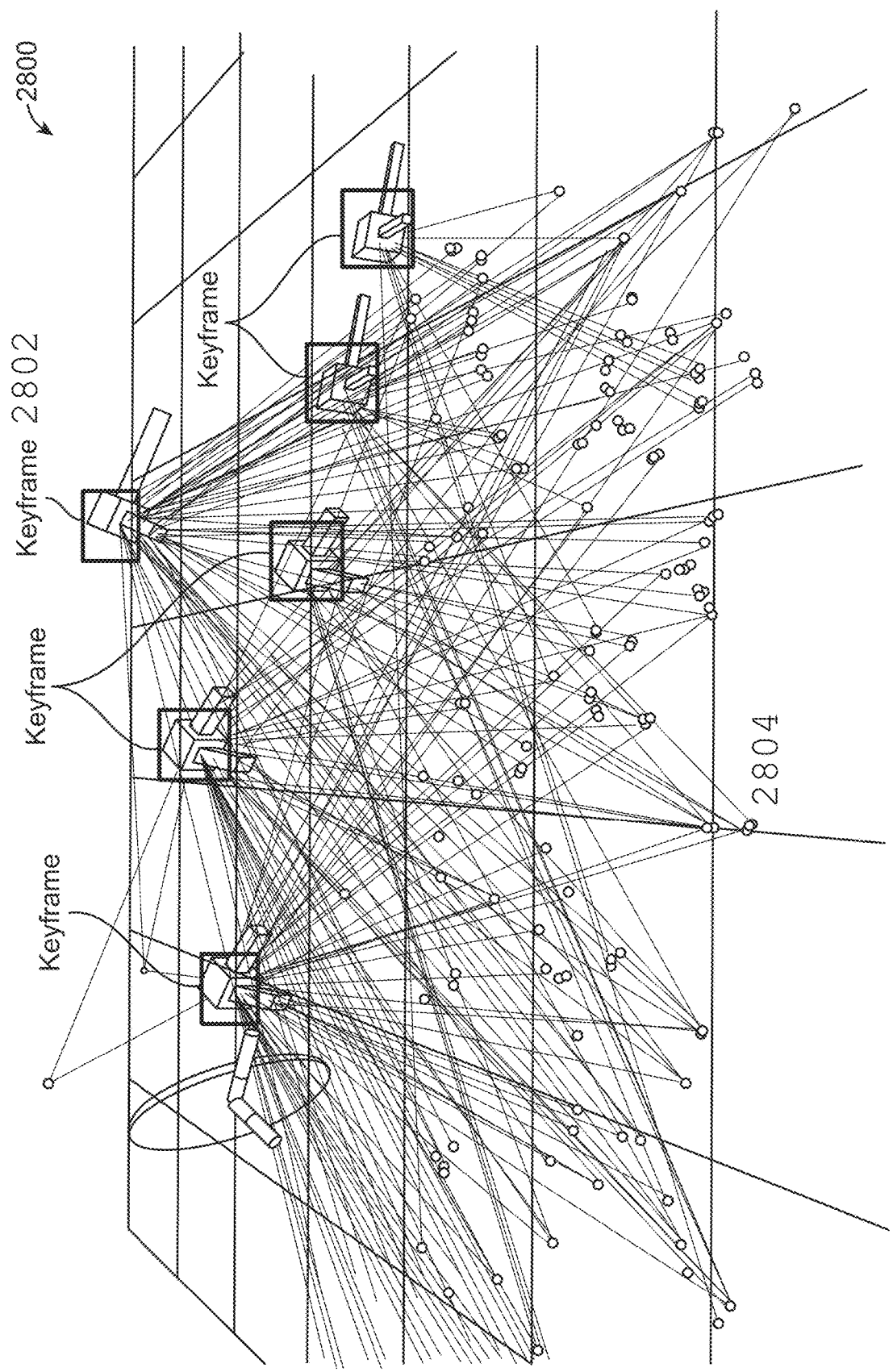
FIG. 28 is a schematic diagram illustrating determining new map points based on a set of keyframes, according to one illustrated embodiment.

Thus, to avoid such a large search operation, the AR system may find new points by render rather than search. In other words, assuming the position of M keyframes are known and each of them has N points, the AR system may project lines (or cones) from N features to the M keyframes. Referring now to FIG. 28, in this particular example, there are 6 keyframes, and lines or rays are rendered (using a graphics card) from the 6 keyframes to the various features.

As can be seen in plot 2800 of FIG. 28 based on the intersection of the rendered lines, new map points may be found. In other words, when two rendered lines intersect, the pixel coordinate of that particular map point in a 3D space may be 2 instead of 1 or 0. Thus, the higher the intersection of the lines at a particular point, the higher the likelihood that there is a map point corresponding to a particular feature in the 3D space. Thus, the intersection of rendered lines may be used to find new map points in a 3D space.

It should be appreciated that for optimization purposes, rather than rendering lines from the keyframes, triangular cones may instead be rendered from the keyframe for more accurate results. The Nth feature may be bisector of the cone, and the half angles to the two side edges may be defined by the camera's pixel pitch, which runs through the lens mapping function on either side of the Nth feature. The interior of the cone may be shaded such that the bisector is the brightest and the edges on either side of the Nth feature may be set of 0.

The camera buffer may be a summing buffer, such that bright spots may represent candidate locations of new features, but taking into account both camera resolution and lens calibration. In other words, projecting cones, rather than lines may help compensate for the fact that certain keyframes are farther away than others that may have captured the features at a closer distance. Thus, a cone rendered from a keyframe that is farther away will be larger (and have a large radius) than one that is rendered from a keyframe that is closer.

It should be appreciated that for optimization purposes, triangles may be rendered from the keyframes instead of lines. Rather than rendering simple rays, render a triangle that is normal to the virtual camera. As discussed previously, the bisector of the triangle is defined by the Nth feature, and the half angles of the two side edges may be defined by the camera's pixel pitch and run through a lens mapping function on either side of the Nth feature. Next the AR system may apply a summing buffer of the camera buffer such that the bright spots represent a candidate location of the features.

Essentially, the AR system may project rays or cones from a number of N unmatched features in a number M prior key frames into a texture of the M+1 keyframe, encoding the keyframe identifier and feature identifier. The AR system may build another texture from the features in the current keyframe, and mask the first texture with the second. All of the colors are a candidate pairing to search for constraints. This approach advantageously turns the O(MN2) search for constraints into an O(MN) render, followed by a tiny O((<M)N(<<N)) search.

As a further example, the AR system may pick new keyframes based on normals. In other words, the virtual key frame from which to view the map points may be selected by the AR system. For instance, the AR system may use the above keyframe projection, but pick the new "keyframe" based on a PCA (Principal component analysis) of the normals of the M keyframes from which {M,N} labels are sought (e.g., the PCA-derived keyframe will give the optimal view from which to derive the labels).

Performing a PCA on the existing M keyframes provides a new keyframe that is most orthogonal to the existing M keyframes. Thus, positioning a virtual key frame at the most orthogonal direction may provide the best viewpoint from which to find new map points in the 3D space. Performing another PCA provides a next most orthogonal direction, and performing a yet another PCA provides yet another orthogonal direction. Thus, it can be appreciated that performing 3 PCAs may provide an x, y and z coordinates in the 3D space from which to construct map points based on the existing M key frames having the N features.

Figure 29:
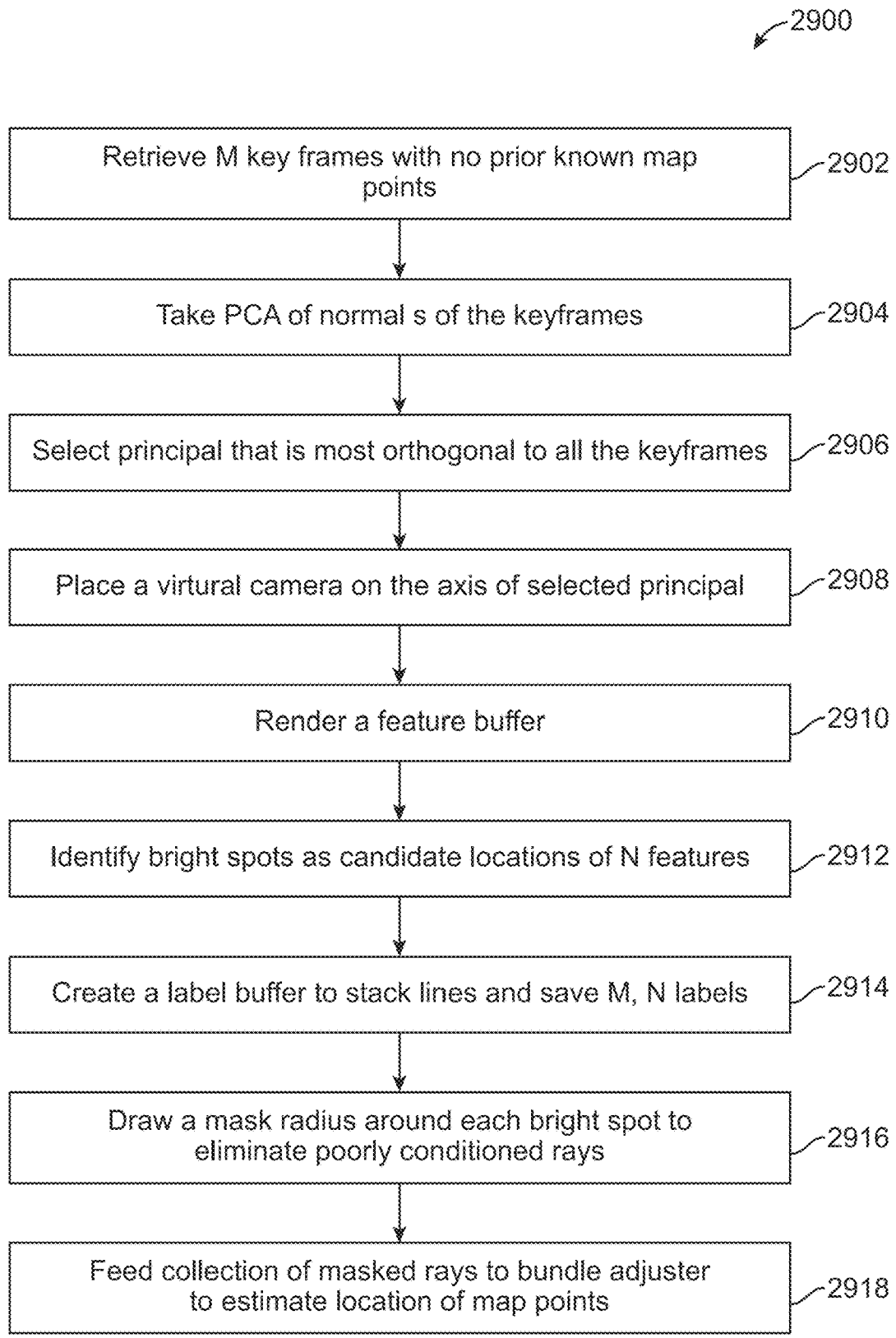
FIG. 29 is a process flow diagram of an exemplary method of determining new map points, according to one illustrated embodiment.

FIG. 29 illustrates an exemplary algorithm 2900 for finding map points from M known keyframes, with no prior known map points. First, the AR system retrieves M keyframes associated with a particular space (step 2902). As discussed previously, M keyframes refers to known keyframes that have captured the particular space. Next, a PCA of the normal of the keyframes is performed to find the most orthogonal direction of the M key frames (step 2904). It should be appreciated that the PCA may produce three principals each of which is orthogonal to the M key frames. Next, the AR system selects the principal that is smallest in the 3D space, and is also the most orthogonal to the view of all the keyframes (step 2906).

After having identified the principal that is orthogonal to the keyframes, the AR system may place a virtual camera on the axis of the selected principal (step 2908). It should be appreciated that the virtual keyframe may be places far away enough so that its field of view includes all the M keyframes.

Next, the AR system may render a feature buffer (step 2910), such that N rays (or cones) are rendered from each of the M key frames to the Nth feature. The feature buffer may be a summing buffer, such that the bright spots (pixel coordinates at which lines N lines have intersected) represent candidate locations of N features. It should be appreciated that the same process described above may be repeated with all three PCA axes, such that map points are found on x, y and z axes.

Next, the system may store all the bright spots in the image as virtual "features" (step 2912). Next, the AR system may create a second "label" buffer at the virtual keyframe to stack the lines (or cones) and saving their {M, N} labels (step 2914). Next, the AR system may draw a "mask radius" around each bright spot in the feature buffer (step 2916). The mask radius represents the angular pixel error of the virtual camera. Next, the AR system may fill the circles and mask the label buffer with the resulting binary image. It should be appreciated that in an optional embodiment, the filling of the above circles may be bright at the center, fading to zero at the circumference.

In the now-masked label buffer, the AR system may, at each masked region, collect the principal rays using the {M, N}-tuple label of each triangle. It should be appreciated that if cones/triangles are used instead of rays, the AR system may only collect triangles where both sides of the triangle are captured inside the circle. Thus, the mask radius essentially acts as a filter that eliminates poorly conditioned rays or rays that have a large divergence (e.g., a ray that is at the edge of a field of view (FOV) or a ray that emanates from far away).

For optimization purposes, the label buffer may be rendered with the same shading as used previously in generated cones/triangles). In another optional optimization embodiment, the AR system may scale the triangle density from one to zero instead of checking the extents (sides) of the triangles. Thus, very divergent rays will effectively raise the noise floor inside a masked region. Running a local threshold detect inside the mark will trivially pull out the centroid from only those rays that are fully inside the mark.

Next, the AR system may feed the collection of masked/optimized rays to a bundle adjuster to estimate the location of map points (step 2918). It should be appreciated that this system is functionally limited to the size of the render buffers that are employed. For example, if the key frames are widely separated, the resulting rays/cones will have lower resolution.

In an alternate embodiment, rather than using PCA to find the orthogonal direction, the virtual key frame may be placed at the location of one of the M key frames. This may be a simpler and effective solution because the M key frame may have already captured the space at the best resolution of the camera. If PCAs are used to find the orthogonal directions at which to place the virtual keyframes, the process above is repeated by placing the virtual camera along each PCA axis and finding map points in each of the axes.

In yet another exemplary algorithm of finding new map points, the AR system may hypothesize map points. Thus, instead of using a label buffer, the AR system hypothesizes map points, for example by performing the following algorithm. The AR system may first get M key frames. Next, the AR system gets the first three principal components from a PCA analysis. Next, the AR system may place a virtual keyframe at each principal. Next, the AR system may render a feature buffer exactly as discussed above at each of the three virtual keyframes.

Since the principal components are by definition orthogonal to each other, rays drawn from each camera outwards may hit each other at a point in 3D space. It should be appreciated that there may be multiple intersections of rays in some instances. Thus, there may now be N features in each virtual keyframe. Next, the AR system may use a geometric algorithm to find the points of intersection. This geometric algorithm may be a constant time algorithm because there may be $N^3$ rays. Next, masking and optimization may be performed in the same manner described above to find the map points in 3D space.

Figure 30:
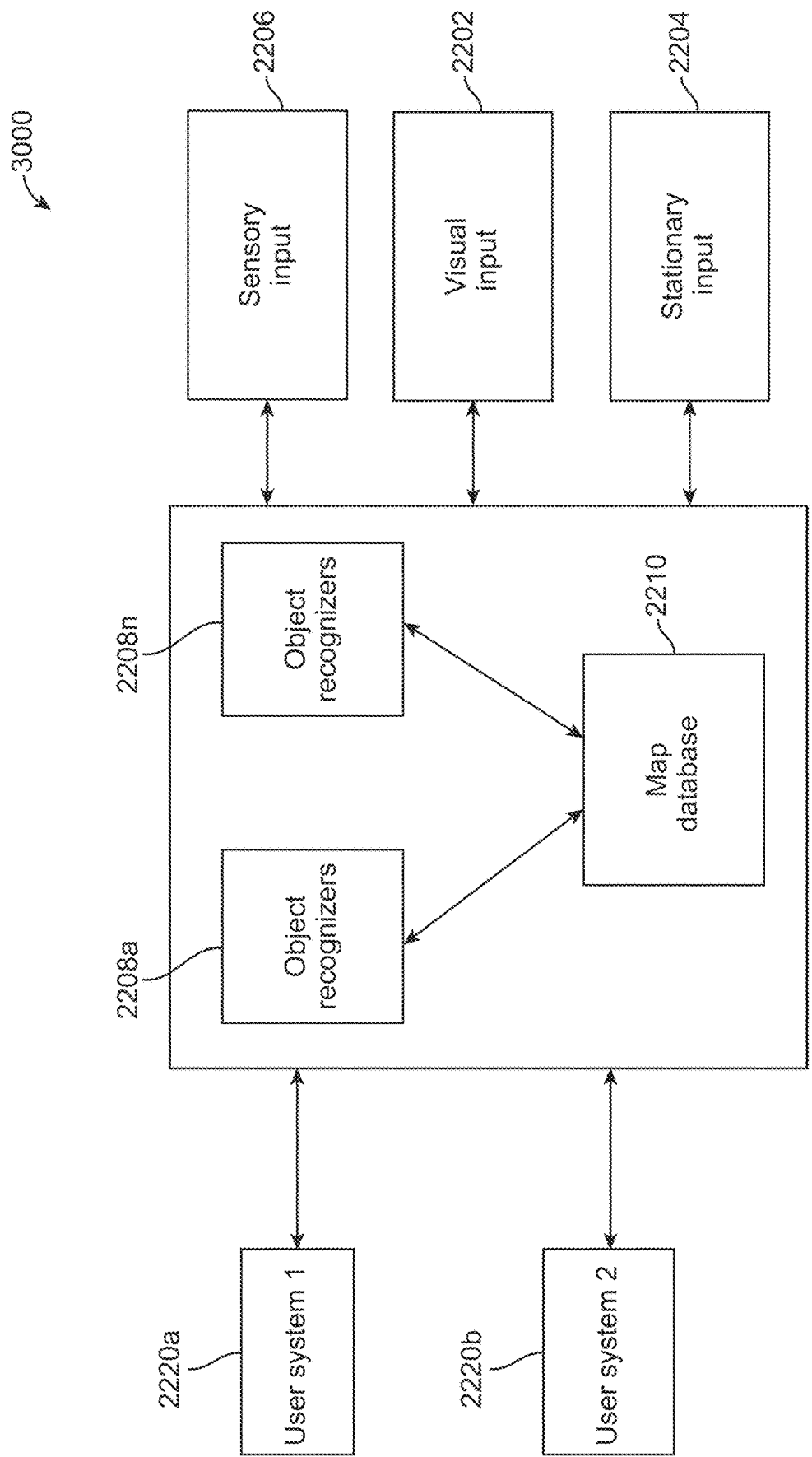
FIG. 30 is a system view diagram of an exemplary AR system, according to one illustrated embodiment.

Referring to process flow diagram 3000 of FIG. 30, on a basic level, the AR system is configured to receive input (e.g., visual input 2202 from the user's wearable system, input from room cameras 2204, sensory input 2206 in the form of various sensors in the system, gestures, totems, eye tracking etc.) from one or more AR systems. The AR systems may constitute one or more user wearable systems, and/or stationary room systems (room cameras, etc.). The wearable AR systems not only provide images from the FOV cameras, they may also be equipped with various sensors (e.g., accelerometers, temperature sensors, movement sensors, depth sensors, GPS, etc.), as discussed above, to determine the location, and various other attributes of the environment of the user. Of course, this information may further be supplemented with information from stationary cameras discussed previously that may provide images and/or various cues from a different point of view. It should be appreciated that image data may be reduced to a set of points, as explained above.

One or more object recognizers 2208 (object recognizers explained in depth above) crawl through the received data (e.g., the collection of points) and recognize and/or map points with the help of the mapping database 2210. The mapping database may comprise various points collected over time and their corresponding objects. It should be appreciated that the various devices, and the map database (similar to the passable world) are all connected to each other through a network (e.g., LAN, WAN, etc.) to access the cloud.

Based on this information and collection of points in the map database, the object recognizers may recognize objects and supplement this with semantic information (as explained above) to give life to the objects. For example, if the object recognizer recognizes a set of points to be a door, the system may attach some semantic information (e.g., the door has a hinge and has a 90 degree movement about the hinge). Over time the map database grows as the system (which may reside locally or may be accessible through a wireless network) accumulates more data from the world.

Once the objects are recognized, the information may be transmitted to one or more user wearable systems 2220. For example, the system may transmit information about a scene happening in California to one or more users in New York. Based on data received from multiple FOV cameras and other inputs, the object recognizers and other software components map the points collected through the various images, recognize objects etc., such that the scene may be accurately "passed over" to a user in a different part of the world. As discussed above, the system may also use a topological map for localization purposes. More particularly, the following discussion will go in depth about various elements of the overall system that enables the interaction between one or more users of the AR system.

Figure 31:
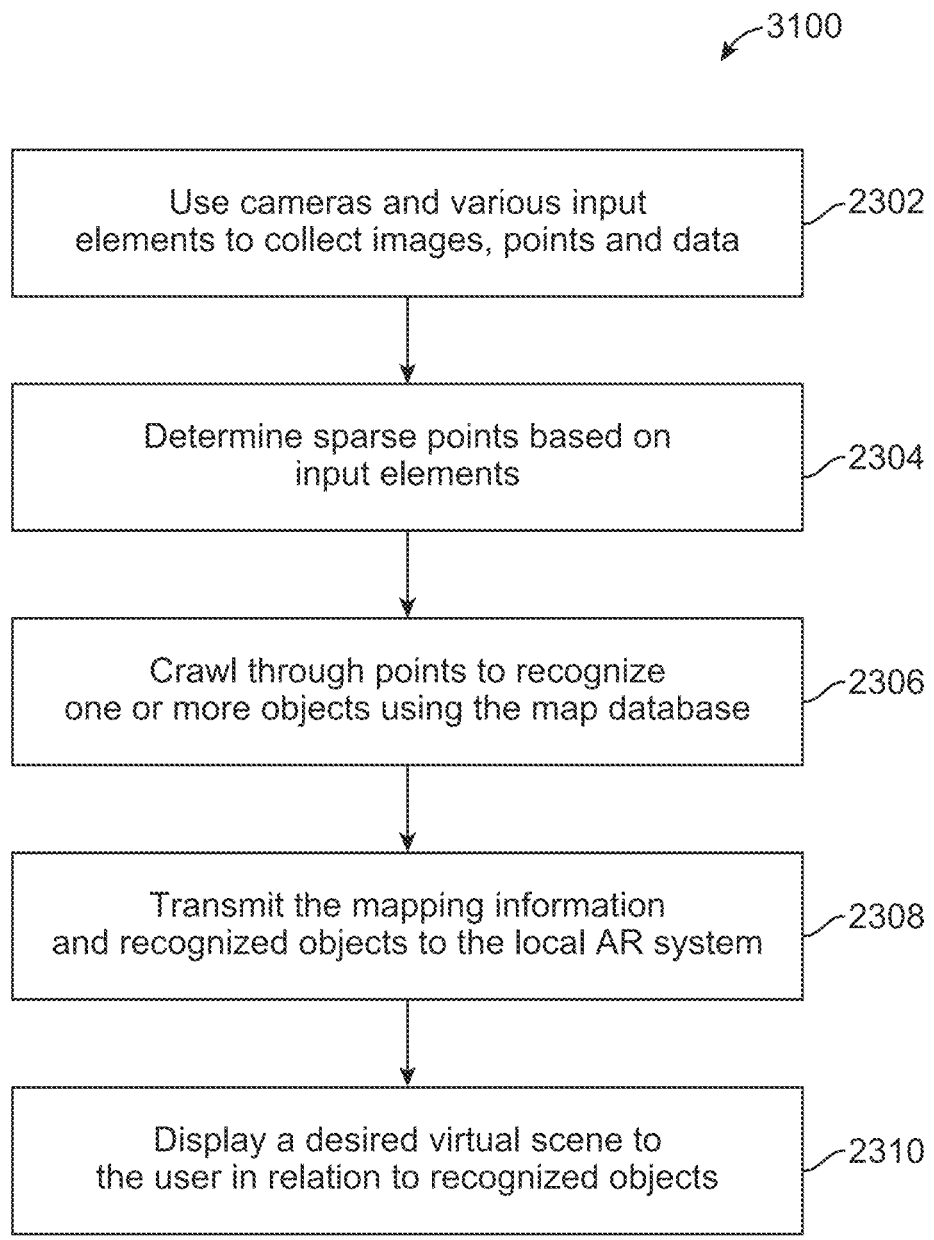
FIG. 31 is a process flow diagram of an exemplary method of rendering virtual content in relation to recognized objects, according to one illustrated embodiment.

FIG. 31 is a process flow diagram 3100 that represents how a virtual scene may be represented to a user of the AR system. For example, the user may be New York, but want to view a scene that is presently going on in California, or may want to go on a walk with a friend who resides in California. First, in 2302, the AR system may receive input from the user and other users regarding the environment of the user. As discussed previously, this may be achieved through various input devices, and knowledge already possessed in the map database.

Figure 32:
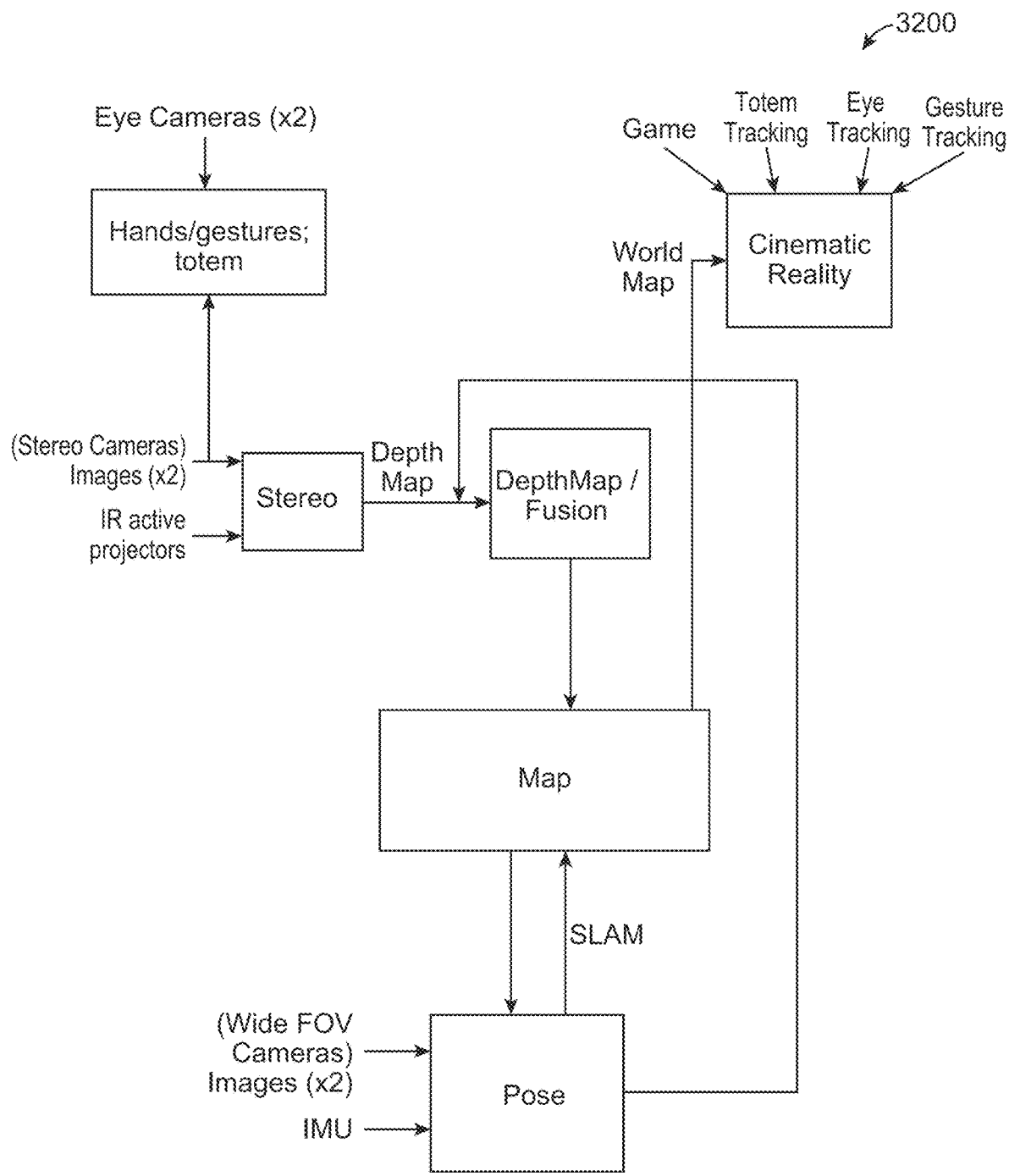
FIG. 32 is a plan view of another embodiment of the AR system, according to one illustrated embodiment.

The user's FOV cameras, sensors, GPS, eye tracking etc., conveys information to the system (step 2302). The system may then determine sparse points based on this information (step 2304). As discussed above, the sparse points may be used in determining pose data etc., that is important in displaying and understanding the orientation and position of various objects in the user's surroundings. The object recognizers may crawl through these collected points and recognize one or more objects using the map database (step 2306). This information may then be conveyed to the user's individual AR system (step 2308), and the desired virtual scene may be accordingly displayed to the user (step 2310). For example, the desired virtual scene (user in CA) may be displayed at the right orientation, position, etc., in relation to the various objects and other surroundings of the user in New York. It should be appreciated that the above flow chart represents the system at a very basic level. FIG. 32 below represents a more detailed system architecture. It should be appreciated that a number of user scenarios detailed below use similar processes as the one described above.

Referring now to FIG. 32, a more detailed system diagram 3200 is described. As shown in FIG. 32, at the center of the system of a Map, which may be a database containing map data for the world. In one embodiment it may partly reside on user-wearable components, and may partly reside at cloud storage locations accessible by wired or wireless network. The Map (or the passable world model) is a significant and growing component which will become larger and larger as more and more users are on the system.

A Pose process may run on the wearable computing architecture and utilize data from the Map to determine position and orientation of the wearable computing hardware or user. Pose data may be computed from data collected on the fly as the user is experiencing the system and operating in the world. The data may comprise images, data from sensors (such as inertial measurement, or "IMU" devices, which generally comprises accelerometer and gyro components), and surface information pertinent to objects in the real or virtual environment.

What is known as a "sparse point representation" may be the output of a simultaneous localization and mapping (or "SLAM"; or "V-SLAM", referring to a configuration wherein the input is images/visual only) process. The system is configured to not only find out wherein the world the various components are, but what the world is made of. Pose is a building block that achieves many goals, including populating the Map and using the data from the Map.

In one embodiment, sparse point position is not completely adequate on its own, and further information is needed to produce a multifocal virtual or augmented reality experience as described above, which may also be termed "Cinematic Reality". Dense Representations, generally referring to depth map information, may be utilized to fill this gap at least in part. Such information may be computed from a process referred to as "Stereo", wherein depth information is determined using a technique such as triangulation or time-of-flight sensing.

Image information and active patterns (such as infrared patterns created using active projectors) may serve as input to the Stereo process. A significant amount of depth map information may be fused together, and some of this may be summarized with surface representation. For example, mathematically definable surfaces are efficient (i.e., relative to a large point cloud) and digestible inputs to things like game engines.

Thus the output of the Stereo process (depth map) may be combined in the Fusion process. Pose may be an input to this Fusion process as well, and the output of Fusion becomes an input to populating the Map process, as shown in the embodiment of FIG. 32. Sub-surfaces may connect with each other, such as in topographical mapping, to form larger surfaces, and the Map becomes a large hybrid of points and surfaces.

To resolve various aspects in a Cinematic Reality process, various inputs may be utilized. For example, in the depicted embodiment, various Game parameters may be inputs to determine that the user or operator of the system is playing a monster battling game with one or more monsters at various locations, monsters dying or running away under various conditions (such as if the user shoots the monster), walls or other objects at various locations, and the like.

The Map may include information regarding where such objects are relative to each other, to be another valuable input to Cinematic Reality. The input from the Map to the Cinematic Reality process may be called the "World Map". Pose relative to the world becomes an input as well and plays a key role to almost any interactive system.

Controls or inputs from the user are another important input. More details on various types of user inputs (e.g., visual input, gestures, totems, audio input, sensory input, etc.) will be described in further detail below. In order to move around or play a game, for example, the user may need to instruct the system regarding what he or she wants to do. Beyond just moving oneself in space, there are various forms of user controls that may be utilized. In one embodiment, a totem or object such as a gun may be held by the user and tracked by the system.

The system preferably will be configured to know that the user is holding the item and understand what kind of interaction the user is having with the item (i.e., if the totem or object is a gun, the system may be configured to understand location and orientation, as well as whether the user is clicking a trigger or other sensed button or element which may be equipped with a sensor, such as an IMU, which may assist in determining what is going on, even with such activity is not within the field of view of any of the cameras.

Hand gesture tracking or recognition may also provide valuable input information. The system may be configured to track and interpret hand gestures for button presses, for gesturing left or right, stop, etc. For example, in one configuration, maybe the user wants to flip through emails or your calendar in a non-gaming environment, or do a "fist bump" with another person or player.

The system may be configured to leverage a minimum amount of hand gesture, which may or may not be dynamic. For example, the gestures may be simple static gestures like open hand for stop, thumbs up for ok, thumbs down for not ok; or a hand flip right or left or up/down for directional commands. One embodiment may start with a fairly limited vocabulary for gesture tracking and interpretation, and eventually become more nuanced and complex.

Eye tracking is another important input (i.e., tracking where the user is looking to control the display technology to render at a specific depth or range). In one embodiment, vergence of the eyes may be determined using triangulation, and then using a vergence/accommodation model developed for that particular person, accommodation may be determined.

With regard to the camera systems, the depicted configuration shows three pairs of cameras: a relative wide field of view ("FOV") or "passive SLAM" pair of cameras arranged to the sides of the user's face, a different pair of cameras oriented in front of the user to handle the Stereo imaging process and also to capture hand gestures and totem/object tracking in front of the user's face. Then there is a pair of Eye Cameras oriented into the eyes of the user so they may attempt to triangulate eye vectors and other information. As noted above, the system may also comprise one or more textured light projectors (such as infrared, or "IR", projectors) to inject texture into a scene.

Calibration of all of these devices (for example, the various cameras, IMU and other sensors, etc.) is important in coordinating the system and components thereof. The system may also be configured to utilize wireless triangulation technologies (such as mobile wireless network triangulation and/or global positioning satellite technology, both of which become more relevant as the system is utilized outdoors). Other devices or inputs such as a pedometer worn by a user, a wheel encoder associated with the location and/or orientation of the user, may need to be calibrated to become valuable to the system.

The display system may also be considered to be an input element from a calibration perspective. In other words, the various elements of the system preferably are related to each other, and are calibrated intrinsically as well (i.e., how they map the real world matrix into measurements; going from real world measurements to matrix may be termed "intrinsics"; we want to know the intrinsics of the devices). For a camera module, the standard intrinsics parameters may include the focal length in pixels, the principal point (intersection of the optical axis with the sensor), and distortion parameters (particularly geometry).

One may also want to consider photogrammetric parameters, if normalization of measurements or radiance in space is of interest. With an IMU module that combines gyro and accelerometer devices, scaling factors may be important calibration inputs. Camera-to-camera calibration also may be key, and may be dealt with, at least in part, by having the three sets of cameras (Eye, Stereo, and World/wide FOV) rigidly coupled to each other.

In one embodiment, the display may have two eye sub-displays, which may be calibrated at least partially in-factory, and partially in-situ due to anatomic variations of the user (location of the eyes relative to the skull, location of the eyes relative to each other, etc.). Thus in one embodiment, a process is conducted at runtime to calibrate the display system for the particular user.

Generally all of the calibration will produce parameters or configurations which may be used as inputs to the other functional blocks, as described above (for example: where are the cameras relative to a helmet or other head-worn module; what is the global reference of the helmet; what are the intrinsic parameters of those cameras so the system can adjust the images on the fly—to know where every pixel in an image corresponds to in terms of ray direction in space; same with the stereo cameras; their disparity map may be mapped into a depth map, and into an actual cloud of points in 3-D; so calibration is fundamental there as well; all of the cameras preferably will be known relative to a single reference frame—a fundamental notion behind calibrating our head mounted system; same with the IMU—generally one will want to determine what the three axes of rotation are relative to the helmet, etc., to facilitate at least some characterization/transformation related thereto.

The map described above is generated using various map points obtained from multiple user devices. Various modes of collecting map points to add on to the Map or the passable world model will be discussed below.

Dense/Sparse Mapping Tracking

As previously noted, there are many ways that one can obtain map points for a given location, where some approaches may generate a large number of (dense) points and other approaches may generate a much smaller number of (sparse) points. However, conventional vision technologies are premised upon the map data being one or the other.

This presents a problem when there is a need to have a single map that corresponds to both sparse and dense sets of data. For example, when in an indoor setting within a given space, there is often the need to store a very dense map of the point within the room, e.g., because the higher level and volume of detail for the points in the room is necessary to fulfill the requirements of many gaming or business applications. On the other hand, in an outdoor setting, there is far less need to store a dense amount of data, and hence it may be far more efficient to represent outdoor spaces using a sparse set of points.

With the wearable device of some embodiments of the invention, the system architecture is capable of accounting for the fact that the user may move from a setting corresponding to a dense mapping (e.g., indoors) to a location corresponding to a sparse mapping (e.g., outdoors), and vice versa. The general idea is that regardless of the nature of the identified point, certain information is obtained for that point, where these points are stored together into a common Map. A normalization process is performed to make sure the stored information for the points is sufficient to allow the system to perform desired functionality for the wearable device. This common Map therefore permits integration of the different types of data, and allows movement of the wearable device with seamless access and use of the Map data.

Figure 33:
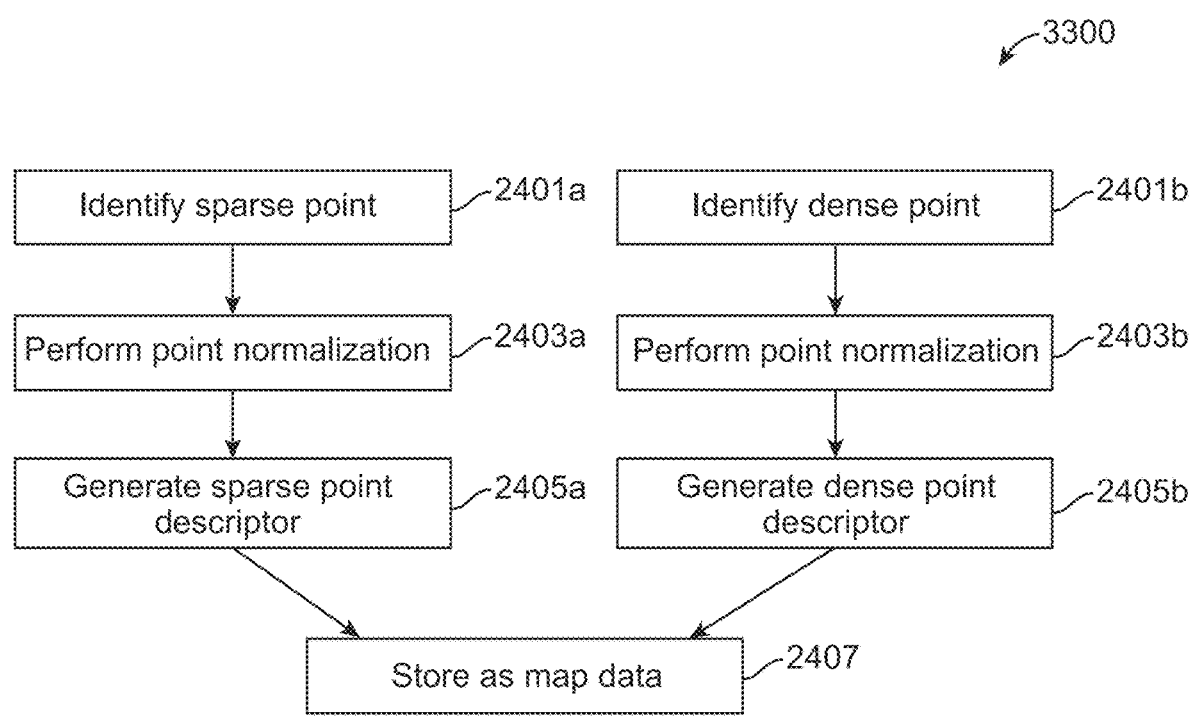
FIG. 33 is a process flow diagram of an exemplary method of identifying sparse and dense points, according to one illustrated embodiment.

FIG. 33 shows a flowchart 3300 of one possible approach to populate the Map with both sparse map data and dense map data, where the path on the left portion addresses sparse points and the path of the right portion addresses dense points.

At 2401a, the process identifies sparse feature points, which may pertain to any distinctive/repeatable visible to the machine. Examples of such distinctive points include corners, circles, triangles, text, etc. Identification of these distinctive features allows one to identify properties for that point, and also to localize the identified point. Various type of information is obtained for the point, including the coordinate of the point as well as other information pertaining to the characteristics of the texture of the region surrounding or adjacent to the point.

Similarly, at 2401b, identification is made of a large number of points within a space. For example, a depth camera may be used to capture a set of 3D points within space that identifies the (x,y,z) coordinate of that point. Some depth cameras may also capture the RGB values along with the D (depth) value for the points. This provides a set of world coordinates for the captured points.

The problem at this point is there are two sets of potentially incompatible points, where one set is sparse (resulting from 2401*a*) and the other set is dense (resulting from 2401*b*). The present invention performs normalization on the captured data to address this potential problem. Normalization is performed to address any aspect of the data that may be needed to facilitate vision functionality needed for the wearable device. For example, at 2403*a*, scale normalization can be performed to normalize the sparse data. Here, a point is identified, and offsets from that point are also identified to determine differences from the identified point to the offsets, where this process is performed to check and determine the appropriate scaling that should be associated with the point.

Similarly, at 2403*b*, the dense data may also be normalized as appropriate to properly scale the identified dense points. Other types of normalization may also be performed, e.g., coordinate normalization to common origin point. A machine learning framework can be used to implement the normalization process, so that the data obtained to normalize a first point is used to normalize a second point, and so on until all necessary points have been normalized.

The normalized point data for both the sparse and dense points are then represented in an appropriate data format. At 2405*a*, a descriptor is generated and populated for each sparse point. Similarly, at 2405*b*, descriptors are generated and populated for the dense points. The descriptors (e.g., using substantially the descriptor format for the A-KAZE algorithm) characterizes each of the points, whether corresponding to sparse or dense data. For example, the descriptor may include information about the scale, orientation, patch data, and/or texture of the point. Thereafter, at 2407, the descriptors are then stored into a common Map to unify the data, including both the sparse and dense data.

During operation of the wearable device, the data that is needed is used by the system. For example, when the user is in a space corresponding to dense data, a large number of points are likely available to perform any necessary functionality using that data. On the other hand, when the user has move to a location corresponding to sparse data, there may be a limited number of points that are used to perform the necessary functionality. The user may be in an outdoor space where only three points are identified. The three points may be used, for example, for object identification. The points may also be used to determine the pose of the user. For example, assume that the user has moved into a room that has already been mapped. The user's device will identify points in the room (e.g., using a mono or stereo camera(s) on the wearable device). An attempt is made to check for the same points/patterns that were previously mapped, e.g., by identifying known points, the user's location can be identified as well as the user's orientation. Given enough identified points in a 3D model of the room, this allows one to determine the pose of the user. If there is a dense mapping, then algorithms appropriate for dense data can be used to make the determination. If the space corresponds to a sparse mapping, then algorithms appropriate for sparse data can be used to make the determination.

Projected Texture Sources

In some locations, there may be a scarcity of feature points from which to obtain texture data for that space. For example, certain rooms may have wide swaths of blank walls for which there are no distinct feature points to identify to obtain the mapping data.

Figure 34:
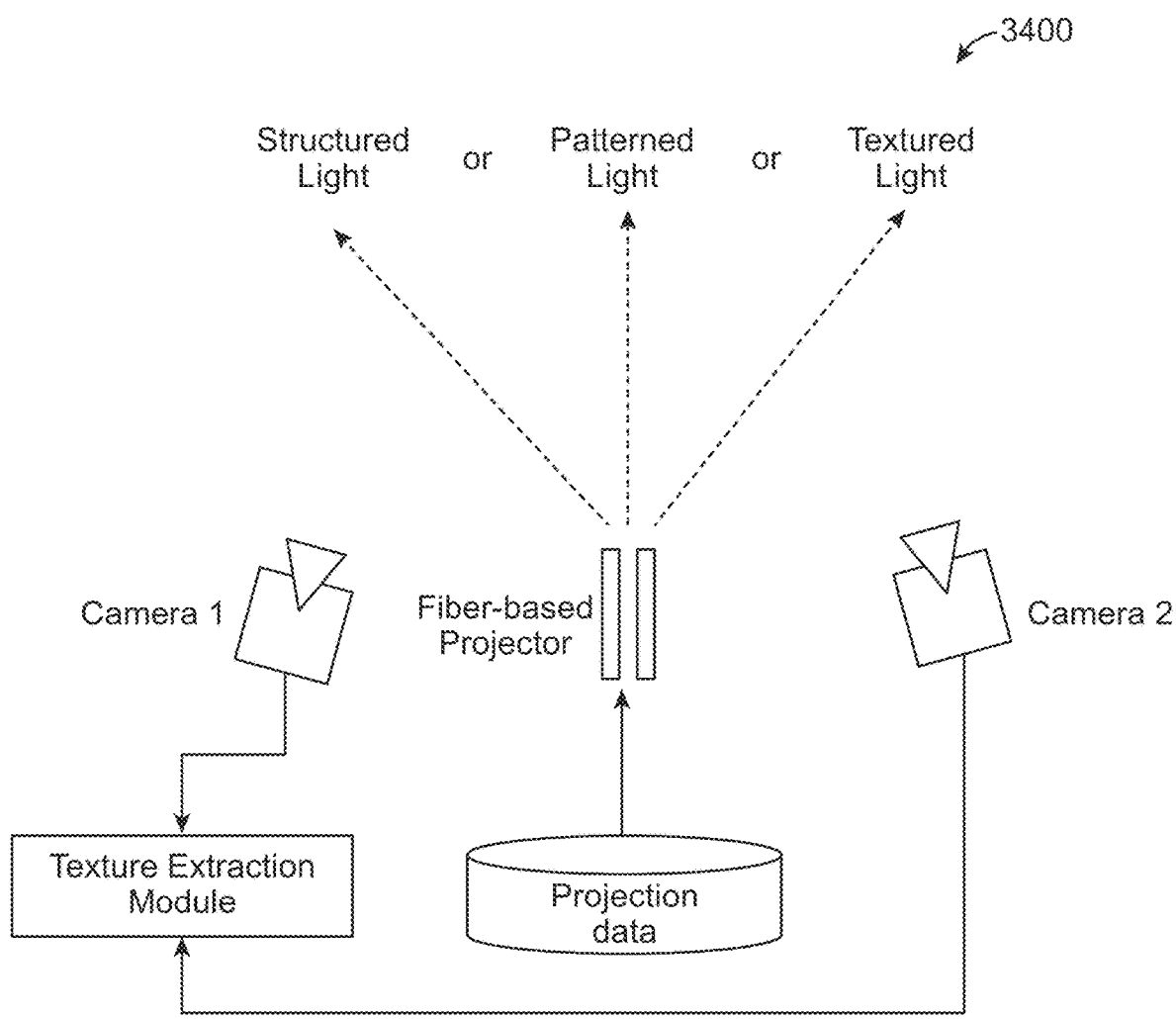
FIG. 34 is a schematic diagram illustrating system components to project textured surfaces, according to one illustrated embodiment.

Some embodiments of the present invention provide a framework for very efficiently and precisely describing the texture of a point, even in the absence of distinct feature points. FIG. 34 illustrates an example approach 3400 that can be taken to implement this aspect of embodiments of the invention. One or more fiber-based projectors are employed to project light that is visible to one or more cameras, such as camera 1 and/or camera 2.

In one embodiment, the fiber-based projector comprises a scanned fiber display scanner that projects a narrow beam of light back and forth at selected angles. The light may be projected through a lens or other optical element, which may be utilized to collect the angularly-scanned light and convert it to one or more bundles of rays.

The projection data to be projected by the fiber-based projector may comprise any suitable type of light. In some embodiments, the projection data comprises structured light having a series of dynamic known patterns, where successive light patterns are projected to identify individual pixels that can be individually addressed and textured. The projection data may also comprise patterned light having a pattern of points to be identified and textured. In yet another embodiment, the projection data comprises textured light, which does not necessarily need to comprise a recognizable pattern, but does include sufficient texture to distinctly identify points within the light data.

In operation, the one or more camera(s) are placed having a recognizable offset from the projector. The points are identified from the captured images from the one or more cameras, and triangulation is performed to determine the requisite location and depth information for the point. With the textured light approach, the textured light permits one to identify points even if there is already some texturing on the projected surface. This is implemented, for example, by having multiple cameras identifying the same point from the projection (either from the textured light or from a real-world object), and then triangulating the correct location and depth information for that identified point. This is advantageous over the structured light and patterned light approaches that realistically need for the projected data to be identifiable.

Using the fiber-based projector for this functionality provides numerous advantages. One advantage is that the fiber-based approach can be used to draw light data exactly where it is desired for texturing purposes. This allows the system to place the visible point exactly where it needs to be projected and/or seen by the camera(s). In effect, this permits a perfectly controllable trigger for a triggerable texture source for generating the texture data. This allows the system o very quickly and easily project and then find the desired point to be textured, and to then triangulate its position and depth.

Another advantage provided by this approach is that some fiber-based projectors are also capable of capturing images. Therefore, in this approach, the cameras can be integrated into projector apparatus, providing savings in terms of cost, device real estate, and power utilization. For example, when two fiber projectors/cameras are used, then this allows a first projector/camera to precisely project light data which is captured by the second projector/camera. Next, the reverse occurs, where the second projector/camera precisely projects the light data to be captured by the first projector/camera. Triangulation can then be performed for the captured data to generate texture information for the point.

As previously discussed, an AR system user may use a wearable structure having a display system positioned in front of the eyes of the user. The display is operatively coupled, such as by a wired lead or wireless connectivity, to a local processing and data module which may be mounted in a variety of configurations. The local processing and data module may comprise a power-efficient processor or controller, as well as digital memory, such as flash memory, both of which may be utilized to assist in the processing, caching, and storage of data a) captured from sensors which may be operatively coupled to the frame, such as image capture devices (such as cameras), microphones, inertial measurement units, accelerometers, compasses, GPS units, radio devices, and/or gyros; and/or b) acquired and/or processed using a remote processing module and/or remote data repository, possibly for passage to the display after such processing or retrieval.

The local processing and data module may be operatively coupled, such as via a wired or wireless communication links, to the remote processing module and remote data repository such that these remote modules are operatively coupled to each other and available as resources to the local processing and data module.

Figure 35:
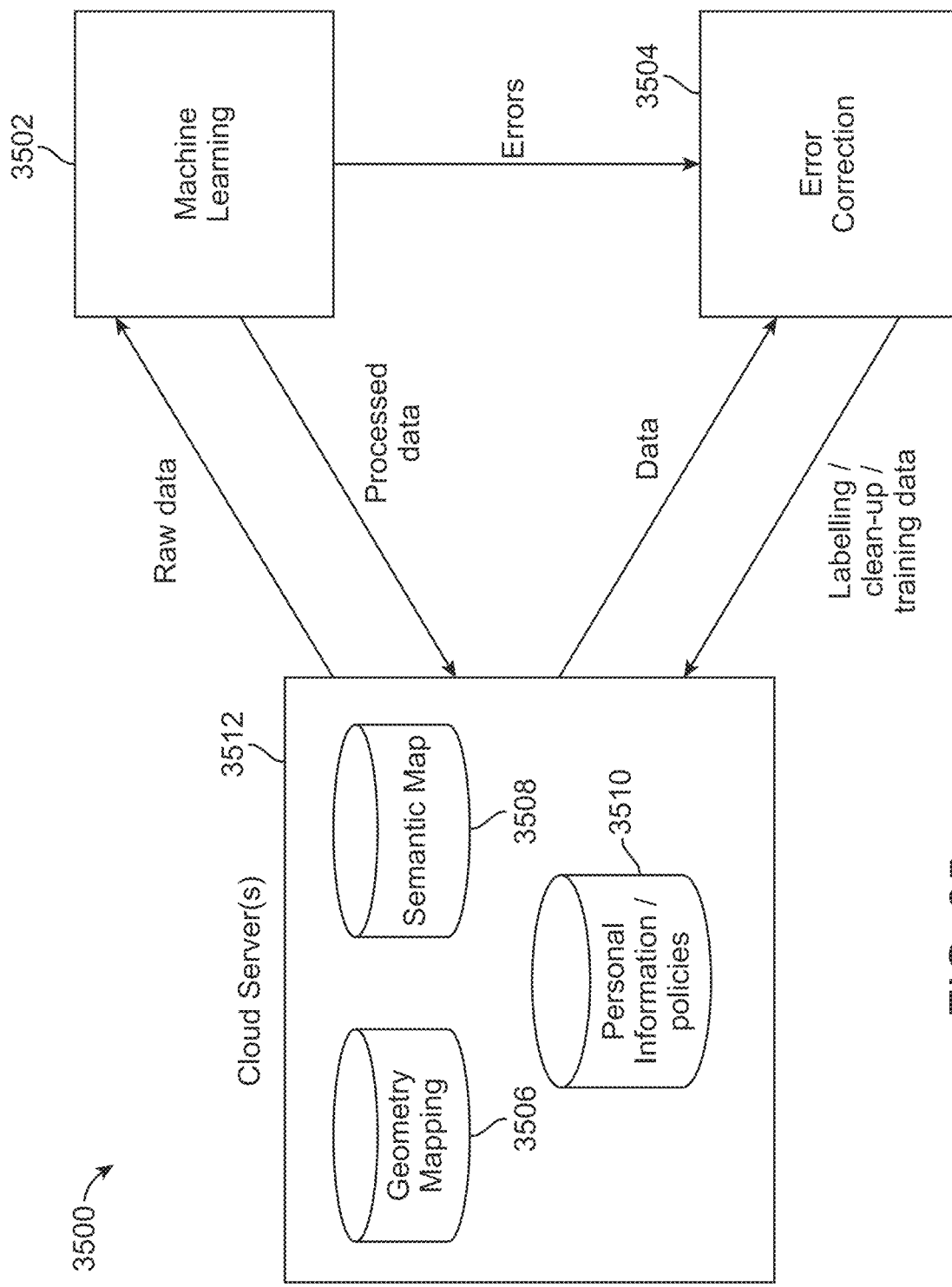
FIG. 35 is a plan view of an exemplary AR system illustrating an interaction between cloud servers, error correction module and a machine learning module, according to one illustrated embodiment.

In some cloud-based embodiments, the remote processing module may comprise one or more relatively powerful processors or controllers configured to analyze and process data and/or image information. FIG. 35 depicts an example architecture 3500 that can be used in certain cloud-based computing embodiments. The cloud-based server(s) 3512 can be implemented as one or more remote data repositories embodied as a relatively large-scale digital data storage facility, which may be available through the internet or other networking configuration in a cloud resource configuration.

Various types of content can be stored in the cloud-based repository. For example, data collected on the fly as the user is experiencing the system and operating in the world. The data may comprise images, data from sensors (such as inertial measurement, or "IMU" devices, which generally comprises accelerometer and gyro components), and surface information pertinent to objects in the real or virtual environment. The system may generate various types of data and metadata from the collected sensor data.

For example, geometry mapping data 3506 and semantic mapping data can be generated and stored within the cloud-based repository. Map data is a type of data that can be cloud-based, which may be a database containing map data for the world. In one embodiment, this data is entirely stored in the cloud. In another embodiment, this Map data partly resides on user-wearable components, and may partly reside at cloud storage locations accessible by wired or wireless network.

Cloud-based processing may be performed to process and/or analyze the data. For example, the semantic map comprise information that provides sematic content usable by the system, e.g., for objects and locations in the world being tracked by the Map. One or more remote servers can be used to perform the processing (e.g., machine learning processing) to analyze sensor data and to identify/generate the relevant semantic map data 3508. As another example, a Pose process may run to determine position and orientation of the wearable computing hardware or user.

This Pose processing can also be performed on a remote server. In one embodiment, the system processing is partially performed on cloud-based servers and partially performed on processors in the wearable computing architecture. In an alternate embodiment, the entirety of the processing is performed on the remote servers. Any suitable partitioning of the workload between the wearable device and the remote server (e.g., cloud-based server) may be implemented, with consideration of the specific work that is required, the relative available resources between the wearable and the server, and the network bandwith availability/requirements.

Cloud-based facilities may also be used to perform quality assurance processing and error corrections for the stored data. Such tasks may include, for example, error correction, labelling tasks, clean-up activities, and generation of training data. Automaton can be used at the remote server to perform these activities. Alternatively, remote "people resources" can also be employed, similar to the Mechanical Turk program provided by certain computing providers.

It should be appreciated that the mapping techniques (e.g., map point collection, pose determination, finding new map points, recognizing objects based on map points, creating the map/passable world model, etc.) described above form the basis of how one or more users interact with the AR system in their respective physical environments. Given that the AR system takes visual/audio/sensory data and converts it into map data to construct a virtual world or map of a virtual world that is stored in the cloud, the AR system is thus able to understand a location, orientation, placement and configuration of physical objects and can accordingly place virtual content in relation to the physical world.

This gives context and meaning to the virtual content that is generated on the user device. For example, rather than haphazardly displaying virtual content to the user (e.g., virtual content that is always displayed on the top left side of the screen, etc.), the AR system may now place virtual content at appropriate orientations/locations based on the user's field of view. For example, virtual content may be displayed on top of various physical objects. Thus, rather than displaying a monster right in the middle of the screen, the monster may appear to be standing on a physical object, for example. Mapping and knowing the real world thus provides a huge advantage in strategically displaying virtual content in a meaningful manner, thereby greatly improving user experience and interaction with the AR system.

Because the AR system is configured to continuously "know" the physical location and orientation of the user's surroundings, and given that the AR system is constantly collecting various types of data regarding the user's environment (e.g., FOV images, eye tracking data, sensory data, audio data, etc.) conventional types of user inputs may not be necessary. For example, rather than the user physically pressing a button or explicitly speaking a command, user input in the AR system may be automatically recognized.

For example, the system may automatically recognize a gesture made by the user's fingers. In another example, the AR system may recognize an input based on eye tracking data. Or, in another example, the AR system may recognize a location, and automatically use that as user input to display virtual content. One important type of user input is gesture recognition in order to perform an action or display virtual content, as will be described below.

Gestures

In some implementations, the AR system may detect and be responsive to one or more finger/hand gestures. These gestures can take a variety of forms and may, for example, be based on inter-finger interaction, pointing, tapping, rubbing, etc. Other gestures may, for example, include 2D or 3D representations of characters (e.g., letters, digits, punctuation). To enter such, a user swipes their finger in the defined character pattern. Other gestures may include thumb/wheel selection type gestures, which may, for example be used with a "popup" circular radial menu which may be rendered in a field of view of a user, according to one illustrated embodiment.

Embodiments of the AR system can therefore recognize various commands using gestures, and in response perform certain functions mapped to the commands. The mapping of gestures to commands may be universally defined, across many users, facilitating development of various applications which employ at least some commonality in user interface. Alternatively or additionally, users or developers may define a mapping between at least some of the gestures and corresponding commands to be executed by the AR system in response to detection of the commands.

For example, a pointed index finger may indicate a command to focus, for example to focus on a particular portion of a scene or virtual content at which the index finger is pointed. A pinch gesture can be made with the tip of the index finger touching a tip of the thumb to form a closed circle, e.g., to indicate a grab and/or copy command. Another example pinch gesture can be made with the tip of the ring finger touching a tip of the thumb to form a closed circle, e.g., to indicate a select command.

Yet another example pinch gesture can be made with the tip of the pinkie finger touching a tip of the thumb to form a closed circle, e.g., to indicate a back and/or cancel command. A gesture in which the ring and middle fingers are curled with the tip of the ring finger touching a tip of the thumb may indicate, for example, a click and/or menu command. Touching the tip of the index finger to a location on the head worn component or frame may indicate a return to home command.

Figure 36A:
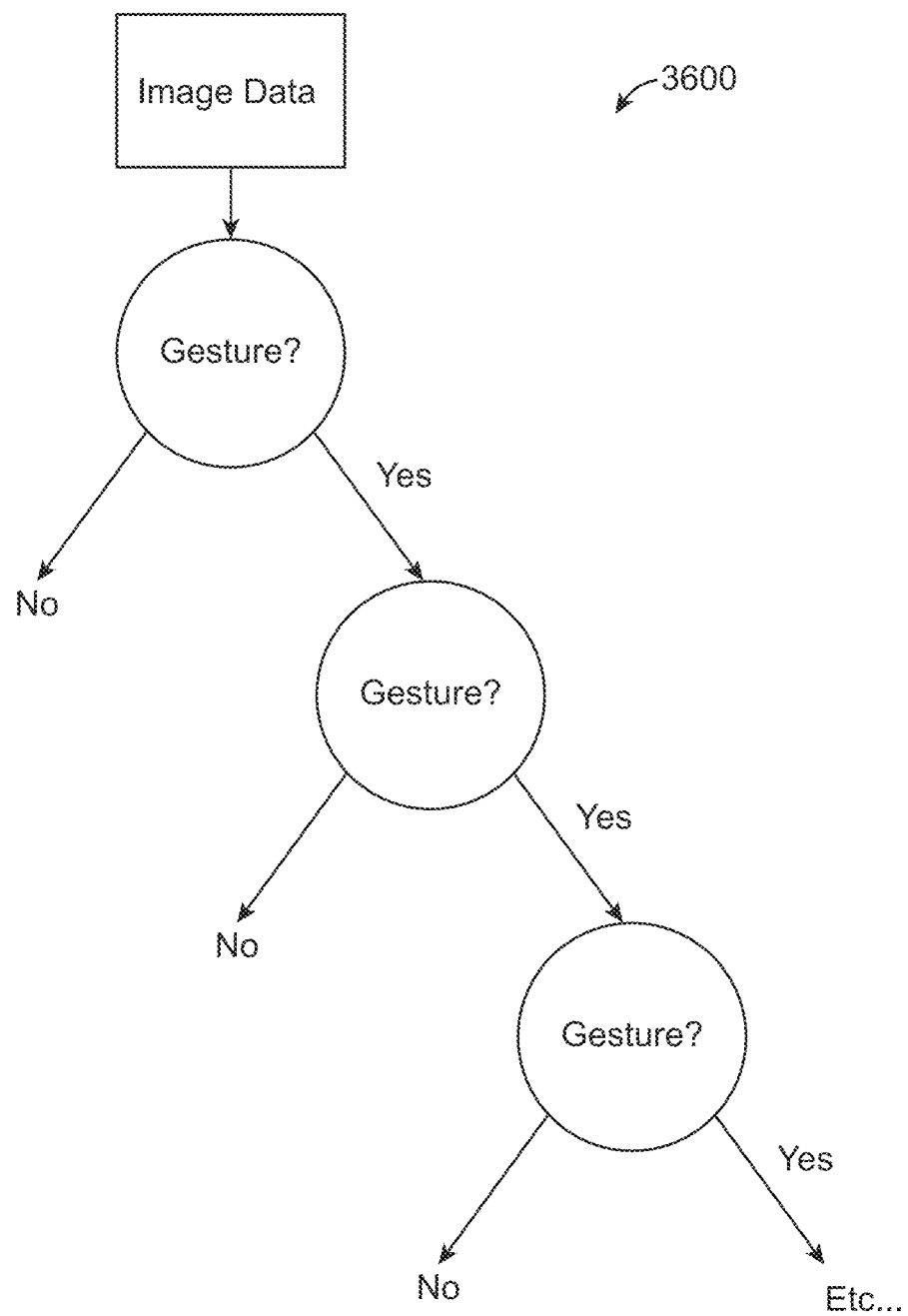
FIGS. 36A-36I are schematic diagrams illustrating gesture recognition, according to one illustrated embodiment.

Embodiments of the invention provide an advanced system and method for performing gesture tracking and identification. In one embodiment, a rejection cascade approach is performed, where multiple stages of gesture analysis is performed upon image data to identify gestures. As shown in the cascade 3600 of FIG. 36A, incoming images (e.g., an RGB image at a depth D) is processed using a series of permissive analysis nodes. Each analysis node performed a distinct step of determining whether the image is identifiable as a gesture.

Each stage in this process performs a targeted computation so that the sequence of different in its totality can be used to efficiently perform the gesture processing. This means, for example, that the amount of processing power at each stage of the process, along with the sequence/order of the nodes, can be used to optimize the ability to remove non-gestures while doing so with minimal computational expenses. For example, computationally less-expensive algorithms may be applied in the earlier stages to remove large numbers of "easier" candidates, thereby leaving smaller numbers of "harder" data to be analyzed in later stages using more computationally expensive algorithms.

Figure 36B:
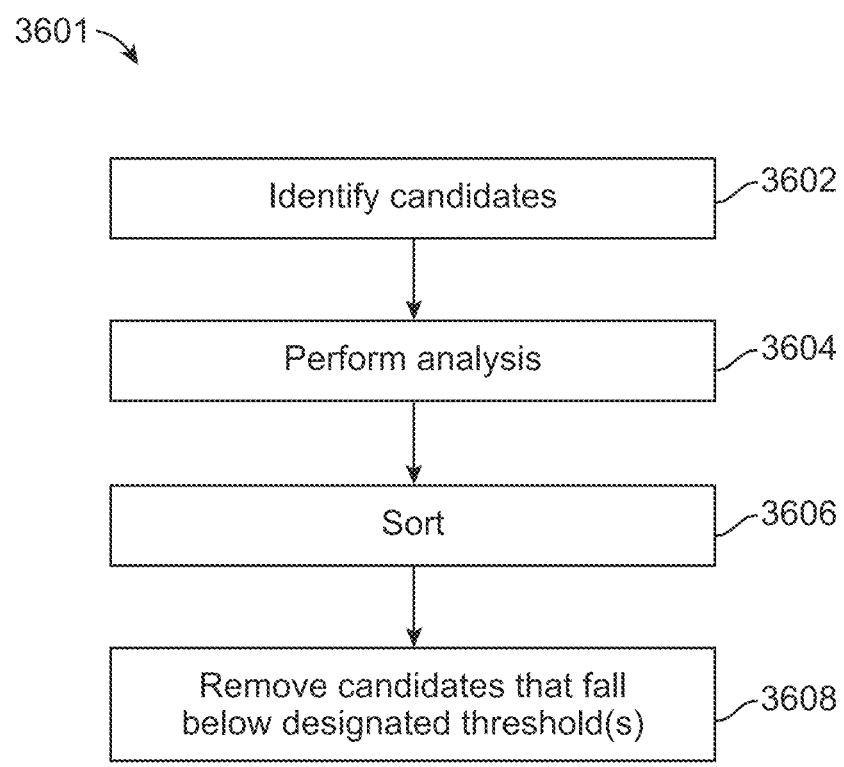

The general approach to perform this type of processing in one embodiment is shown in the flowchart 3601 of FIG. 36B. The first step is to generate candidates for the gesture processing (step 3602). These include, for example, images captured from sensor measurements of the wearable device, e.g., from camera(s) mounted on the wearable device. Next, analysis is performed on the candidates to generate analysis data (step 3604). For example, one type of analysis may be to check on whether the contour of the shapes (e.g., fingers) in the image is sharp enough. Sorting is then performed on the analyzed candidates (step 3606). Finally, any candidate that corresponds to a scoring/analysis value that is lower than a minimum threshold is removed from consideration (step 3608).

Figure 36C:
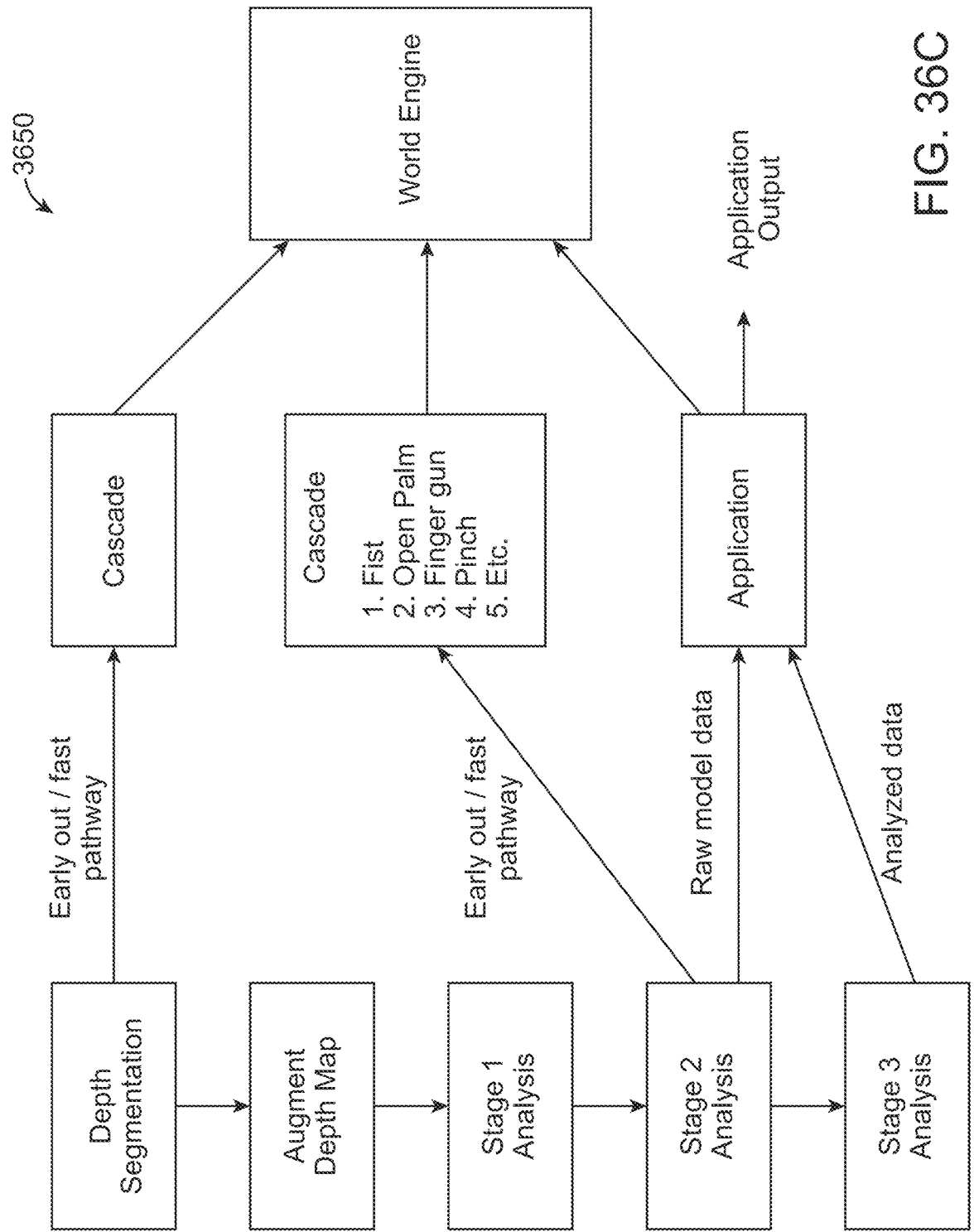
Figure 36D:
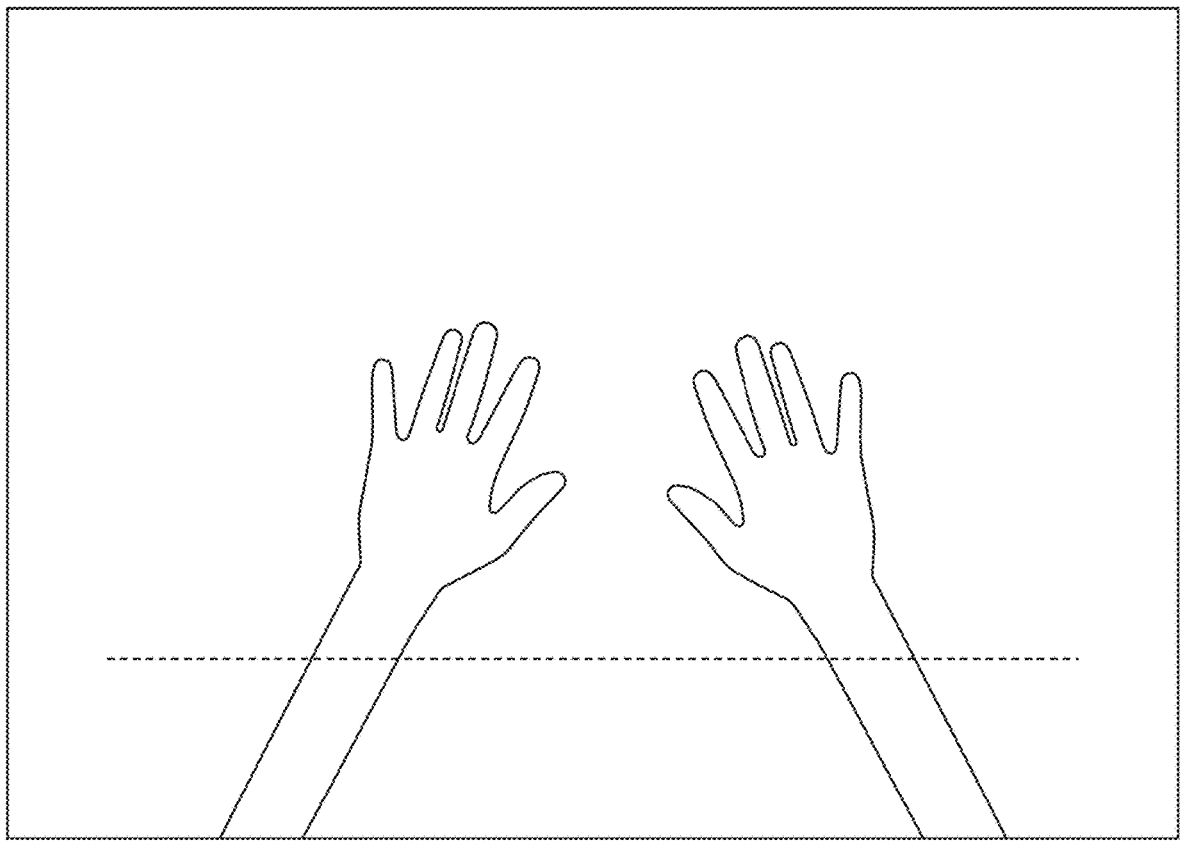

FIG. 36C depicts a more detailed approach 3650 for gesture analysis according to one embodiment of the invention. The first action is to perform depth segmentation upon the input data. For example, typically the camera providing the data inputs (e.g., the camera producing RGB+depth data) will be mounted on the user's head, where the camera FOV (field of view) will cover the range in which the human could reasonably perform gestures. As shown in illustration 3660 of FIG. 36D, a line search can be performed through the data (e.g., from the bottom of the FOV).

If there are identifiable points along that line, then potentially a gesture has been identified. Performing this analysis over a series of lines can be used to generate the depth data. In some embodiment, this type of processing can be quite sparse—perhaps where 50 points are acquired relatively really quickly. Of course, different kinds of line series can be employed, e.g., in additional to or instead of flat lines across the bottom, smaller diagonal lines are employed in the area where there might be a hand/arm.

Any suitable pattern may be employed, selecting ones that are most effective at detecting gestures. In some embodiments, a confidence-enhanced depth map is obtained, where the data is flood filled from cascade processing where a "flood feel" is performed to check for and filter whether the identified object is really a hand/arm. The confidence enhancement can be performed, for example, by getting a clear map of the hand and then checking for the amount of light is reflected off the hand in the images to the sensor, where the greater amount of light corresponds to a higher confidence level to enhance the map.

From the depth data, one can cascade to perform immediate/fast processing, e.g., where the image data is amenable to very fast recognition of a gesture. This works best for very simple gestures and/or hand/finger positions.

In many cases, deeper processing is to be performed to augment the depth map. For example, one type of depth augmentation is to perform depth transforms upon the data. Another type of augmentation is to check for geodesic distances from specified point sets, such as boundaries, centroids, etc. For example, from a surface location, a determination is made of the distance to various points on the map. This attempts to find, for example, the farthest point to the tip of the fingers (by finding the end of the fingers). The point sets may be from the boundaries (e.g., outline of hand) or centroid (e.g., statistical central mass location).

Figure 36E:
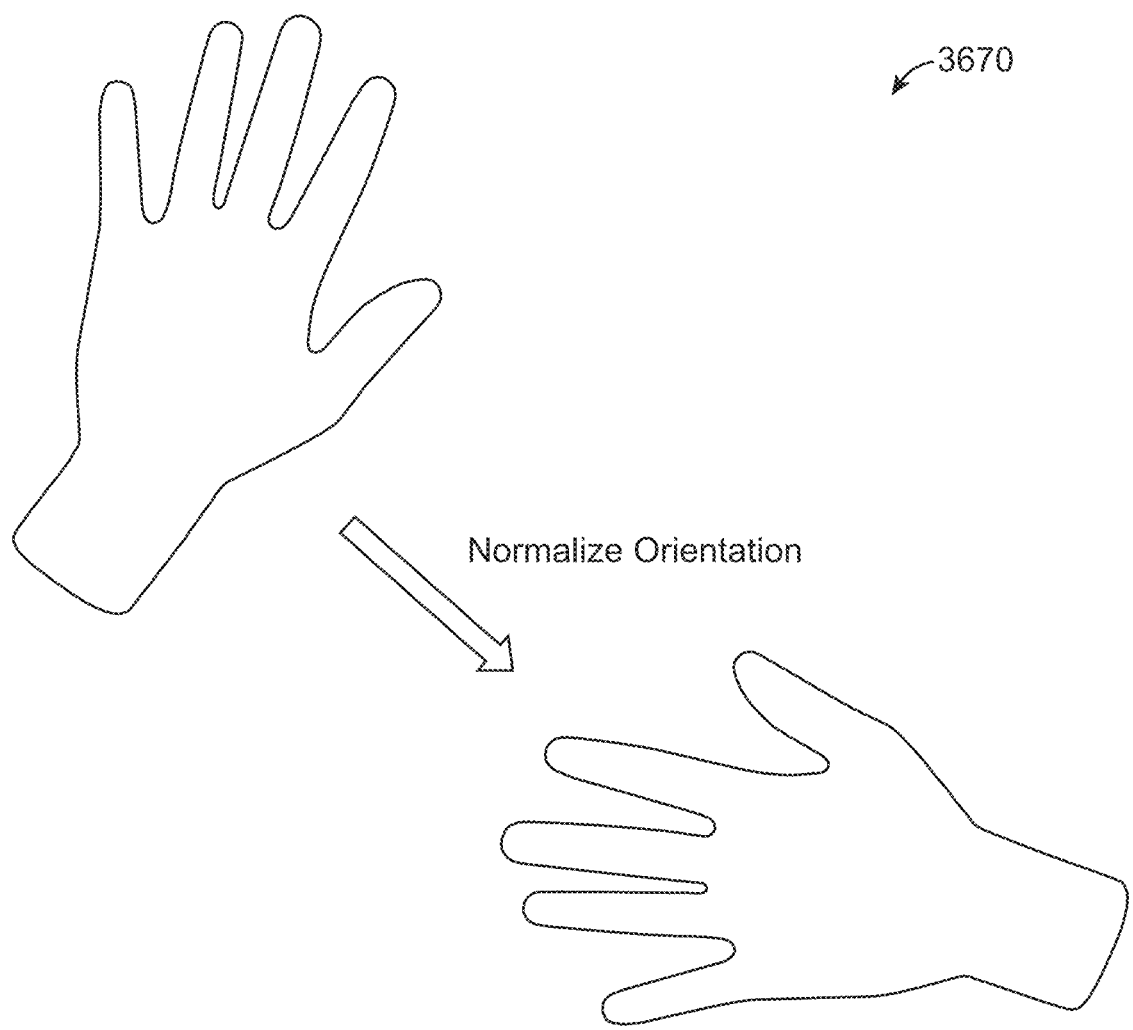

Surface normalization may also be calculated. In addition, curvatures may also be estimated, which identifies how fast a contour turns—and to perform a filtering process to go over the points and removing concave points from fingers. In some embodiments, orientation normalization may be performed on the data. To explain, consider that a given image of the hand may be captured with the hand in different positions. However, the analysis may be expecting a canonical position of the image data of the hand. In this situation, as shown in illustration 3670 of FIG. 36E, the mapped data may be re-oriented to change to a normalized/canonical hand position.

Figure 36F:
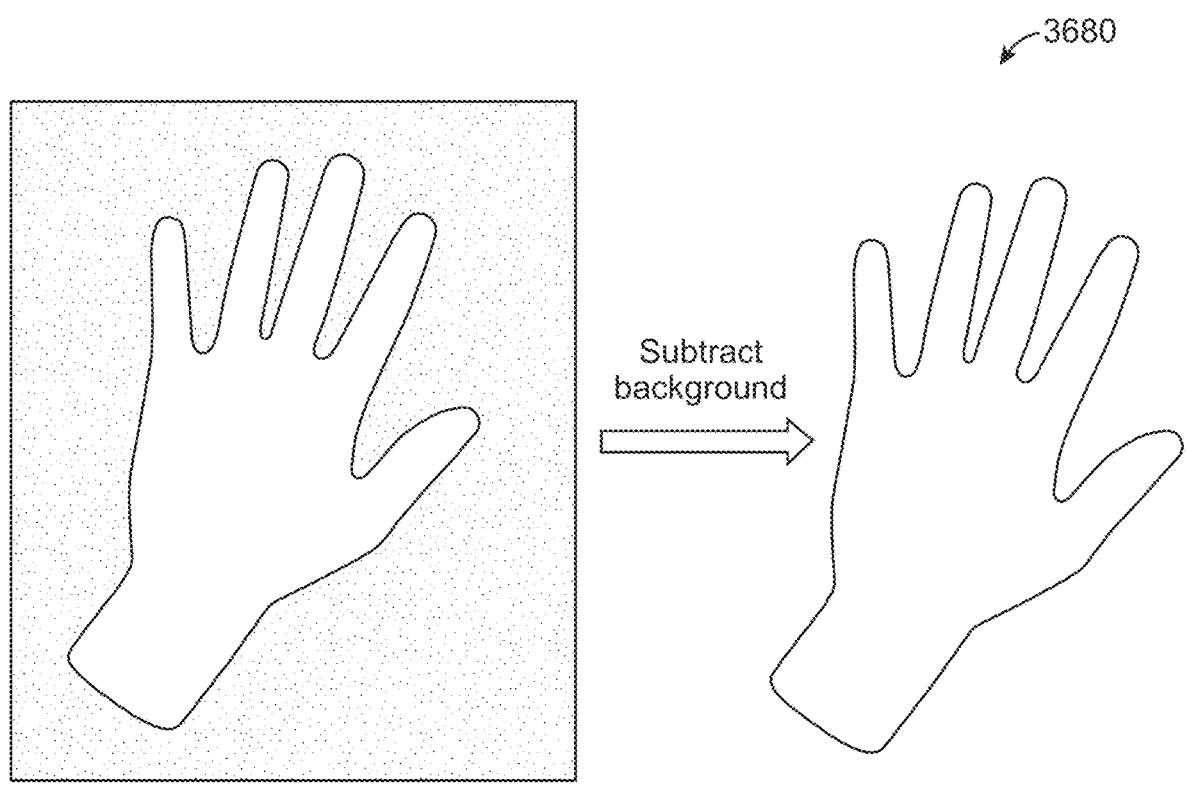

One advantageous approach in some embodiments of invention is to perform background subtraction on the data. In many cases, a known background exists in a scene, e.g., the pattern of a background wall. In this situation, the map of the object to be analyzed can be enhanced by removing the background image data. An example of this process is shown in illustration 3680 of FIG. 36F, where the left portion of the figure shows an image of a hand over some background image data. The right-hand portion of the figure shows the results of removing the background from the image, leaving the augmented hand data with increased clarity and focus.

Figure 36G:
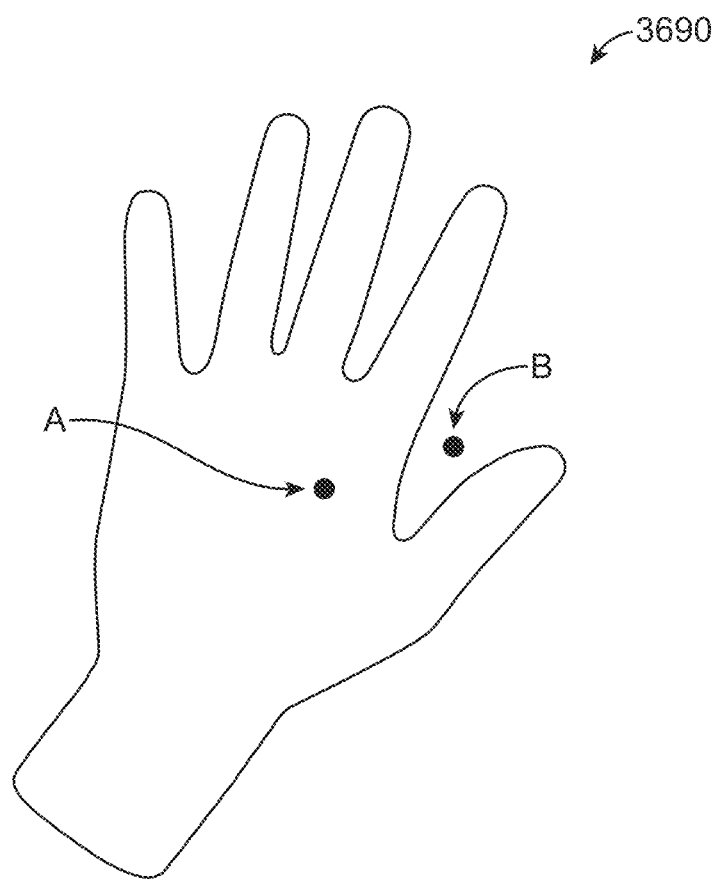

Depth comparisons may also be performed upon points in the image to identify the specific points that pertain to the hand (as opposed to the background non-hand data). For example, as shown in illustration 3690 of FIG. 36G, it can be seen a first point A is located at a first depth and a second point B is located at a significantly different second depth.

In this situation, the difference in the depths of these two points makes it very evident that they likely belong to different objects. Therefore, if one knows that the depth of the hand is at the same depth value as point A, then one can conclude that point A is part of the hand. On the other hand, since the depth value for point B is not the same as the depth of the hand, then one can readily conclude that point B is not part of the hand.

At this point a series of analysis stages is performed upon the depth map. Any number of analysis stages can be applied to the data. The present embodiment shows three stages, but one of ordinary skill in the art would readily understand that any other number of stages (either smaller or larger) may be used as appropriate for the application to which the invention is applied.

In the current embodiment, stage 1 analysis is performed using a classifier mechanism upon the data. For example, a classification/decision forest can be used to apply a series of yes/no decisions in the analysis to identify the different parts of the hand for the different points in the mapping.

This identifies, for example, whether a particular point belongs to the palm portion, back of hand, non-thumb finger, thumb, fingertip, and/or finger joint. Any suitable classifier can be used for this analysis stage. For example, a deep learning module or a neural network mechanism can be used instead of or in addition to the classification forest. In addition, a regression forest (e.g., using a Hough transformation) can be used in addition to the classification forest.

Figure 36H:
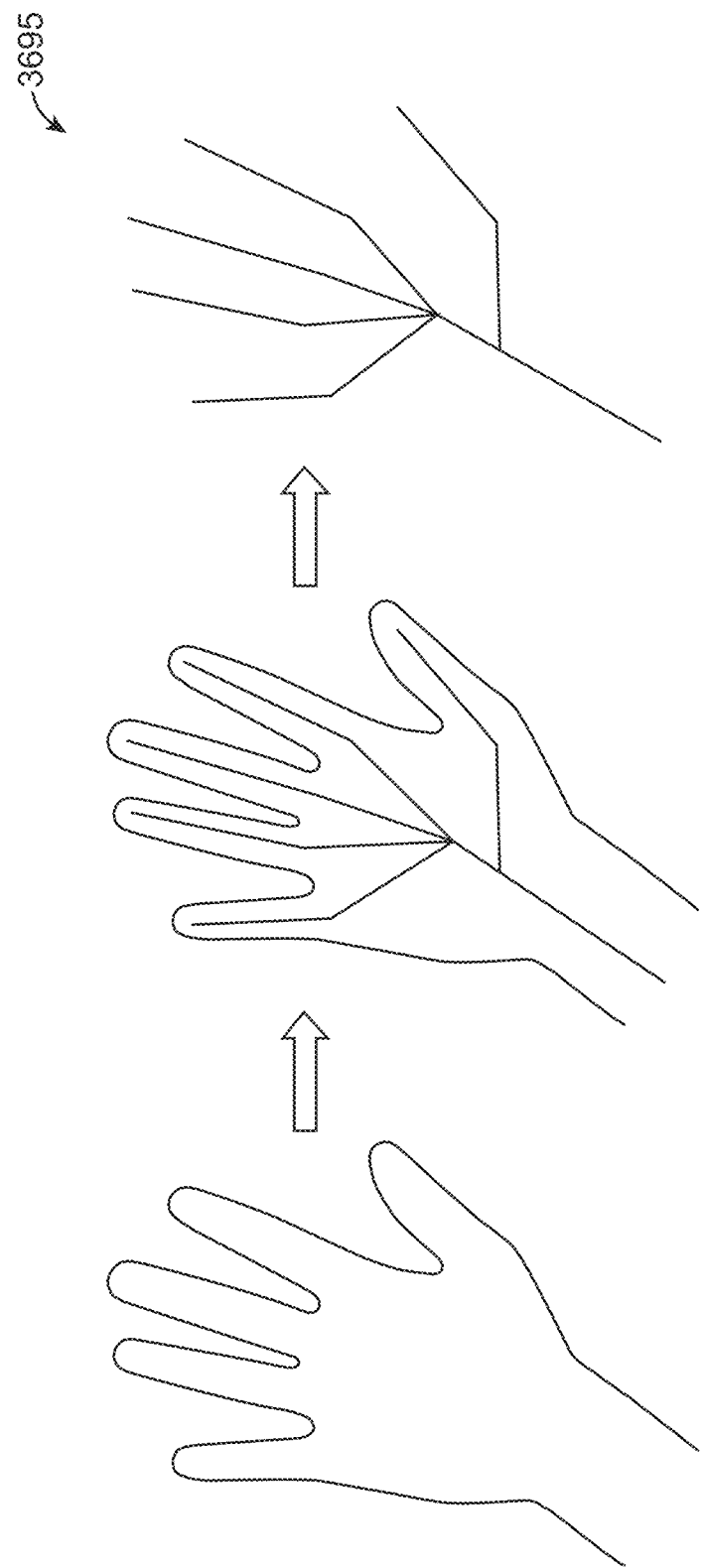

The next stage of analysis (stage 2) can be used to further analysis the mapping data. For example, analysis can be performed to identify joint locations, articular, or to perform skeletonization on the data. Illustration 3695 of FIG. 36H provides an illustration of skeletonization, where an original map of the hand data is used to identify the locations of bones/joints within the hand, resulting in a type of "stick" figure model of the hand/hand skeleton. This type of model provides with clarity a very distinct view of the location of the fingers and the specific orientation and/or configuration of the hand components. Labelling may also be applied at this stage to the different parts of the hand.

Figure 36I:
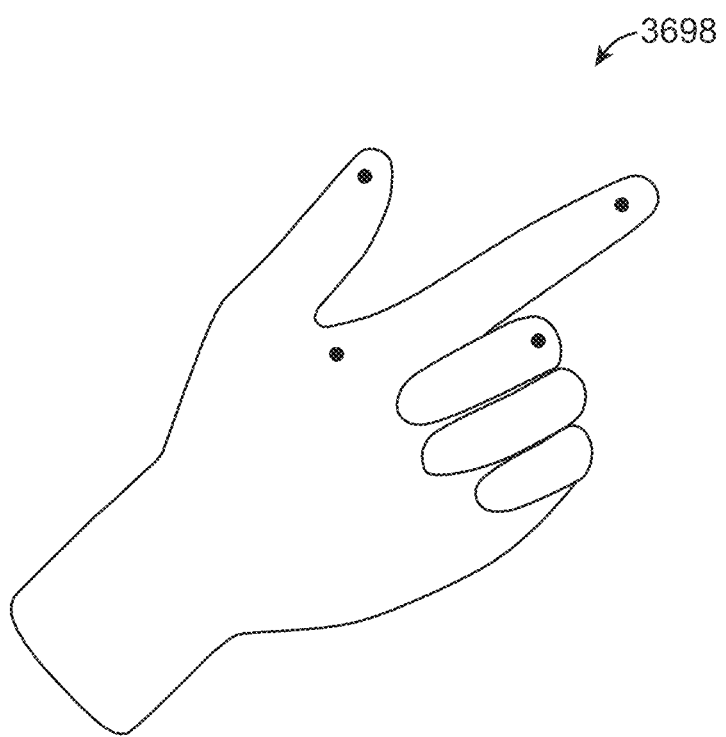

At this point, it is possible that the data is now directly consumable by a downstream application without requiring any further analysis. Thus may occur, for example, if the downstream application itself includes logic to perform additional analysis/computations upon the model data. In addition, the system can also optionally cascade to perform immediate/fast processing, e.g., where the data is amenable to very fast recognition of a gesture, such as the (1) first gesture; (2) open palm gesture; (3) finger gun gesture; (4) pinch; etc. For example, as shown in illustration 3698 of FIG. 36I, various points on the hand mapping (e.g., point on extended thumb and point on extended first finger) can be used to immediately identify a pointing gesture. The outputs will then proceed to a world engine, e.g., to take action upon a recognized gesture.

In addition, deeper processing can be performed in the stage 3 analysis. This may involve, for example, using a decision forest/tree to classify the gesture. This additional processing can be used to identify the gesture, determine a hand pose, identify context dependencies, and/or any other information as needed.

Prior/control information can be applied in any of the described steps to optimize processing. This permits some biasing for the analysis actions taken in that stage of processing. For example, for game processing, previous action taken in the game can be used to bias the analysis based upon earlier hand positions/poses. In addition, a confusion matrix can be used to more accurately perform the analysis.

Figure 37:
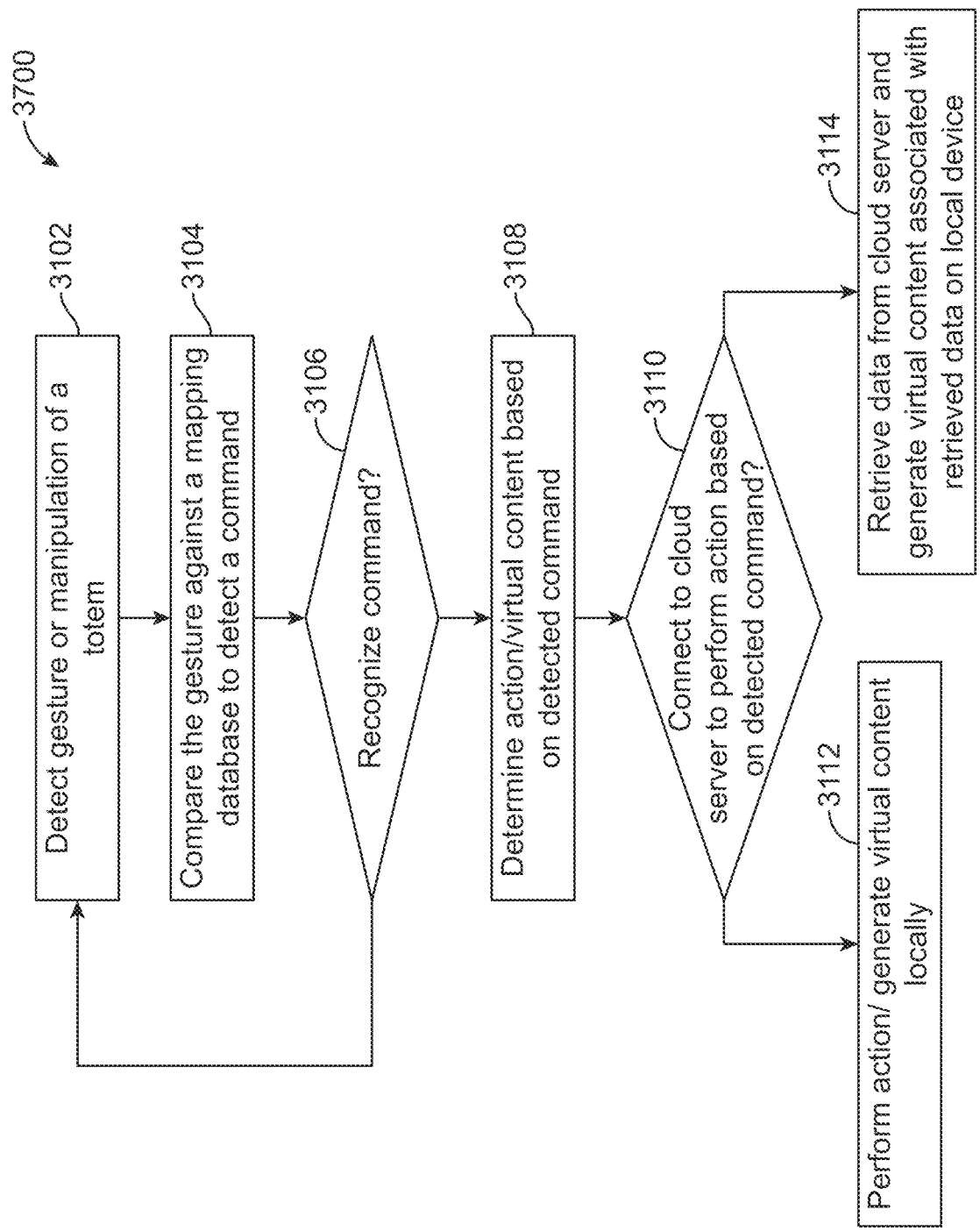
FIG. 37 is a process flow diagram of an exemplary method of performing an action based on a recognized gesture, according to one illustrated embodiment.

Using the principles of gesture recognition discussed above, the AR system may use visual input gathered from the user's FOV cameras and recognize various gestures that may be associated with a predetermined command or action. Referring now to flowchart 3700 of FIG. 37, in step 3102, the AR system may detect a gesture as discussed in detail above.

As described above, the movement of the fingers or a movement of the totem may be compared to a database to detect a predetermined command, in step 3104. If a command is detected, the AR system determines the desired action and/or desired virtual content based on the gesture, in step 3108. If the gesture or movement of the totem does not correspond to any known command, the AR system simply goes back to detecting other gestures or movements to step 3102.

In step 3108, the AR system determines the type of action necessary in order to satisfy the command. For example, the user may want to switch an application, or may want to turn a page, may want to generate a user interface, may want to connect to a friend located at another physical location, etc. Based on the desired action/virtual content, the AR system determines whether to retrieve information from the cloud servers, or whether the action can be performed using local resources on the user device, in step 3110.

For example, if the user simply wants to turn a page of a virtual book, the required data may already have been downloaded or may reside entirely on the local device, in which case, the AR system simply retrieves data associated with the next page and may display the next page to the user. Similarly, if the user wants to create a user interface such that the user can draw a picture in the middle of space, the AR system may simply generate a virtual drawing surface in the desired location without needing data from the cloud.

Data associated with many applications and capabilities may be stored on the local device such that the user device does not need to unnecessarily connect to the cloud or access the passable world model. Thus, if the desired action can be performed locally, local data may be used to display virtual content corresponding to the detected gesture (step 3112).

Alternatively, in step 3114, if the system needs to retrieve data from the cloud or the passable world model, the system may send a request to the cloud network, retrieve the appropriate data and send it back to the local device such that the action or virtual content may be appropriated displayed to the user. For example, if the user wants to connect to a friend at another physical location, the AR system may need to access the passable world model to retrieve the necessary data associated with the physical form of the friend in order to render it accordingly at the local user device.

Thus, based on the user's interaction with the AR system, the AR system may create many types of user interfaces as desired by the user. The following represent some exemplary embodiments of user interfaces that may be created in a similar fashion to the exemplary process described above.

It should be appreciated that the above process is simplified for illustrative purposes, and other embodiments may include additional steps based on the desired user interface. The following discussion goes through various types of finger gestures, that may all be recognized and used such that the AR system automatically performs an action and/or presents virtual content to the user that is either derived from the cloud or retrieved locally.

Finger Gestures

Finger gestures can take a variety of forms and may, for example, be based on inter-finger interaction, pointing, tapping, rubbing, etc.

Other gestures may, for example, include 2D or 3D representations of characters (e.g., letters, digits, punctuation). To enter such, a user swipes their finger in the defined character pattern. In one implementation of a user interface, the AR system renders three circles, each circle with specifically chosen characters (e.g., letters, digits, punctuation) arranged circumferentially around the periphery. The user can swipe through the circles and letters to designate a character selection or input. In another implementation, the AR system renders a keyboard (e.g., QWERTY keyboard) low in the user's field of view, proximate a position of the user's dominate hand in a bent-arm position. The user can than perform a swipe-like motion through desired keys, and then indicate that the swipe gesture selection is complete by performing another gesture (e.g., thumb-to-ring finger gesture) or other proprioceptive interaction.

Other gestures may include thumb/wheel selection type gestures, which may, for example be used with a "popup" circular radial menu which may be rendered in a field of view of a user, according to one illustrated embodiment.

Figure 38:
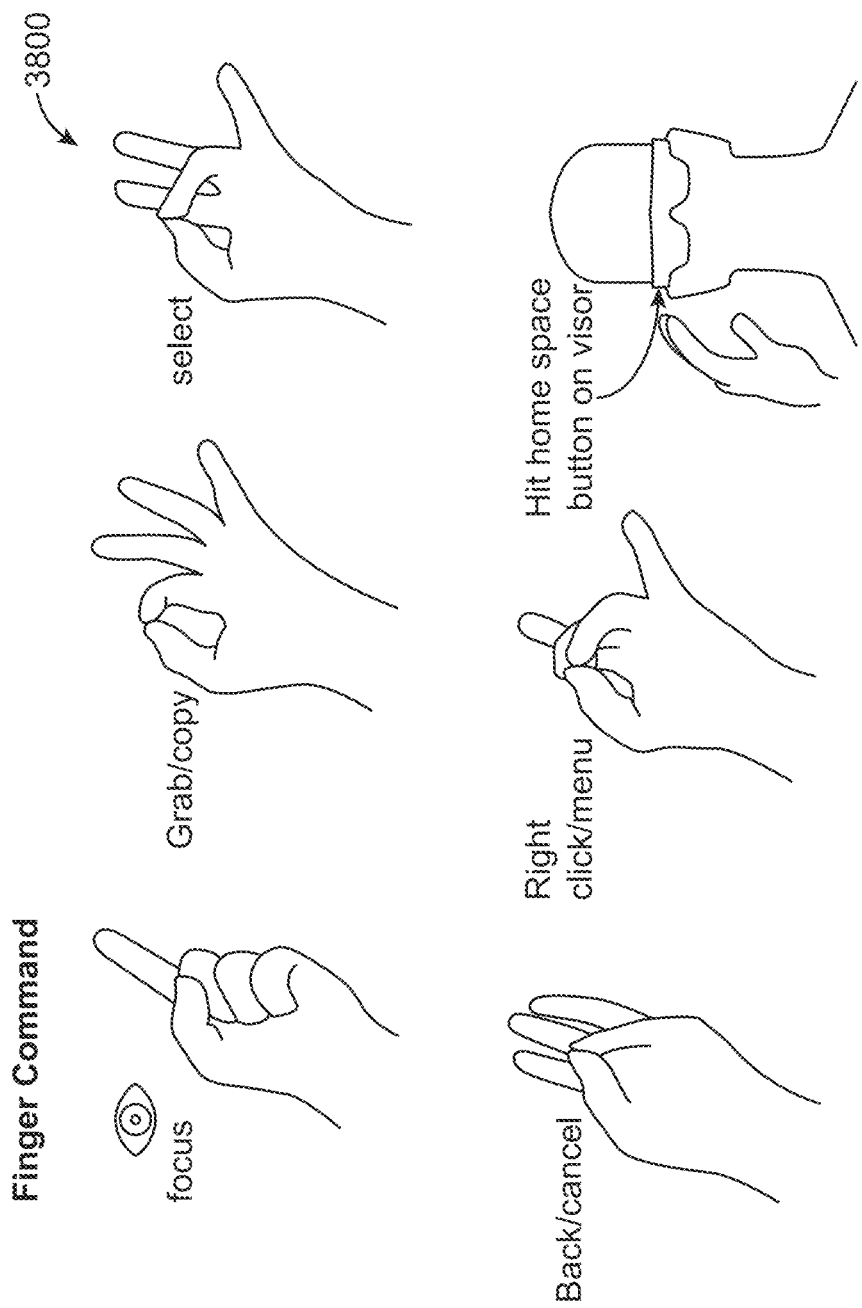
FIG. 38 is a plan view illustrating various finger gestures, according to one illustrated embodiment.

Gestures 3800 of FIG. 38 shows a number of additional gestures. The AR system recognizes various commands, and in response performs certain functions mapped to the commands. The mapping of gestures to commands may be universally defined, across many users, facilitating development of various applications which employ at least some commonality in user interface. Alternatively or additionally, users or developers may define a mapping between at least some of the gestures and corresponding commands to be executed by the AR system in response to detection of the commands.

In the top row left-most position, a pointed index finger may indicate a command to focus, for example to focus on a particular portion of a scene or virtual content at which the index finger is pointed. In the top row middle position, a first pinch gesture with the tip of the index finger touching a tip of the thumb to form a closed circle may indicate a grab and/or copy command. In the top row right-most position, a second pinch gesture with the tip of the ring finger touching a tip of the thumb to form a closed circle may indicate a select command.

In the bottom row left-most position, a third pinch gesture with the tip of the pinkie finger touching a tip of the thumb to form a closed circle may indicate a back and/or cancel command. In the bottom row middle position, a gesture in which the ring and middle fingers are curled with the tip of the ring finger touching a tip of the thumb may indicate a click and/or menu command. In the bottom row right-most position, touching the tip of the index finger to a location on the head worn component or frame may indicate a return to home command. Such may cause the AR system to return to a home or default configuration, for example displaying a home or default menu.

It should be appreciated that there may be many more types of user input not limited to the ones discussed above. For example, the system may measure neurological signals and use that as an input for the system. The system may have a sensor that tracks brain signals and map it against a table of commands. In other words, the user input is simply the user's thoughts, that may be measured by the user's brain signals. This may also be referred to as subvocalization sensing. Such a system may also include apparatus for sensing EEG data to translate the user's "thoughts" into brain signals that may be decipherable by the system.

Totems

Similar to the above process where the AR system is configured to recognize various gestures and perform actions based on the gestures, the user may also use totems, or designated physical objects to control the AR system, or otherwise provide input to the system.

The AR system may detect or capture a user's interaction via tracking (e.g., visual tracking) of a totem. Numerous types of totems may be employed in embodiments of the invention, including for example:

Existing Structures
Actively Marked Totems
Passively Marked Totems
Camera/Sensor Integration
Totem Controller Object Any suitable existing physical structure can be used as a totem. For example, in gaming applications, a game object (e.g., tennis racket, gun controller, etc.) can be recognized as a totem. One or more feature points can be recognized on the physical structure, providing a context to identify the physical structure as a totem. Visual tracking can be performed of the totem, employing one or more cameras to detect a position, orientation, and/or movement (e.g., position, direction, distance, speed, acceleration) of the totem with respect to some reference frame (e.g., reference frame of a piece of media, the real world, physical room, user's body, user's head).

Actively marked totems comprise some sort of active lighting or other form of visual identification. Examples of such active marking include (a) flashing lights (e.g., LEDs); (b) lighted pattern groups; (c) reflective markers highlighted by lighting; (d) fiber-based lighting; (e) static light patterns; and/or (f) dynamic light patterns. Light patterns can be used to uniquely identify specific totems among multiple totems.

Passively marked totems comprise non-active lighting or identification means. Examples of such passively marked totems include textured patterns and reflective markers.

The totem can also incorporate one or more cameras/sensors, so that no external equipment is need to track the totem. Instead, the totem will track itself and will provide its own location, orientation, and/or identification to other devices. The on-board camera are used to visually check for feature points, to perform visual tracking to detect a position, orientation, and/or movement (e.g., position, direction, distance, speed, acceleration) of the totem itself and with respect to a reference frame. In addition, sensors mounted on the totem (such as a GPS sensor or accelerometers) can be used to detect the position and location of the totem.

A totem controller object is a device that can be mounted to any physical structure, and which incorporates functionality to facilitate tracking/identification of the totem. This allows any physical structure to become a totem merely by placing or affixing the totem controller object to that physical structure. The totem controller object may be a powered object that includes a battery to power electronics on the object. The totem controller object may include communications, e.g., wireless communications infrastructure such as an antenna and wireless networking modem, to exchange messages with other devices. The totem controller object may also include any active marking (such as LEDs or fiber-based lighting), passive marking (such as reflectors or patterns), or cameras/sensors (such as cameras, GPS locator, or accelerometers).

As briefly described above, totems may be used to, for example, to provide a virtual user interface. The AR system may, for example, render a virtual user interface to appear on the totem.

The totem may take a large variety of forms. For example, the totem may be an inanimate object. For instance, the totem may take the form of a piece or sheet of metal (e.g., aluminum). A processor component of an individual AR system, for instance a belt pack, may serve as a totem.

The AR system may, for example, replicate a user interface of an actual physical device (e.g., keyboard and/or trackpad of a computer, a mobile phone) on what is essentially a "dumb: totem. As an example, the AR system may render the user interface of an Android® phone onto a surface of an aluminum sheet. The AR system may detect interaction with the rendered virtual user interface, for instance via a front facing camera, and implement functions based on the detected interactions.

For example, the AR system may implement one or more virtual actions, for instance render an updated display of Android® phone, render video, render display of a Webpage. Additionally or alternatively, the AR system may implement one or more actual or non-virtual actions, for instance send email, send text, and/or place a phone call. This may allow a user to select a desired user interface to interact with from a set of actual physical devices, for example various models of iPhones, iPads, Android based smartphones and/or tablets, or other smartphones, tablets, or even other types of appliances which have user interfaces such as televisions, DVD/Blu-ray players, thermostats, etc.

Thus a totem may be any object on which virtual content can be rendered, including for example a body part (e.g., hand) to which virtual content can be locked in a user experience (UX) context. In some implementations, the AR system can render virtual content so as to appear to be coming out from behind a totem, for instance appearing to emerge from behind a user's hand, and slowly wrapping at least partially around the user's hand. The AR system detects user interaction with the virtual content, for instance user finger manipulation with the virtual content which wrapped partially around the user's hand.

Alternatively, the AR system may render virtual content so as to appear to emerge from a palm of the user's hand, and detection user fingertip interaction or manipulate of that virtual content. Thus, the virtual content may be locked to a reference from of a user's hand. The AR system may be responsive to various user interactions or gestures, including looking at some item of virtual content, moving hands, touching hands to themselves or to the environment, other gestures, opening and/or closing eyes, etc.

As described herein, the AR system may employ body center rendering, user center rendering, propreaceptic tactile interactions, pointing, eye vectors, totems, object recognizers, body sensor rendering, head pose detection, voice input, environment or ambient sound input, and the environment situation input.

Figure 39:
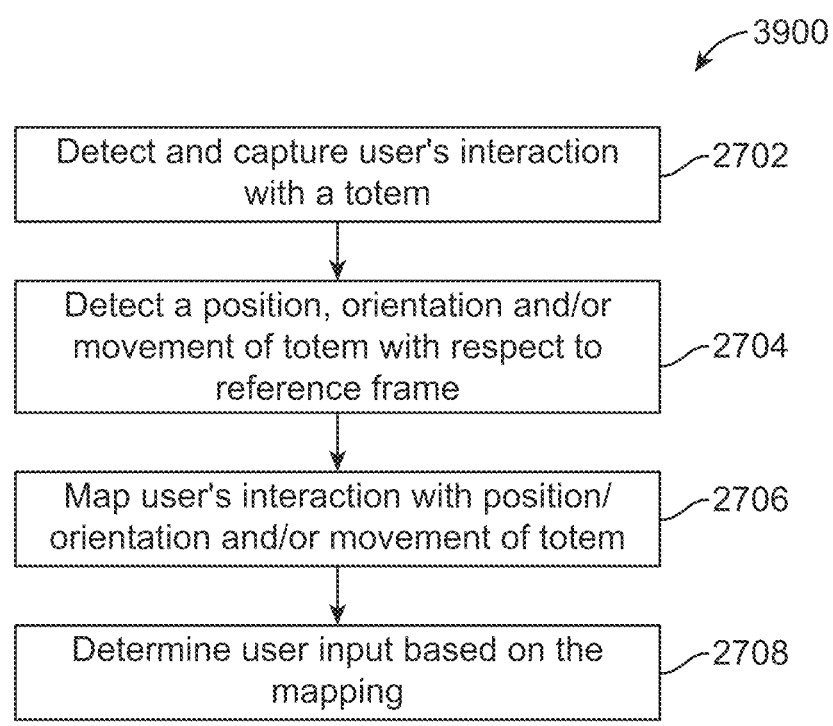
FIG. 39 is a process flow diagram of an exemplary method of determining user input based on a totem, according to one illustrated embodiment.

Referring now to flowchart 3900 of FIG. 39, an exemplary process of detecting a user input through a totem is described. In step 2702, the AR system may detect a motion of a totem. It should be appreciated that the user may have already designated one or more physical objects as a totem during set-up, for example. The user may have multiple totems. For example, the user may have designated one totem for a social media application, another totem for playing games, etc. The movement of the totem may be recognized through the user's FOV cameras, for example.

Or, the movement may be detected through sensors (e.g., haptic glove, image sensors, hand tracking devices, etc.) and captured.

Based on the detected and captured gesture or input through the totem, the AR system detects a position, orientation and/or movement of the totem with respect to a reference frame, in step 2704. The reference frame may be set of map points based on which the AR system translates the movement of the totem to an action or command. In step 2706, the user's interaction with the totem is mapped. Based on the mapping of the user interaction with respect to the reference frame 2704, the system determines the user input.

For example, the user may move a totem or physical object back and forth to signify turning a virtual page and moving on to a next page. In order to translate this movement with the totem the AR system may first need to recognize the totem as one that is routinely used for this purpose. For example, the user may use a playful wand on his desk to move it back and forth to signify turning a page.

The AR system, through sensors, or images captured of the wand, may first detect the totem, and then use the movement of the wand with respect to the reference frame to determine the input. For example, the reference frame, in this case may simply be a set of map points associated with the stationary room. When the wand is moved back and forth, the map points of the wand change with respect to those of the room, and a movement may thus be detected. This movement may then be mapped against a mapping database that is previously created to determine the right command. For example, when the user first starts using the user device, the system may calibrate certain movements and define them as certain commands.

For example, moving a wand back and forth for a width of at least 2 inches may be a predetermined command to signify that the user wants to turn a virtual page. There may be a scoring system such that when the movement matches the predetermined gesture to a certain threshold value, the movement and the associated input is recognized, in one embodiment. When the detected movement matches a predetermined movement associated with a command stored in the map database, the AR system recognizes the command, and then performs the action desired by the user (e.g., display the next page to the user). The following discussion delves into various physical objects that may be used as totems, all of which use a similar process as the one described in FIG. 39.

Figure 40:
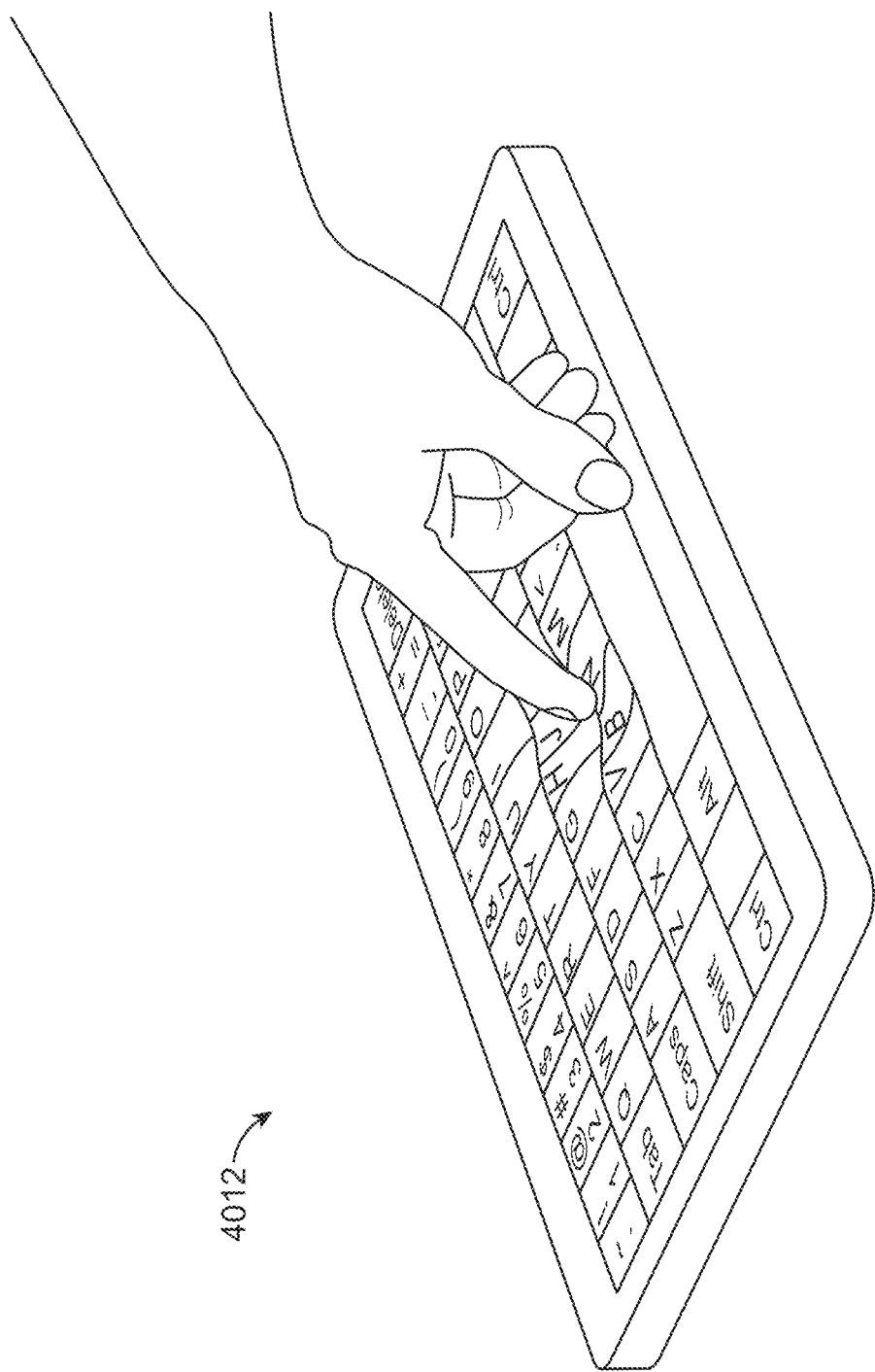
FIG. 40 illustrates an exemplary totem in the form of a virtual keyboard, according to one illustrated embodiment.

FIG. 40 shows a totem 4012 according to one illustrated embodiment, which may be used as part of a virtual keyboard implementation. The totem may have generally rectangular profile and a soft durometer surface. The soft surface provides some tactile perception to a user as the user interacts with the totem via touch.

As described above, the AR system may render the virtual keyboard image in a user's field of view, such that the virtual keys, switches or other user input components appear to reside on the surface of the totem. The AR system may, for example, render a 4D light field which is projected directly to a user's retina. The 4D light field allows the user to visually perceive the virtual keyboard with what appears to be real depth.

The AR system may also detect or capture user interaction with the surface of the totem. For example, the AR system may employ one or more front facing cameras to detect a position and/or movement of a user's fingers. In particularly, the AR system may identify from the captured images, any interactions of the user's fingers with various portions of the surface of the totem. The AR system maps the locations of those interactions with the positions of virtual keys, and hence with various inputs (e.g., characters, numbers, punctuation, controls, functions). In response to the inputs, the AR system may cause the inputs to be provided to a computer or some other device.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

Figure 41A:
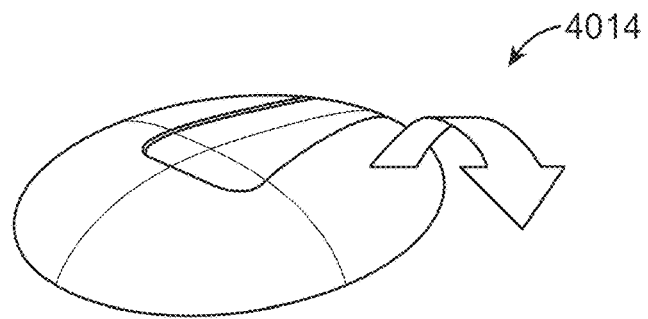
FIGS. 41A-41C illustrates another exemplary totem in the form of a mouse, according to one illustrated embodiment.

FIG. 41A shows a top surface of a totem 4014 according to one illustrated embodiment, which may be used as part of a virtual mouse implementation.

The top surface of the totem may have generally ovoid profile, with hard surface portion, and one or more soft surface portions to replicate keys of a physical mouse. The soft surface portions do not actually need to implement switches, and the totem may have no physical keys, physical switches or physical electronics. The soft surface portion(s) provides some tactile perception to a user as the user interacts with the totem via touch.

The AR system may render the virtual mouse image in a user's field of view, such that the virtual input structures (e.g., keys, buttons, scroll wheels, joystick, thumbstick) appear to reside on the top surface of the totem. The AR system may, for example, render a 4D light field which is projected directly to a user's retina to provide the visual perception of the virtual mouse with what appears to be real depth. Similar to the exemplary method outlined with reference to FIG. 39, the AR system may also detect or capture movement of the totem by the user, as well as, user interaction with the surface of the totem.

For example, the AR system may employ one or more front facing cameras to detect a position and/or movement of the mouse and/or interaction of a user's fingers with the virtual input structures (e.g., keys). The AR system maps the position and/or movement of the mouse. The AR system maps user interactions with the positions of virtual input structures (e.g., keys), and hence with various inputs (e.g., controls, functions). In response to the position, movements and/or virtual input structure activations, the AR system may cause corresponding inputs to be provided to a computer or some other device.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

Figure 41B:
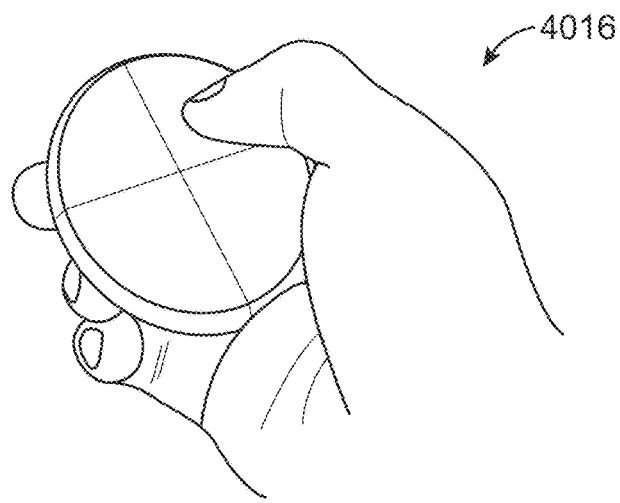

FIG. 41B shows a bottom surface of the totem 4016 of FIG. 41A, according to one illustrated embodiment, which may be used as part of a virtual trackpad implementation.

The bottom surface of the totem may be flat with a generally oval or circular profile. The bottom surface may be a hard surface. The totem may have no physical input structures (e.g., keys, buttons, scroll wheels), no physical switches and no physical electronics.

The AR system may optionally render a virtual trackpad image in a user's field of view, such that the virtual demarcations appear to reside on the bottom surface of the totem. Similar to the exemplary method outlined with reference to FIG. 39, the AR system detects or captures a user's interaction with the bottom surface of the totem. For example, the AR system may employ one or more front facing cameras to detect a position and/or movement of a user's fingers on the bottom surface of the totem. For instance, the AR system may detect one or more static positions of one or more fingers, or a change in position of one or more fingers (e.g., swiping gesture with one or more fingers, pinching gesture using two or more fingers).

The AR system may also employ the front facing camera(s) to detect interactions (e.g., tap, double tap, short tap, long tap) of a user's fingers with the bottom surface of the totem. The AR system maps the position and/or movement (e.g., distance, direction, speed, acceleration) of the user's fingers along the bottom surface of the totem. The AR system maps user interactions (e.g., number of interactions, types of interactions, duration of interactions) with the bottom surface of the totem, and hence with various inputs (e.g., controls, functions). In response to the position, movements and/or interactions, the AR system may cause corresponding inputs to be provided to a computer or some other device.

Figure 41C:
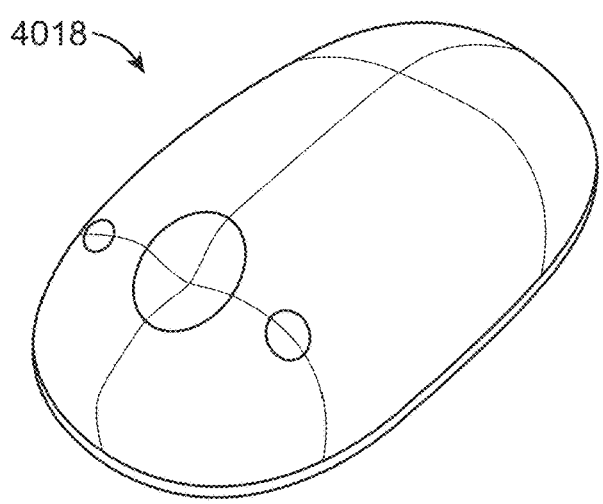

FIG. 41C shows a top surface of a totem 4108 according to another illustrated embodiment, which may be used as part of a virtual mouse implementation.

The totem of FIG. 41C is similar in many respects to that of the totem of FIG. 41A. Hence, similar or even identical structures are identified with the same reference numbers. Only significant differences are discussed below.

The top surface of the totem of FIG. 41C includes one or more indents or depressions at one or more respective locations on the top surface where the AR system with render keys or other structures (e.g., scroll wheel) to appear. Operation of this virtual mouse is similar to the above described implementations of virtual mice.

Figure 42A:
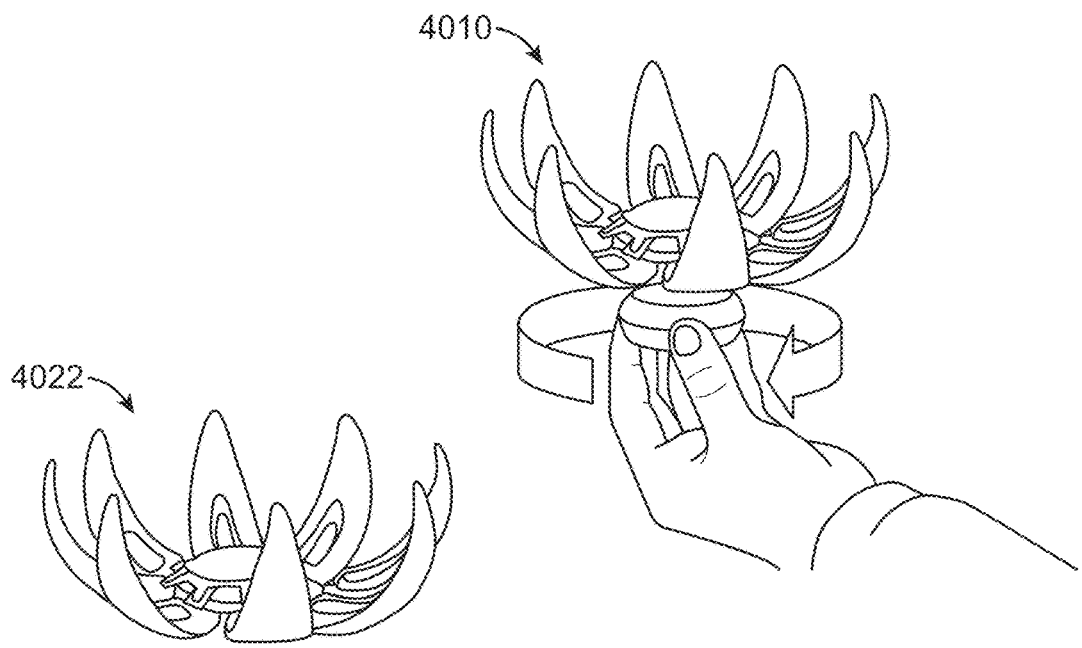
FIGS. 42A-42C illustrates another exemplary totem in the form of a lotus structure, according to one illustrated embodiment.

FIG. 42A shows an orb totem 4020 with a flower petal-shaped (e.g., Lotus flower) virtual user interface according to another illustrated embodiment.

The totem may have a spherical shape with either a hard outer surface or a soft outer surface. The outer surface of the totem may have texture to facilitate a sure grip by the user. The totem may have no physical keys, physical switches or physical electronics.

The AR system renders the flower petal-shaped virtual user interface image in a user's field of view, so as to appear to be emanating from the totem. Each of the petals may correspond to a function, category of functions, and/or category of content or media types, tools and/or applications.

The AR system may optionally render one or more demarcations on the outer surface of the totem. Alternatively or additionally, the totem may optionally bear one or more physical demarcations (e.g., printed, inscribed) on the outer surface. The dernarcation(s) may assist the user in visually orienting the totem with the flower petal-shaped virtual user interface.

The AR system detects or captures a user's interaction with the totem. For example, the AR system may employ one or more front facing cameras to detect a position, orientation, and/or movement (e.g., rotational direction, magnitude of rotation, angular speed, angular acceleration)

of the totem with respect to some reference frame (e.g., reference frame of the flower petal-shaped virtual user interface, real world, physical room, user's body, user's head) (similar to exemplary process flow diagram of FIG. 39).

For instance, the AR system may detect one or more static orientations or a change in orientation of the totem or a demarcation on the totem. The AR system may also employ the front facing camera(s) to detect interactions (e.g., tap, double tap, short tap, long tap, fingertip grip, enveloping grasp) of a user's fingers with outer surface of the totem. The AR system maps the orientation and/or change in orientation (e.g., distance, direction, speed, acceleration) of the totem to user selections or inputs. The AR system optionally maps user interactions (e.g., number of interactions, types of interactions, duration of interactions) with the outer surface of the totem, and hence with various inputs (e.g., controls, functions). In response to the orientations, changes in position (e.g., movements) and/or interactions, the AR system may cause corresponding inputs to be provided to a computer or some other device.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

Figure 42B:
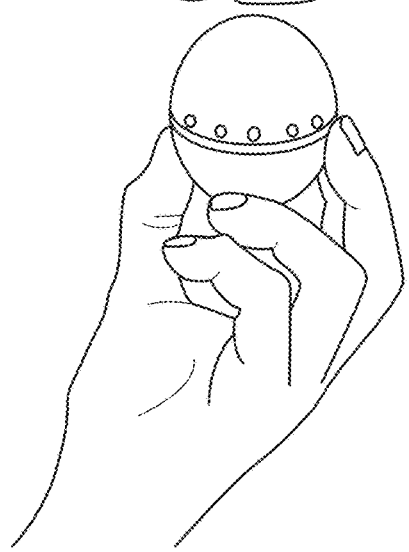

FIG. 42B shows an orb totem 4022 with a flower petal-shaped (e.g., Lotus flower) virtual user interface according to another illustrated embodiment.

The totem of FIG. 42B is similar in many respects to that of the totem of FIG. 42A. Hence, similar or even identical structures are identified with the same reference numbers. Only significant differences are discussed below.

The totem is disc shaped, having a top surface and bottom surface which may be flat or domed, as illustrated in FIG. 42B. That is a radius of curvature may be infinite or much larger than a radius of curvature of a peripheral edge of the totem.

The AR system renders the flower petal-shaped virtual user interface image in a user's field of view, so as to appear to be emanating from the totem. As noted above, each of the petals may correspond to a function, category of functions, and/or category of content or media types, tools and/or applications.

Operation of this virtual mouse is similar to the above described implementations of virtual mice.

Figure 42C:
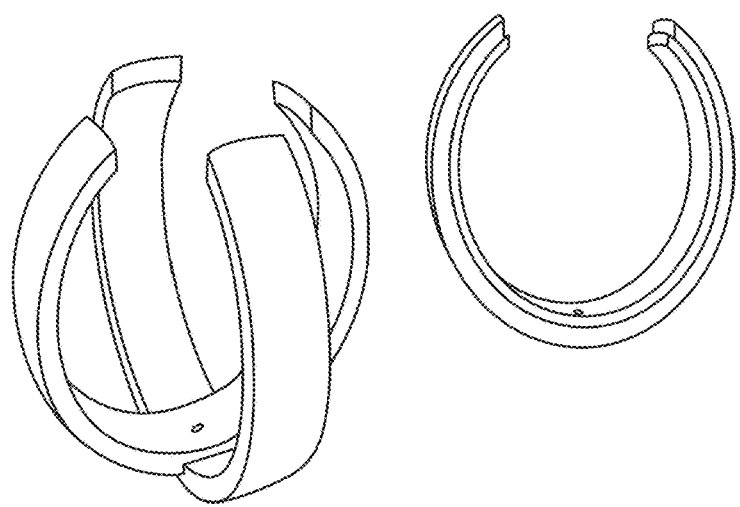

FIG. 42C shows an orb totem 4024 in a first configuration and a second configuration, according to another illustrated embodiment.

In particular, the totem has a number of arms or elements which are selectively moveable or positionable with respect to each other. For example, a first arm or pair of arms may be rotated with respect to a second arm or pair of arms. The first arm or pair of arms may be rotated from a first configuration to a second configuration. Where the arms are generally arcuate, as illustrated, in the first configuration the arms form an orb or generally spherical structure. In the second configuration, the second arm or pairs of arms align with the first arm or pairs of arms to form an partial tube with a C-shaped profile.

The arms may have an inner diameter sized large enough to receive a wrist or other limb of a user. The inner diameter may be sized small enough to prevent the totem from sliding off the limb during use. For example, the inner diameter may be sized to comfortably receive a wrist of a user, while not sliding past a hand of the user. This allows the totem to take the form of a bracelet, for example when not in use, for convenient carrying. A user may then configure the totem into an orb shape for use, in a fashion similar to the orb totems described above. The totem may have no physical keys, physical switches or physical electronics.

Notably, the virtual user interface is omitted from FIG. 42C. The AR system may render a virtual user interface in any of a large variety of forms, for example the flower petal-shaped virtual user interface previously illustrated and discussed.

Figure 43A:
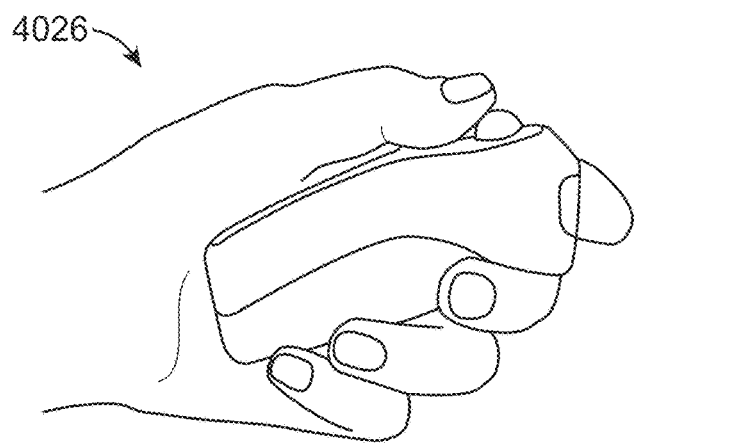
FIGS. 43A-43D illustrates other exemplary totems.

FIG. 43A shows a handheld controller shaped totem 4026, according to another illustrated embodiment. The totem has a gripping section sized and configured to comfortably fit in a user's hand. The totem may include a number of user input elements, for example a key or button and a scroll wheel. The user input elements may be physical elements, although not connected to any sensor or switches in the totem, which itself may have no physical switches or physical electronics.

Alternatively, the user input elements may be virtual elements rendered by the AR system. Where the user input elements are virtual elements, the totem may have depressions, cavities, protrusions, textures or other structures to tactile replicate a feel of the user input element.

The AR system detects or captures a user's interaction with the user input elements of the totem. For example, the AR system may employ one or more front facing cameras to detect a position and/or movement of a user's fingers with respect to the user input elements of the totem (similar to exemplary process flow diagram of FIG. 39). For instance, the AR system may detect one or more static positions of one or more fingers, or a change in position of one or more fingers (e.g., swiping or rocking gesture with one or more fingers, rotating or scrolling gesture, or both).

The AR system may also employ the front facing camera(s) to detect interactions (e.g., tap, double tap, short tap, long tap) of a user's fingers with the user input elements of the totem. The AR system maps the position and/or movement (e.g., distance, direction, speed, acceleration) of the user's fingers with the user input elements of the totem. The AR system maps user interactions (e.g., number of interactions, types of interactions, duration of interactions) of the user's fingers with the user input elements of the totem, and hence with various inputs (e.g., controls, functions). In response to the position, movements and/or interactions, the AR system may cause corresponding inputs to be provided to a computer or some other device.

Figure 43B:
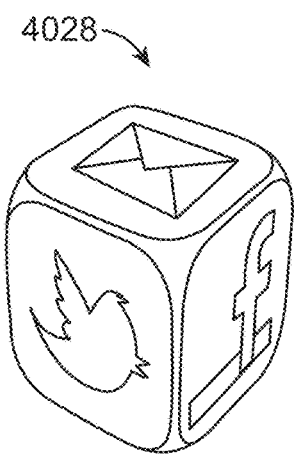

FIG. 43B shows a block shaped totem 4028, according to another illustrated embodiment. The totem may have the shape of a cube with six faces, or some other three-dimensional geometric structure. The totem may have a hard outer surface or a soft outer surface. The outer surface of the totem may have texture to facilitate a sure grip by the user. The totem may have no physical keys, physical switches or physical electronics.

The AR system renders a virtual user interface image in a user's field of view, so as to appear to be on the face(s) of the outer surface of the totem. Each of the faces, and corresponding virtual input prompt, may correspond to a function, category of functions, and/or category of content or media types, tools and/or applications.

The AR system detects or captures a user's interaction with the totem. For example, the AR system may employ one or more front facing cameras to detect a position, orientation, and/or movement (e.g., rotational direction, magnitude of rotation, angular speed, angular acceleration) of the totem with respect to some reference frame (e.g., reference frame of the real world, physical room, user's body, user's head) (similar to exemplary process flow diagram of FIG. 39). For instance, the AR system may detect one or more static orientations or a change in orientation of the totem.

The AR system may also employ the front facing camera(s) to detect interactions (e.g., tap, double tap, short tap, long tap, fingertip grip, enveloping grasp) of a user's fingers with outer surface of the totem. The AR system maps the orientation and/or change in orientation (e.g., distance, direction, speed, acceleration) of the totem to user selections or inputs. The AR system optionally maps user interactions (e.g., number of interactions, types of interactions, duration of interactions) with the outer surface of the totem, and hence with various inputs (e.g., controls, functions). In response to the orientations, changes in position (e.g., movements) and/or interactions, the AR system may cause corresponding inputs to be provided to a computer or some other device.

In response to the orientations, changes in position (e.g., movements) and/or interactions, the AR system may change one or more aspects of the rendering the virtual user interface cause corresponding inputs to be provided to a computer or some other device. For example, as a user rotates the totem, different faces may come into the user's field of view, while other faces rotate out of the user's field of view. The AR system may respond by rendering virtual interface elements to appear on the now visible faces, which were previously hidden from the view of the user. Likewise, the AR system may respond by stopping the rendering of virtual interface elements which would otherwise appear on the faces now hidden from the view of the user.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

Figure 43C:
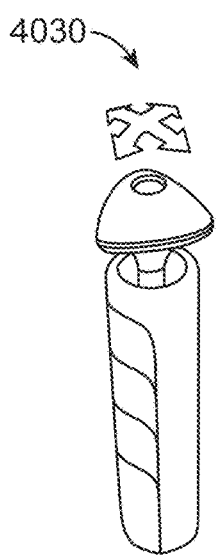

FIG. 43C shows a handheld controller shaped totem 4030, according to another illustrated embodiment. The totem has a gripping section sized and configured to comfortably fit in a user's hand, for example a cylindrically tubular portion. The totem may include a number of user input elements, for example a number of pressure sensitive switches and a joy or thumbstick. The user input elements may be physical elements, although not connected to any sensor or switches in the totem, which itself may have no physical switches or physical electronics.

Alternatively, the user input elements may be virtual elements rendered by the AR system. Where the user input elements are virtual elements, the totem may have depressions, cavities, protrusions, textures or other structures to tactile replicate a feel of the user input element.

The AR system detects or captures a user's interaction with the user input elements of the totem. For example, the AR system may employ one or more front facing cameras to detect a position and/or movement of a user's fingers with respect to the user input elements of the totem (similar to exemplary process flow diagram of FIG. 39). For instance, the AR system may detect one or more static positions of one or more fingers, or a change in position of one or more fingers (e.g., swiping or rocking gesture with one or more fingers, rotating or scrolling gesture, or both).

The AR system may also employ the front facing camera(s) to detect interactions (e.g., tap, double tap, short tap, long tap) of a user's fingers with the user input elements of the totem. The AR system maps the position and/or movement (e.g., distance, direction, speed, acceleration) of the user's fingers with the user input elements of the totem. The AR system maps user interactions (e.g., number of interactions, types of interactions, duration of interactions) of the user's fingers with the user input elements of the totem, and hence with various inputs (e.g., controls, functions). In response to the position, movements and/or interactions, the AR system may cause corresponding inputs to be provided to a computer or some other device.

Figure 43D:
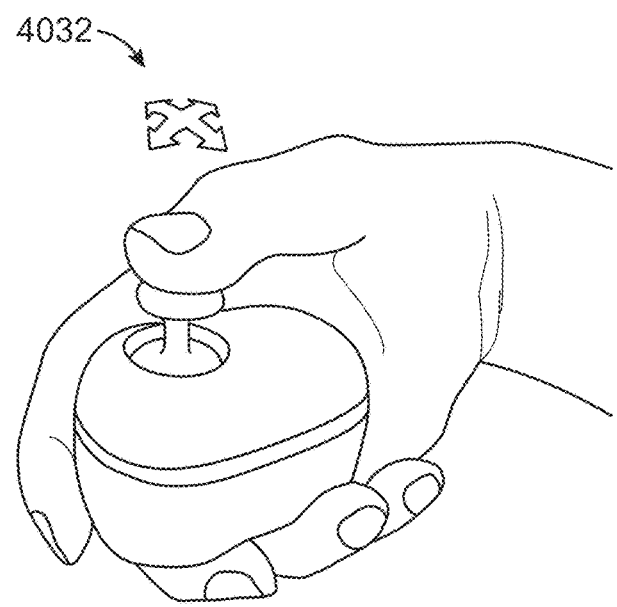

FIG. 43D shows a handheld controller shaped totem 4032, according to another illustrated embodiment. The totem has a gripping section sized and configured to comfortably fit in a user's hand. The totem may include a number of user input elements, for example a key or button and a joy or thumbstick. The user input elements may be physical elements, although not connected to any sensor or switches in the totem, which itself may have no physical switches or physical electronics. Alternatively, the user input elements may be virtual elements rendered by the AR system. Where the user input elements are virtual elements, the totem may have depressions, cavities, protrusions, textures or other structures to tactile replicate a feel of the user input element.

The AR system detects or captures a user's interaction with the user input elements of the totem. For example, the AR system may employ one or more front facing cameras to detect a position and/or movement of a user's fingers with respect to the user input elements of the totem (similar to exemplary process flow diagram of FIG. 39). For instance, the AR system may detect one or more static positions of one or more fingers, or a change in position of one or more fingers (e.g., swiping or rocking gesture with one or more fingers, rotating or scrolling gesture, or both). The AR system may also employ the front facing camera(s) to detect interactions (e.g., tap, double tap, short tap, long tap) of a user's fingers with the user input elements of the totem.

The AR system maps the position and/or movement (e.g., distance, direction, speed, acceleration) of the user's fingers with the user input elements of the totem. The AR system maps user interactions (e.g., number of interactions, types of interactions, duration of interactions) of the user's fingers with the user input elements of the totem, and hence with various inputs (e.g., controls, functions). In response to the position, movements and/or interactions, the AR system may cause corresponding inputs to be provided to a computer or some other device.

Figure 44A:
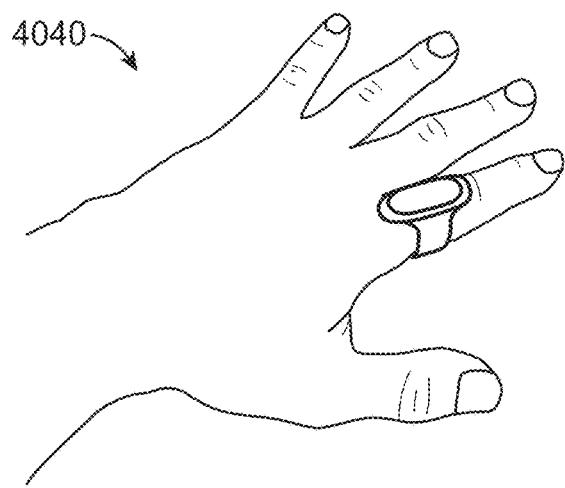
FIGS. 44A-44C illustrates exemplary totems in the form of rings, according to one illustrated embodiment.

FIG. 44A shows a ring totem 4034, according one illustrated embodiment. In particular, the ring totem has a tubular portion and an interaction portion physically coupled to the tubular portion. The tubular and interaction portions may be integral, and may be formed as or from a single unitary structure. The tubular portion has an inner diameter sized large enough to receive a finger of a user therethrough. The inner diameter may be sized small enough to prevent the totem from sliding off the finger during normal use. This allows the ring totem to be comfortably worn even when not in active use, ensuring availability when needed. The ring totem may have no physical keys, physical switches or physical electronics.

The AR system may render a virtual user interface in any of a large variety of forms. For example, the AR system may render a virtual user interface in the user's field of view as to appear as if the virtual user interface element(s) reside on the interaction surface. Alternatively, the AR system may render a virtual user interface as the flower petal-shaped virtual user interface previously illustrated and discussed, emanating from the interaction surface.

The AR system detects or captures a user's interaction with the totem. For example, the AR system may employ one or more front facing cameras to detect a position, orientation, and/or movement (e.g., position, direction, distance, speed, acceleration) of the user's finger(s) with respect to interaction surface in some reference frame (e.g., reference frame of the interaction surface, real world, physical room, user's body, user's head) (similar to exemplary process flow diagram of FIG. 39). For instance, the AR system may detect one or more locations of touches or a change in position of a finger on the interaction surface.

The AR system may also employ the front facing camera(s) to detect interactions (e.g., tap, double tap, short tap, long tap, fingertip grip, enveloping grasp) of a user's fingers with the interaction surface of the totem. The AR system maps the position, orientation, and/or movement of the finger with respect to the interaction surface to a set of user selections or inputs. The AR system optionally maps other user interactions (e.g., number of interactions, types of interactions, duration of interactions) with the interaction surface of the totem, and hence with various inputs (e.g., controls, functions). In response to the position, orientation, movement, and/or other interactions, the AR system may cause corresponding inputs to be provided to a computer or some other device.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

Figure 44B:
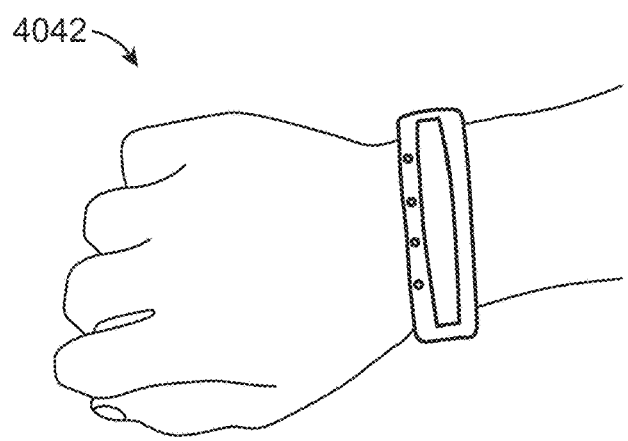

FIG. 44B shows a bracelet totem 4036, according one illustrated embodiment. In particular, the bracelet totem has a tubular portion and a touch surface physically coupled to the tubular portion. The tubular portion and touch surface may be integral, and may be formed as or from a single unitary structure. The tubular portion has an inner diameter sized large enough to receive a wrist or other limb of a user.

The inner diameter may be sized small enough to prevent the totem from sliding off the limb during use. For example, the inner diameter may be sized to comfortably receive a wrist of a user, while not sliding past a hand of the user. This allows the bracelet totem to be worn whether in active use or not, ensuring availability when desired. The bracelet totem may have no physical keys, physical switches or physical electronics.

The AR system may render a virtual user interface in any of a large variety of forms. For example, the AR system may render a virtual user interface in the user's field of view as to appear as if the virtual user interface element(s) reside on the touch surface. Alternatively, the AR system may render a virtual user interface as the flower petal-shaped virtual user interface previously illustrated and discussed, emanating from the touch surface.

The AR system detects or captures a user's interaction with the totem (similar to exemplary process flow diagram of FIG. 39). For example, the AR system may employ one or more front facing cameras to detect a position, orientation, and/or movement (e.g., position, direction, distance, speed, acceleration) of the user's finger(s) with respect to touch surface in some reference frame (e.g., reference frame of the touch surface, real world, physical room, user's body, user's head). For instance, the AR system may detect one or more locations of touches or a change in position of a finger on the touch surface.

The AR system may also employ the front facing camera(s) to detect interactions (e.g., tap, double tap, short tap, long tap, fingertip grip, enveloping grasp) of a user's fingers with the touch surface of the totem. The AR system maps the position, orientation, and/or movement of the finger with respect to the touch surface to a set of user selections or inputs. The AR system optionally maps other user interactions (e.g., number of interactions, types of interactions, duration of interactions) with the touch surface of the totem, and hence with various inputs (e.g., controls, functions). In response to the position, orientation, movement, and/or other interactions, the AR system may cause corresponding inputs to be provided to a computer or some other device.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

Figure 44C:
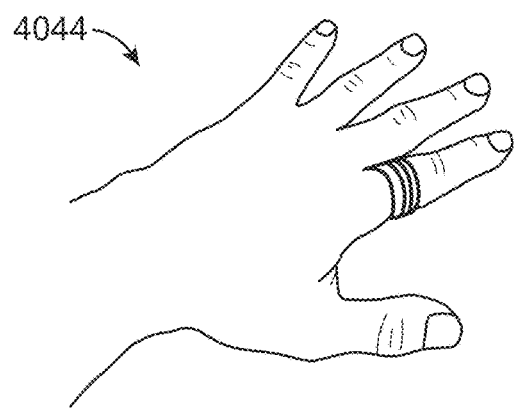

FIG. 44C shows a ring totem 4038, according another illustrated embodiment. In particular, the ring totem has a tubular portion and an interaction portion physically rotatably coupled to the tubular portion to rotate with respect thereto. The tubular portion has an inner diameter sized large enough to receive a finger of a user there through. The inner diameter may be sized small enough to prevent the totem from sliding off the finger during normal use.

This allows the ring totem to be comfortably worn even when not in active use, ensuring availability when needed. The interaction portion may itself be a closed tubular member, having a respective inner diameter received about an outer diameter of the tubular portion. For example, the interaction portion may be journaled or slideable mounted to the tubular portion. The interaction portion is accessible from an exterior surface of the ring totem. The interaction portion may, for example, be rotatable in a first rotational direction about a longitudinal axis of the tubular portion. The interaction portion may additionally be rotatable in a second rotational, opposite the first rotational direction about the longitudinal axis of the tubular portion. The ring totem may have no physical switches or physical electronics.

The AR system may render a virtual user interface in any of a large variety of forms. For example, the AR system may render a virtual user interface in the user's field of view as to appear as if the virtual user interface element(s) reside on the interaction portion. Alternatively, the AR system may render a virtual user interface as the flower petal-shaped virtual user interface previously illustrated and discussed, emanating from the interaction portion.

The AR system detects or captures a user's interaction with the totem (similar to exemplary process flow diagram of FIG. 39). For example, the AR system may employ one or more front facing cameras to detect a position, orientation, and/or movement (e.g., position, direction, distance, speed, acceleration) of the interaction portion with respect to the tubular portion (e.g., finger receiving portion) in some reference frame (e.g., reference frame of the tubular portion, real world, physical room, user's body, user's head).

For instance, the AR system may detect one or more locations or orientations or changes in position or orientation of the interaction portion with respect to the tubular portion. The AR system may also employ the front facing camera(s) to detect interactions (e.g., tap, double tap, short tap, long tap, fingertip grip, enveloping grasp) of a user's fingers with the interaction portion of the totem.

The AR system maps the position, orientation, and/or movement of the interaction portion with respect the tubular portion to a set of user selections or inputs. The AR system optionally maps other user interactions (e.g., number of interactions, types of interactions, duration of interactions) with the interaction portion of the totem, and hence with various inputs (e.g., controls, functions). In response to the position, orientation, movement, and/or other interactions, the AR system may cause corresponding inputs to be provided to a computer or some other device.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

Figure 45A:
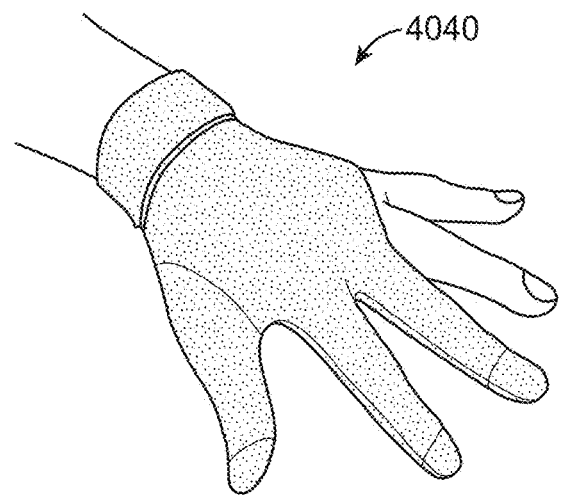
FIGS. 45A-45C illustrates exemplary totems in the form of a haptic glove, a pen and a paintbrush, according to one illustrated embodiment.

FIG. 45A shows a glove-shaped haptic totem 4040, according one illustrated embodiment. In particular, the glove-shaped haptic totem is shaped like a glove or partial glove, having an opening for receiving a wrist and one or more tubular glove fingers (three shown) sized to receive a user's fingers. The glove-shaped haptic totem may be made of one or more of a variety of materials. The materials may be elastomeric or may otherwise conform the shape or contours of a user's hand, providing a snug but comfortable fit.

The bracelet totem may have no physical keys, physical switches or physical electronics. The AR system may render a virtual user interface in any of a large variety of forms. For example, the AR system may render a virtual user interface in the user's field of view as to appear as if the virtual user interface element(s) is inter-actable via the glove-shaped haptic totem. For example, the AR system may render a virtual user interface as one of the previously illustrated and/or described totems or virtual user interfaces.

The AR system detects or captures a user's interaction via visual tracking of the user's hand and fingers on which the glove-shaped haptic totem is worn (similar to exemplary process flow diagram of FIG. 39). For example, the AR system may employ one or more front facing cameras to detect a position, orientation, and/or movement (e.g., position, direction, distance, speed, acceleration) of the user's hand and/or finger(s) with respect to some reference frame (e.g., reference frame of the touch surface, real world, physical room, user's body, user's head).

For instance, the AR system may detect one or more locations of touches or a change in position of a hand and/or fingers. The AR system may also employ the front facing camera(s) to detect interactions (e.g., tap, double tap, short tap, long tap, fingertip grip, enveloping grasp) of a user's hands and/or fingers. Notably, the AR system may track the glove-shaped haptic totem instead of the user's hands and fingers. The AR system maps the position, orientation, and/or movement of the hand and/or fingers to a set of user selections or inputs.

The AR system optionally maps other user interactions (e.g., number of interactions, types of interactions, duration of interactions), and hence with various inputs (e.g., controls, functions). In response to the position, orientation, movement, and/or other interactions, the AR system may cause corresponding inputs to be provided to a computer or some other device.

Additionally or alternatively, the AR system may render the virtual user interface differently in response to select user interactions. For instance, some user interactions may correspond to selection of a particular submenu, application or function. The AR system may respond to such selection by rendering a new set of virtual interface elements, based at least in part on the selection. For instance, the AR system render a submenu or a menu or other virtual interface element associated with the selected application or functions. Thus, the rendering by AR system may be context sensitive.

The glove-shaped haptic totem includes a plurality of actuators, which are responsive to signals to provide haptic sensations such as pressure and texture. The actuators may take any of a large variety of forms, for example piezoelectric elements, and/or micro electrical mechanical structures (MEMS).

The AR system provides haptic feedback to the user via the glove-shaped haptic totem. In particular, the AR system provides signals to the glove-shaped haptic totem to replicate a sensory sensation of interacting with a physical object which a virtual object may represent. Such may include providing a sense of pressure and/or texture associated with a physical object.

Thus, the AR system may cause a user to feel a presence of a virtual object, for example including various structural features of the physical object such as edges, corners, roundness, etc. The AR system may also cause a user to feel textures such as smooth, rough, dimpled, etc.

Figure 45B:
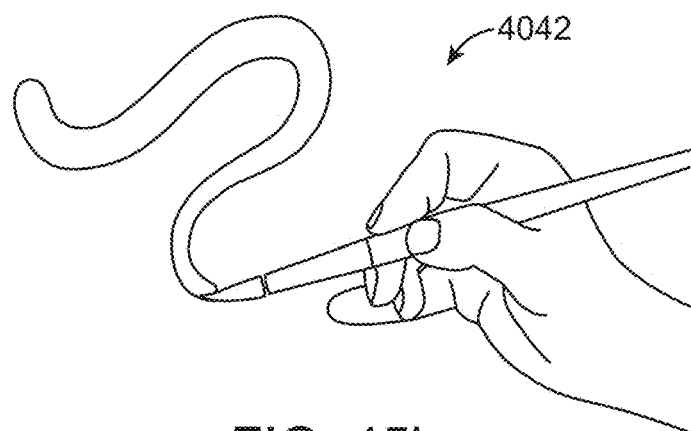

FIG. 45B shows a stylus or brush shaped totem 4042, according one illustrated embodiment. The stylus or brush shaped totem includes an elongated handle, similar to that of any number of conventional stylus or brush. In contrast to conventional stylus or brush, the stylus or brush has a virtual tip or bristles.

In particular, the AR system may render a desired style of virtual tip or bristle to appear at an end of the physical stylus or brush. The tip or bristle may take any conventional style including narrow or wide points, flat bristle brushed, tapered, slanted or cut bristle brushed, natural fiber bristle brushes (e.g., horse hair), artificial fiber bristle brushes, etc. Such advantageously allows the virtual tip or bristles to be replaceable.

The AR system detects or captures a user's interaction via visual tracking of the user's hand and/or fingers on the stylus or brush and/or via visual tracking of the end of the stylus or brush (similar to exemplary process flow diagram of FIG. 39). For example, the AR system may employ one or more front facing cameras to detect a position, orientation, and/or movement (e.g., position, direction, distance, speed, acceleration) of the user's hand and/or finger(s) and/or end of the stylus or brush with respect to some reference frame (e.g., reference frame of a piece of media, the real world, physical room, user's body, user's head).

For instance, the AR system may detect one or more locations of touches or a change in position of a hand and/or fingers. Also for instance, the AR system may detect one or more locations of the end of the stylus or brush and/or an orientation of the end of the stylus or brush with respect to, for example, a piece of media or totem representing a piece of media.

The AR system may additionally or alternatively detect one or more change in locations of the end of the stylus or brush and/or change in orientation of the end of the stylus or brush with respect to, for example, the piece of media or totem representing the piece of media. The AR system may also employ the front facing camera(s) to detect interactions (e.g., tap, double tap, short tap, long tap, fingertip grip, enveloping grasp) of a user's hands and/or fingers or of the stylus or brush.

The AR system maps the position, orientation, and/or movement of the hand and/or fingers and/or end of the stylus or brush to a set of user selections or inputs. The AR system optionally maps other user interactions (e.g., number of interactions, types of interactions, duration of interactions), and hence with various inputs (e.g., controls, functions). In response to the position, orientation, movement, and/or other interactions, the AR system may cause corresponding inputs to be provided to a computer or some other device.

Additionally or alternatively, the AR system may render a virtual image of markings made by the user using the stylus or brush, taking into account the visual effects that would be achieved by the selected tip or bristles.

The stylus or brush may have one or more haptic elements (e.g., piezoelectric elements, MEMS elements), which the AR system control to provide a sensation (e.g., smooth, rough, low friction, high friction) that replicate a feel of a selected point or bristles, as the selected point or bristles pass over media. The sensation may also reflect or replicate how the end or bristles would interact with different types of physical aspects of the media, which may be selected by the user. Thus, paper and canvass may produce two different haptic responses.

Figure 45C:
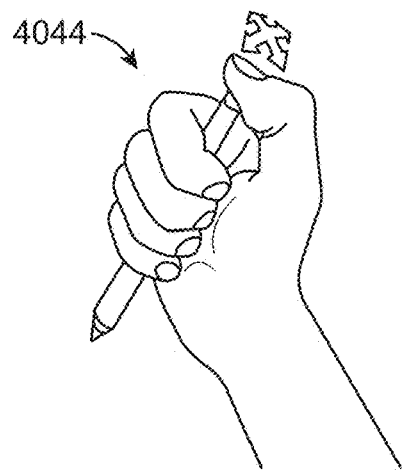

FIG. 45C shows a pen shaped totem 4044, according one illustrated embodiment.

The pen shaped totem includes an elongated shaft, similar to that of any number of conventional pen, pencil, stylus or brush. The pen shaped totem has a user actuatable joy or thumbstick located at one end of the shaft. The joy or thumbstick is moveable with respect to the elongated shaft in response to user actuation.

The joy or thumbstick may, for example, be pivotally movable in four directions (e.g., forward, back, left, right). Alternatively, the joy or thumbstick may, for example, be movable in all directions four directions, or may be pivotally moveable in any angular direction in a circle, for example to navigate. Notably, the joy or thumbstick is not coupled to any switch or electronics.

Instead of coupling the joy or thumbstick to a switch or electronics, the AR system detects or captures a position, orientation, or movement of the joy or thumbstick. For example, the AR system may employ one or more front facing cameras to detect a position, orientation, and/or movement (e.g., position, direction, distance, speed, acceleration) of the joy or thumbstick with respect to some reference frame (e.g., reference frame of the elongated shaft.

Additionally, the AR system may employ one or more front facing cameras to detect a position, orientation, and/or movement (e.g., position, direction, distance, speed, acceleration) of the user's hand and/or finger(s) and/or end of the pen shaped totem with respect to some reference frame (e.g., reference frame of the elongated shaft, of a piece of media, the real world, physical room, user's body, user's head) (similar to exemplary process flow diagram of FIG. 39). For instance, the AR system may detect one or more locations of touches or a change in position of a hand and/or fingers.

Also for instance, the AR system may detect one or more locations of the end of the pen shaped totem and/or an orientation of the end of the pen shaped totem with respect to, for example, a piece of media or totem representing a piece of media. The AR system may additionally or alternatively detect one or more change in locations of the end of the pen shaped totem and/or change in orientation of the end of the pen shaped totem with respect to, for example, the piece of media or totem representing the piece of media. The AR system may also employ the front facing camera(s) to detect interactions (e.g., tap, double tap, short tap, long tap, fingertip grip, enveloping grasp) of a user's hands and/or fingers with the joy or thumbstick or the elongated shaft of the pen shaped totem.

The AR system maps the position, orientation, and/or movement of the hand and/or fingers and/or end of the joy or thumbstick to a set of user selections or inputs. The AR system optionally maps other user interactions (e.g., number of interactions, types of interactions, duration of interactions), and hence with various inputs (e.g., controls, functions). In response to the position, orientation, movement, and/or other interactions, the AR system may cause corresponding inputs to be provided to a computer or some other device.

Additionally or alternatively, the AR system may render a virtual image of markings made by the user using the pen shaped totem, taking into account the visual effects that would be achieved by the selected tip or bristles.

The pen shaped totem may have one or more haptic elements (e.g., piezoelectric elements, MEMS elements), which the AR system control to provide a sensation (e.g., smooth, rough, low friction, high friction) that replicate a feel of passing over media.

Figure 46A:
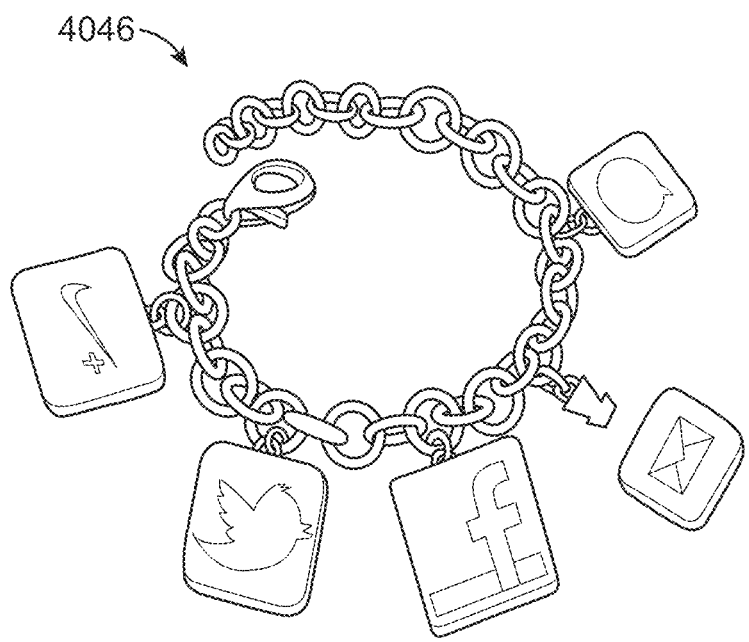
FIGS. 46A-46B illustrated exemplary totems in the form of a keychain and a charm bracelet, according to one illustrated embodiment.

FIG. 46A shows a charm chain totem 4046, according one illustrated embodiment.

The charm chain totem includes a chain and a number of charms. The chain may include a plurality of interconnected links which provides flexibility to the chain. The chain may also include a closure or clasp which allows opposite ends of the chain to be securely coupled together. The chain and/or clasp may take a large variety of forms, for example single strand, multi-strand, links or braided. The chain and/or clasp may be formed of any variety of metals, or other non-metallic materials.

A length of the chain should accommodate a portion of a user's limb when the two ends are clasped together. The length of the chain should also be sized to ensure that the chain is retained, even loosely, on the portion of the limb when the two ends are clasped together. The chain may be worn as a bracket on a wrist of an arm or on an ankle of a leg. The chain may be worn as a necklace about a neck.

The charms may take any of a large variety of forms. The charms may have a variety of shapes, although will typically take the form of plates or discs. While illustrated with generally rectangular profiles, the charms may have any variety of profiles, and different charms on a single chain may have respective profiles which differ from one another. The charms may be formed of any of a large variety of metals, or non-metallic materials.

Each charm may bear an indicia, which is logically associable in at least one computer- or processor-readable non-transitory storage medium with a function, category of functions, category of content or media types, and/or tools or applications which is accessible via the AR system.

Adding on the exemplary method of using totems described in FIG. 39, the AR system may detect or captures a user's interaction with the charms of FIG. 46A. For example, the AR system may employ one or more front facing cameras to detect touching or manipulation of the charms by the user's fingers or hands. For instance, the AR system may detect a selection of a particular charm by the user touching the respective charm with their finger or grasping the respective charm with two or more fingers.

Further, the augmented reality may detect a position, orientation, and/or movement (e.g., rotational direction, magnitude of rotation, angular speed, angular acceleration) of a charm with respect to some reference frame (e.g., reference frame of the portion of the body, real world, physical room, user's body, user's head). The AR system may also employ the front facing camera(s) to detect other interactions (e.g., tap, double tap, short tap, long tap, fingertip grip, enveloping grasp) of a user's fingers with a charm. The AR system maps selection of the charm to user selections or inputs, for instance selection of a social media application.

The AR system optionally maps other user interactions (e.g., number of interactions, types of interactions, duration of interactions) with the charm, and hence with various inputs (e.g., controls, functions) with the corresponding application. In response to the touching, manipulation or other interactions with the charms, the AR system may cause corresponding applications to be activated and/or provide corresponding inputs to the applications.

Additionally or alternatively, the AR system may render the virtual user interface differently in response to select user interactions. For instance, some user interactions may correspond to selection of a particular submenu, application or function. The AR system may respond to such selection by rendering a set of virtual interface elements, based at least in part on the selection. For instance, the AR system render a submenu or a menu or other virtual interface element associated with the selected application or functions. Thus, the rendering by AR system may be context sensitive.

Figure 46B:
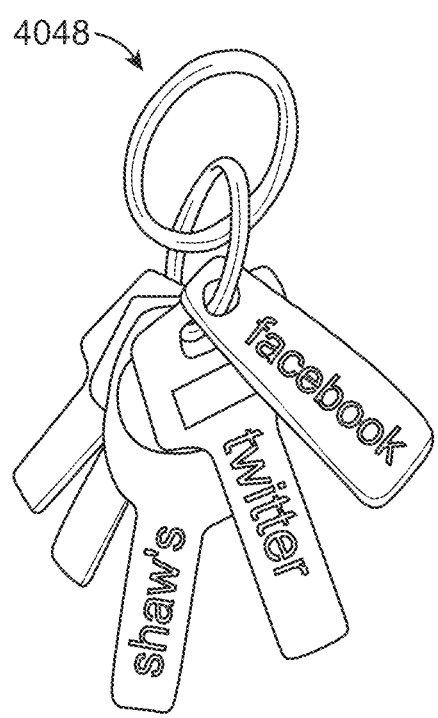

FIG. 46B shows a keychain totem 4048, according one illustrated embodiment. The keychain totem includes a chain and a number of keys. The chain may include a plurality of interconnected links which provides flexibility to the chain. The chain may also include a closure or clasp which allows opposite ends of the chain to be securely coupled together. The chain and/or clasp may take a large variety of forms, for example single strand, multi-strand, links or braided. The chain and/or clasp may be formed of any variety of metals, or other non-metallic materials.

The keys may take any of a large variety of forms. The keys may have a variety of shapes, although will typically take the form of conventional keys, either with or without ridges and valleys (e.g., teeth). In some implementations, the keys may open corresponding mechanical locks, while in other implementations the keys only function as totems and do not open mechanical locks. The keys may have any variety of profiles, and different keys on a single chain may have respective profiles which differ from one another. The keys may be formed of any of a large variety of metals, or non-metallic materials. Various keys may be different colors from one another.

Each key may bear an indicia, which is logically associable in at least one computer- or processor-readable non-transitory storage medium with a function, category of functions, category of content or media types, and/or tools or applications which is accessible via the AR system.

The AR system detects or captures a user's interaction with the keys (similar to exemplary process flow diagram of FIG. 39). For example, the AR system may employ one or more front facing cameras to detect touching or manipulation of the keys by the user's fingers or hands. For instance, the AR system may detect a selection of a particular key by the user touching the respective key with their finger or grasping the respective key with two or more fingers.

Further, the augmented reality may detect a position, orientation, and/or movement (e.g., rotational direction, magnitude of rotation, angular speed, angular acceleration) of a key with respect to some reference frame (e.g., reference frame of the portion of the body, real world, physical room, user's body, user's head). The AR system may also employ the front facing camera(s) to detect other interactions (e.g., tap, double tap, short tap, long tap, fingertip grip, enveloping grasp) of a user's fingers with a key.

The AR system maps selection of the key to user selections or inputs, for instance selection of a social media application. The AR system optionally maps other user interactions (e.g., number of interactions, types of interactions, duration of interactions) with the key, and hence with various inputs (e.g., controls, functions) with the corresponding application. In response to the touching, manipulation or other interactions with the keys, the AR system may cause corresponding applications to be activated and/or provide corresponding inputs to the applications.

User Interfaces

Using the principles of gesture tracking and/or totem tracking discussed above, the AR system is configured to create various types of user interfaces for the user to interact with. With the AR system, any space around the user may be converted into a user interface such that the user can interact with the system. Thus, the AR system does not require a physical user interface such as a mouse/keyboard, etc. (although totems may be used as reference points, as described above), but rather a virtual user interface may be created anywhere and in any form to help the user interact with the AR system.

In one embodiment, there may be predetermined models or templates of various virtual user interfaces. For example, during set-up the user may designate a preferred type or types of virtual UI (e.g., body centric UI, head—centric UI, hand-centric UI, etc.) Or, various applications may be associated with their own types of virtual UI. Or, the user may customize the UI to create one that he/she may be most comfortable with. For example, the user may simply, using a motion of his hands "draw" a virtual UI in space and various applications or functionalities may automatically populate the drawn virtual UI.

Before delving into various embodiments of user interfaces, an exemplary process 4100 of interacting with a user interface with be briefly described.

Figure 47:
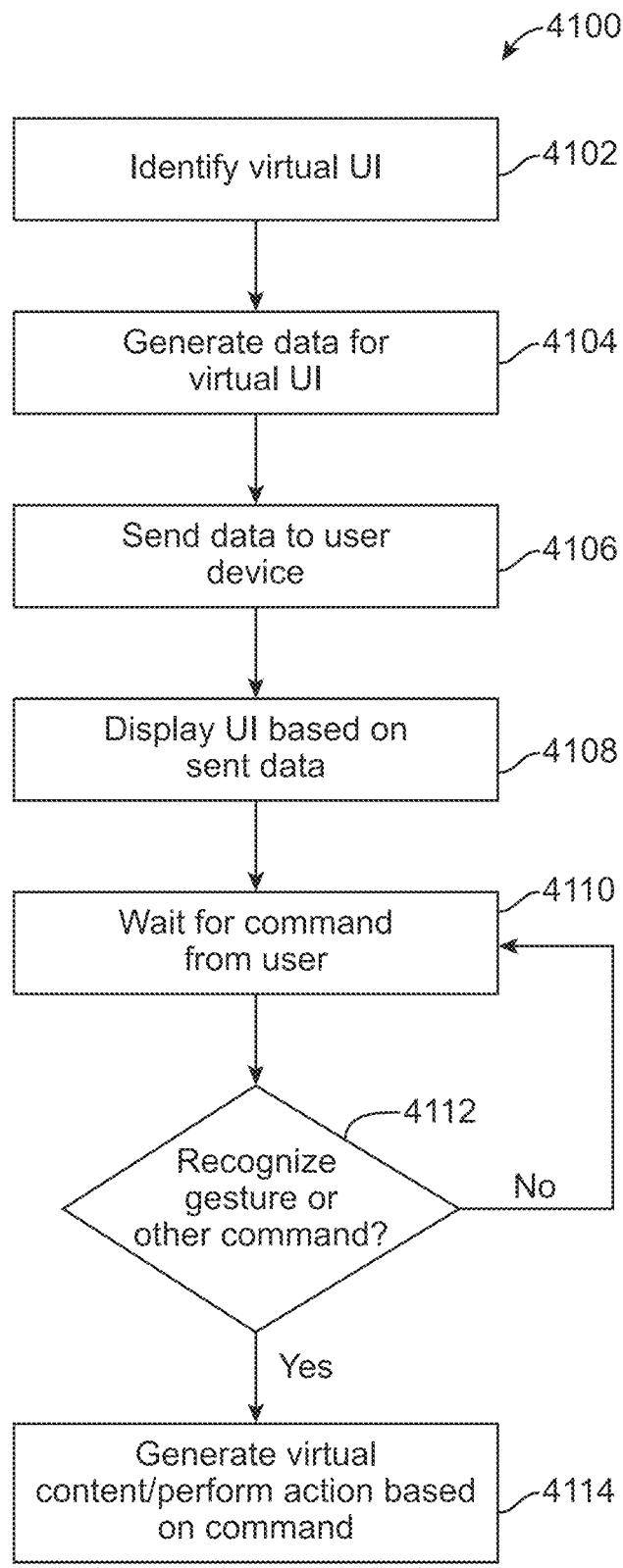
FIG. 47 is a process flow diagram of an exemplary method of generating a virtual user interface, according to one illustrated embodiment.

Referring now to flowchart 4100 of FIG. 47, in step 4102, the AR system may identify a particular UI. The type of UI may be predetermined by the user. The system may identify that a particular UI needs to be populated based on a user input (e.g—gesture, visual data, audio data, sensory data, direct command, etc.). In step 4104, the AR system may generate data for the virtual UI. For example, data associated with the confines, general structure, shape of the UI etc. may be generated. In addition, the AR system may determine map coordinates of the user's physical location so that the AR system can display the UI in relation to the user's physical location.

For example, if the UI is body centric, the AR system may determine the coordinates of the user's physical stance such that a ring UI can be displayed around the user. Or, if the UI is hand centric, the map coordinates of the user's hands may need to be determined. It should be appreciated that these map points may be derived through data received through the FOV cameras, sensory input, or any other type of collected data.

In step 4106, the AR system may send the data to the user device from the cloud. Or the data may be sent from a local database to the display components. In step 4108, the UI is displayed to the user based on the sent data.

Once the virtual UI has been created, the AR system may simply wait for a command from the user to generate more virtual content on the virtual UI in step 4110. For example, the UI maybe a body centric ring around the user's body. The AR system may then wait for the command, and if it is recognized (step 4112), virtual content associated with the command may be displayed to the user. The following are various examples of user interfaces that may be created for the user. However the process flow diagram will be similar to that described above.

Figure 48A:
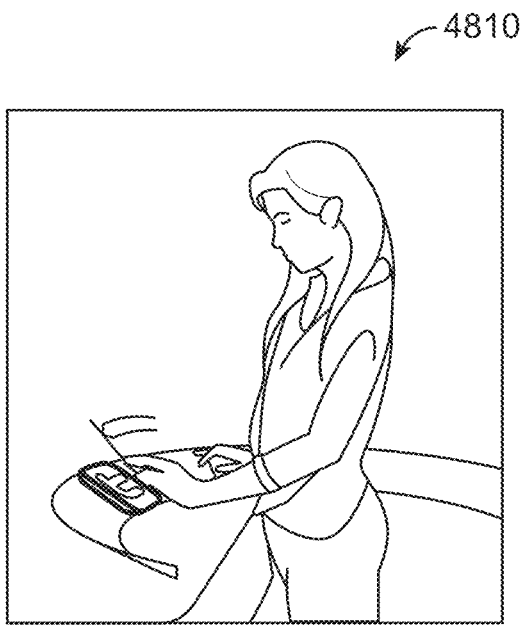
FIGS. 48A-48C illustrate various user interfaces through which to interact with the AR system, according to the illustrated embodiments.

FIG. 48A shows a user interacting via gestures with a user interface virtual construct rendered by the AR system, according to one illustrated embodiment.

In particular, FIG. 48A (scene 4810) shows the user interacting with a generally annular layout or configuration virtual user interface of various user selectable virtual icons. The user selectable virtual icons may represent applications (e.g., social media application, Web browser, electronic mail application), functions, menus, virtual rooms or virtual spaces, etc.

The user may, for example, perform a swipe gesture. The AR system detects the swipe gesture, and interprets the swipe gesture as an instruction to render the generally annular layout or configuration user interface. The AR system then renders the generally annular layout or configuration virtual user interface into the user's field of view so as to appear to at least partially surround the user, spaced from the user at a distance that is within arm's reach of the user.

Figure 48B:
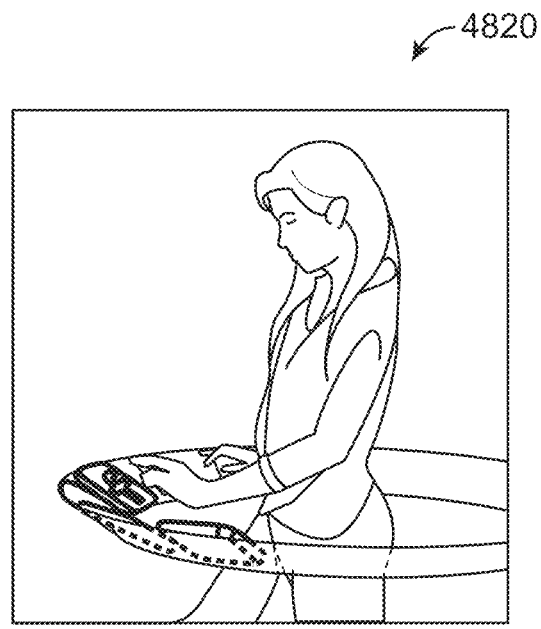

FIG. 48B (scene 4820) shows a user interacting via gestures, according to one illustrated embodiment. The generally annular layout or configuration virtual user interface may present the various user selectable virtual icons in a scrollable form. The user may gesture, for example with a sweeping motion of a hand, to cause scrolling through various user selectable virtual icons. For instance, the user may make a sweeping motion to the user's left or to the user' right, in order to cause scrolling in the left (i.e., counter-clockwise) or right (i.e., clockwise) directions, respectively.

In particular, FIG. 48B shows the user interacting with the generally annular layout or configuration virtual user interface of various user selectable virtual icons of FIG. 48A. Identical or similar physical and/or virtual elements are identified using the same reference numbers as in FIG. 48A, and discussion of such physical and/or virtual elements will not be repeated in the interest of brevity.

The user may, for example, perform a point or touch gesture, proximally identifying one of the user selectable virtual icons. The AR system detects the point or touch gesture, and interprets the point or touch gesture as an instruction to open or execute a corresponding application, function, menu or virtual room or virtual space. The AR system then renders appropriate virtual content based on the user selection.

Figure 48C:
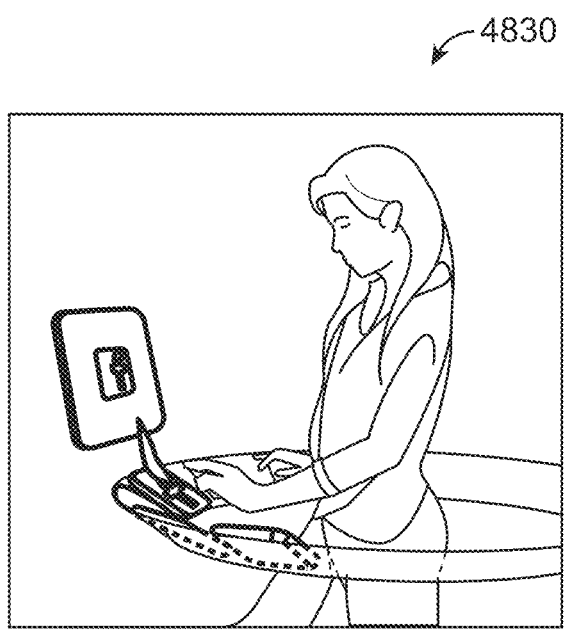

FIG. 48C (scene 4830) shows the user interacting with the generally annular layout or configuration virtual user interface of various user selectable virtual icons. Identical or similar physical and/or virtual elements are identified using the same reference numbers as in FIG. 48A, and discussion of such physical and/or virtual elements will not be repeated in the interest of brevity.

In particular, the user selects one of the user selectable virtual icons. In response, the AR system opens or executes a corresponding application, function, menu or virtual room or virtual space. For example, the AR system may render a virtual user interface for a corresponding application as illustrated in FIG. 48C. Alternatively, the AR system may render a corresponding virtual room or virtual space based on the user selection.

Figure 49:
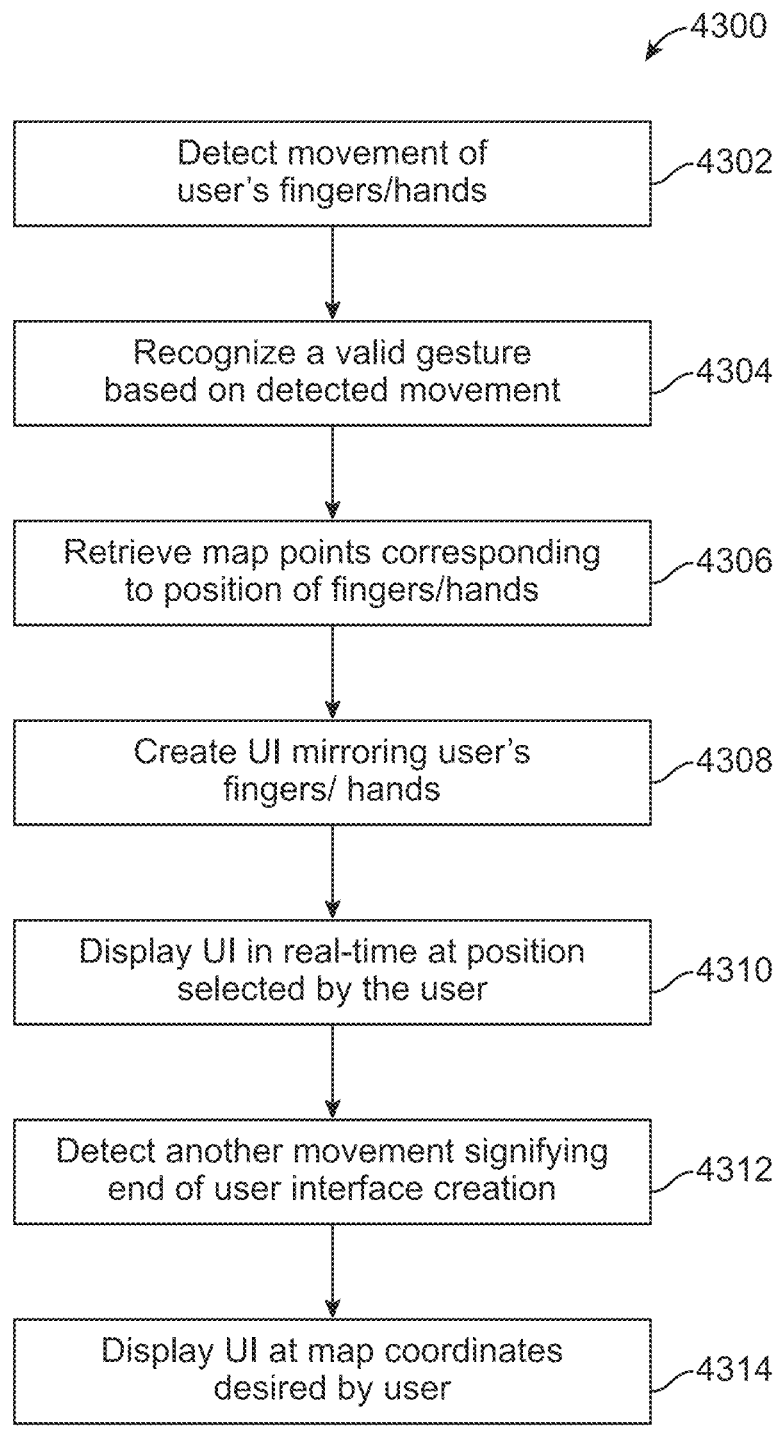
FIG. 49 is a process flow diagram of an exemplary method of constructing a customized user interface, according to one illustrated embodiment.

As discussed above, virtual user interfaces may also be created through user gestures. Before delving into various embodiments of creating UIs, FIG. 49 is an exemplary process flow diagram 4300 of creating user interfaces based on the user's gestures/finger or hand position. In step 4302, the AR system detects a movement of the user's fingers or hands.

This movement may be a predetermined gesture signifying that the user wants to create an interface (the AR system may compare the gesture to a map of predetermined gestures, for example). Based on this, the AR system may recognize the gesture as a valid gesture in step 4304. In step 4304, the AR system may retrieve through the cloud server, a set of map points associated with the user's position of fingers/hands in order to display the virtual UI at the right location, and in real-time with the movement of the user's fingers or hands. In step 4306, the AR system creates the UI that mirrors the user's gestures, and displayed the UI in real-time at the right position using the map points (step 4308).

The AR system may then detect another movement of the fingers hands or another predetermined gesture indicating to the system that the creation of user interface is done (step 4310). For example the user may stop making the motion of his fingers, signifying to the AR system to stop "drawing" the UI. In step 4312, the AR system displays the UI at the map coordinates equal to that of the user's fingers/hands when making the gesture indicating to the AR system that the user desires creations of a customized virtual UI. The following figures go through various embodiments of virtual UI constructions, all of which may be created using similar processes as described above.

Figure 50A:
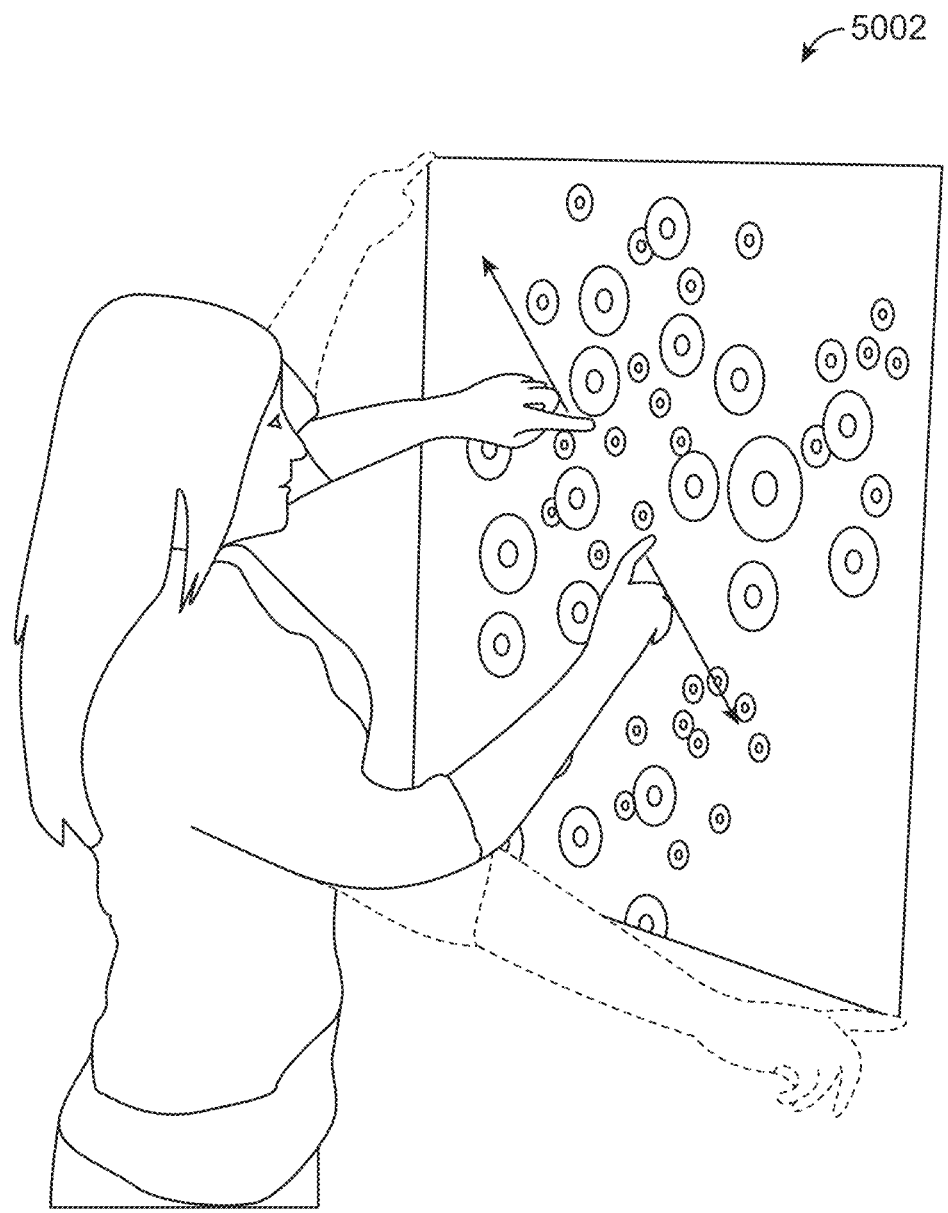
FIGS. 50A-50C illustrate users creating user interfaces, according to one illustrated embodiment.

FIG. 50A (scene 5002) shows a user interacting via gestures with a user interface virtual construct rendered by an AR system according to one illustrated embodiment.

In particular, FIG. 50A shows a user performing a gesture to create a new virtual work portal or construct in hovering in space in a physical environment or hanging or glued to a physical surface such as a wall of a physical environment. The user may, for example, perform a two arm gesture, for instance dragging outward from a center point to locations where an upper left and a lower right corner of the virtual work portal or construct should be located. The virtual work portal or construct may, for example, be represented as a rectangle, the user gesture establishing not only the position, but also the dimensions of the virtual work portal or construct.

The virtual work portal or construct may provide access to other virtual content, for example to applications, functions, menus, tools, games, and virtual rooms or virtual spaces. The user may employ various other gestures for navigating once the virtual work portal or construct has been created or opened.

Figure 50B:

FIG. 50B (scene 5004) shows a user interacting via gestures with a user interface virtual construct rendered by an AR system, according to one illustrated embodiment.

In particular, FIG. 50B shows a user performing a gesture to create a new virtual work portal or construct on a physical surface of a physical object that serves as a totem. The user may, for example, perform a two finger gesture, for instance an expanding pinch gesture, dragging outward from a center point to locations where an upper left and a lower right corner of the virtual work portal or construct should be located. The virtual work portal or construct may, for example, be represented as a rectangle, the user gesture establishing not only the position, but also the dimensions of the virtual work portal or construct.

The virtual work portal or construct may provide access to other virtual content, for example to applications, functions, menus, tools, games, and virtual rooms or virtual spaces. The user may employ various other gestures for navigating once the virtual work portal or construct has been created or opened.

Figure 50C:
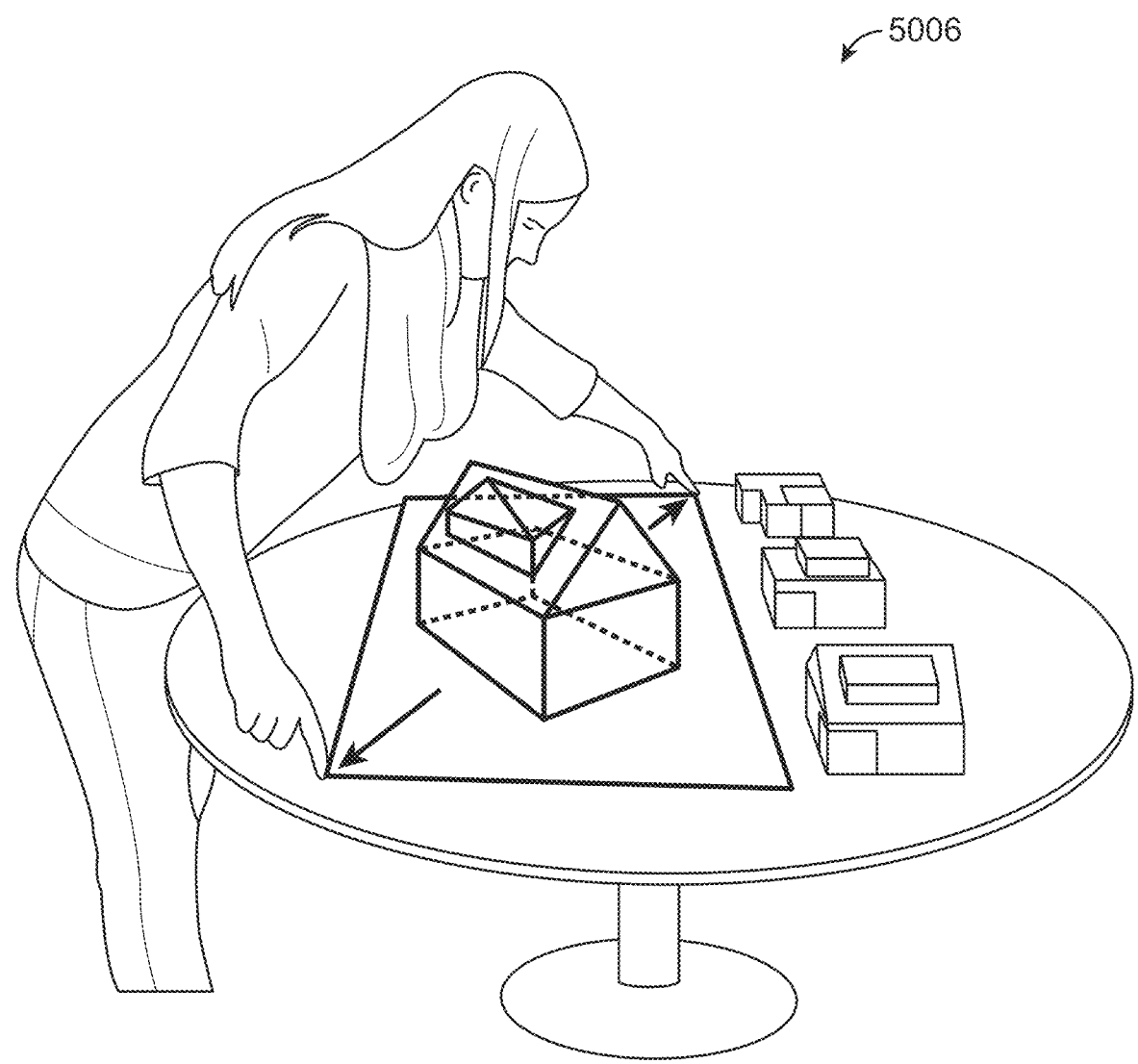

FIG. 50C (scene 5006) shows a user interacting via gestures with a user interface virtual construct rendered by an AR system, according to one illustrated embodiment.

In particular, FIG. 50C shows a user performing a gesture to create a new virtual work portal or construct on a physical surface such as a top surface of a physical table or desk. The user may, for example, perform a two arm gesture, for instance dragging outward from a center point to locations where an upper left and a lower right corner of the virtual work portal or construct should be located. The virtual work portal or construct may, for example, be represented as a rectangle, the user gesture establishing not only the position, but also the dimensions of the virtual work portal or construct.

As illustrated in FIG. 50C, specific application, functions, tools, menus, models, or virtual rooms or virtual spaces can be assigned or associated to specific physical objects or surfaces. Thus, in response to a gesture performed on or proximate a defined physical structure or physical surface, the AR system automatically opens the respective application, functions, tools, menus, model, or virtual room or virtual space associated with the physical structure or physical surface, eliminating the need to navigate the user interface.

As previously noted, a virtual work portal or construct may provide access to other virtual content, for example to applications, functions, menus, tools, games, three-dimensional models, and virtual rooms or virtual spaces. The user may employ various other gestures for navigating once the virtual work portal or construct has been created or opened.

Figure 51C:
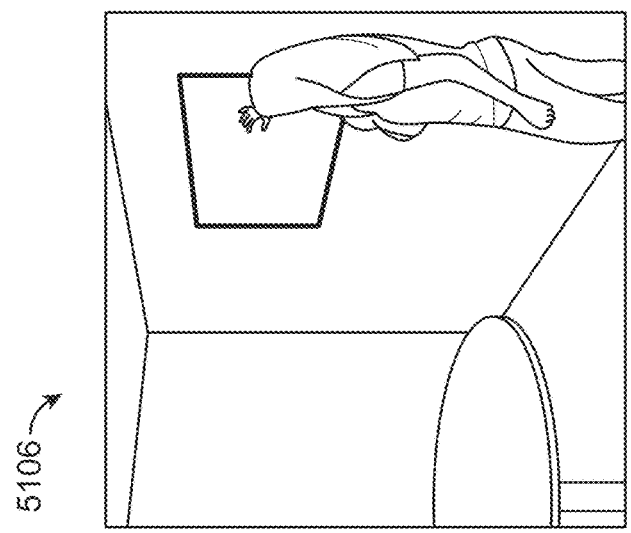
FIGS. 51A-51C illustrate interacting with a user interface created in space, according to one illustrated embodiment.
Figure 51B:
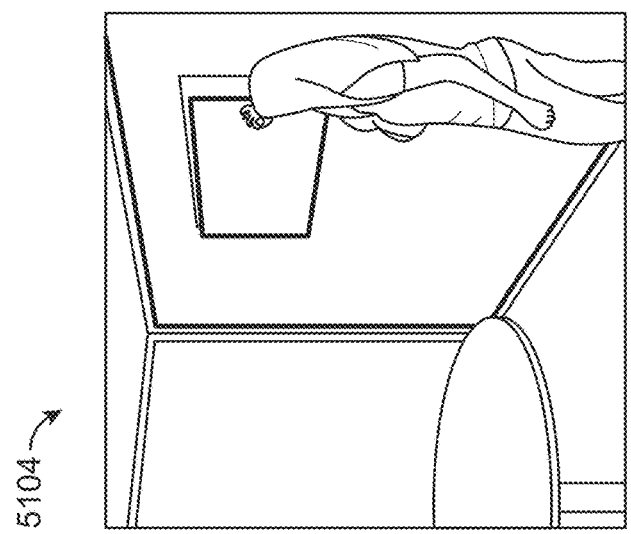
Figure 51A:
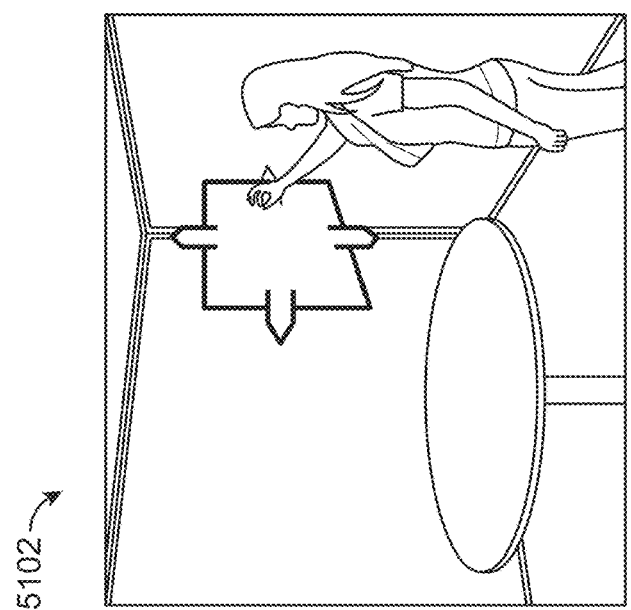

FIGS. 51A-51C (scenes 5102-5106) show a user interacting via gestures with a user interface virtual construct rendered by an AR system (not shown in FIGS. 51A-51C), according to one illustrated embodiment.

The user interface may employ either or both of at least two distinct types of user interactions, denominated as direct input or proxy input. Direct input corresponds to conventional drag and drop type user interactions, in which the user selects an iconification of an instance of virtual content, for example with a pointing device (e.g., mouse, trackball, finger) and drags the selected icon to a target (e.g., folder, other iconification of for instance an application).

Proxy input corresponds to a user selecting an iconification of an instance of virtual content by looking or focusing one the specific iconification with the user's eyes, then executing some other action (s) (e.g., gesture), for example via a totem. A further distinct type of user input is denominated as a throwing input. Throwing input corresponds to a user making a first gesture (e.g., grasping or pinching) to select selects an iconification of an instance of virtual content, followed by a second gesture (e.g., arm sweep or throwing motion towards target) to indicate a command to move the virtual content at least generally in a direction indicated by the second gesture. The throwing input will typically include a third gesture (e.g., release) to indicate a target (e.g., folder, other iconification of for instance an application).

The third gesture may be performed when the user's hand is aligned with the target or at least proximate the target. The third gesture may be performed when the user's hand is moving in the general direction of the target but not yet aligned or proximate with the target, assuming that there is no other virtual content proximate the target which would render the intended target ambiguous to the AR system.

Thus, the AR system detects and responds to gestures (e.g., throwing gestures, pointing gestures) which allow freeform location specification of a location at which virtual content should be rendered or moved. For example, where a user desires a virtual display, monitor or screen, the user may specify a location in the physical environment in the user's field of view in which to cause the virtual display, monitor or screen to appear.

This contrasts from gesture input to a physical device, where the gesture may cause the physical device to operate (e.g., ON/OFF, change channel or source of media content), but does not change a location of the physical device.

Additionally, where a user desires to logically associate a first instance of virtual content (e.g., icon representing file) with a second instance (e.g., icon representing storage folder or application), the gesture defines a destination for the first instance of virtual content.

In particular, FIG. 51A shows the user performing a first gesture to select a virtual content in the form of a virtual work portal or construct. The user may for example, perform a pinch gesture, pinching and appear to hold the virtual work portal or construct between a thumb and index finger. In response to the AR system detecting a selection (e.g., grasping, pinching or holding) of a virtual work portal or construct, the AR system may re-render the virtual work portal or construct with visual emphasis, for example as show in in FIG. 51A.

The visual emphasis cues the user at to which piece of virtual content the AR system has detected as being selected, allowing the user to correct the selection if necessary. Other types of visual cues or emphasis may be employed, for example highlighting, marqueeing, flashing, color changes, etc.

In particular, FIG. 51B shows the user performing a second gesture to move the virtual work portal or construct to a physical object, for example a surface of a wall, on which the user wishes to map the virtual work portal or construct. The user may, for example, perform a sweeping type gesture while maintaining the pinch gesture. In some implementations, the AR system may determine which physical object the user intends, for example based on either proximity and/or a direction of motion.

For instance, where a user makes a sweeping motion toward a single physical object, the user may perform the release gesture with their hand short of the actual location of the physical object. Since there are no other physical objects in proximate or in line with the sweeping gesture when the release gesture is performed, the AR system can unambiguously determine the identity of the physical object that the user intended. This may in some ways be thought of as analogous to a throwing motion.

In response to the AR system detecting an apparent target physical object, the AR system may render a visual cue positioned in the user's field of view so as to appear co-extensive with or at least proximate the detected intended target. For example, the AR system may render a boarder that encompasses the detected intended target as shown in FIG. 49B.

The AR system may also continue render the virtual work portal or construct with visual emphasis, for example as shown in FIG. 49B. The visual emphasis cues the user as to which physical object or surface the AR system has detected as being selected, allowing the user to correct the selection if necessary. Other types of visual cues or emphasis may be employed, for example highlighting, marqueeing, flashing, color changes, etc.

In particular, FIG. 51C shows the user performing a third gesture to indicate a command to map the virtual work portal or construct to the identified physical object, for example a surface of a wall, to cause the AR system to map the virtual work portal or construct to the physical object. The user may, for example, perform a release gesture, releasing the pinch to simulate releasing the virtual work portal or construct.

Figure 52A:
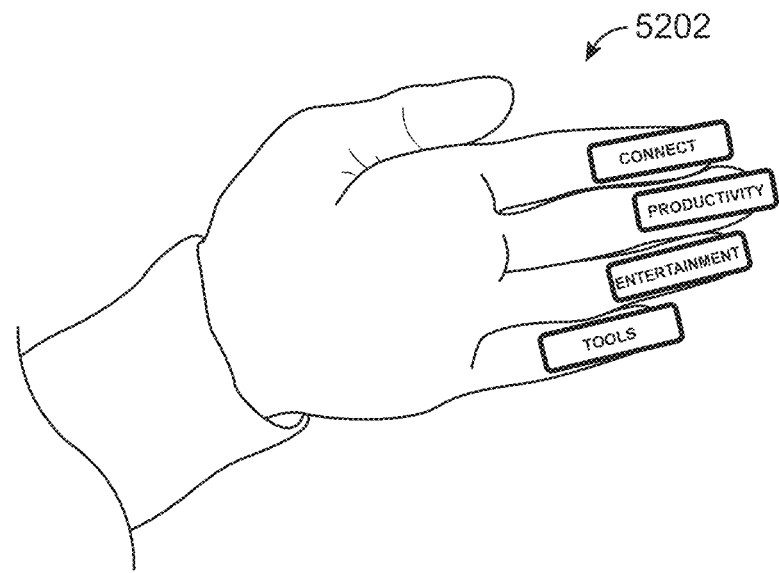
FIGS. 52A-52C are schematic diagrams illustrating creation of a user interface on a palm of the user, according to one illustrated embodiment.
Figure 52B:
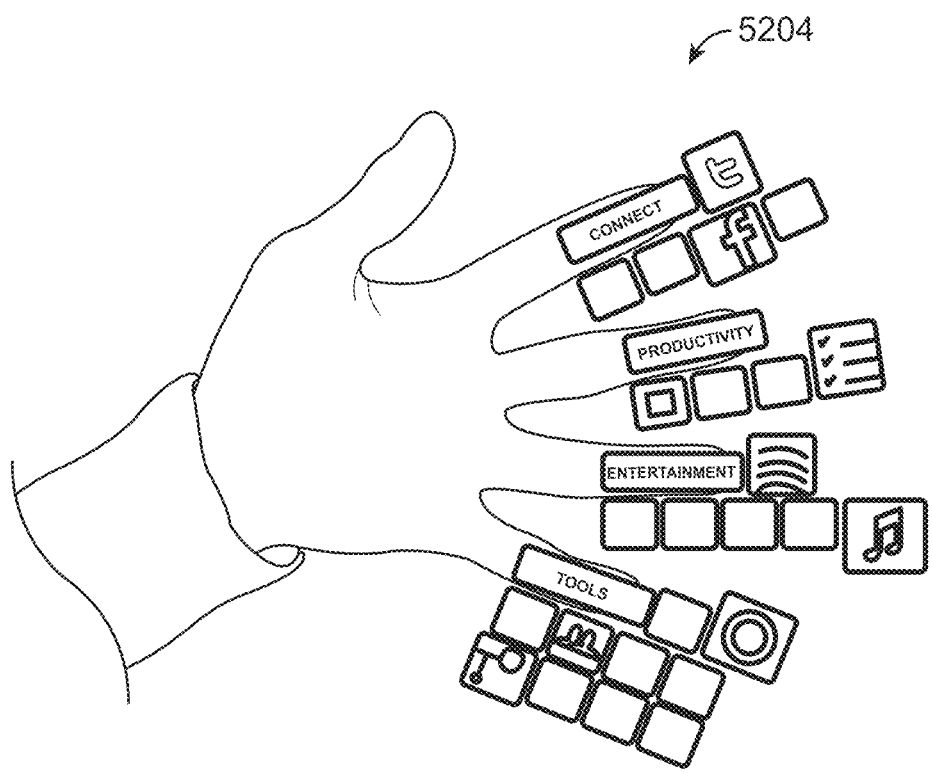
Figure 52C:
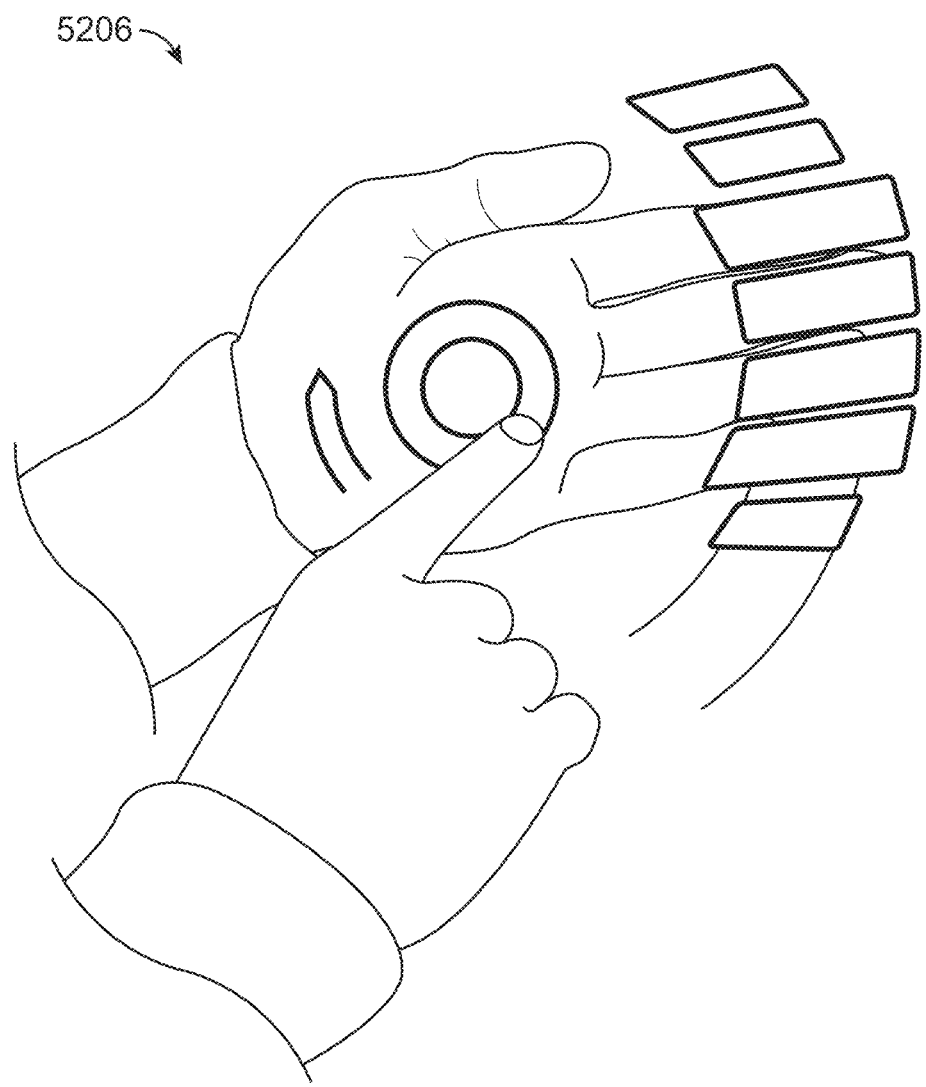

FIGS. 52A-52C (scenes 5202-5206) show a number of user interface virtual constructs rendered by an AR system (not shown in FIGS. 52A-52C) in which a user's hand serves as a totem, according to one illustrated embodiment. It should be appreciated that FIGS. 52A-C may follow the process flow diagram of FIG. 47 in order to create a user interface on the user's hands.

As illustrated in FIG. 52A, in response to detecting a first defined gesture (e.g., user opening or displaying open palm of hand, user holding up hand), the AR system renders a primary navigation menu in a field of view of the user so as to appear to be on or attached to a portion of the user's hand. For instance, a high level navigation menu item, icon or field may be rendered to appear on each finger other than the thumb. The thumb may be left free to serve as a pointer, which allows the user to select a desired one of the high level navigation menu item or icons via one of second defined gestures, for example by touch the thumb to the corresponding fingertip.

The menu items, icons or fields may, for example, represent user selectable virtual content, for instance applications, functions, menus, tools, models, games, and virtual rooms or virtual spaces.

As illustrated in FIG. 52B, in response to detecting a third defined gesture (e.g., user spreads fingers apart), the AR system expands the menus, rendering an a lower level navigation menu in a field of view of the user so as to appear to be on or attached to a portion of the user's hand. For instance, a number of lower level navigation menu items or icons may be rendered to appear on each of the fingers other than the thumb. Again, the thumb may be left free to serve as a pointer, which allows the user to select a desired one of the lower level navigation menu item or icons by touch the thumb to a corresponding portion of the corresponding finger.

As illustrated in FIG. 52C, in response to detecting a fourth defined gesture (e.g., user making circling motion in palm of hand with finger from other hand), the AR system scrolls through the menu, rendering fields of the navigation menu in a field of view of the user so as to appear to be on or attached to a portion of the user's hand. For instance, a number of fields may appear to scroll successively from one finger to the next. New fields may scroll into the field of view, entering form one direction (e.g., from proximate the thumb) and other fields may scroll from the field of view, existing from the other direction (e.g., proximate the pinkie finger). The direction of scrolling may correspond to a rotational direction of the finger in the palm. For example the fields may scroll in one direction in response to a clockwise rotation gesture and scroll in a second, opposite direction, in response to a counterclockwise rotation gesture.

User Scenarios—Interacting with Passable World Model and/or Multiple Users

Using the principles of gesture tracking/UI creation, etc. a few exemplary user applications will now be described. The applications described below may have hardware and/or software components that may be separate installed onto the system, in some embodiments. In other embodiments, the system may be used in various industries, etc. and may be modified to achieve some of the embodiments below.

Prior to delving into specific applications or user scenarios, an exemplary process of receiving and updating information from the passable world model will be briefly discussed. The passable world model, discussed above, allows multiple users to access the virtual world stored on a cloud server and essentially pass on a piece of their world to other users. For example, similar to other examples discussed above, a first user of an AR system in London may want to conference in with a second user of the AR system currently located in New York.

The passable world model may enable the first user to pass on a piece of the passable world that constitutes the current physical surroundings of the first user to the second user, and similarly pass on a piece of the passable world that constitutes an avatar of the second user such that the second user appears to be in the same room as the first user in London. In other words, the passable world allows the first user to transmit information about the room to the second user, and simultaneously allows the second user to create an avatar to place himself in the physical environment of the first user. Thus, both users are continuously updating, transmitting and receiving information from the cloud, giving both users the experience of being in the same room at the same time.

Figure 53:
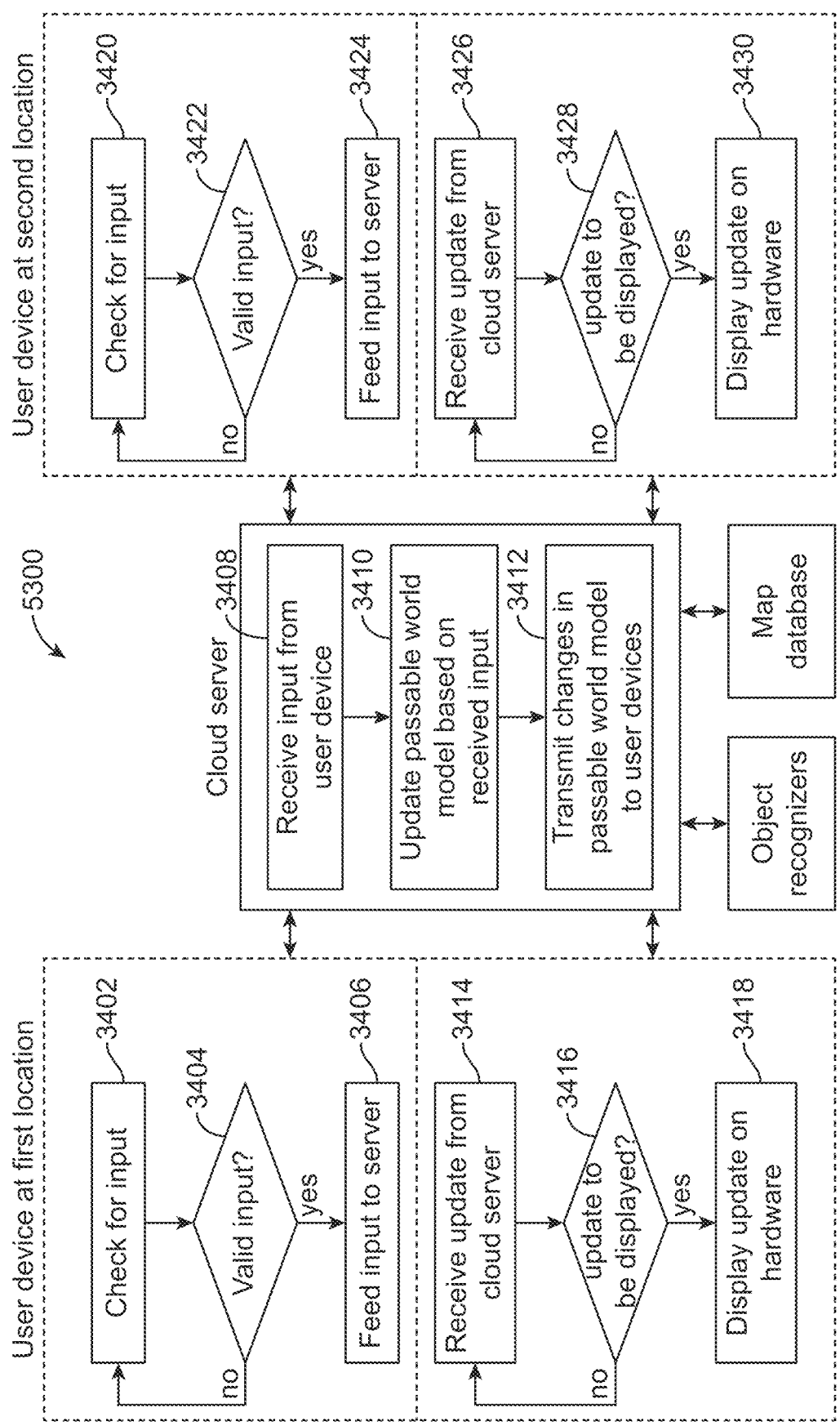
FIG. 53 is a process flow diagram of an exemplary method of retrieving information from the passable world model and interacting with other users of the AR system, according to one illustrated embodiment.

Referring to FIG. 53, an exemplary process 5300 of how data is communicated back and forth between two users located at two separate physical locations is disclosed. It should be appreciated that each input system (e.g., sensors, cameras, eye tracking, audio, etc.) may have a process similar to the one below. For illustrative purposes, the input of the following system may be input from the FOV cameras (e.g., cameras that capture the FOV of the users).

In step 3402, the AR system may check for input from the cameras. For example, following the above example, the user in London may be in a conference room, and may be drawing some figures on the white board. This may or may not constitute input for the AR system. Since the passable world is constantly being updated and built upon data received from multiple users, the virtual world existing on the cloud becomes increasingly precise, such that only new information needs to be updated to the cloud.

For example, if the user simply moved around the room, there may already have been enough 3D points, pose data information, etc. such that the user device of the user in New York is able to project the conference room in London without actively receiving new data from the user in London. However, if the user in London is adding new information, such as drawing a figure on the board in the conference room, this may constitute input that needs to be transmitted to the passable world model, and passed over to the user in New York. Thus, in step 3404, the user device checks to see if the received input is valid input. If the received input is not valid, there is wait loop in place such that the system simply checks for more input 3402

If the input is valid, the received input is fed to the cloud server in step 3406. For example, only the updates to the board may be sent to the server, rather than sending data associated with all the points collected through the FOV camera.

On the cloud server, in step 3408, the input is received from the user device, and updated into the passable world model in step 3410. As discussed in other system architectures described above, the passable world model on the cloud server may have processing circuitry, multiple databases, including a mapping database with both geometric and topological maps, object recognizers and other suitable software components.

In step 3410, based on the received input 3408, the passable world model is updated. The updates may then be sent to various user devices that may need the updated information, in step 3412. Here, the updated information may be sent to the user in New York such that the passable world that is passed over to the user in New York can also view the first user's drawing as a picture is drawn on the board in the conference room in London.

It should be appreciated that the second user's device may already be projecting a version of the conference room in London, based on existing information in the passable world model, such that the second user in New York perceives being in the conference room in London. In step 3426, the second user device receives the update from the cloud server. In step 3428, the second user device may determine if the update needs to be displayed. For example, certain changes to the passable world may not be relevant to the second user and may not be updated. In step 3430, the updated passable world model is displayed on the second user's hardware device. It should be appreciated that this process of sending and receiving information from the cloud server is performed rapidly such that the second user can see the first user drawing the figure on the board of the conference room almost as soon as the first user performs the action.

Similarly, input from the second user is also received in steps 3420-3424, and sent to the cloud server and updated to the passable world model. This information may then be sent to the first user's device in steps 3414-3418. For example, assuming the second user's avatar appears to be sitting in the physical space of the conference room in London, any changes to the second user's avatar (which may or may not mirror the second user's actions/appearance) must also be transmitted to the first user, such that the first user is able to interact with the second user.

In one example, the second user may create a virtual avatar resembling himself, or the avatar may be a bee that hovers around the conference room in London. In either case, inputs from the second user (for example, the second user may shake his head in response to the drawings of the first user), are also transmitted to the first user such that the first user can gauge the second user's reaction. In this case, the received input may be based on facial recognition and changes to the second user's face may be sent to the passable world model, and then passed over to the first user's device such that the change to the avatar being projected in the conference room in London is seen by the first user.

Figure 54:
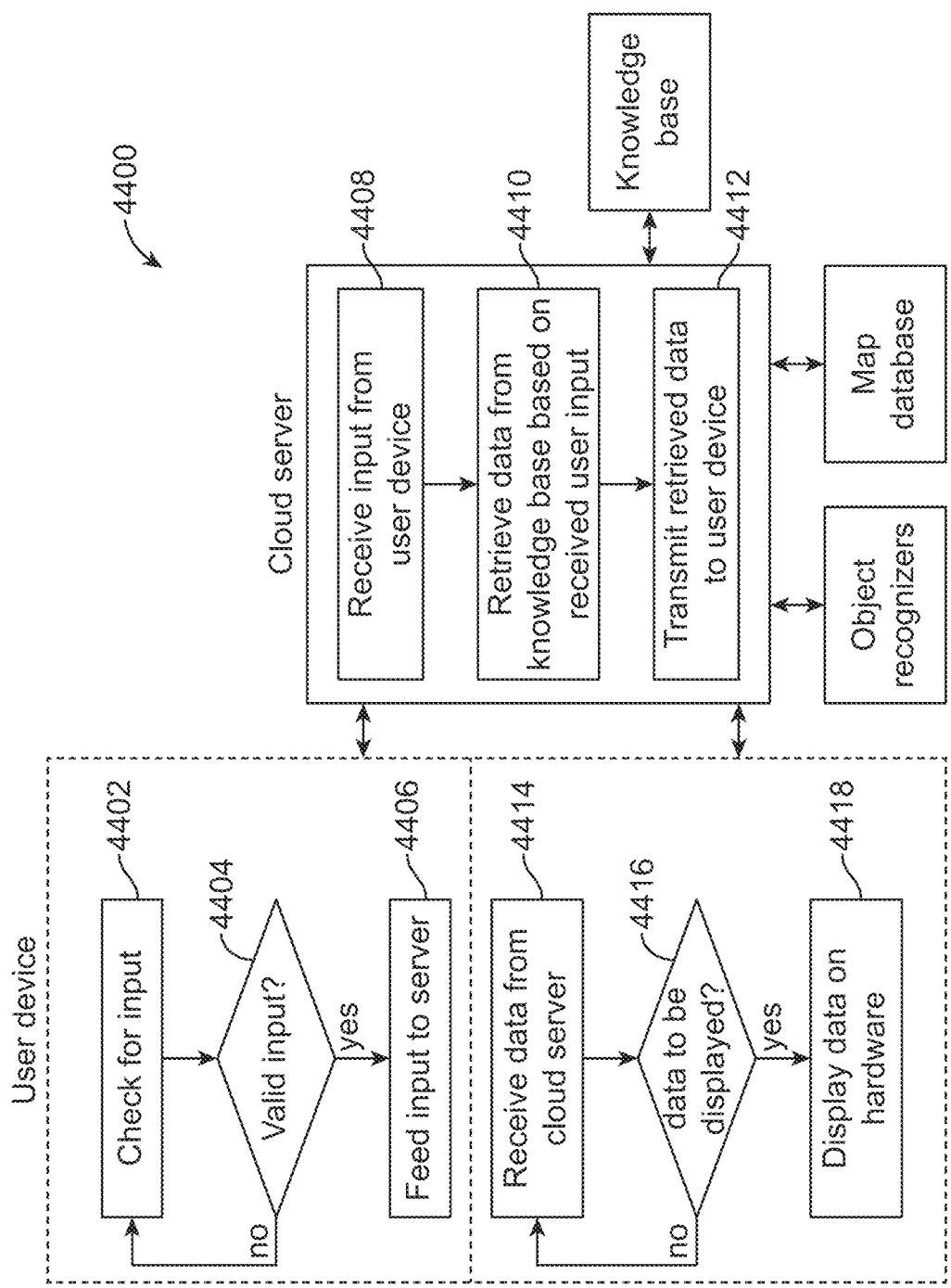
FIG. 54 is a process flow diagram of an exemplary method of retrieving information from a knowledge based in the cloud based on received input, according to one illustrated embodiment.

Similarly, there may be many other types of input that are effectively passed back and forth between multiple users of the AR system. Although the particular examples may change, all interactions between a user of the AR system and the passable world is similar to the process described above, with reference to FIG. 53. While the above process flow diagram describes interaction between multiple users accessing and passing a piece of the passable world to each other, FIG. 54 is an exemplary process flow diagram 4400 illustrating interaction between a single user and the AR system. The user may access and interact with various applications that require data retrieved from the cloud server.

In step 4402, the AR system checks for input from the user. For example, the input may be visual, audio, sensory input, etc. indicating that the user requires data. For example, the user may want to look up information about an advertisement he may have just seen on a virtual television. In step 4404, the system determines if the user input is valid. If the user input is valid, in step 4406, the input is fed into the server. On the server side, when the user input is received in step 4408, appropriate data is retrieved from a knowledge base in step 4410. As discussed above, there may be multiple knowledge databases connected to the cloud server from which to retrieve data. In step 4412, the data is retrieved and transmitted to the user device requesting data.

Back on the user device, the data is received from the cloud server in step 4414. In step 4416, the system determines when the data needs to be displayed in the form of virtual content, and if it does, the data is displayed on the user hardware 4418.

As discussed briefly above, many user scenarios may involve the AR system identifying real-world activities and automatically performing actions and/or displaying virtual content based on the detected real-world activity. For example, the AR system recognizes the user activity (e.g., cooking) and then creates a user interface that floats around the user's frame of reference providing useful information/virtual content associated with the activity. Similarly, many other uses can be envisioned, some of which will be described in user scenarios below.

Figure 55:
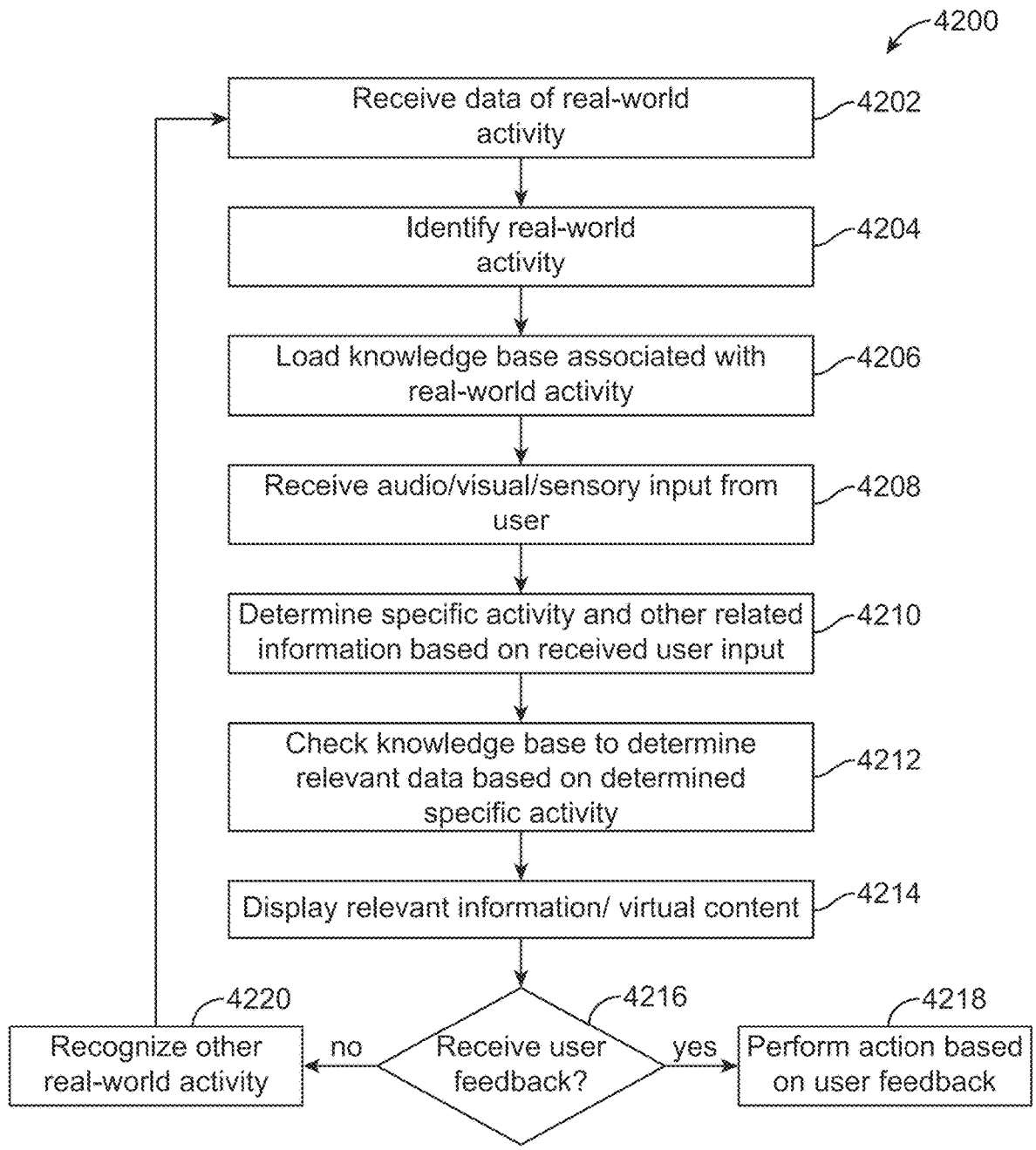
FIG. 55 is a process flow diagram of an exemplary method of recognizing a real-world activity, according to one illustrated embodiment.

Referring now to FIG. 55, an exemplary process flow diagram 4200 of recognizing real-world activities will be briefly described. In step 4202, the AR system may receive data corresponding to a real-world activity. For example, the data may be visual data, audio data, sensory data, etc.. Based on the received data, the AR system may identify the real-world activity in step 4204.

For example, the captured image of a user cutting vegetables may be recorded, and when compared to a mapping database, the AR system may recognize that the user is cooking, for example. Based on the identified real-world activity, the AR system may load a knowledge base associated with the real-world activity in step 4206, using the process flow diagram of FIG. 54, for example. Or, the knowledge base may be a locally stored knowledge base.

Once the knowledge base has been loaded, the AR system may rely on specific activities within the broad category to determine useful information to be displayed to the user. For example, the AR system may have retrieved information related to cooking, but may only need to display information about a particular recipe that the user is currently making. Or the AR system may only need to display information about cooking which is determined based on receiving further input from the user, in step 4208.

The AR system may then determine the specific activity in step 4210, similar to step 4202-4204, based on the received input regarding the specific activity. In step 4212, the AR system may check the loaded knowledge base to determine relevant data associated with the specific activity and display the relevant information/virtual content in the user interface (e.g., floating user interface). In step 4216, the AR system determines whether further user feedback is received. In steps 4218 and 4220, the user either performs an action based on user feedback or simply waits for further feedback related to the real-world activity. The following user scenarios may use one or more of the process flow diagrams outlined above.

Figure 56A:
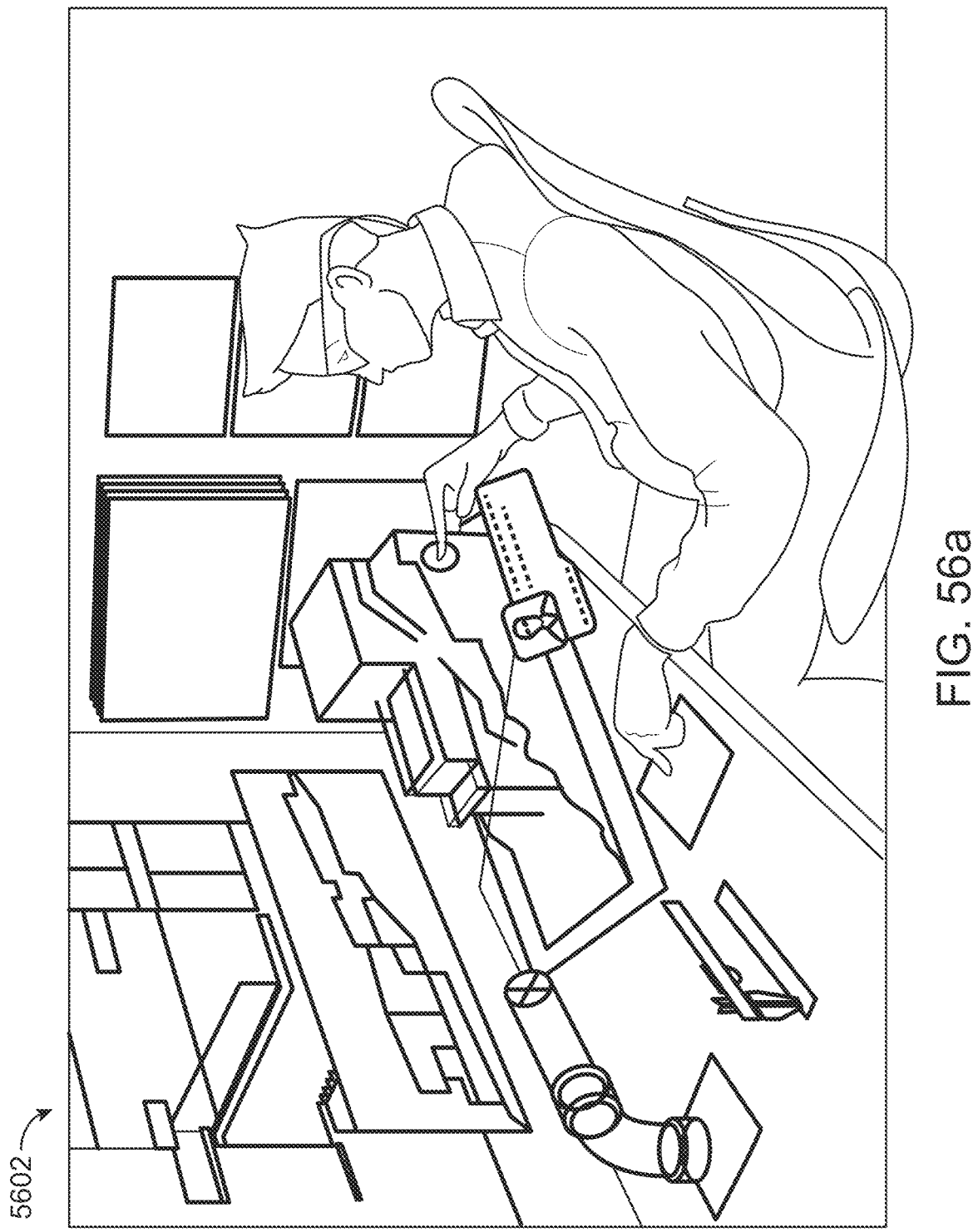
FIGS. 56A-56B illustrate a user scenario of a user interacting with the AR system in an office environment, according to one illustrated embodiment.

FIG. 56A shows a user sitting in a physical office space, and using an AR system to experience a virtual room or virtual space in the form of a virtual office, at a first time, according to one illustrated embodiment.

The physical office may include one or more physical objects, for instance walls, floor (not shown), ceiling (not shown), a desk and chair. The user may wear a head worn AR system, or head worn component of an AR system. The head worn AR system or component is operable to render virtual content in a field of view of the user. For example, the head worn AR system or component may render virtual objects, virtual tools and applications onto the retina of each eye of the user.

As illustrated the AR system renders a virtual room or virtual space in the form of a virtual office, in which the user performs their occupation or job. Hence, the virtual office is populated with various virtual tools or applications useful in performing the user's job. The virtual tools or applications may for example include various virtual objects or other virtual content, for instance two-dimensional drawings or schematics, two-dimensional images or photographs, and a three-dimensional architectural model.

The virtual tools or applications may for example include tools such as a ruler, caliper, compass, protractor, templates or stencils, etc. The virtual tools or applications may for example include interfaces for various software applications, for example interfaces for email, a Web browser, word processor software, presentation software, spreadsheet software, voicemail software, etc. Some of the virtual objects may be stacked or overlaid with respect to one another. The user may select a desired virtual object with a corresponding gesture.

Based on the recognized gesture, the AR system may map the gesture, and recognize the command. The command may be to move the user interface, and may then display the next virtual object. For instance, the user may page through documents or images with a finger flicking gesture to iteratively move through the stack of virtual objects. Some of the virtual objects may take the form of menus, selection of which may cause rendering of a submenu. The user scenario illustrated in FIGS. 56A-56B (scenes 5602 and 5604) may utilize aspects of the process flow diagrams illustrated in FIGS. 54 and 55.

Figure 56B:
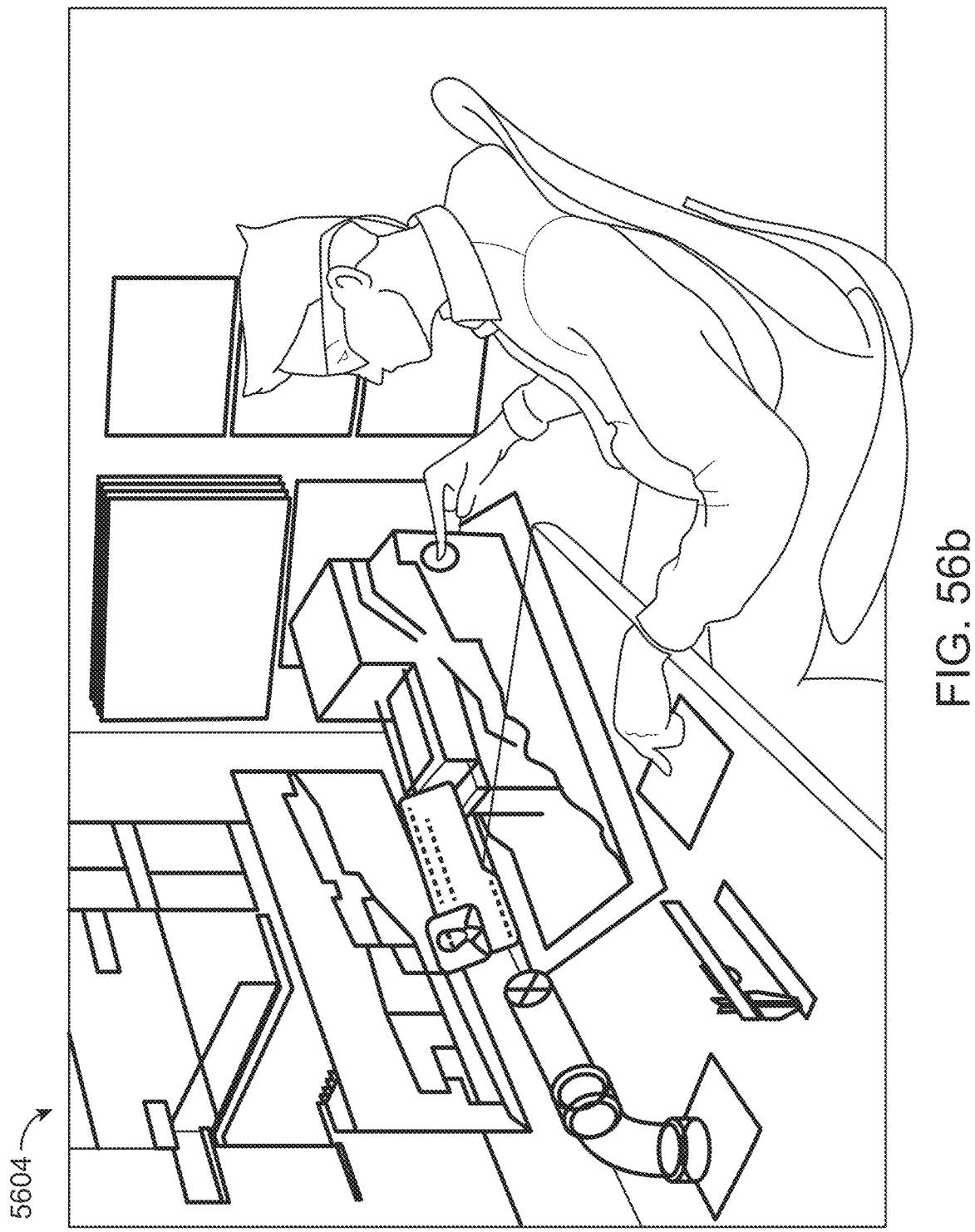

FIG. 56B shows the user in the physical office employing the virtual office of FIG. 56A, at a second time, according to one illustrated embodiment. The physical office of FIG. 56B is identical to that of FIG. 56A, and the virtual office of FIG. 56B is similar to the virtual office of FIG. 56A.

At the second time, the AR system may present (i.e., render) a virtual alert or notification to the user in the virtual office. The virtual alert may be based on data retrieved from the cloud. Or for example, the virtual alert may be based on identifying a real-world activity, as described in FIG. 55. For example, the AR system may render a visual representation of a virtual alert or notification in the user's field of view. The AR system may additionally or alternatively render an aural representation of a virtual alert or notification.

Figure 57:
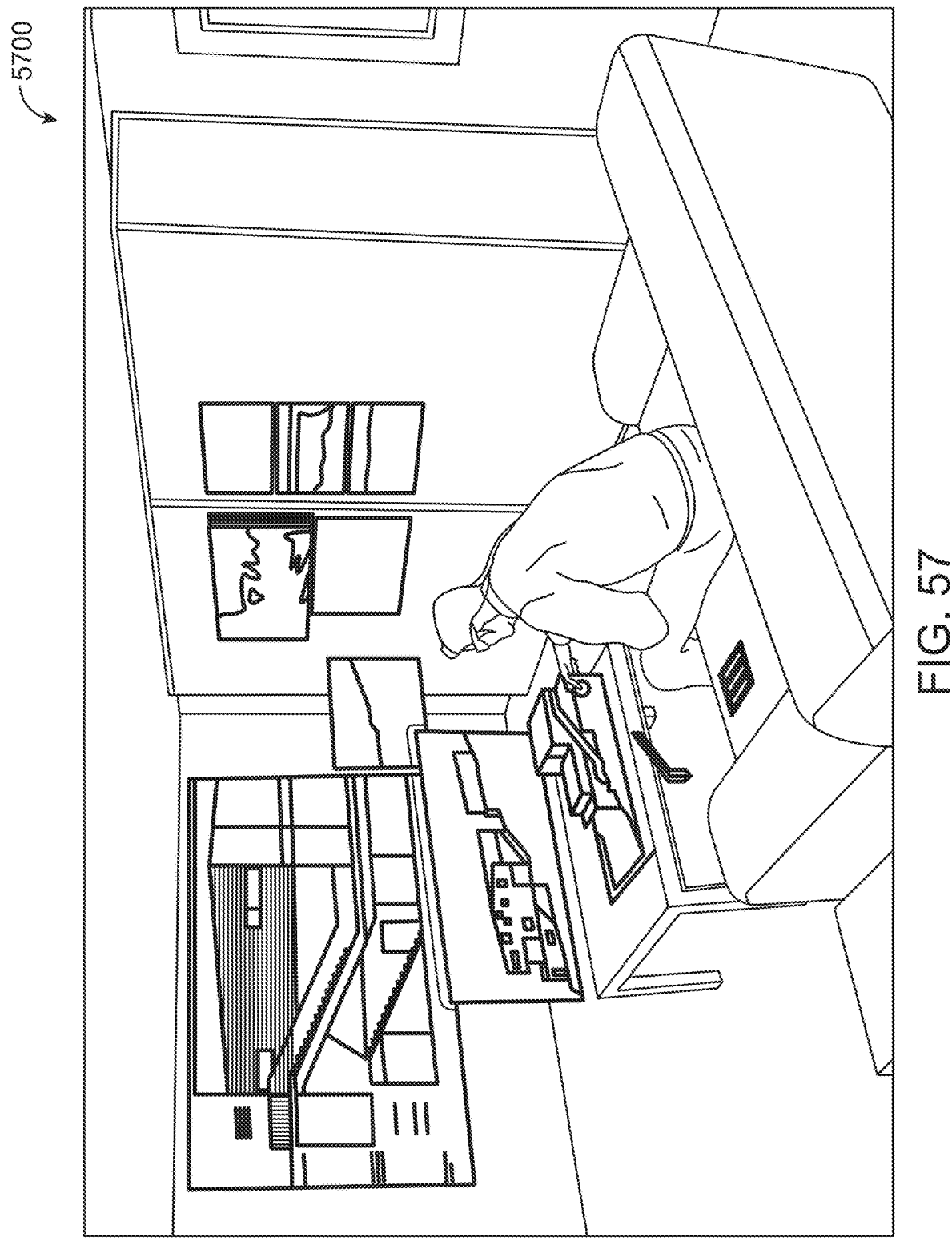
FIG. 57 is another user scenario diagram illustrating creating an office environment in the user's living room, according to one illustrated embodiment.

FIG. 57 (scene 5700) shows a user sitting in a physical living room space, and using an AR system to experience a virtual room or virtual space in the form of a virtual office, at a first time, according to one illustrated embodiment.

The physical living room may include one or more physical objects, for instance walls, floor, ceiling, a coffee table and sofa. The user may wear a head worn AR system, or head worn component of an AR system. The head worn AR system or component is operable to render virtual content in a field of view of the user. For example, the head worn AR system or component may render virtual objects, virtual tools and applications onto the retina of each eye of the user.

As illustrated the AR system renders a virtual room or virtual space in the form of a virtual office, in which the user performs their occupation or job. Hence, the virtual office is populated with various virtual tools or applications useful in performing the user's job. This may be based on received inputs by the user, based on which the AR system may retrieve data from the cloud and display the virtual tools to the user.

As FIGS. 56A and 57 illustrate, a virtual office may be portable, being renderable in various different physical environments. It thus may be particularly advantageous if the virtual office renders identically in a subsequent use to its appearance or layout as the virtual office appeared in in a most previous use or rendering. Thus, in each subsequent use or rendering, the same virtual objects will appear and the various virtual objects may retain their same spatial positions relative to one another as in a most recently previous rendering of the virtual office.

In some implementations, this consistency or persistence of appearance or layout from one use to next subsequent use, may be independent of the physical environments in which the virtual space is rendered. Thus, moving from a first physical environment (e.g., physical office space) to a second physical environment (e.g., physical living room) will not affect an appearance or layout of the virtual office.

The user may, for example select a specific application (e.g., camera application), for use while in a specific virtual room or virtual space (e.g., office space).

Figure 58:
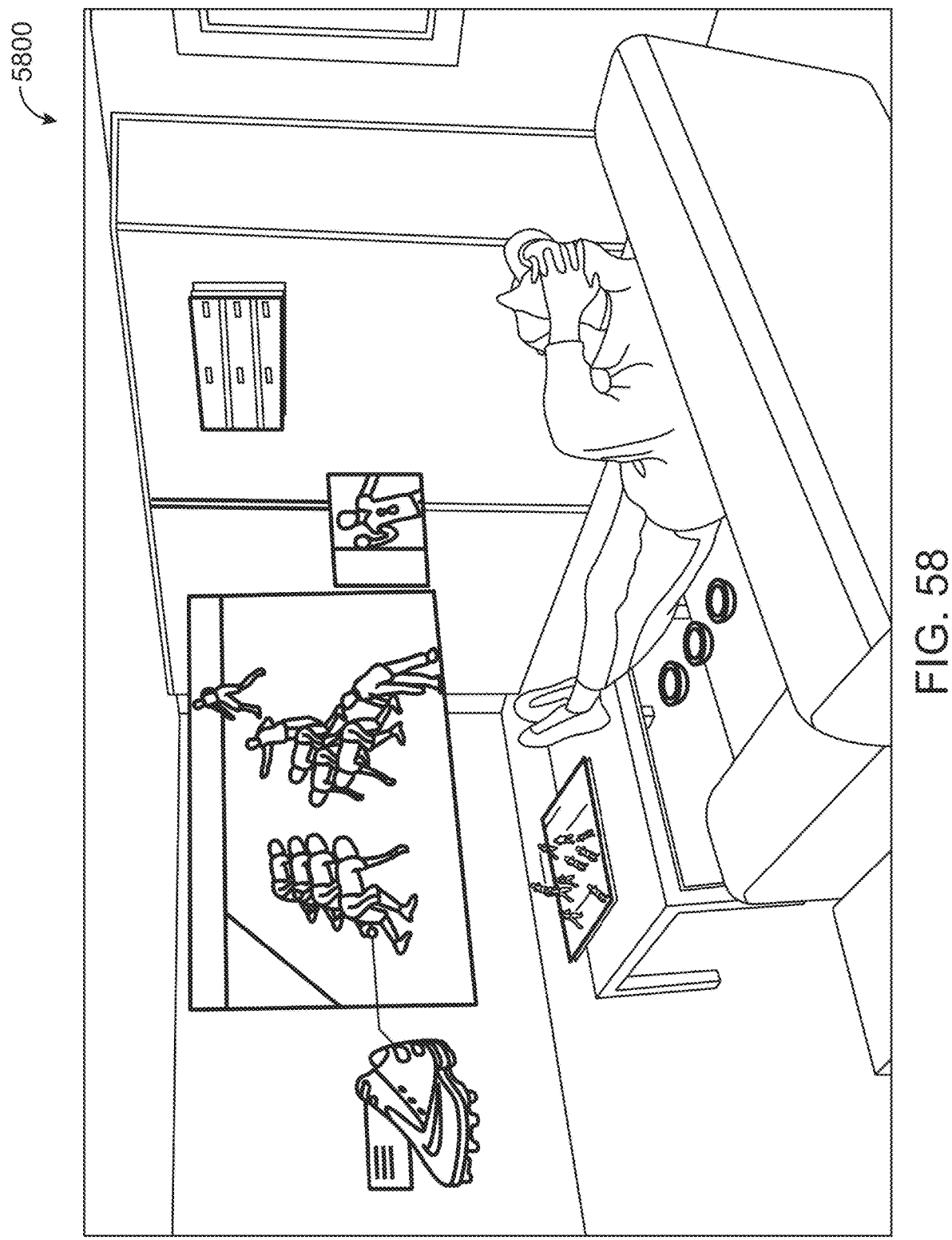
FIG. 58 is another user scenario diagram illustrating a user watching virtual television in the user's living room, according to one illustrated embodiment.

FIG. 58 (scene 5800) shows a user sitting in a physical living room space, and using an AR system to experience a virtual room or virtual space in the form of a virtual entertainment or media room, at a first time, according to one illustrated embodiment.

The user may wear a head worn AR system, or head worn component of an AR system. The head worn AR system or component is operable to render virtual content in a field of view of the user. For example, the head worn AR system or component may render virtual objects, virtual tools and applications onto the retina of each eye of the user.

As illustrated the AR system renders a virtual room or virtual space in the form of a virtual entertainment or media room, in which the user relaxes and/or enjoys entertainment or consumes media (e.g., programs, movies, games, music, reading). Hence, the virtual entertainment or media room is populated with various virtual tools or applications useful in enjoying entertainment and/or consuming media.

The AR system may render the virtual entertainment or media room with a virtual television or primary screen.

Since the AR system may render virtual content to a user's retina, the virtual television or primary screen can be rendered to any desired size. The virtual television or primary screen could even extend beyond the confines of the physical room. The AR system may render the virtual television or primary screen to replicate any know or yet to be invented physical television.

Thus, the AR system may render the virtual television or primary screen to replicate a period or classic television from the 1950s, 1960, or 1970s, or may replicate any current television. For example, the virtual television or primary screen may be rendered with an outward appears of a specific make and model and year of a physical television. Also for example, the virtual television or primary screen may be rendered with the same picture characteristics of a specific make and model and year of a physical television. Likewise, the AR system may render sound to have the same aural characteristics as sound from a specific make and model and year of a physical television.

The AR system also renders media content to appear as if the media content was being displayed by the virtual television or primary screen. The AR system may retrieve data from the cloud, such that virtual television displaying virtual content that is streamed from the passable world model, based on received user input indicating that the user wants to watch virtual television. Here, the user may also create the user interface, to specify the confines of the user interface or virtual television, similar to the process flow diagram of FIG. 49 discussed above. The media content may take any of a large variety for forms, including television programs, movies, video conference or calls, etc.

The AR system may render the virtual entertainment or media room with one or more additional virtual televisions or secondary screens. Additional virtual televisions or secondary screens may enable the user to enjoy second screen experiences.

For instance, a first secondary screen may allow the user to monitor a status of a fantasy team or player in a fantasy league (e.g., fantasy football league), including various statistics for players and teams. Again, based on user input received from the user regarding the type of virtual content desired and a location of the virtual content, the AR system may retrieve data from the cloud server and display it at the location desired by the user, as per process flow diagrams of FIGS. 49, 54 and 55.

Additionally or alternatively, a second or more secondary screens may allow the user to monitor other activities, for example activities tangentially related to the media content on the primary screen. For instance, a second or additional secondary screens may display a listing of scores in games from around a conference or league while the user watches one of the games on the primary screen.

Also for instance, a second or additional secondary screens may display highlights from games from around a conference or league, while the user watches one of the games on the primary screen. One or more of the secondary screens may be stacked as illustrated FIG. 30, allowing a user to select a secondary screen to bring to a top, for example via a gesture. For instance, the user may use a gesture to toggle through the stack of secondary screens in order, or may use a gesture to select a particular secondary screen to bring to a foreground relative to the other secondary screens.

The AR system may render the virtual entertainment or media room with one or more three-dimensional replay or playback tablets. The three-dimensional replay or playback tablets may replicate in miniature, a pitch or playing field of a game the user is watching on the primary display, for instance providing a "God's eye view." The three-dimensional replay or playback tablets may, for instance, allow the user to enjoy on-demand playback or replay of media content that appears on the primary screen. This may include user selection of portions of the media content to be play backed or replayed.

This may include user selection of special effects, for example slow motion replay, stopping or freezing replay, or speeding up or fast motion replay to be faster than actual time. Such may additionally allow a user to add or introduce annotations into the display. For example, the user may gesture to add annotations marking a receiver's route during a replay of a play in a football game, or to mark a blocking assignment for a linemen or back.

The three-dimensional replay or playback tablet may even allow a user to add a variation (e.g., different call) that modifies how a previous play being reviewed plays out. For example, the user may specify a variation in a route run by a receiver, or a blocking assignment assigned to a lineman or back. The AR system may use the fundamentals parameters of the actual play, modifying one or more parameters, and then executing a game engine on the parameters to play out a previous play executed in an actual physical game but with the user modification(s). For example, the user may track an alternative route for a wide receiver. The AR system has all makes no changes to the actions of the players, except the selected wide receiver, the quarterback, and any defensive players who would cover the wide receiver.

An entire virtual fantasy play may be played out, which may even produce a different outcome than the actual play. This may occur, for example, during an advertising break or time out during the game. This allows the user to test their abilities as an armchair coach or player. A similar approach could be applied to other sports. For example, the user may make a different play call in a replay of a basketball game, or may call for a different pitch in a replay of a baseball game, to name just a few examples. Use of a game engine allows the AR system to introduce an element of statistical chance, but within the confines of what would be expected in real games.

The AR system may render additional virtual content, for example 3D virtual advertisements. The subject matter or content of the 3D virtual advertisements may, for example, be based at least in part on the content of what is being played or watched on the virtual television or primary screen. The AR system may detect a real-world activity and then automatically display virtual content based on the virtual content similar to the process flow described in FIG. 55 above.

The AR system may render virtual controls. For example, the AR system may render virtual controls mapped in the user's field of vision so as to appear to be within arm's reach of the user. The AR system may monitor of user gestures toward or interaction with the virtual controls, and cause corresponding actions in response to the gestures or interactions.

The AR system allows users to select a virtual room or space to be rendered to the user's field of view, for example as a 4D light field. For example, the AR system may include a catalog or library of virtual rooms or virtual spaces to select from. The AR system may include a generic or system wide catalog or library of virtual rooms or virtual spaces, which are available to all users. The AR system may include an entity specific catalog or library of virtual rooms or virtual spaces, which are available to a subset of users, for example users who are all affiliated with a specific entity such as a business, institution or other organization. The AR system may include a number of user specific catalogs or libraries of virtual rooms or virtual spaces, which are available to respective specific users or others who are authorized or granted access or permission by the respective specific user.

The AR system allows users to navigate from virtual space to virtual space. For example, a user may navigate between a virtual office space and a virtual entertainment or media space. As discussed herein, the AR system may be responsive to certain user input to allow navigation directly from one virtual space to another virtual space, or to toggle or browse through a set of available virtual spaces. The set of virtual spaces may be specific to a user, specific to an entity to which a user belongs, and/or may be system wide or generic to all users.

To allow user selection of and/or navigation between virtual rooms or virtual spaces, the AR system may be responsive to one or more of, for instance, gestures, voice commands, eye tracking, and/or selection of physical buttons, keys or switches for example carried by a head worn component, belt pack or other physical structure of the individual AR system. The user input may be indicative of a direct selection of a virtual space or room, or may cause a rendering of a menu or submenus to allow user selection of a virtual space or room.

Figure 59:
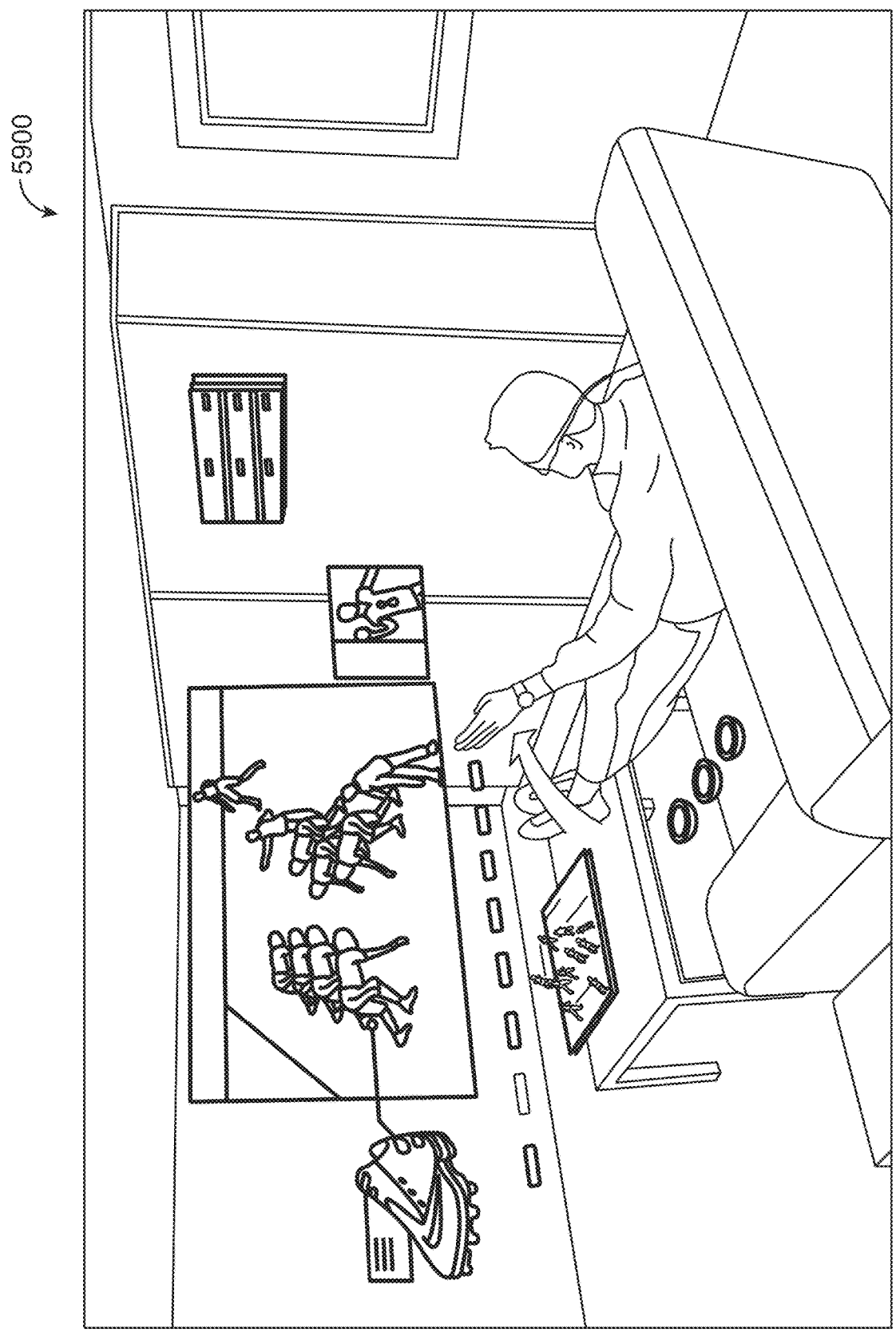
FIG. 59 is another user scenario diagram illustrating the user of FIG. 54 interacting with the virtual television through hand gestures, according to one illustrated embodiment.

FIG. 59 (scene 5900) shows a user sitting in a physical living room space, and using an AR system to experience a virtual room or virtual space in the form of a virtual entertainment or media room, at a first time, according to one illustrated embodiment.

The physical living room may include one or more physical objects, for instance walls, floor, ceiling, a coffee table and sofa. As previously noted, the user may wear a head worn AR system, or head worn component of an AR system, operable to render virtual content in a field of view of the user. For example, the head worn AR system or component may render virtual objects, virtual tools and applications onto the retina of each eye of the user.

The AR system may store a set of virtual rooms or spaces that are logically associated with a specific physical location, physical room or physical space. For example, the AR system may store a mapping between a physical location, physical room or physical space and one or more virtual rooms or spaces. For instance, the AR system may store a mapping between a user's physical living room and a virtual entertainment or media room.

Also for instance, the AR system may store a mapping between the user's physical living room and a number of other virtual rooms or spaces (e.g., office space). The AR system may determine a current location of a user, and detect a specific user gesture (single headed arrow). Based on knowledge of the user's current physical location, and in response to the gesture, the AR system may render virtual content that scrolls or toggles through the set of virtual rooms or virtual spaces mapped or otherwise associated with the specific physical space. For example, the AR system may render the virtual content associated with a next one of the virtual rooms or spaces in a set As illustrated in FIG. 59, the AR system may render a user interface tool which provides a user with a representation of choices of virtual rooms or virtual spaces, and possibly a position of a currently selected virtual room or virtual space in a set of virtual room or virtual space available to the user. As illustrated, the representation takes the form of a line of marks or symbols, with each marking representing a respective one of the virtual rooms or virtual spaces available to the user. A currently selected one of the virtual rooms or virtual spaces is visually emphasized, to assist the user in navigating forward or backward through the set.

Figure 60A:
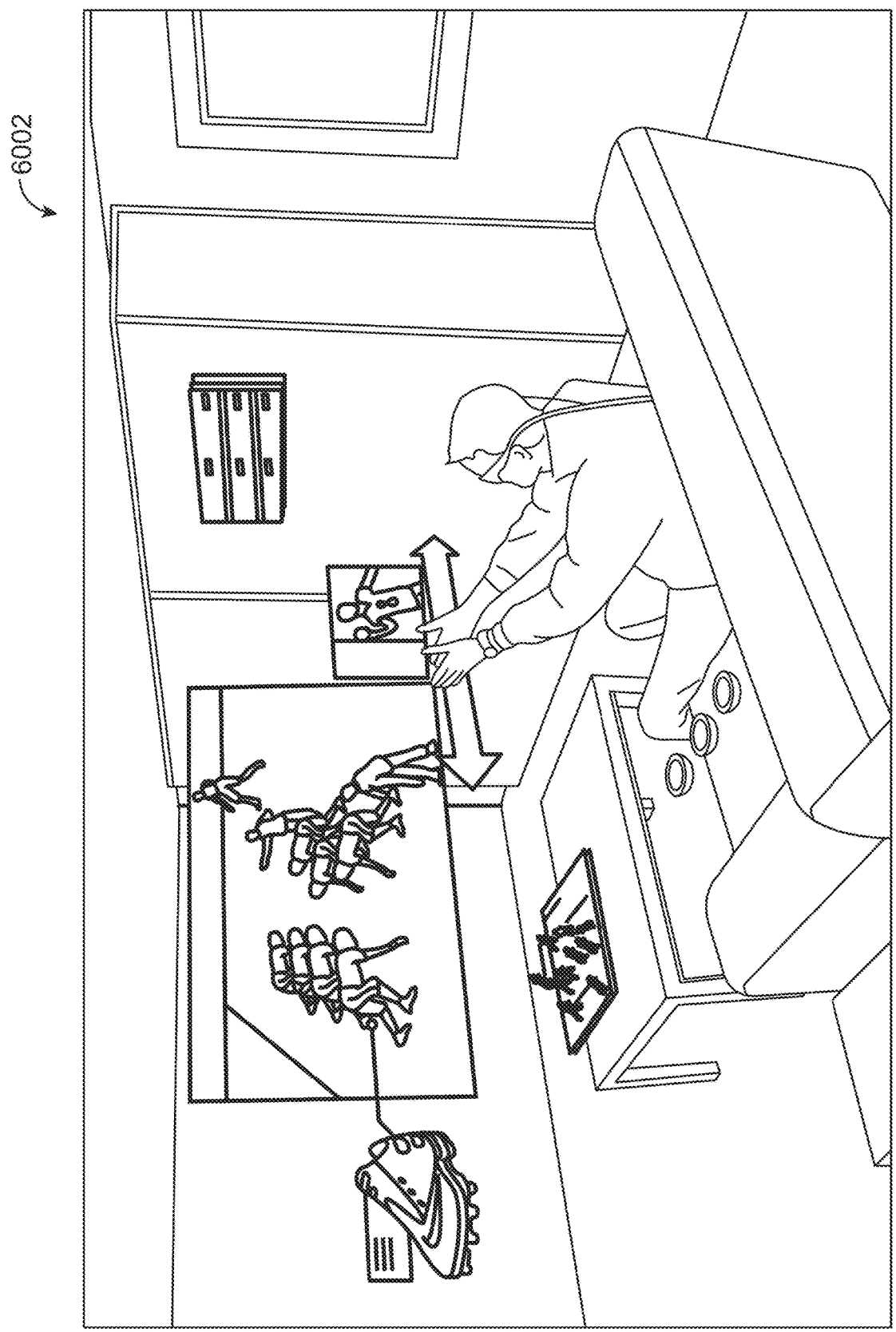
FIGS. 60A-60B illustrates the user of FIGS. 58 and 59 interacting with the AR system using other hand gestures, according to one illustrated embodiment.
Figure 60B:
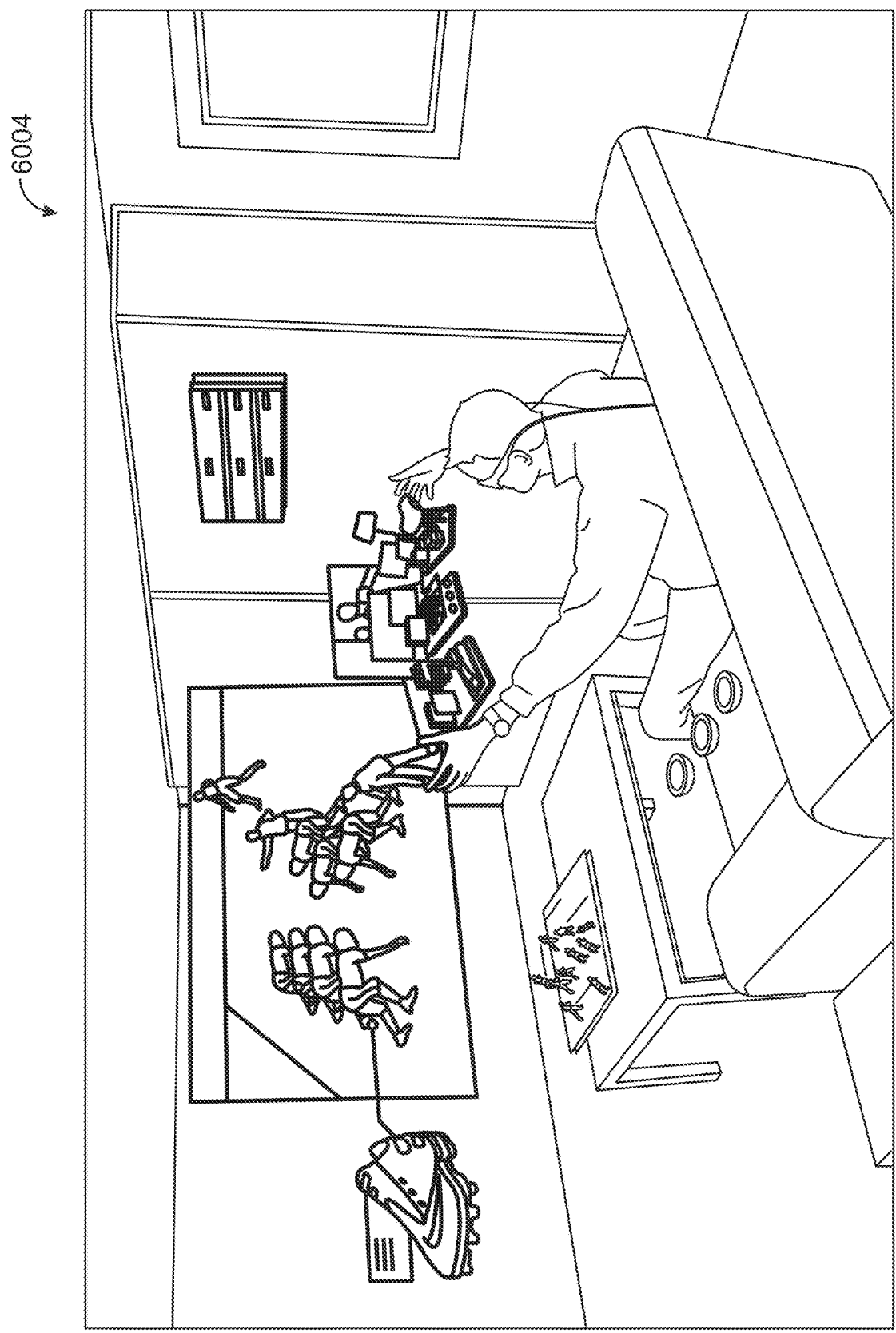

FIGS. 60A, 60B (scenes 6002 and 6004) show a user sitting in a physical living room space, and using an AR system to experience a virtual room or virtual space in the form of a virtual entertainment or media room, the user executing gestures to interact with a user interface virtual construct, according to one illustrated embodiment.

The physical living room may include one or more physical objects, for instance walls, floor, ceiling, a coffee table and sofa. As previously noted, the user may wear a head worn AR system, or head worn component of an AR system, operable to render virtual content in a field of view of the user. For example, the head worn AR system or component may render virtual objects, virtual tools and applications onto the retina of each eye of the user.

As illustrated in FIG. 60A, the user executes a first gesture (illustrated by double headed arrow), to open an icon based cluster user interface virtual construct (FIG. 60B). The gesture may include movement of the user's arms and/or hands or other parts of the user's body, for instance head pose or eyes. Alternatively, the user may use spoken commands to access the icon based cluster user interface virtual construct (FIG. 60B). If a more comprehensive menu is desired, the user may use a different gesture.

As illustrated in FIG. 60B, the icon based cluster user interface virtual construct provides a set of small virtual representations of a variety of different virtual rooms or spaces from which a user may select. This virtual user interface provides quick access to virtual rooms or virtual spaces via representations of the virtual rooms or virtual spaces. The small virtual representations are themselves essentially non-functional, in that they do not include functional virtual content. Thus, the small virtual representations are non-functional beyond being able to cause a rendering of a functional representation of a corresponding virtual room or space in response to selection of one of the small virtual representations.

The set of small virtual representations may correspond to a set or library of virtual rooms or spaces available to the particular user. Where the set includes a relatively large number of choices, the icon based cluster user interface virtual construct may, for example, allow a user to scroll through the choice. For example, in response to a second gesture, an AR system may re-render the icon based cluster user interface virtual construct with the icons shifted in a first direction (e.g., toward user's right), with one icon falling out of a field of view (e.g., right-most icon) and a new icon entering the field of view. The new icon corresponds to a respective virtual room or virtual space that was not displayed, rendered or shown in a temporally most immediately preceding rendering of the icon based cluster user interface virtual construct. A third gesture may, for example, cause the AR system to scroll the icons in the opposite direction (e.g., toward user's left) similar to process flow diagram of FIG. 37).

In response to a user selection of a virtual room or virtual space, the AR system may render virtual content associated with the virtual room or virtual space to appear in the user's field of view. The virtual content may be mapped or "glued" to the physical space. For example, the AR system may render some or all of the virtual content positioned in the user's field of view to appear as if the respective items or instances of virtual content are on various physical surfaces in the physical space, for instance walls, tables, etc. Also for example, the AR system may render some or all of the virtual content positioned in the user's field of view to appear as if the respective items or instances of virtual content are floating in the physical space, for instance within reach of the user.

Figure 61A:
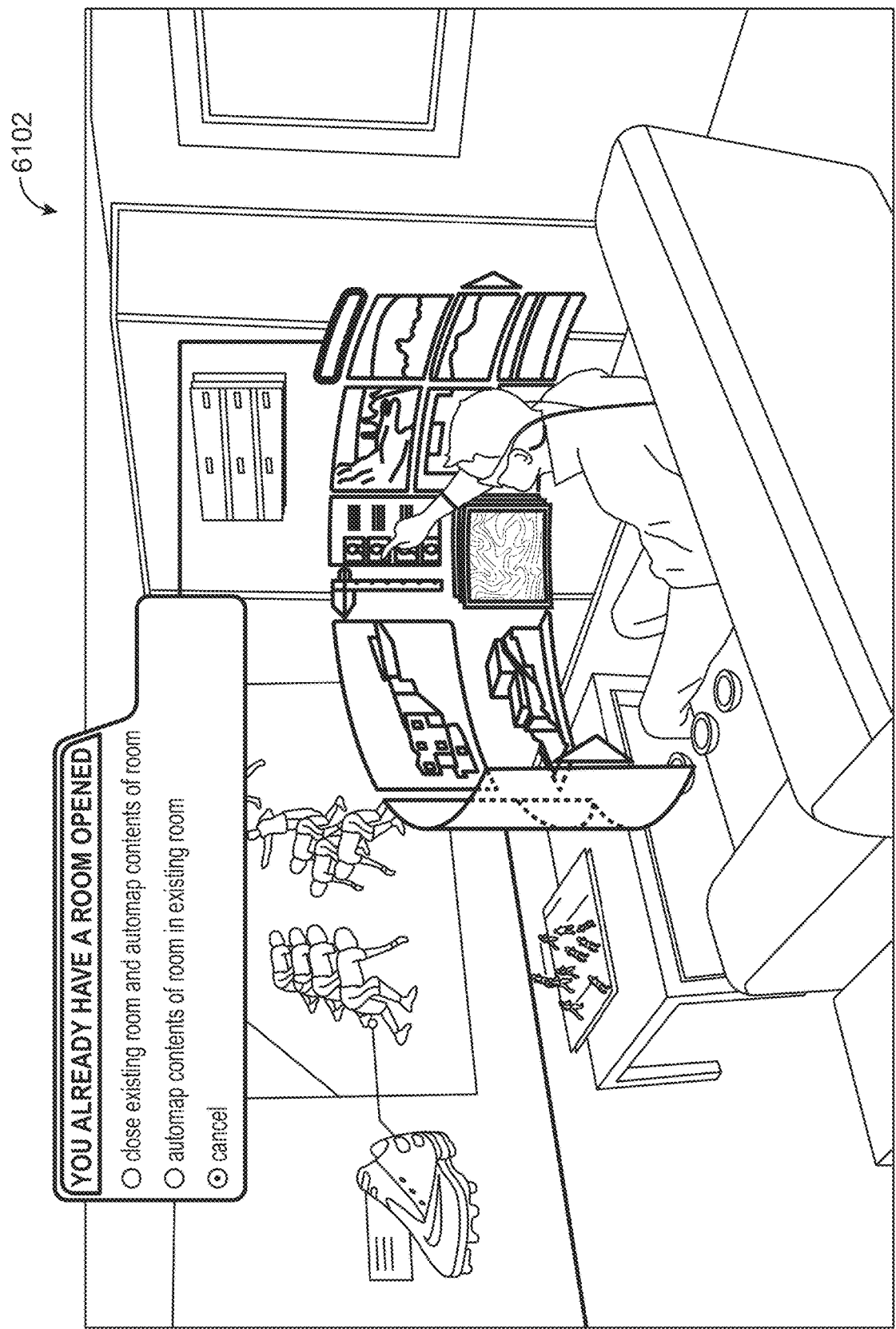
FIGS. 61A-61E illustrate other applications opened by the user of FIGS. 58-60 by interacting with various types of user interfaces, according to one illustrated embodiment.

FIG. 61A shows a user sitting in a physical living room space, and using an AR system to experience a virtual room or virtual space in the form of a virtual entertainment or media room, the user executing gestures to interact with a user interface virtual construct, according to one illustrated embodiment.

The physical living room may include one or more physical objects, for instance walls, floor, ceiling, a coffee table and sofa. As previously noted, the user may wear a head worn AR system, or head worn component of an AR system, operable to render virtual content in a field of view of the user. For example, the head worn AR system or component may render virtual objects, virtual tools and applications onto the retina of each eye of the user.

As illustrated in FIG. 61A (scene 6102), the AR system may render a functional group or pod user interface virtual construct, so at to appear in a user's field of view, preferably appearing to reside within a reach of the user. The pod user interface virtual construct includes a plurality of virtual room or virtual space based applications, which conveniently provides access from one virtual room or virtual space to functional tools and applications which are logically associated with another virtual room or virtual space. The pod user interface virtual construct forms a mini work station for the user.

As previously discussed, the AR system may render virtual content at any apparent or perceived depth in the virtual space. Hence, the virtual content may be rendered to appear or seem to appear at any depth in the physical space onto which the virtual space is mapped. Implementation of intelligent depth placement of various elements or instances of virtual content may advantageously prevent clutter in the user's field of view.

As previously noted, the AR system may render virtual content so as to appear to be mounted or glued to a physical surface in the physical space, or may render the virtual content so as to appear to be floating in the physical space. Thus, the AR system may render the pod user interface virtual construct floating within the reach of the user, while concurrently rendering a virtual room or space (e.g., virtual entertainment or media room or space) spaced farther away for the user, for instance appear to be glued to the walls and table.

The AR system detects user interactions with the pod user interface virtual construct or the virtual content of the virtual room or space. For example, the AR system may detect swipe gestures, for navigating through context specific rooms. The AR system may render a notification or dialog box, for example, indicating that the user is in a different room. The notification or dialog box may query the use with respect to what action that the user would like the AR system to take (e.g., close existing room and automatically map contents of room, automatically map contents of room to existing room, or cancel).

Figure 61B:
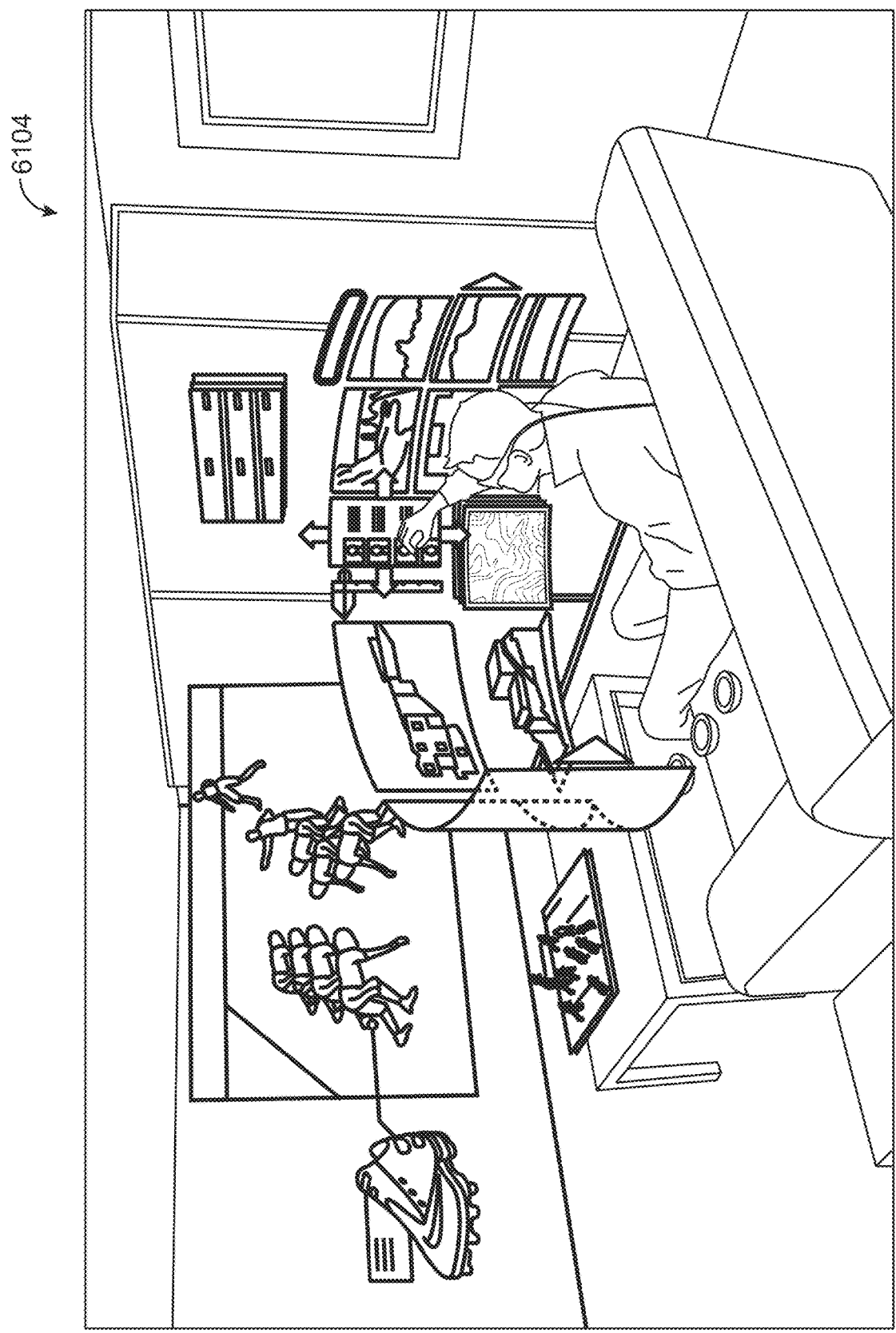

FIG. 61B (scene 6104) shows a user sitting in a physical living room space, and using an AR system to experience a virtual room or virtual space in the form of a virtual entertainment or media room, the user executing gestures to interact with a user interface virtual construct, according to one illustrated embodiment.

The physical living room may include one or more physical objects, for instance walls, floor, ceiling, a coffee table and sofa. As previously noted, the user may wear a head worn AR system, or head worn component of an AR system, operable to render virtual content in a field of view of the user. For example, the head worn AR system or component may render virtual objects, virtual tools and applications onto the retina of each eye of the user.

As illustrated in FIG. 61B, the AR system may render a functional group or pod user interface virtual construct, so at to appear in a user's field of view, preferably appearing to reside within a reach of the user. The pod user interface virtual construct includes a plurality of user selectable representations of virtual room or virtual space based applications, which conveniently provides access from one virtual room or virtual space to functional tools and applications which are logically associated with another virtual room or virtual space. The pod user interface virtual construct forms a mini work station for the user. This interface allows a user to conveniently navigate existing virtual rooms or virtual spaces to find specific applications, without having to necessarily render full-scale versions of the virtual rooms or virtual spaces along with the fully functional virtual content that goes along with the full-scale versions.

As illustrated in FIG. 61B, the AR system detects user interactions with the pod user interface virtual construct or the virtual content of the virtual room or space. For example, the AR system may detect a swipe or pinch gesture, for navigating to and opening context specific virtual rooms or virtual spaces. The AR system may render a visual effect to indicate which of the representations is selected.

Figure 61C:
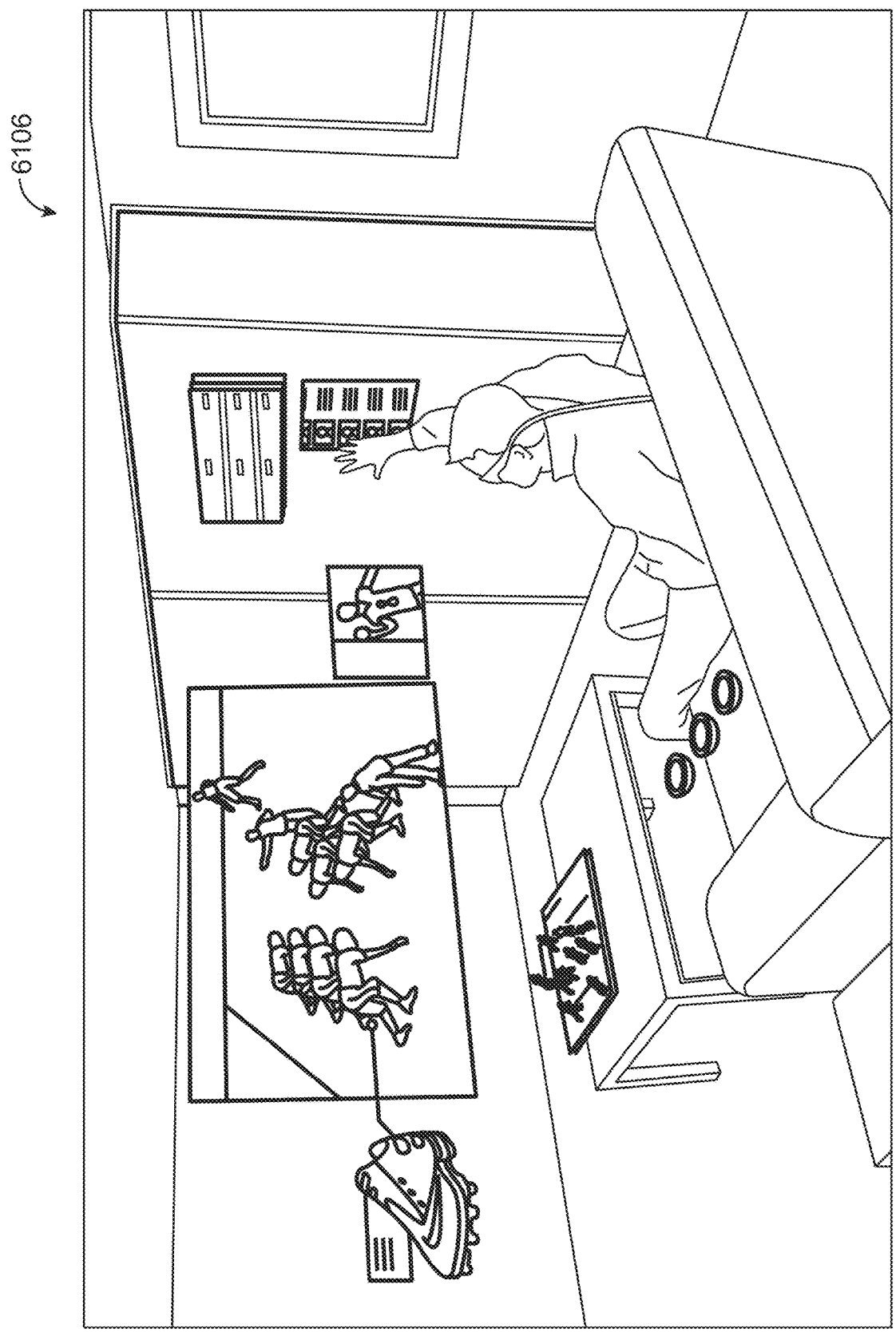

FIG. 61C (scene 6106) shows a user sitting in a physical living room space, and using an AR system to experience a virtual room or virtual space in the form of a virtual entertainment or media room, the user executing gestures to interact with a user interface virtual construct, according to one illustrated embodiment.

As illustrated in FIG. 61C, the AR system may render a selected application in the field of view of the user, in response to a selection of a representation, such as the selection illustrated in FIG. 61B. In particular, the AR system may render a fully functional version of the selected application to the retina of the eyes of the user, for example so as to appear on a physical surface (e.g., wall) of the physical room or physical space (e.g., living room). Notably, the selected application an application normally logically associated with another virtual room or virtual space than the virtual room or virtual space which the user is experiencing. For example, the user may select a social networking application, a Web browsing application, or an electronic mail (email) application from, for example, a virtual work space, while viewing a virtual entertainment or media room or space. Based on this selection, the AR system may retrieve data associated with the application from the cloud server and transmit to the local device, and then may display the retrieved data in the form of the web browsing application, electronic mail, etc. (Similar to process flow of FIG. 54).

Figure 61D:
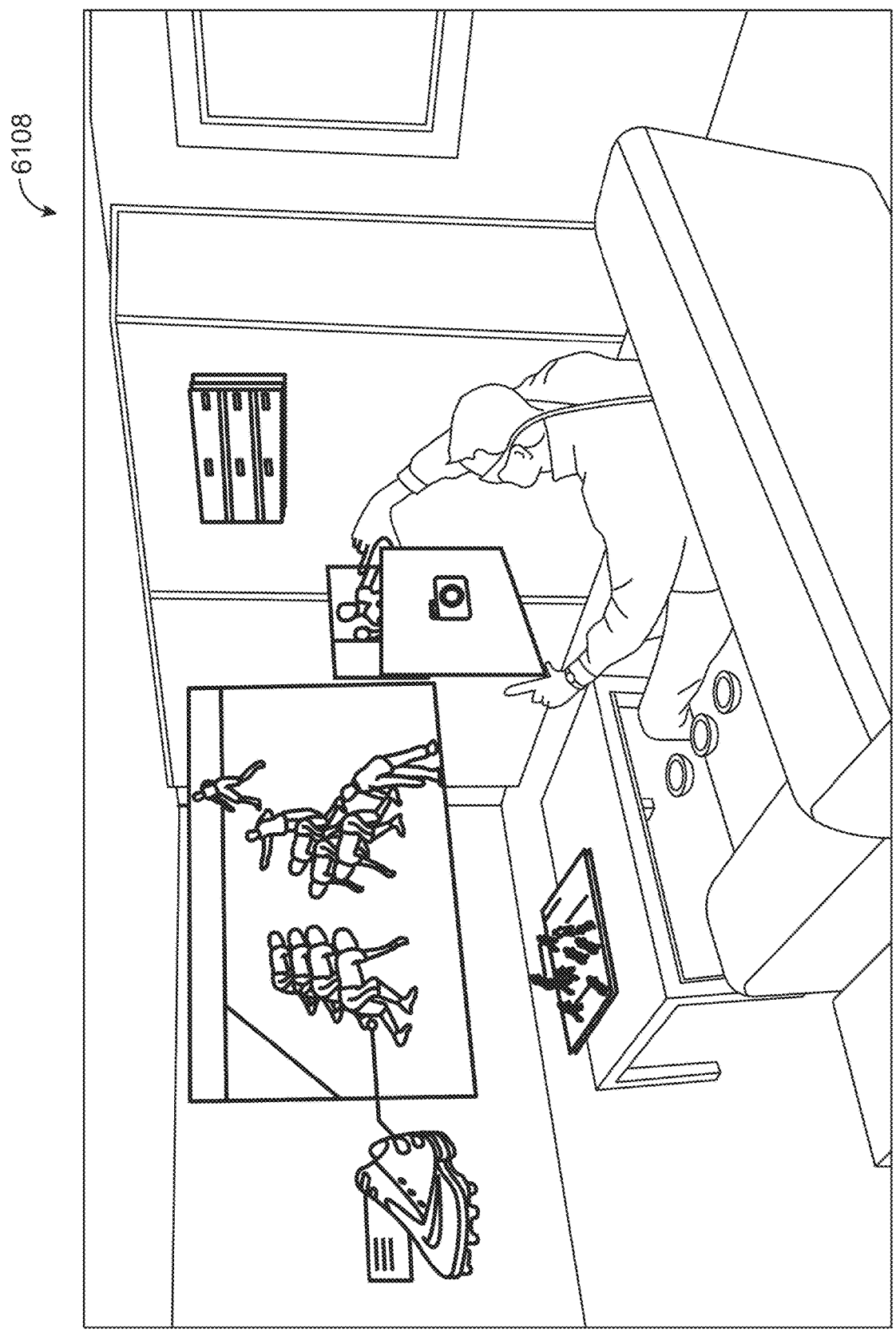

FIG. 61D (scene 6108) shows a user sitting in a physical living room space, and using an AR system to experience a virtual room or virtual space in the form of a virtual entertainment or media room, the user executing gestures to interact with a user interface virtual construct, according to one illustrated embodiment.

The physical living room may include one or more physical objects, for instance walls, floor, ceiling, a coffee table and sofa. As previously noted, the user may wear a head worn AR system, or head worn component of an AR system, operable to render virtual content in a field of view of the user. For example, the head worn AR system or component may render virtual objects, virtual tools and applications onto the retina of each eye of the user.

As illustrated in FIG. 61D, the user may perform a defined gesture, which serves as a hot key for a commonly used application (e.g., camera application). The AR system detects the user's gesture, interprets the gesture, and opens or executes the corresponding application. For example, the AR system may render the selected application or a user interface of the selected application in the field of view of the user, in response to the defined gesture. In particular, the AR system may render a fully functional version of the selected application or application user interface to the retina of the eyes of the user, for example so as to appear with arm's reach of the user.

A camera application may include a user interface that allows the user to cause the AR system to capture images or image data. For example, the camera application may allow the user to cause outward facing cameras on a body or head worn component of an individual AR system to capture images or image data (e.g., 4D light field) of a scene that is in a field of view of the outward facing camera(s) and/or the user.

Defined gestures are preferably intuitive. For example, an intuitive two handed pinch type gesture for opening a camera application or camera user interface is illustrated in FIG. 61D. The AR system may recognize other types of gestures. The AR system may store a catalog or library of gestures, which maps gestures to respective applications and/or functions. Gestures may be defined for all commonly used applications. The catalog or library of gestures may be specific to a particular user. Alternatively or additionally, the catalog or library of gestures may be specific to a specific virtual room or virtual space. Alternatively, the catalog or library of gestures may be specific to a specific physical room or physical space. Alternatively or additionally, the catalog or library of gestures may be generic across a large number of users and/or a number of virtual rooms or virtual spaces.

As noted above, gestures are preferably intuitive, particular with relation to the particular function, application or virtual content to which the respective gesture is logically associated or mapped. Additionally, gestures should be ergonomic. That is the gestures should be comfortable to be performed by users of a wide variety of body sizes and abilities. Gestures also preferably involve a fluid motion, for instance an arm sweep. Defined gestures are preferably scalable. The set of defined gestures may further include gestures which may be discretely performed, particular where discreetness would be desirable or appropriate. On the other hand, some defined gestures should not be discrete, but rather should be demonstrative, for example gestures indicating that a user intends to capture images and/or audio of others present in an environment. Gestures should also be culturally acceptable, for example over a large range of cultures. For instance, certain gestures which are considered offensive in one or more cultures should be avoided.

A number of proposed gestures are set out in Table A, below.

TABLE A

Swipe to the side (Slow)
Spread hands apart
Bring hands together
Small wrist movements (as opposed to large arm movements)
Touch body in a specific place (arm, hand, etc.)

TABLE A-continued

Wave
Pull hand back
Swipe to the side (slow)
Push forward
Flip hand over
Close hand
Swipe to the side (Fast)
Pinch-thumb to forefinger
Pause (hand, finger, etc.)
Stab (Point)

Figure 61E:

FIG. 61E (scene 6110) shows a user sitting in a physical living room space, and using an AR system to experience a virtual room or virtual space in the form of a virtual entertainment or media room, the user executing gestures to interact with a user interface virtual construct, according to one illustrated embodiment.

As illustrated in FIG. 61E, the AR system renders a comprehensive virtual dashboard menu user interface, for example rendering images to the retina of the user's eyes. The virtual dashboard menu user interface may have a generally annular layout or configuration, at least partially surrounding the user, with various user selectable virtual icons spaced to be within arm's reach of the user.

The AR system detects the user's gesture or interaction with the user selectable virtual icons of the virtual dashboard menu user interface, interprets the gesture, and opens or executes a corresponding application. For example, the AR system may render the selected application or a user interface of the selected application in the field of view of the user, in response to the defined gesture. For example, the AR system may render a fully functional version of the selected application or application user interface to the retina of the eyes of the user.

As illustrated in FIG. 61E, the AR system may render media content where the application is a source of media content (e.g., ESPN Sports Center®, Netflix®). The AR system may render the application, application user interface or media content to overlie other virtual content. For example, the AR system may render the application, application user interface or media content to overlie a display of primary content on a virtual primary screen being displayed in the virtual room or space (e.g., virtual entertainment or media room or space).

Figure 62A:
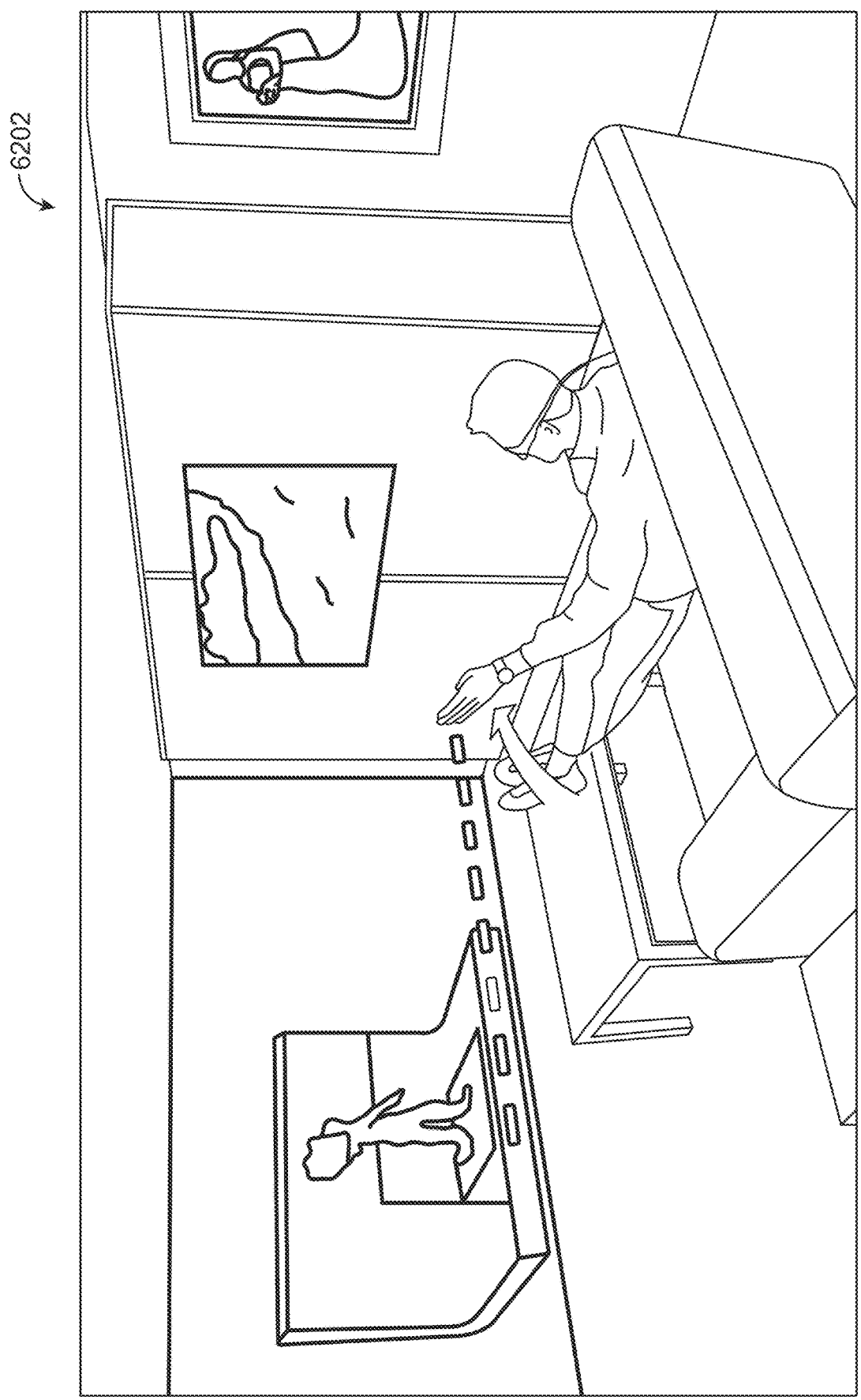
FIGS. 62A-62D illustrate the user of FIGS. 58-61 changing a virtual skin of the user's living room, according to one illustrated embodiment.

FIG. 62A (scene 6202) shows a user sitting in a physical living room space, and using an AR system to experience a first virtual décor (i.e., aesthetic skin or aesthetic treatment), the user executing gestures to interact with a user interface virtual construct, according to one illustrated embodiment.

Figure 65A:
FIGS. 65A-65C illustrates the user of FIGS. 58-64 selecting a movie to watch on a virtual television screen, according to one illustrated embodiment.

The AR system allows a user to change (i.e., re-skin) a virtual décor of a physical room or physical space. For example, as illustrated in FIG. 65A, a user may gesture to bring up a first virtual décor, for example a virtual fireplace with a virtual fire and first and second virtual pictures.

The first virtual décor (e.g., first skin) is mapped to the physical structures of the physical room or space (e.g., physical living room). Based on the gesture, the AR system (similar to process flow of FIG. 54) retrieves data associated with the virtual décor and transmits back to the user device. The retrieved data is then displayed based on the map coordinates of the physical room or space.

As also illustrated in FIG. 62A, the AR system may render a user interface tool which provides a user with a representation of choices of virtual décor, and possibly a position of a currently selected virtual décor in a set of virtual décor available to the user. As illustrated, the representation takes the form of a line of marks or symbols, with each marking representing a respective one of the virtual décor available to the user. A currently selected one of the virtual décor is visually emphasized, to assist the user in navigating forward or backward through the set. The set of virtual décor may be specific to the user, specific to a physical room or physical space, or may be shared by two or more users.

Figure 62B:
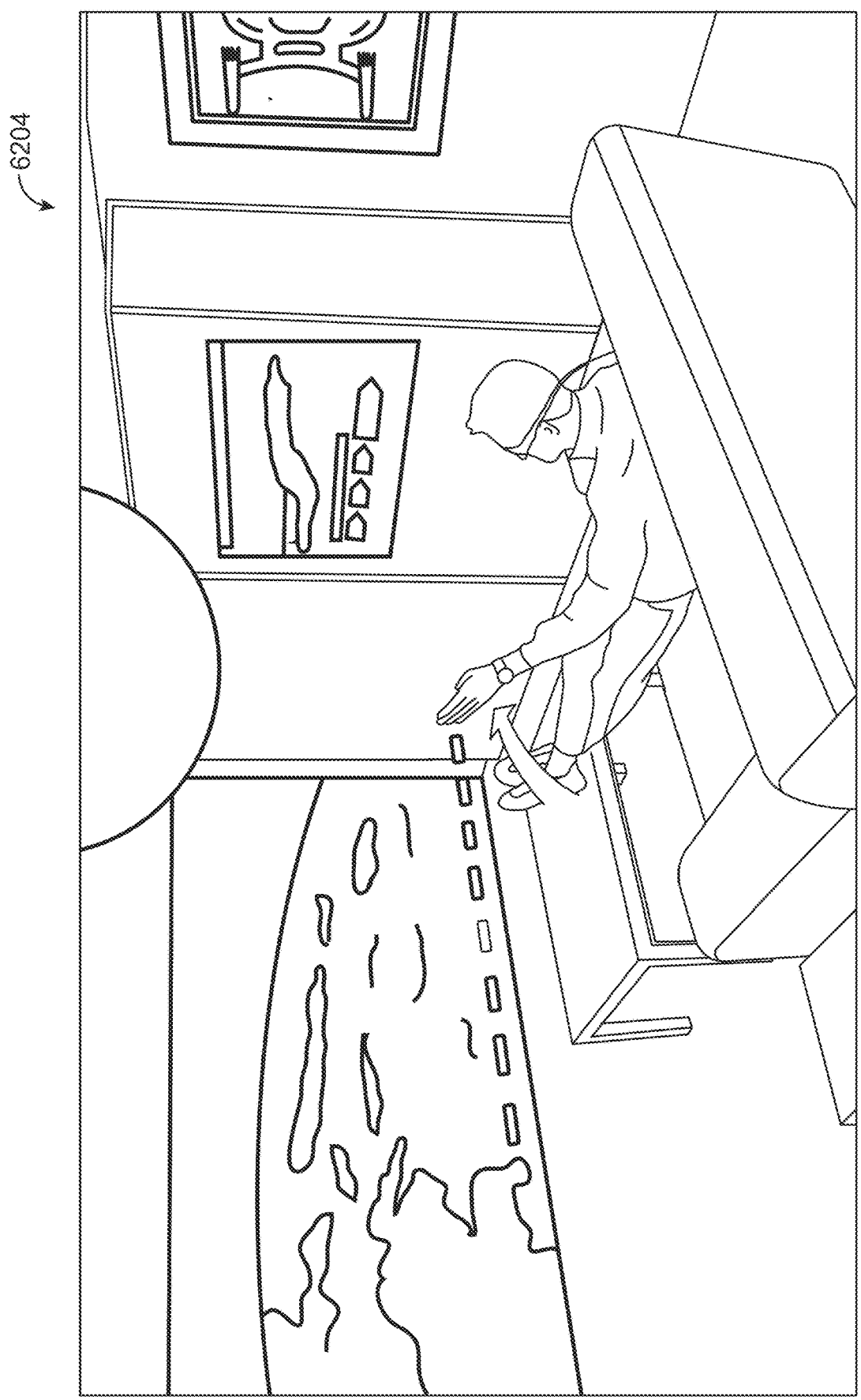

FIG. 62B (scene 6204) shows a user sitting in a physical living room space, and using an AR system to experience a second virtual décor (i.e., aesthetic skin or aesthetic treatment), the user executing gestures to interact with a user interface virtual construct, according to one illustrated embodiment.

As illustrated in FIG. 62B, a user may gesture to bring up a second virtual décor, different from the first virtual décor. The second virtual décor may, for example, replicate a command deck of a spacecraft (e.g., Starship) with a view of a planet, technical drawings or illustrations of the spacecraft, and a virtual lighting fixture or luminaire. The gesture to bring up the second virtual décor may be identical to the gesture to bring up the first virtual décor, the user essentially toggling, stepping or scrolling through a set of defined virtual decors for the physical room or physical space (e.g., physical living room). Alternatively, each virtual décor may be associated with a respective gesture.

As illustrated, a user interface tool may indicate that which of the set of virtual decors is currently selected and mapped to the physical room or space.

Figure 62C:
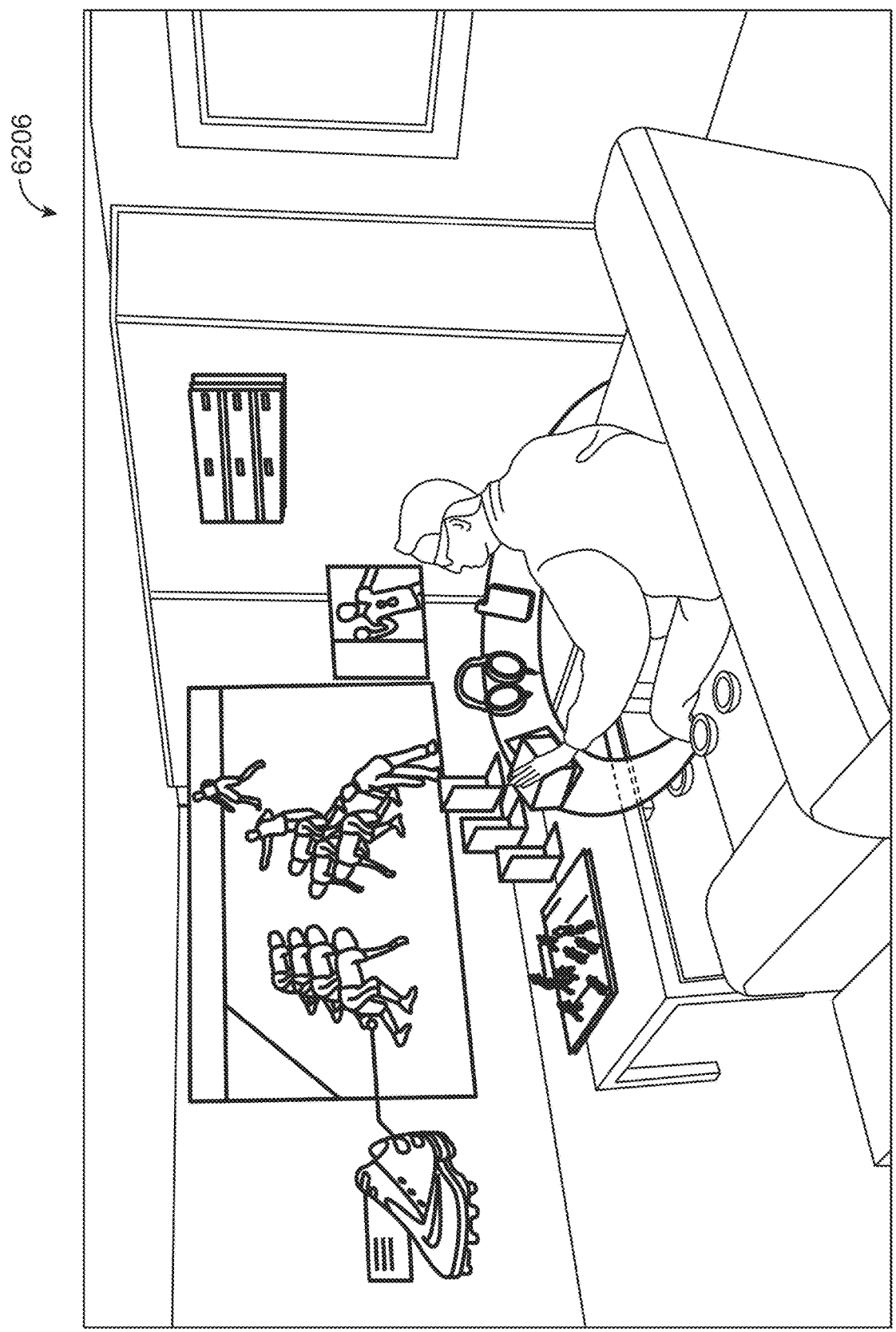

FIG. 62C (scene 6206) shows a user sitting in a physical living room space, and using an AR system to experience a third virtual décor (i.e., aesthetic skin or aesthetic treatment), the user executing gestures to interact with a user interface virtual construct, according to one illustrated embodiment.

The physical living room is illustrated as being identical to that of FIG. 62A. As previously noted, the user may wear a head worn AR system, or head worn component of an AR system, operable to render virtual content in a field of view of the user. Identical or similar physical and/or virtual elements are identified using the same reference numbers as in FIG. 81A, and discussion of such physical and/or virtual elements will not be repeated in the interest of brevity.

Figure 62D:

As illustrated in FIG. 62C, a user may gesture to bring up a third virtual décor, different from the first and the second virtual decors. The third virtual décor may, for example, replicate a view of a beach scene and a different virtual picture. The gesture to bring up the third virtual décor may be identical to the gesture to bring up the first and the second virtual decors, the user essentially toggling, stepping or scrolling through a set of defined virtual decors for the physical room or physical space (e.g., physical living room). Alternatively, each virtual décor may be associated with a respective gesture. Similarly, the user may enjoy a fourth virtual décor as well as shown in FIG. 62D (scene 6208)

As illustrated, a user interface tool may indicate that which of the set of virtual decors is currently selected and mapped to the physical room or space.

Figure 63:
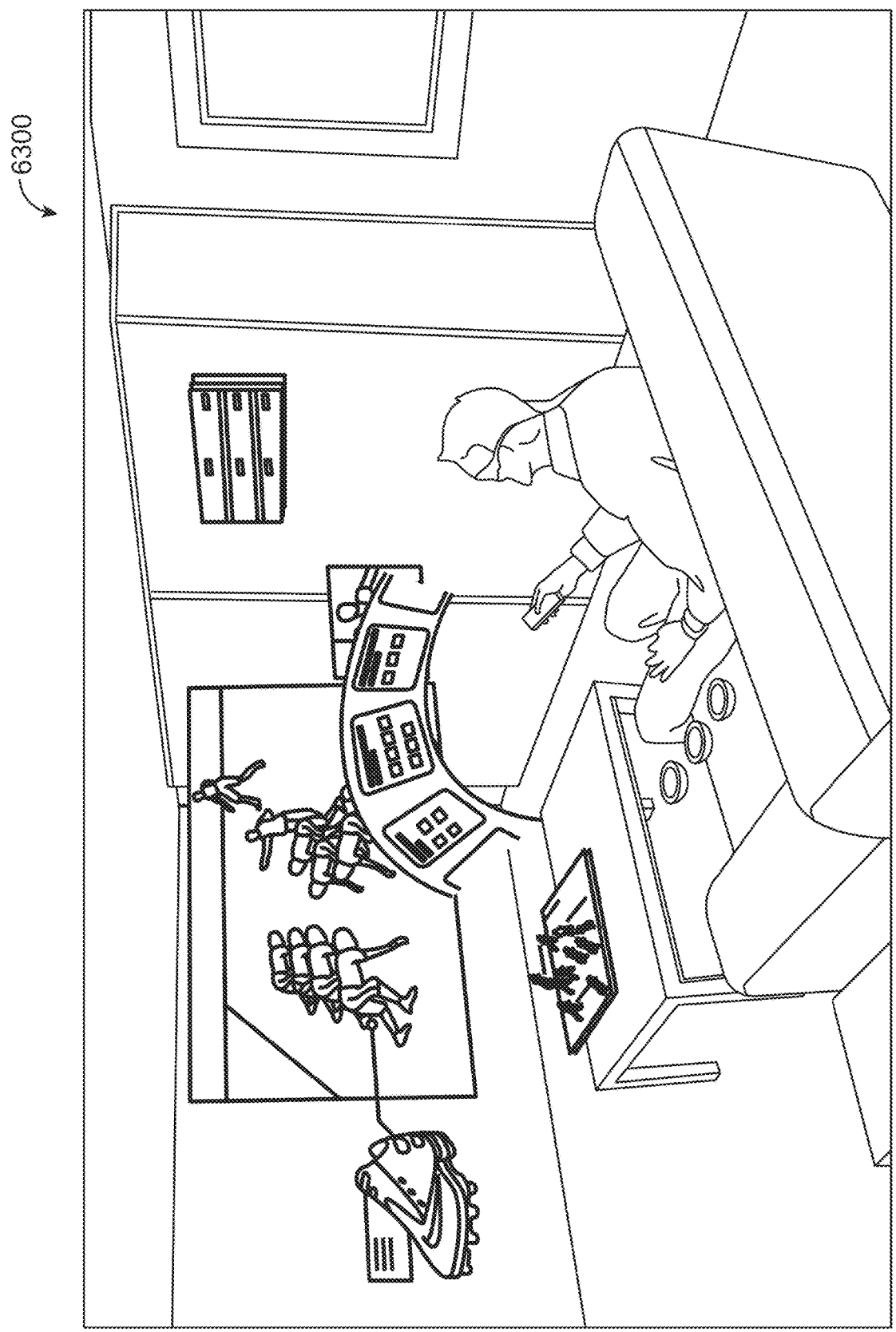
FIG. 63 illustrates the user of FIGS. 58-61 using a totem to interact with the AR system, according to one illustrated embodiment.

FIG. 63 (scene 6300) shows a user sitting in a physical living room space, and using an AR system to experience a virtual room or virtual space in the form of a virtual entertainment or media room, the user executing gestures to interact with a user interface virtual construct, according to one illustrated embodiment.

As illustrated in FIG. 63, the AR system may render a hierarchical menu user interface virtual construct including a plurality of virtual tablets or touch pads, so at to appear in a user's field of view, preferably appearing to reside within a reach of the user. These allow a user to navigate a primary menu to access user defined virtual rooms or virtual spaces, which are a feature of the primary navigation menu. The various functions or purposes of the virtual rooms or virtual spaces may be represented iconically. Based on the user's gestures, various icons of the user interface may be moved or selected by the user. The AR system may retrieve data from the cloud server, similar to the process flow of FIG. 54, as needed.

FIG. 63 shows a user sitting in a physical living room space, and using an AR system to experience a virtual room or virtual space in the form of a virtual entertainment or media room, the user executing gestures to interact with a user interface virtual construct to provide input by proxy, according to one illustrated embodiment.

As illustrated in FIG. 63, the AR system may render a user interface virtual construct including a plurality of user selectable virtual elements, so at to appear in a user's field of view. The user manipulates a totem to interact with the virtual elements of the user interface virtual construct. The user, may for example, point a front of the totem at a desired one of the elements.

The user may also interact with the totem, for example tapping or touching on a surface of the totem, indicating a selection of the element at which the totem is pointing or aligned. The AR system detects the orientation of the totem and the user interactions with the totem, interpreting such as a selection of the element at which the totem is pointing or aligned. The AR system the executes a corresponding action, for example opening an application, opening a submenu, or rendering a virtual room or virtual space corresponding to the selected element.

The totem may replicate a remote control, for example remote controls commonly associated with televisions and media players. In some implementations, the totem may be an actual remote control for an electronic device (e.g., television, media player, media streaming box), however the AR system may not actually received any wireless communications signals from the remote control. The remote control may even not have batteries, yet still function as a totem since the AR system is relies on image that capture position, orientation and interactions with the totem (e.g., remote control).

Figure 64A:
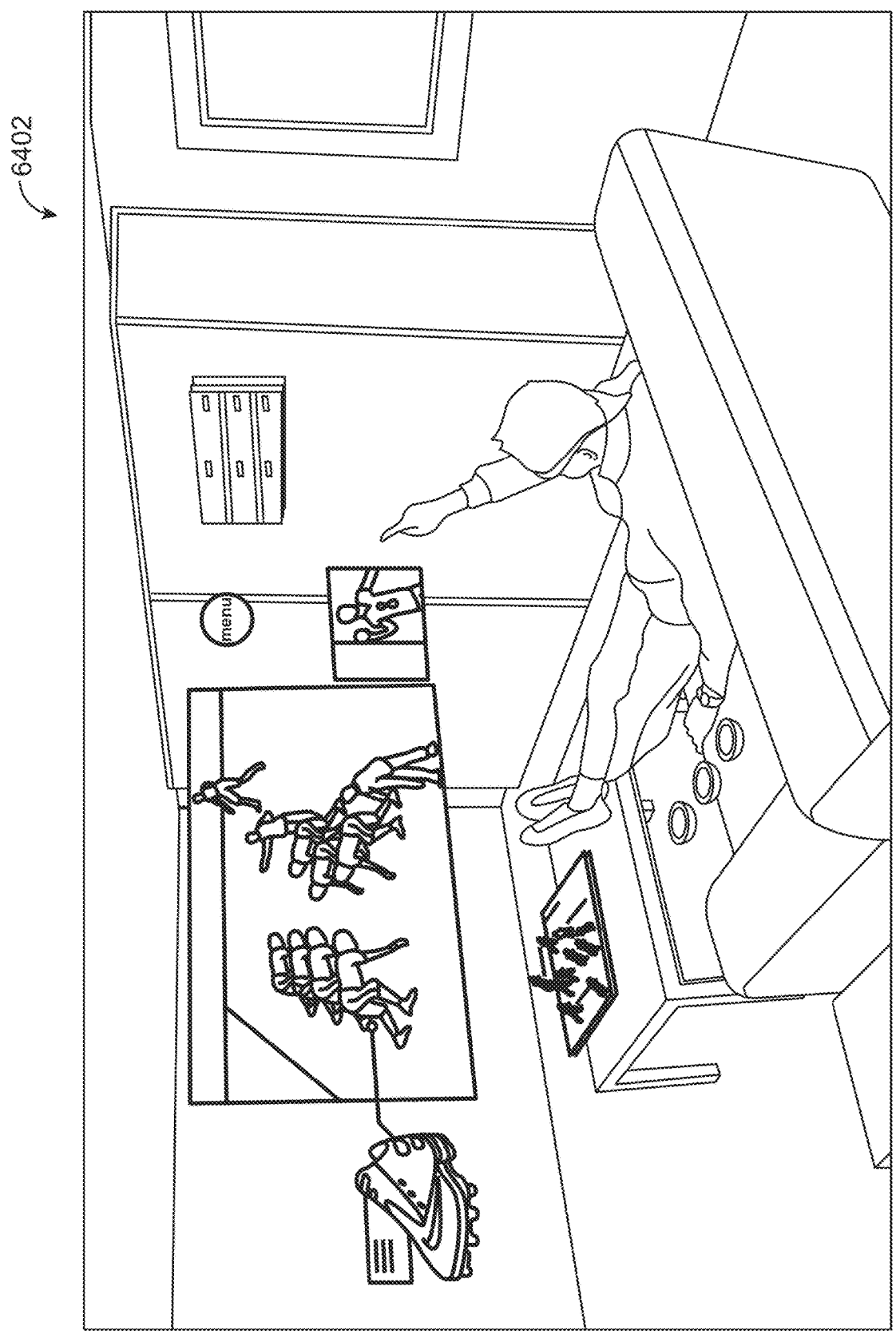
FIG. 64A-64B illustrates the user of FIGS. 58-63 using a physical object as a user interface, according to one illustrated embodiment.
Figure 64B:
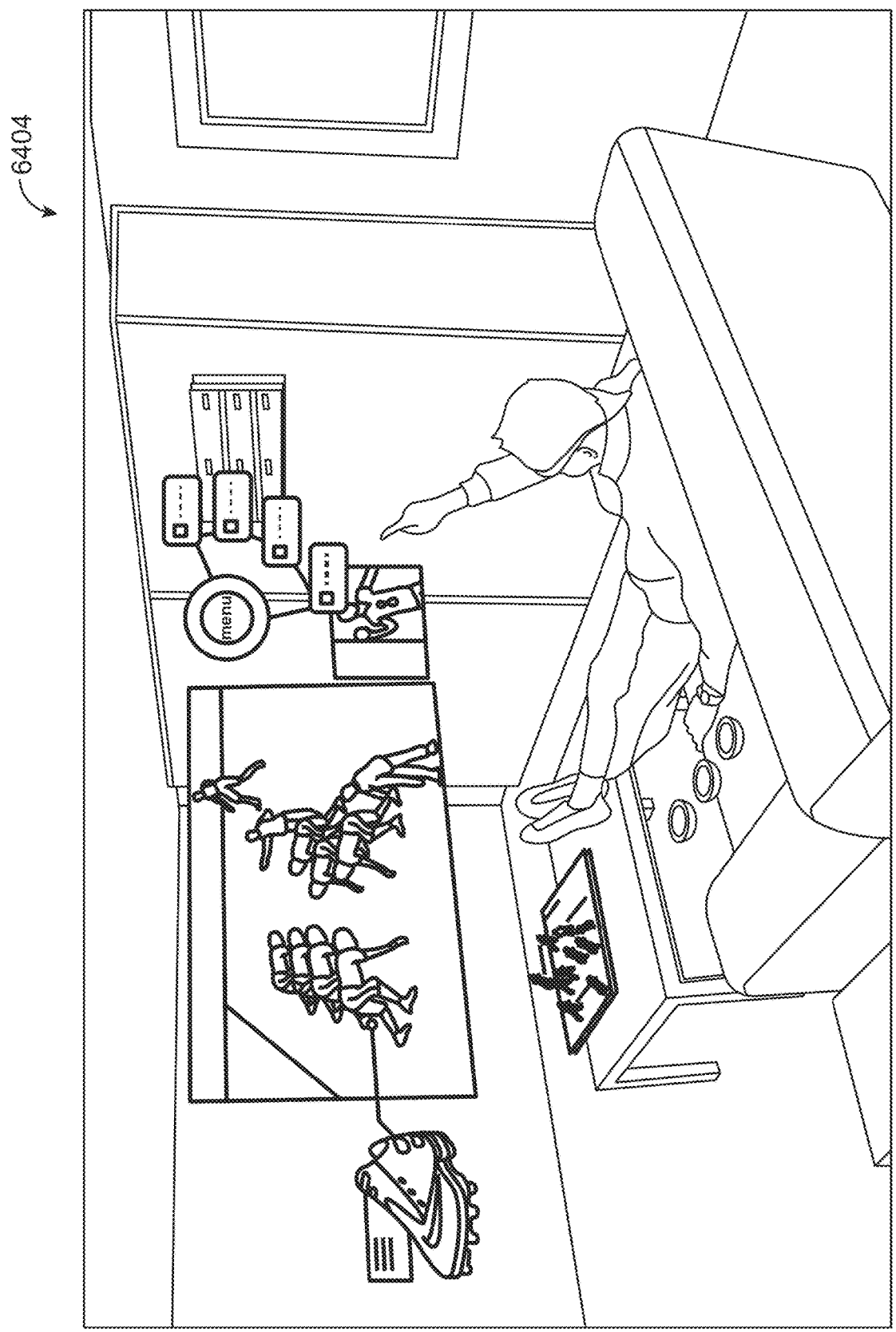

FIGS. 64A and 64B (scenes 6402 and 6404) show a user sitting in a physical living room space, and using an AR system to experience a virtual room or virtual space in the form of a virtual entertainment or media room, the user executing gestures to interact with a user interface virtual construct to provide input, according to one illustrated embodiment.

As illustrated in FIG. 64A, the AR system may render a user interface virtual construct including an expandable menu icon that is always available. The AR system may consistently render the expandable menu icon in a given location in the user's field of view, or preferably in a peripheral portion of the user's field of view, for example an upper right corner. Alternatively, AR system may consistently render the expandable menu icon in a given location in the physical room or physical space.

As illustrated in FIG. 64B, the user may gesture at or toward the expandable menu icon to expand the expandable menu construct. In response, the AR system may render the expanded expandable menu construct to appear in a field of view of the user. The expandable menu construct may expand to reveal one or more virtual rooms or virtual spaces available to the user. The AR system may consistently render the expandable menu in a given location in the user's field of view, or preferably in a peripheral portion of the user's field of view, for example an upper right corner. Alternatively, AR system may consistently render the expandable menu in a given location in the physical room or physical space.

FIG. 65A (scene 6502) shows a user sitting in a physical living room space, and using an AR system to experience a virtual décor (i.e., aesthetic skin or aesthetic treatment), the user executing pointing gestures to interact with a user interface virtual construct, according to one illustrated embodiment.

As illustrated in FIG. 65A, the AR system may render a user interface tool which includes a number of pre-mapped menus. For instance, the AR system may render a number of poster-like virtual images corresponding to respective pieces of entertainment or media content (e.g., movies, sports events), from which the user can select via one or more pointing gestures. The AR system may render the poster-like virtual images to, for example, appear to the user as if hanging or glued to a physical wall of the living room. Again, the AR system detects the map coordinates of the room, and displays the virtual posters in the right size and at the right orientation with respect to the mapped coordinates, such that the posters appear to be placed on the wall of the room.

The AR system detects the user's gestures, for example pointing gestures which may include pointing a hand or arm toward one of the poster-like virtual images. The AR system recognizes the pointing gesture or projection based proxy input, as a user selection intended to trigger delivery of the entertainment or media content which the poster-like virtual image represents. The AR system may render an image of a cursor, with the cursor appearing to be projected toward a position in which the user gestures. The AR system causes the cursor to tracking the direction of the user's gestures, providing visual feedback to the user, and thereby facilitating aiming to allow projection based proxy input.

Figure 65B:

FIG. 65B (scene 6504) shows a user sitting in a physical living room space, and using an AR system to experience a virtual décor (i.e., aesthetic skin or aesthetic treatment), the user executing touch gestures to interact with a user interface virtual construct, according to one illustrated embodiment.

As illustrated in FIG. 65B, the AR system may render a user interface tool which includes a number of pre-mapped menus. For instance, the AR system may render a number of poster-like virtual images corresponding to respective pieces of entertainment or media content (e.g., movies, sports events), from which the user can select via one or more touch gestures. The AR system may render the poster-like virtual images to, for example, appear to the user as if hanging or glued to a physical wall of the living room.

The AR system detects the user's gestures, for example touch gestures which includes touches at least proximate an area in which one of the poster-like virtual images appears to be rendered. The AR system recognizes the touching gesture or virtual tablet or touch pad like interaction, as a user selection intended to trigger delivery of the entertainment or media content which the poster-like virtual image represents.

Figure 65C:

FIG. 65C (6506) shows a user sitting in a physical living room space, and using an AR system to experience a piece of entertainment or media content, the user executing touch gestures to interact with a user interface virtual construct, according to one illustrated embodiment.

As illustrated in FIG. 65C, in response a user selection, the AR system renders a display of the selected entertainment or media content, and/or associated virtual menus (e.g., high level virtual navigation menu, for instance a navigation menu that allows selection of primary feature, episode, of extras materials). For example, the AR system may render a display of the selected entertainment or media content to the retina of the user's eyes, so that the selected entertainment or media content appears in the field of view of the user as if displayed on a wall of the physical space. As illustrated in FIG. 65C, the display of the selected entertainment or media content may replace at least a portion of the first virtual décor.

As illustrated in FIG. 65C, in response the user selection, the AR system may also render a virtual tablet type user interface tool, which provides a more detailed virtual navigation menu than the high level virtual navigation menu. The more detailed virtual navigation menu may include some or all of the menu options of the high level virtual navigation menu, as well as additional options (e.g., retrieve additional content, play interactive game associated with media title or franchise, scene selection, character exploration, actor exploration, commentary). For instance, the AR system may render the detailed virtual navigation menu to, for example, appear to the user as if sitting on a top surface of a table, within arm's reach of the user.

The AR system detects the user's gestures, for example touch gestures which includes touches at least proximate an area in which the more detailed virtual navigation menu appears to be rendered. The AR system recognizes the touching gesture or virtual tablet or touch pad like interaction, as a user selection intended to effect delivery of the associated entertainment or media content.

Referring now to FIGS. 66A-66J (scenes 6102-6120), another user scenario is illustrated. FIGS. 66A-66J illustrate an AR system implemented retail experience, according to one illustrated embodiment.

As illustrated, a mother and daughter each wearing respective individual AR systems receive an augmented reality experience while shopping in a retail environment, for example a supermarket. As explained herein, the AR system may provide entertainment as well as facilitate the shopping experience. For example, the AR system may render virtual content, for instance virtual characters which may appear to jump from a box or carton, and/or offer virtual coupons for selected items. The AR system may render games, for example games based on locations throughout the store and/or based on items on shopping list, list of favorites, or a list of promotional items. The augmented reality environment encourages children to play, while moving through each location at which a parent or accompanying adult needs to pick up an item. Even adults may play.

In another embodiment, the AR system may provide information about food choices, and may help users with their health/weight/lifestyle goals. The AR system may render the calorie count of various foods while the user is consuming it, thus educating the user on his/her food choices. If the user is consuming unhealthy food, the AR system may warn the user about the food so that the user is able to make an informed choice.

The AR system may subtly render virtually coupons, for example using radio frequency identification (RFID) transponders and communications. For example, referring back to process flow of FIG. 55, the AR system may recognize the real world activity (shopping), and load information from the knowledge database regarding shopping.

Based on recognizing the specific activity, the system may unlock metadata, or display virtual content based on the recognized specific activity. For example, the AR system may render visual affects tied or proximately associated with items, for instance causing a glowing affect around box glows to indicate that there is metadata associated with the item. The metadata may also include or link to a coupon for a discount or rebate on the item. The AR system may detect user gestures, and for example unlocking metadata in response to defined gestures.

The AR system may recognize different gestures for different items. For example, as explained herein, a virtual animated creature may be rendered so as to appear to pop out of a box holding a coupon for the potential purchaser or customer. For example, the AR system may render virtual content that makes a user perceive a box opening. The AR system allows advertising creation and/or delivery at the point of customer or consumer decision.

The AR system may render virtual content which replicates a celebrity appearance. For example, the AR system may render a virtual appearance of a celebrity chef at a supermarket, as will be described further below. The AR system may render virtual content which assists in cross-selling of products. For example, one or more virtual affects may cause a bottle of wine to recommend a cheese that goes well with the wine. The AR system may render visual and/or aural affects which appear to be proximate the cheese, in order to attract a shopper's attention. The AR system may render one or more virtual affects in the field of the user that cause the user to perceive the cheese recommending certain crackers. The AR system may render friends who may provide opinions or comments regarding the various produces (e.g., wine, cheese, crackers).

The AR system may render virtual affects within the user's field of view which are related to a diet the user is following. For example, the affects may include an image of a skinny version of the user, which is rendered in response to the user looking at a high calorie product. This may include an aural oral reminder regarding the diet. Similar to above (refer to process flow of FIG. 55), the AR system recognizes visual input (here, a high calorie product) and automatically retrieves data corresponding to the skinny version of the user to display. The system also uses map coordinates of the high calorie product to display the skinny version of the user right next to the physical product.

Figure 66A:
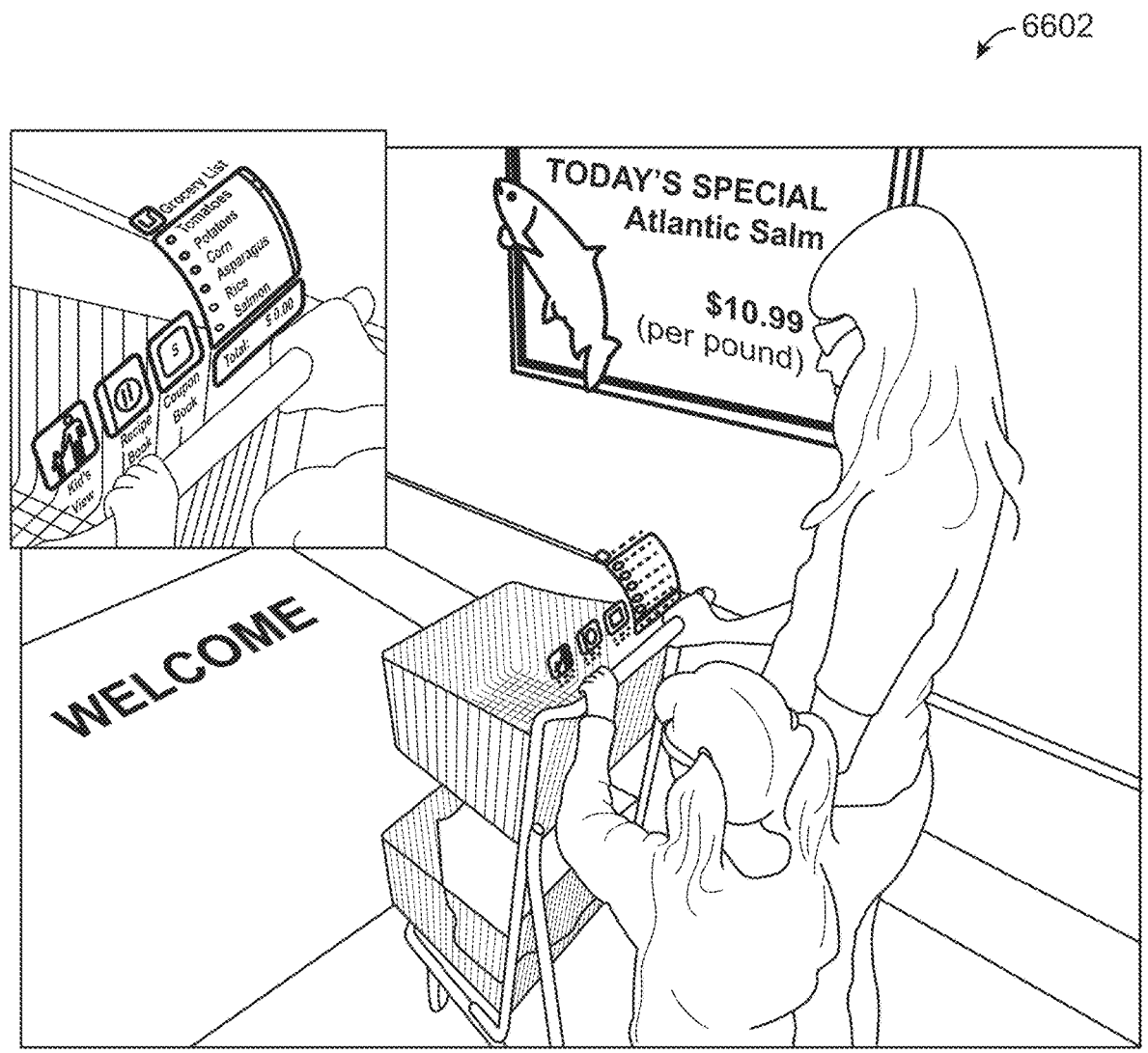

In particular, FIG. 66A shows mother with her daughter in tow, pushing a shopping cart from an entrance of a grocery store. The AR system recognizes the presence of a shopping cart or a hand on the shopping cart, and determines a location of the user and/or shopping cart. Based on such, the AR system automatically launches a set of relevant applications, rendering respective user interfaces of the applications to the user's field of view. In other words, similar to the process flow of FIG. 55, the AR system recognizes the specific activity as shopping, and automatically retrieves data associated with the relevant applications to be displayed in a floating user interface.

Applications may, for example, include a virtual grocery list. The grocery list may be organized by user defined criteria (e.g., dinner recipes). The virtual grocery list may be generated before the user leaves home, or may be generated at some later time, or even generated on the fly, for example in cooperation with one of the other applications. The applications may, for example, include a virtual coupon book, which includes virtual coupons redeemable for discounts or rebates on various products. The applications may, for example, include a virtual recipe book, which includes various recipes, table of contents, indexes, and ingredient lists.

Selection of a virtual recipe may cause the AR system to update the grocery list. In some implementations, the AR system may update the grocery list based on knowledge of the various ingredients the user already has at home, whether in a refrigerator, freezer or cupboard. The AR system may collect this information throughout the day as the user works in the kitchen of their home. The applications may, for example, include a virtual recipe builder. The recipe builder may build recipes around defined ingredients.

For example, the user may enter a type of fish (e.g., Atlantic salmon), and the recipe builder will generate a recipe that uses the ingredient. Selection of a virtual recipe generated by the recipe builder may cause the AR system to update the grocery list. In some implementations, the AR system may update the grocery list based on knowledge of the various ingredients the user already has at home. The applications may, for example, include a virtual calculator, which may maintain a running total of cost of all items in the shopping cart.

Figure 66B:

FIG. 66B shows mother with her daughter in a produce section. The mother weighs a physical food item on a scale. The AR system automatically determines the total cost of the item (e.g., price per pound multiplied by weight) enters the amount into the running total cost. The AR system automatically updates the 'smart' virtual grocery list to reflect the item. The AR system automatically updates the 'smart' virtual grocery list based on location to draw attention to items on the grocery list that are nearby the present location.

For example, the AR system may update the rendering of the virtual grocery list to visually emphasize certain items (e.g., focused on fruits and vegetables in the produce section). Such may include highlighting items on the list or moving close by items to a top of the list. Further, the AR system may render visual effects in the field of view of the user such that the visual affects appear to be around or proximate nearby physical items that appear on the virtual grocery list.

Figure 66C:

FIG. 66C shows the child selecting a virtual icon to launch a scavenger hunt application. The scavenger hunt application makes the child's shopping experience more engaging and educational. The scavenger hunt application may present a challenge, for example, involving locating food items from different countries around the world. Points are added to the child's score as she identifies food items and puts them in her virtual shopping cart. Based on the input received by the child, the AR system may retrieve data related to the scavenger hunt from the cloud (e.g., instructions for the scavenger hunt, etc.) and transmit back to the user device so that the scavenger hunt instructions are timely displayed to the child.

Figure 66D:
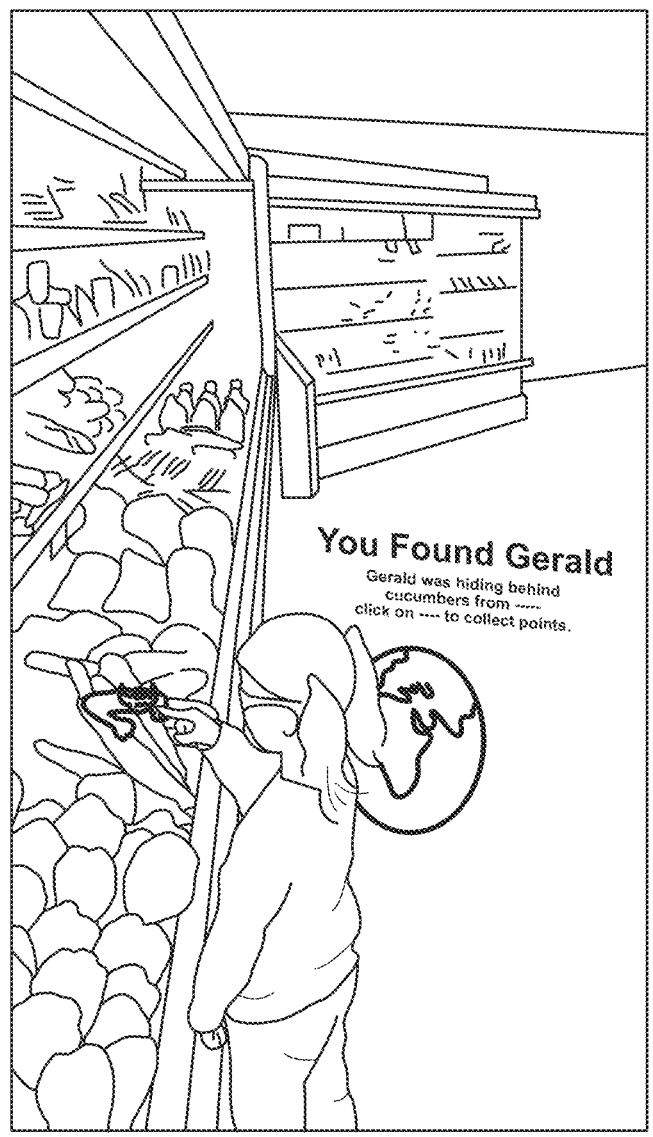

FIG. 66D shows the child finding and gesturing toward a bonus virtual icon, in the form of a friendly monster or an avatar. The AR system may render unexpected or bonuses virtual content to the field of view of the child to provide a more entertaining and engaging user experience. The AR system, detects and recognizes the gesture of pointing toward the monster, and unlocks the metadata associated with the friendly monster or avatar. By gesturing toward the monster, the AR system recognizes the map coordinates of the monster, and therefore unlocks it based on the user's gesture. The bonus information is then retrieved from the cloud and displayed in the appropriate map coordinates next to the friendly monster, for instance.

Figure 66E:
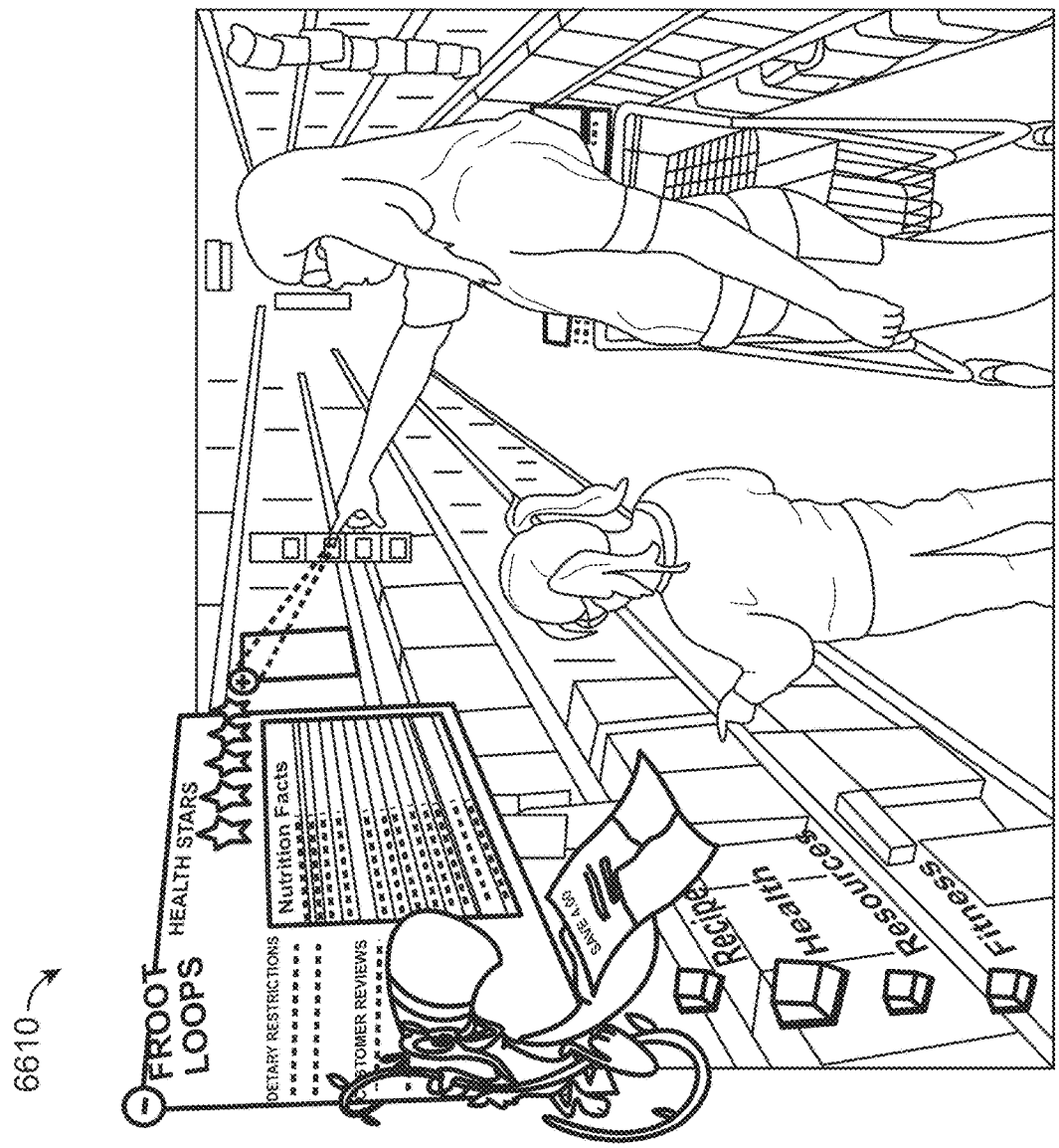

FIG. 66E show the mother and daughter in a cereal aisle. The mother selects a particular cereal to explore additional information, for example via a virtual presentation of metadata. The metadata may, for example, include: dietary restrictions, nutritional information (e.g., health stars), product reviews and/or product comparisons, or customer comments. Rendering the metadata virtually allow the metadata to be presented in a way that is easily readable, particular for adults how may have trouble reading small type or fonts. Similar to the process flow of FIG. 55, the system may recognize the real-world activity/real-world object, retrieve data associated with it, and appropriately display the virtual information associated with the particular cereal.

As also illustrated in FIG. 66E, an animated character (e.g., Toucan Sam®) is rendered and may be presented to the customers with any virtual coupons that are available for a particular item. The AR system may render coupons for a given product to all passing customers, or only to customers who stop. Alternatively or additionally, the AR system may render coupons for a given product to customers who have the given product on their virtual grocery list, or only to those who have a competing product on their virtual grocery list. Alternatively or additionally, the AR system may render coupons for a given product based on knowledge of a customer's past or current buying habits and/or contents of the shopping cart. Here, similar to FIG. 55, the AR system may recognize the real-world activity, load the knowledge base associated with the virtual coupons, and based on the user's specific interest or specific activity, may display the relevant virtual coupons to the user.

Figure 66F:

As illustrated in FIG. 66F, the AR system may render an animated character (e.g., friendly monster) in the field of view of at least the child. The AR system may render the animated character so as to appear to be climbing out of a box (e.g., cereal box). The sudden appearance of the animated character may prompt the child to start a game (e.g., Monster Battle). The child can animate or bring the character to life with a gesture. For example, a flick of the wrist may cause the AR system to render the animated character bursting through the cereal boxes.

Figure 66G:

FIG. 66G shows the mother at an end of an aisle, watching a virtual celebrity chef (e.g., Mario Batali) presentation via the AR system. The celebrity chef may demonstrate a simple recipe to customers. All ingredients used in the demonstrated recipe may be available at the end cap. This user scenario may utilize the process flow of FIGS. 53 and 54. The AR system essentially allows the celebrity chef to pass over a piece of his world to multiple users. Here, based on detecting a location at the store, the AR system retrieves data from the passable world associated with the celebrity chef's live performance, and sends back the relevant information to the user's device.

In some instances, the AR system may present the presentation live. This may permit questions to be asked of the celebrity chef by customers at various retail locations. In other instances, the AR system may present a previously recorded presentation.

The AR system may capture the celebrity chef presentation via, for example, a 4D light field. The presentation may likewise be presented via a 4D light field provided to the retina of the user's eyes. This provides a realistic sense of depth, and the ability to circle to the sides and perceive the celebrity as if actually present in the retail environment.

In some implementations, the AR system may capture images of the customers, for example via inward facing cameras carried by each customer's individual head worn component. The AR system may provide a composited virtual image to the celebrity of a crowd composed of the various customers.

FIG. 66H shows the mother in a wine section of the grocery store. The mother may search for a specific wine using a virtual user interface of an application. The application may be a wine specific application, an electronic book, or a more general Web browser. In response to selection of a wine, the AR system may render a virtual map in the field of view of the user, with directions for navigating to the desired wine (similar to the process flow of FIG. 47).

The AR, based on user input, identifies the user interface desired by the user, retrieves data associated with the user interface, and displays the user interface along the right map coordinates in the physical space of the user. Here, for example, the location at which the user interface is rendered may be tied to the map coordinates of the shopping cart. Thus, when the shopping cart moves, the user interface moves along with the shopping cart as well.

While the mother is walking through the aisles, the AR system may capture may render data, which appear to be attached or at least proximate respective bottles of wines to which the data relates. The data may, for example, include recommendations from friends, wines that appear on a customer's personal wine list, and/or recommendations from experts. The data may additionally or alternatively include food parings for the particular wine.

Figure 66I:
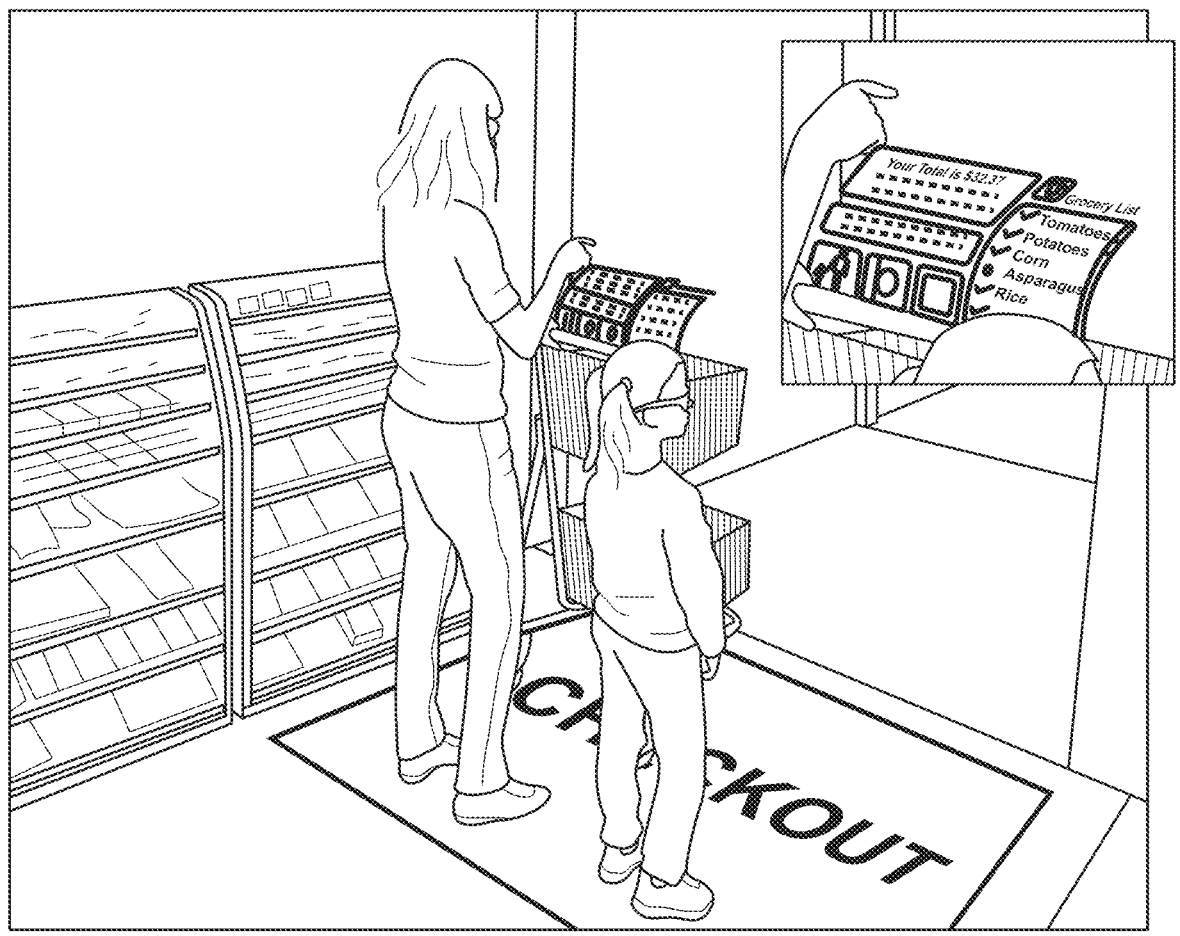

FIG. 66I shows the mother and child concludes their shopping experience. The mother and child may, for example, by walking onto, across or through a threshold. The threshold may be implemented in any of a large variety of fashions, for example as a suitably marked map. The AR system detects passage over or through the threshold, and in response totals up the cost of all the groceries in the shopping cart. The AR system may also provide a notification or reminder to the user, identifying any items on the virtual grocery list where are not in the shopping cart and thus may have been forgotten. The customer may complete the check-out through a virtual display,—no credit card necessary.

Figure 66J:
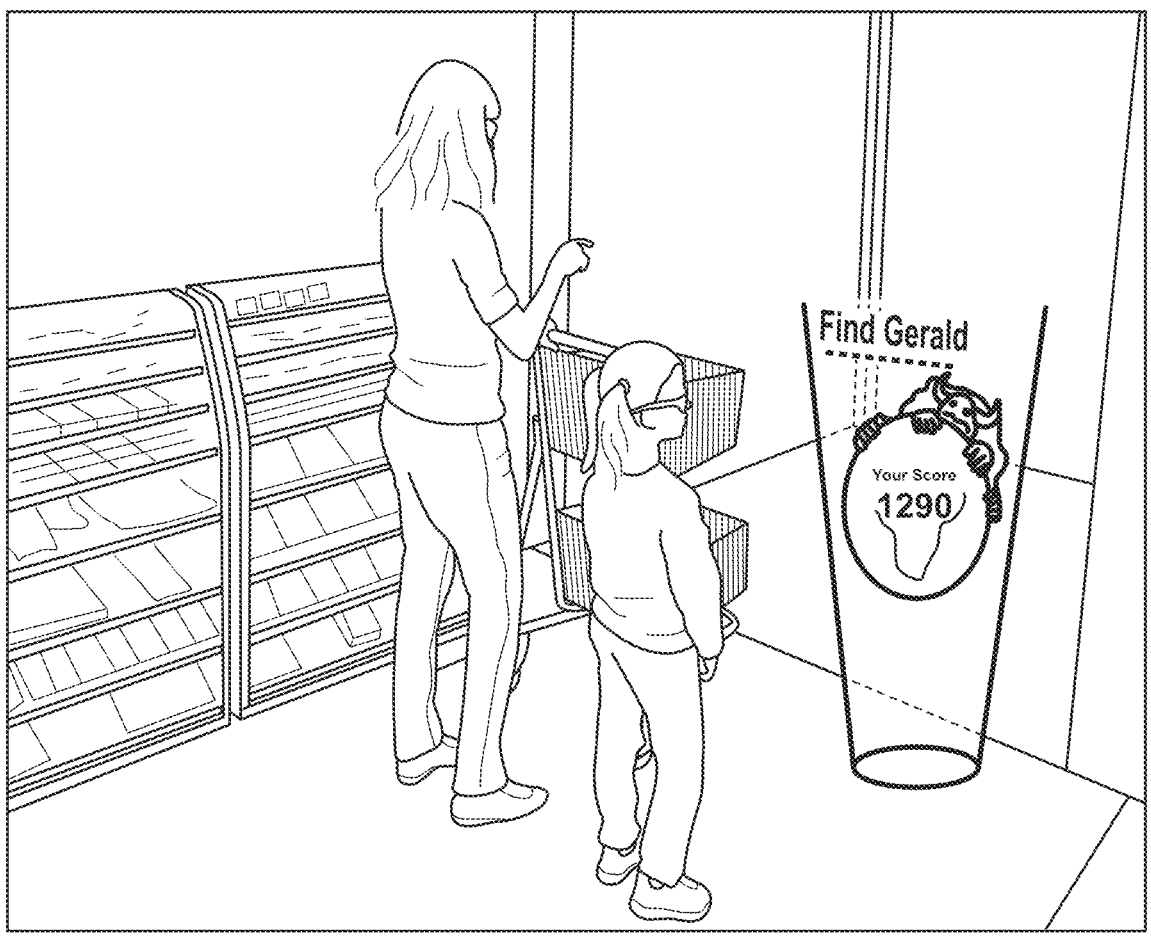

As illustrated in FIG. 66J, at the end of the shopping experience, the child receives a summary of her scavenger hunt gaming experience, for example including her previous high score. The AR system may render the summary as virtual content, at least in the field of view of the child.

Figure 67:
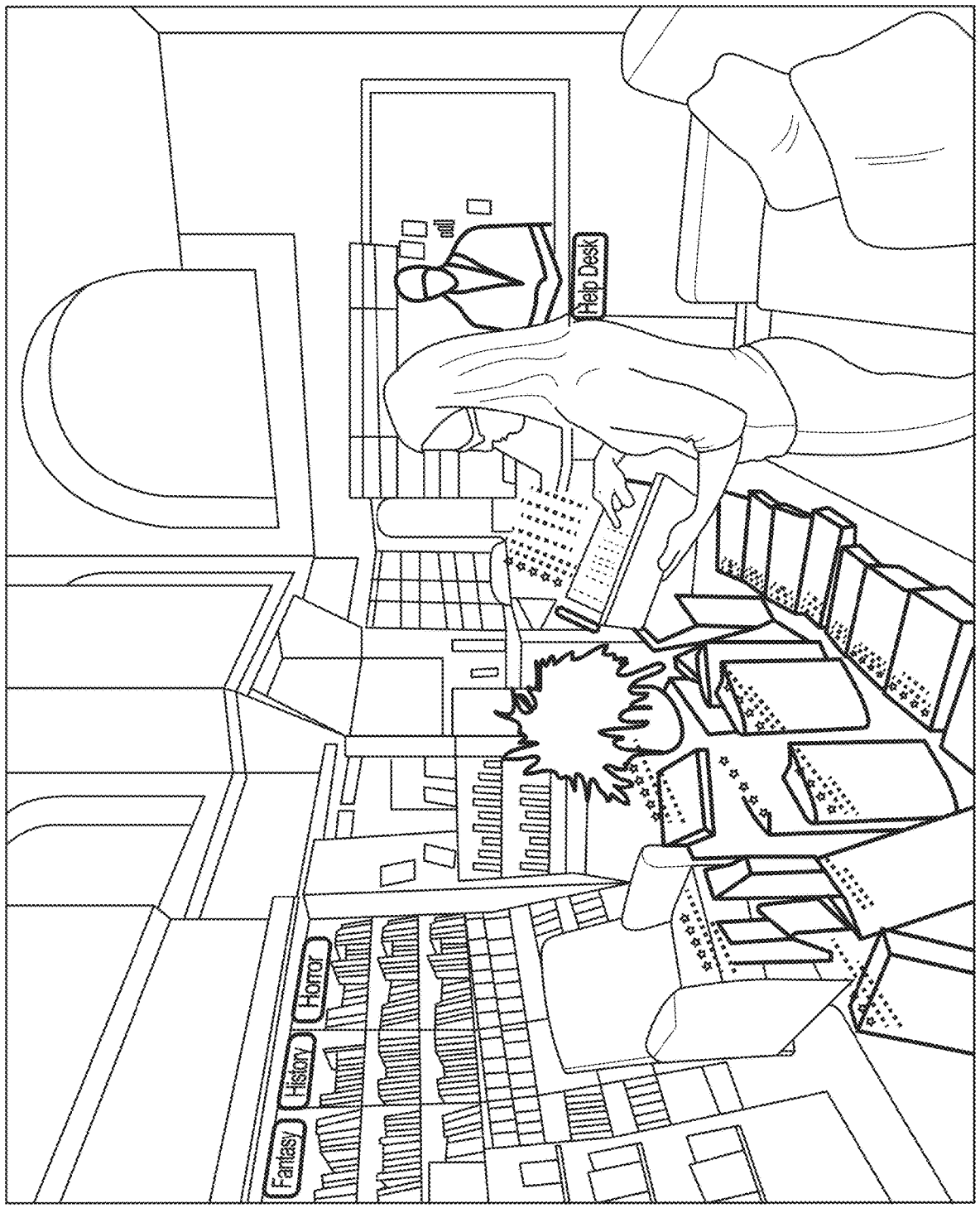
FIG. 67 illustrates another user scenario of a user browsing through a virtual bookstore, according to one illustrated embodiment.

FIG. 67 (scene 6700) shows a customer employing an AR system in a retail environment, for example a bookstore, according to one illustrated embodiment. The customer opens up a book totem. The AR system detects the opening of the book totem, and in response renders an immersive virtual bookstore experience in the user's field of view. The virtual bookstore experience may, for example, include reviews of books, suggestions, and author comments, presentations or readings. The AR system may render additional content, for example virtual coupons.

The virtual environment combines the convenience of an online bookstore with the experience of a physical environment.

User Experience Health Care Example

FIGS. 68A-68F (scenes 6802-6812) illustrate use of an AR system in a health care related application or physical environment, which may include recovery and/or rehabilitation, according to one illustrated embodiment.

Figure 68A:
FIGS. 68A-68F illustrates user scenario of using the AR system in various healthcare and recreational settings, according to one illustrated embodiment.

In particular, FIG. 68A shows a surgeon and surgical team, including a virtually rendered consulting or visiting surgeon, conducting a pre-operative planning session for an upcoming mitral valve replacement procedure. Each of the health care providers is wearing a respective individual AR system.

As noted above, the AR system renders a visual representation of the consulting or visiting surgeon. As discussed herein, the visual representation may take many forms, from a very simple representation to a very realistic representation.

The AR system renders a patient's pre-mapped anatomy (e.g., heart) in 3D for the team to analyze during the planning. The AR system may render the anatomy using a light field, which allows viewing from any angle or orientation. For example, the surgeon could walk around the heart to see a back side thereof.

The AR system may also render patient information. For instance, the AR system may render some patient information (e.g., identification information) so as to appear on a surface of a physical table. Also for instance, the AR system may render other patient information (e.g., medical images, vital signs, charts) so as to appear on a surface of one or more physical walls. Similar to the process flow of FIG. 55, the AR system may detect and recognize input (e.g—here the users may explicitly request to see virtual representation of the pre-mapped anatomy of the heart). Here, based on input, the AR system may retrieve the data from the cloud server, and transmit it back to the user's devices. The system also uses the map coordinates of the room to display the virtual content in the center of the room so that it can be viewed by multiple users sitting around the table.

Figure 68B:
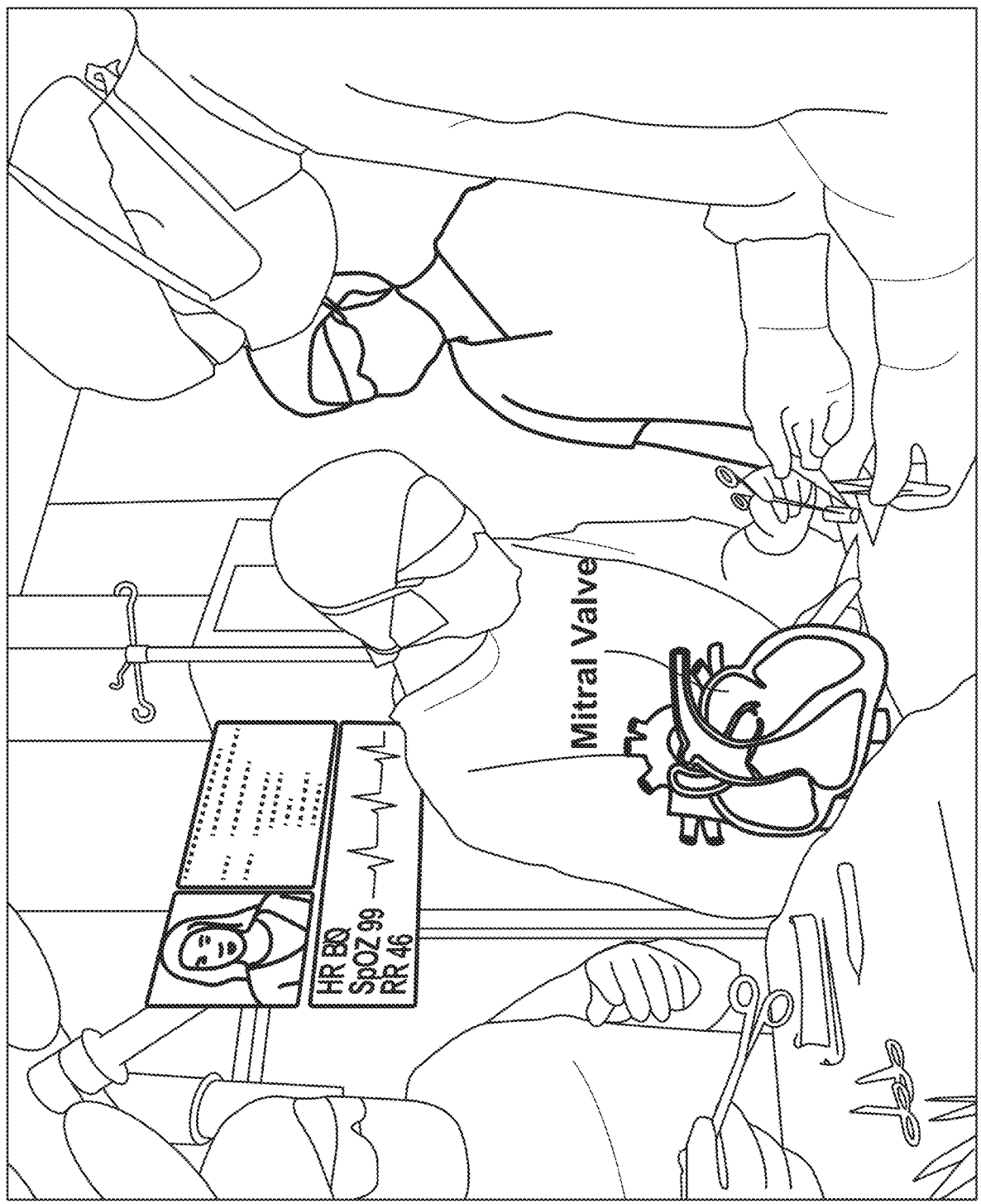

As illustrated in FIG. 68B, the surgeon is able to reference the pre-mapped 3D anatomy (e.g., heart) during the procedure. Being able to reference the anatomy in real time, may for example, improve placement accuracy of a valve repair. Outward pointed cameras capture image information from the procedure, allowing a medical student to observe virtually via the AR system from her remote classroom. The AR system makes a patient's information readily available, for example to confirm the pathology, and avoid any critical errors.

Figure 68C:

FIG. 68C shows a post-operative meeting or debriefing between the surgeon and patient. During the post-operative meeting, the surgeon is able to describe how the surgery went using a cross section of virtual anatomy or virtual 3D anatomical model of the patient's actual anatomy. The AR system allows the patient's spouse to join the meeting virtually while at work. Again, the AR system may render a light field which allows the surgeon, patient and spouse to inspect the virtual 3D anatomical model of the patient's actual anatomy from a desired angle or orientation.

Figure 68D:

FIG. 68D shows the patient convalescing in a hospital room. The AR system allows the patient to perceive any type of relaxing environment that the patient may desire, for example a tranquil beach setting. Here, similar to process flow of FIG. 54, the AR system retrieves data associated with the beach setting from the cloud, maps the room coordinates in order to display the beach setting virtual décor along the desired wall of the hospital room.

Figure 68E:
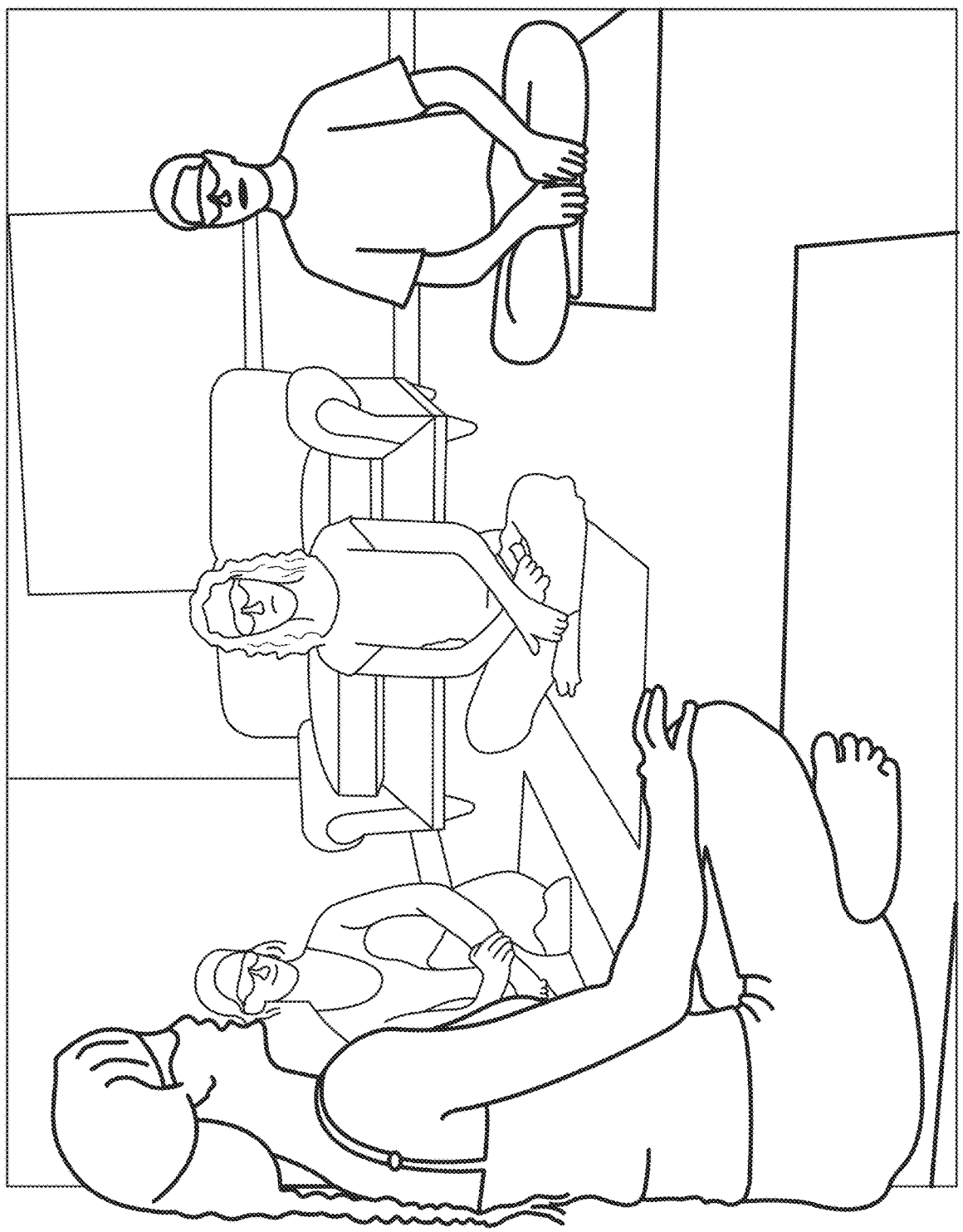

As illustrated in FIG. 68E, the patient may practice yoga or participate in some other rehabilitation during the hospital stay and/or after discharge. The AR system allows the patient to perceive a friend virtually rendered in a virtual yoga class. Similar to process flow of FIG. 53, multiple users are able to pass a piece of their passable world to each other.

More specifically, the AR system updates the passable world model based on the changes to the each of the user's position, location, and image data, as seen by their FOV cameras and other image sources, determines the 3D points based on the images captured by the FOV cameras, and recognizes various objects (and attaches semantic information). Here, information regarding the physical space is continually updated in the passable world model which is transmitted to the other users that are not physically present in the room where the first user is doing yoga. Similarly, information about the other user's movements etc. are also updated on the passable world model, which is transmitted to the first user such that the user views the avatars of the user in the same physical room.

Figure 68F:
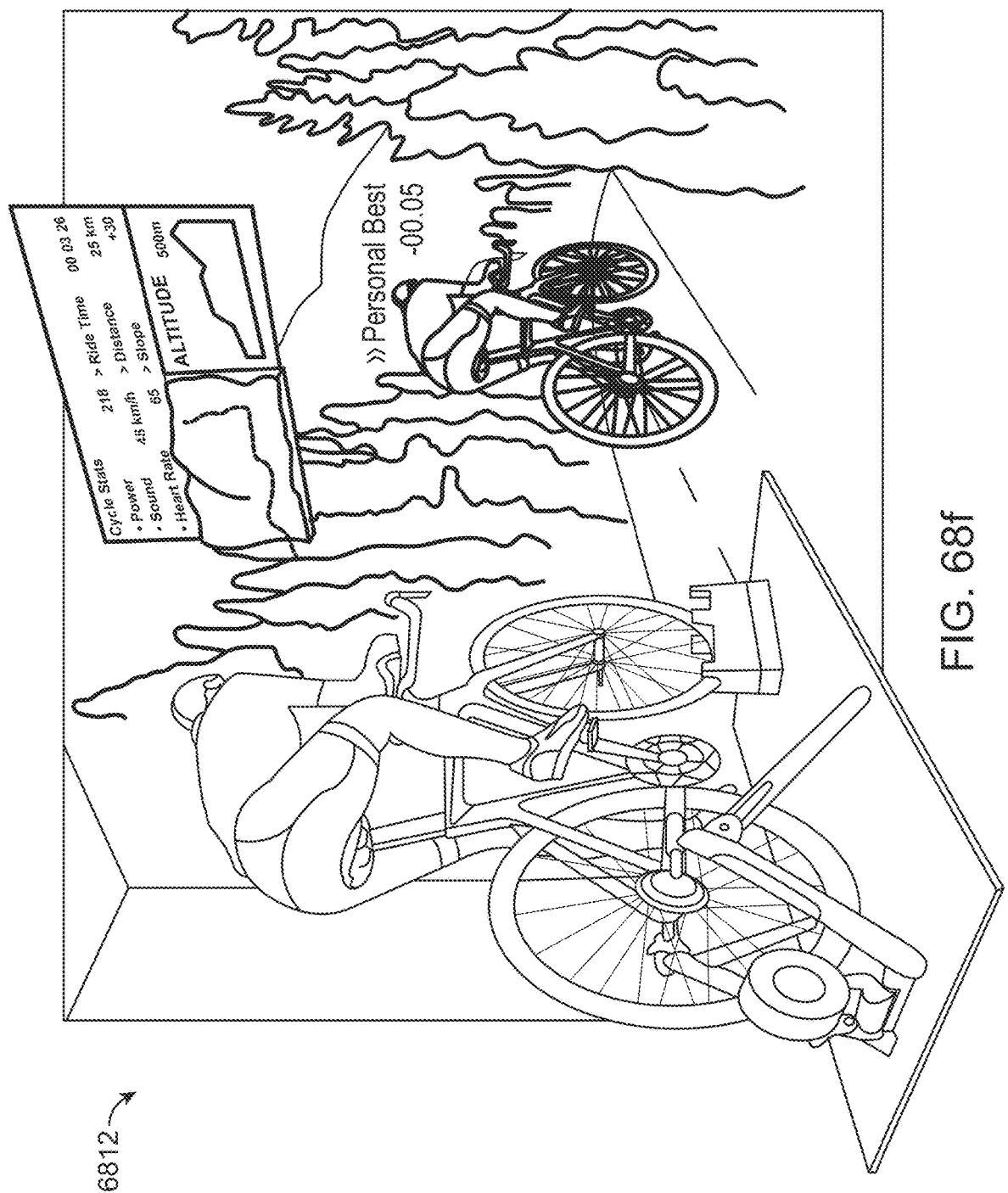

As illustrated in FIG. 68F, the patient may participate in rehabilitation, for example riding on a stationary bicycle during the hospital stay and/or after discharge. The AR system renders, in the user's field of view, information about the simulated cycling route (e.g., map, altitude, and distance), patient's performance statistics (e.g., power, speed, heart rate, ride time). The AR system render a virtual biking experience, for example including an outdoor scene, replicating a ride course such as a favorite physical route.

Additionally or alternatively, the AR system renders a virtual avatar as a motivational tool. The virtual avatar may, for example, replicate a previous ride, allowing the patient to compete with their own personal best time. Here, similar to the process flow of FIG. 55, the AR system detects the user's real-world activity (cycling) and loads a knowledge based related to cycling. Based on the user's specific activity (e.g., speed of cycling, etc.), the AR system may retrieve relevant information (e.g, statistics, motivational tools, etc.) and display the information to the user at the appropriate location by mapping the coordinates of the physical space at which the user is cycling.

User Experience Work/Manual Labor Example

Figure 69:
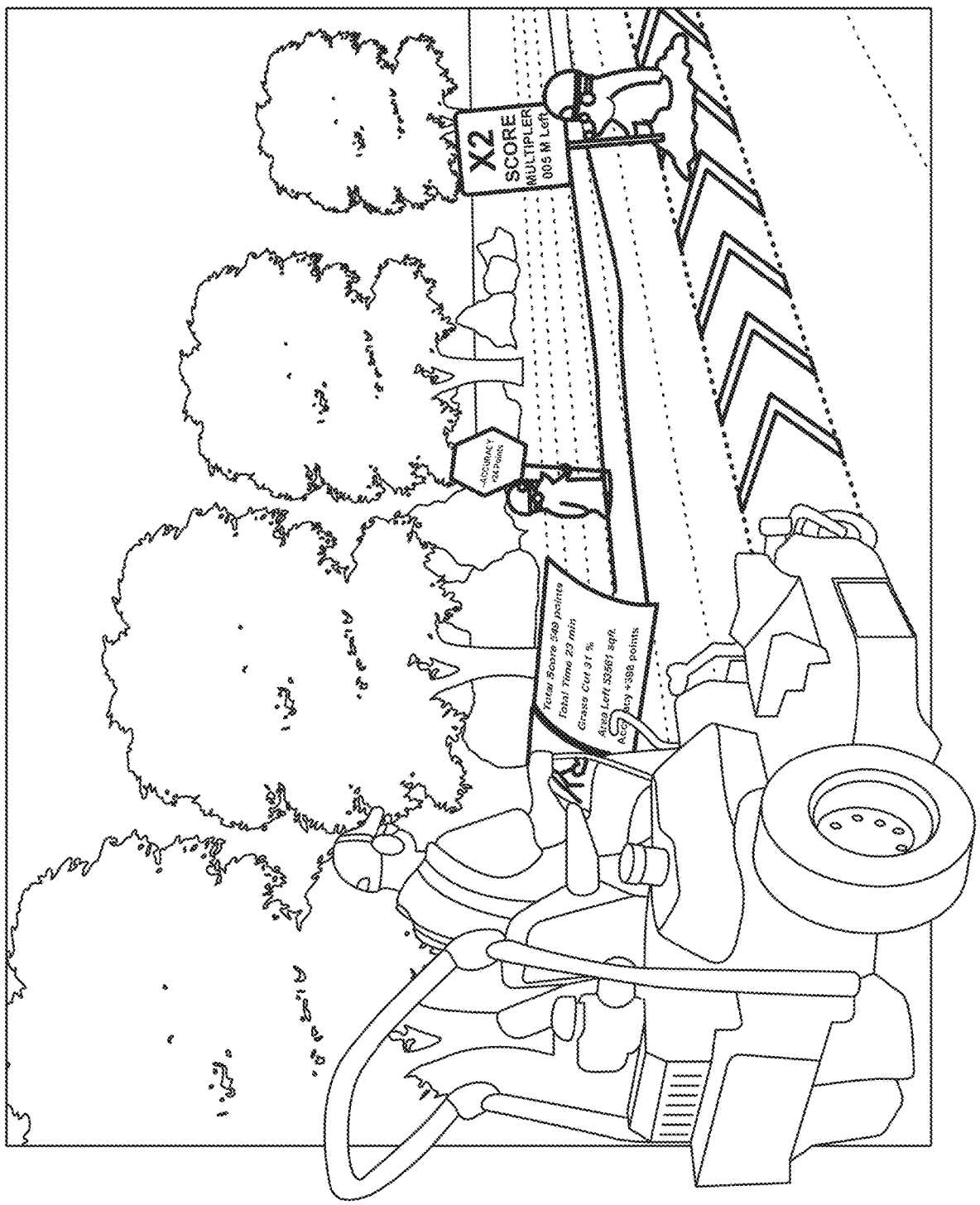
FIG. 69 illustrates yet another user scenario of a user interacting with the AR system at a golf course, according to one illustrated embodiment.

FIG. 69 (scene 6900) shows a worker employing an AR system in a work environment, according to one illustrated embodiment.

In particular, FIG. 69 shows a landscaping worker operating machinery (e.g., lawn mower). Like many repetitive jobs, cutting grass can be tedious. Workers may lose interest after some period of time, increasing the probability of an accident. Further, it may be difficult to attract qualified workers, or to ensure that workers are performing adequately.

The worker wears an individual AR system, which renders virtual content in the user's field of view to enhance job performance. For example, the AR system may render a virtual game, where the goal is to follow a virtually mapped pattern. Points are received for accurately following the pattern and hitting certain score multipliers before they disappear. Points may be deducted for straying from the pattern or straying too close to certain physical objects (e.g., trees, sprinkler heads, roadway).

While only one example environment is illustrated, this approach can be implemented in a large variety of work situations and environments. For example, a similar approach can be used in warehouses for retrieving items, or in retail environments for stacking shelves, or for sorting items such as mail. This approach may reduce or eliminate the need for training, since a game or pattern may be provided for many particular tasks.

Any of the devices/servers in the above-described systems may include a bus or other communication mechanism for communicating information, which interconnects subsystems and devices, such as processor, system memory (e.g., RAM), static storage device (e.g., ROM), disk drive (e.g., magnetic or optical), communication interface (e.g., modem or Ethernet card), display (e.g., CRT or LCD), input device (e.g., keyboard, touchscreen). The system component performs specific operations by the processor executing one or more sequences of one or more instructions contained in system memory.

Such instructions may be read into system memory from another computer readable/usable medium, such as static storage device or disk drive. In alternative embodiments, hard-wired circuitry may be used in place of or in combination with software instructions to implement the invention. Thus, embodiments of the invention are not limited to any specific combination of hardware circuitry and/or software. In one embodiment, the term "logic" shall mean any combination of software or hardware that is used to implement all or part of the invention.

The term "computer readable medium" or "computer usable medium" as used herein refers to any medium that participates in providing instructions to processor 1407 for execution. Such a medium may take many forms, including but not limited to, non-volatile media and volatile media. Non-volatile media includes, for example, optical or magnetic disks, such as disk drive. Volatile media includes dynamic memory, such as system memory. Common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer can read.

In an embodiment of the invention, execution of the sequences of instructions to practice the invention is performed by a single computing system. According to other embodiments of the invention, two or more computing systems coupled by a communication link (e.g., LAN, PTSN, or wireless network) may perform the sequence of instructions required to practice the invention in coordination with one another. The system component may transmit and receive messages, data, and instructions, including program, i.e., application code, through communication link and communication interface. Received program code may be executed by the processor as it is received, and/or stored in disk drive, or other non-volatile storage for later execution.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method for generating virtual content in a three-dimensional (3D) physical environment of a user, the method performed by at least one processor and comprising:

based on analyzing data acquired from at least one sensor, identifying a gesture of the user, the gesture including a pose of the user;

identifying a physical surface in the 3D physical environment of the user based at least partly on the identified gesture;

receiving an indication to initiate an interaction with the physical surface;

selecting a subset of user interface (UI) operations from a set of available UI operations associated with the physical surface based on contextual information associated with the physical surface; and generating a display instruction for presenting the subset of UI operations as at least a portion of virtual content that is presented in a 3D view as an overlay to the physical surface.

2. The method of claim 1, wherein the pose includes one or more of an eye pose and a head pose.

3. The method of claim 1, wherein the indication to initiate the interaction with the physical surface comprises one or more of an actuation of a UI device, the gesture of the user, and a change in the gesture of the user.

4. The method of claim 1, wherein generating the display instruction for presenting the subset of UI operations in the 3D view comprises
   generating a virtual menu comprising the subset of UI operations,
   determining a spatial location of the virtual menu based on a characteristic of the physical surface, and
   generating a display instruction for presenting the virtual menu at the spatial location in the 3D physical environment of the user.

5. The method of claim 1, wherein the method further comprises:
   determining, from a set of available virtual objects, virtual objects that are interactable by the user in the 3D physical environment based at least partly on the contextual information associated with the physical surface,
   wherein the subset of UI operations is selected based on the subset of UI operations being configured for interacting with the virtual objects.

6. The method of claim 1, further comprising determining the contextual information associated with the physical surface,
   wherein selecting the subset of UI operations from the set of available UI operations associated with the physical surface is based at least partly on the contextual information.

7. The method of claim 6, wherein
   the contextual information comprises an orientation of the physical surface, and
   selecting the subset of UI operations includes identifying UI operations that can be performed on the physical surface having the orientation.

8. The method of claim 1, wherein
   the subset of UI operations are presented in a virtual work portal in the virtual content, and
   one or more dimensions and a position of the virtual work portal are based at least partly on the gesture.

9. A system generating virtual content in a three-dimensional (3D) physical environment of a user, the system comprising:
   at least one sensor configured to acquire gesture data, the gesture including a pose of the user;
   at least one processor configured to
   analyze the gesture data from the at least one sensor,
   identify a gesture of the user base on analyzing the gesture data,
   identify a physical surface in the 3D physical environment of the user based at least partly on the identified gesture,
   receive an indication to initiate an interaction with the physical surface,
   select a subset of user interface (UI) operations from a set of available UI operations associated with the physical surface based on contextual information associated with the physical surface, and
   generate a display instruction for presenting the subset of UI operations as at least a portion of virtual content that is presented in a 3D view as an overlay to the physical surface; and
   an augmented reality (AR) display system configured to present the subset of UI operations as at least a portion of virtual content that is presented in a 3D view as an overlay to the physical surface.

10. The system of claim 9, wherein the pose includes one or more of an eye pose and a head pose.

11. The system of claim 9, wherein the indication to initiate the interaction with the physical surface comprises one or more of an actuation of a UI device, the gesture of the user, and a change in the gesture of the user.

12. The system of claim 9, wherein the at least one processor being configured to generate the display instruction for presenting the subset of UI operations in the 3D view comprises the at least one processor being configured to
   generate a virtual menu comprising the subset of UI operations,
   determine a spatial location of the virtual menu based on a characteristic of the physical surface, and
   generate a display instruction for presenting the virtual menu at the spatial location in the 3D physical environment of the user.

13. The system of claim 9, wherein the at least one processor is also configured to determine, from a set of available virtual objects, virtual objects that are interactable by the user in the 3D physical environment based at least partly on the contextual information associated with the physical surface, and
   wherein the subset of UI operations is selected based on the subset of UI operations being configured for interacting with the virtual objects.

14. The system of claim 9, wherein the at least one processor is also configured to
   determine the contextual information associated with the physical surface, and
   select the subset of UI operations from the set of available UI operations associated with the physical surface based at least partly on the contextual information.

15. The system of claim 14, wherein the contextual information comprises an orientation of the physical surface, and
   wherein the at least one processor is also configured to identify UI operations that can be performed on the physical surface having the orientation to select the subset of UI operations.

16. The system of claim 9, wherein
   the subset of UI operations are presented in a virtual work portal in the virtual content, and
   one or more dimensions and a position of the virtual work portal are based at least partly on the gesture.

* * * * *

EX PARTE REEXAMINATION CERTIFICATE (13022nd)

United States Patent
Abovitz et al.

(10) Number: US 11,060,858 C1
(45) Certificate Issued: Sep. 8, 2025

(54) METHOD AND SYSTEM FOR GENERATING A VIRTUAL USER INTERFACE RELATED TO A TOTEM

(71) Applicant: MAGIC LEAP, INC., Plantation, FL (US)

(72) Inventors: Rony Abovitz, Weston, FL (US); Brian T. Schowengerdt, Seattle, WA (US); Mathew D. Watson, Bellevue, WA (US)

(73) Assignee: MAGIC LEAP, INC., Plantation, FL (US)

Reexamination Request:
No. 90/014,986, Mar. 22, 2022

Reexamination Certificate for:
Patent No.: 11,060,858
Issued: Jul. 13, 2021
Appl. No.: 16/410,617
Filed: May 13, 2019

Related U.S. Application Data

(63) Continuation of application No. 14/707,253, filed on May 8, 2015, now Pat. No. 10,288,419, which is a continuation of application No. 14/696,347, filed on Apr. 24, 2015, now Pat. No. 9,612,403, which is a continuation of application No. 14/331,218, filed on Jul. 14, 2014, now Pat. No. 9,671,566, said application No. 14/707,253 is a continuation-in-part of application No. 14/641,376, filed on Mar. 17, 2015, now Pat. No. 9,874,749.

(60) Provisional application No. 61/845,907, filed on Jul. 12, 2013, provisional application No. 62/012,273, filed on Jun. 14, 2014.

(51) Int. Cl.
*G02B 6/10* (2006.01)
*G02B 6/34* (2006.01)
*G06V 40/20* (2022.01)
*G06V 20/10* (2022.01)
*G16H 40/20* (2018.01)

(52) U.S. Cl.
CPC .............. *G06V 40/28* (2022.01); *G06V 20/10* (2022.01); *G16H 40/20* (2018.01)

(58) Field of Classification Search
CPC .................................................. G02B 27/0172
See application file for complete search history.

(56) References Cited

To view the complete listing of prior art documents cited during the proceeding for Reexamination Control Number 90/014,986, please refer to the USPTO's Patent Electronic System.

*Primary Examiner* — Joseph R Pokrzywa

(57) ABSTRACT

A waveguide apparatus includes a planar waveguide and at least one optical diffraction element (DOE) that provides a plurality of optical paths between an exterior and interior of the planar waveguide. A phase profile of the DOE may combine a linear diffraction grating with a circular lens, to shape a wave front and produce beams with desired focus. Waveguide apparati may be assembled to create multiple focal planes. The DOE may have a low diffraction efficiency, and planar waveguides may be transparent when viewed normally, allowing passage of light from an ambient environment (e.g., real world) useful in AR systems. Light may be returned for temporally sequentially passes through the planar waveguide. The DOE(s) may be fixed or may have dynamically adjustable characteristics. An optical coupler system may couple images to the waveguide apparatus from a projector, for instance a biaxially scanning cantilevered optical fiber tip.

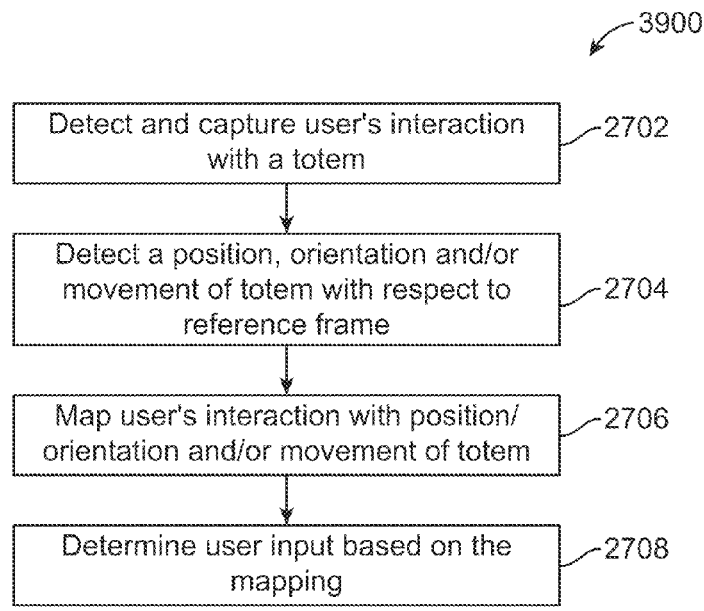

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3, 8-11 and 16 are determined to be patentable as amended.

Claims 4-7 and 12-15, dependent on an amended claim, are determined to be patentable.

New claims 17-38 are added and determined to be patentable.

1. A method for generating virtual content in a three-dimensional (3D) physical environment of a user, the method performed by at least one processor and comprising:
   based on analyzing data acquired from at least one sensor, identifying a gesture of [the] *a* user, the gesture including a pose of the user, *wherein the pose comprises a movement, a position, a change in position, an orientation, or a change in orientation pertaining to one or more hands, one or more wrists, or one or more fingers of the user*;
   identifying a physical surface *of a physical totem* in the 3D physical environment of the user based at least partly on the [identified] gesture, *wherein the physical surface is external to the user*;
   receiving an indication *by at least a portion of a body of the user* to initiate an interaction *indicative of an action undertaken by the user* with *respect to at least a portion of* the physical surface, *wherein the indication pertains to a first position, a first orientation, or a first movement pertaining to the at least the portion of the body of the user relative to the physical surface*;
   in response to the interaction by the user, selecting a subset of user interface (UI) operations from a set of available UI operations associated with the physical surface based on contextual information, *wherein the contextual information corresponds to the interaction and is* associated with *one or more locations of the at least the portion of* the physical surface; [and]
   generating a display instruction for presenting the subset of UI operations as at least a portion of virtual content that is presented in a 3D view as an overlay to the physical surface; *and*
   *rendering at least the at least the portion of the virtual content onto or with respect to the physical surface.*

2. The method of claim 1, *further comprising:*
   *generating a first set of UI operations or structures on at least a portion of the physical surface prior to receiving the indication of the interaction, wherein*
      *the subset of UI operations is selected from the set of UI operations to modify the first set of UI operations or structures based at least in part upon the first position, the first orientation, or the first movement of the at least the portion of the body of the user relative to the physical surface,*
      *the pose further includes one or more of an eye pose and a head pose, and*
      *the pose pertains to at least one of a direction of the movement or the change in position or the change in orientation, a magnitude of the movement or the change in position or the change in orientation, a speed of the movement or the change in position or the change in orientation, or an acceleration pertaining to the one or more hands, the one or more wrists, or the one or more fingers of the user.*

3. The method of claim 1, wherein the indication to initiate the interaction with *the at least the portion of* the physical surface comprises one or more of an actuation of a UI device, [the] *a different* gesture of the user, and a change in the gesture of the user, *and the pose further includes one or more of a hand pose and a pose of one or more fingers of the user.*

8. The method of claim 1, wherein
   the subset of UI operations [are] *is* presented in a virtual work portal in the virtual content, and
   one or more dimensions and a position of the virtual work portal are based at least partly on the gesture.

9. A system generating virtual content in a three-dimensional (3D) physical environment of a user, the system comprising:
   at least one sensor configured to acquire gesture data *pertaining to a gesture of a user, the gesture including a pose of the user, wherein the pose comprises a movement, a position, a change in position, an orientation, or a change in orientation pertaining to one or more hands, one or more wrists, or one or more fingers of the user*;
   at least one processor configured to*:*
      analyze the gesture data [from] *acquired by* the at least one sensor,
      identify [a] *the* gesture of the user base on analyzing the gesture data,
      identify a physical surface *of a physical totem* in the 3D physical environment of the user based at least partly on the identified gesture, *wherein the physical surface is external to the user,*
      receive an indication *by at least a portion of a body of the user* to initiate an interaction *indicative of an action undertaken by the user* with *respect to at least a portion of* the physical surface, *wherein the indication pertains to a first position, a first orientation, or a first movement of the at least the portion of the body of the user relative to the physical surface,*
      in response to the interaction by the user, select a subset of user interface (UI) operations from a set of available UI operations associated with the physical surface based on contextual information, *wherein the contextual information corresponds to the interaction and is* associated with *one or more locations of the at least the portion of* the physical surface, and
      generate a display instruction for presenting the subset of UI operations as at least a portion of virtual content that is presented in a 3D view as an overlay to the physical surface; and
   an augmented reality (AR) display system configured to present the subset of UI operations as at least a portion of virtual content that is presented in a 3D view as an overlay to the physical surface.

10. The system of claim 9, *the at least one processor further configured to generate a first set of UI operations or structures on at least a portion of the physical surface prior to receiving the indication of the interaction, wherein the subset of UI operations is selected from the set of UI operations to modify the first set of UI operations or* structures based at least in part upon the first position, the first orientation, or the first movement of the at least the portion of the body of the user relative to the physical surface, and the pose includes one or more of an eye pose, and a head pose.

11. The system of claim 9, wherein the indication to initiate the interaction with *the at least the portion of* the physical surface comprises one or more of an actuation of a UI device, [the] *a different* gesture of the user, and a change in the gesture of the user, *and the pose further includes one or more of a hand pose and a pose of one or more fingers of the user.*

16. The system of claim 9, wherein
the subset of UI operations [are] *is* presented in a virtual work portal in the virtual content, and
one or more dimensions and a position of the virtual work portal are based at least partly on the gesture.

17. *The method of claim 1, further comprising:*
*mapping the first position, the first orientation, or the first movement of the at least the portion of the body of the user relative to the physical surface to one or more respective UI operations or structures; and*
*mapping the first position, the first orientation, or the first movement of the at least the portion of the body of the user relative to the physical surface to one or more respective inputs based at least in part upon a result of mapping the first position, the first orientation, or the first movement of the at least the portion of the body of the user relative to the physical surface, wherein*
*the one or more respective inputs comprise at least one of a character, a number, a punctuation, a control, or a function.*

18. *The method of claim 1, further comprising:*
*respectively rendering different subsets of UI operations or structures in response to different interactions by the user, wherein respectively rendering different subsets of UI operations or structures comprises rendering a new set of UI operations or structures based at least in part upon a corresponding interaction.*

19. *The method of claim 18, wherein respectively rendering the different subsets of UI operations or structures comprises:*
*respectively mapping positions, orientations, or movements of a plurality of fingers of the user relative to the physical surface to respective UI operations or structures; and*
*respectively mapping the positions, orientations, or movements of the plurality of fingers of the user relative to the physical surface to a plurality of respective inputs based at least in part upon the respective UI operations or structures, wherein*
*the plurality of respective inputs comprises two or more of a character, a number, a punctuation, a control, a function, or a combination thereof.*

20. *The method of claim 1, wherein identifying the physical surface in the 3D physical environment of the user based at least partly on the gesture comprises:*
*identifying a subset of data pertaining to a portion of the 3D physical environment based at least in part upon the gesture, wherein the subset of data includes a set of points;*
*recognizing a first type of surface with a first object recognizer with a first object recognizer; and*
*recognizing the physical surface from a plurality of subtypes of the first type using a second object recognizer, wherein the plurality of subtypes are different from each other.*

21. *The method of claim 1, further comprising:*
*recognizing a first gesture by the user to interact with a virtual UI construct;*
*selecting a user selectable virtual room or virtual space-based application or function from the virtual construct based at least in part upon the first gesture from the user;*
*receiving a second gesture for navigating through a plurality of context-specific virtual rooms or context-specific spaces, wherein the plurality of context-specific virtual rooms or context-specific spaces is respectively associated with a plurality of plurality of user selectable virtual room or virtual space-based applications or functions;*
*rendering a context-specific virtual room or a context-specific virtual space that includes a fully functional construct for the application or the function to at least one eye of the user; and*
*providing a notification to the user that the user is in the context-specific virtual room or the context-specific virtual space.*

22. *The method of claim 21, further comprising:*
*populating the subset of UI operations or structures with a virtual workstation, wherein the virtual workstation comprises the plurality of user selectable virtual room or virtual space-based applications; and*
*providing navigation to each of the plurality of virtual room or virtual space-based applications or the plurality of context-specific virtual rooms or context-specific spaces in the subset of UI operations or structures.*

23. *The method of claim 1, further comprising:*
*mapping one or more characteristics of the interaction to one or more respective operations or structures in the subset of UI operations or structures, wherein*
*the one or more characteristics of the interaction comprise a number of actions pertaining to the interaction, a type of the interaction from a plurality of types of interactions, or a temporal duration of the interaction,*
*the subset of UI operations or structures includes one or more keys, one or more buttons, one or more scroll wheels, one or more joysticks, or one or more thumb sticks,*
*the physical surface is devoid of physical or electronic structures that correspond to the subset of UI operations or structures, and*
*the interaction includes performing at least one of tapping, touching, double tapping, short tapping, or long tapping the physical surface with a part of a body of the user, fingertip gripping, enveloping grasp of one or more fingers of the user.*

24. *The method of claim 1, further comprising:*
*rendering an emphasis on the physical surface for indicating that the physical surface has been identified based at least in part upon the gesture; and*
*rendering one or more demarcations on the physical surface for orienting the physical surface or the subset of UI operations or structures, wherein*
*the interaction comprises an action performed by the user on at least a portion of the subset of UI operations or structures,*
*the gesture includes at least one of a user touching the physical surface, a user presenting a pose with one or more arms or one or more fingers with respect to the physical surface, and* the physical surface includes one or more indents or depressions at one or more respective locations at which one or more UI operations or structures are rendered.

25. The method of claim 1, wherein the gesture is performed by the user when at least a portion of the one or more hands, one or more wrists, or one or more fingers of the user is in contact with the physical totem.

26. The method of claim 25, further comprising:
detecting a first interaction with a first location on the physical totem, wherein
the first location on the physical totem corresponds to a first UI operation of the subset of UI operations;
issuing a computer command to execute the first UI operation in response to the first interaction, wherein the physical totem comprises a physical object that has no physical or electronic structures that correspond to the first UI operation for implementing the first UI operation.

27. The method of claim 25, wherein the physical totem comprises a totem controller that includes functionality to facilitate self-tracking of the physical totem, wherein the totem controller is mountable to a plurality of different physical objects including the physical totem so as to transform the plurality of different physical objects into corresponding totems.

28. The method of claim 25, further comprising replicating an electronic controller from the totem object to provide a plurality of actual or non-virtual actions at least by rendering at least the subset of UI operations which, when interacted upon by user interactions via corresponding gestures with respect to corresponding locations on the physical totem, respectively correspond to the plurality of control functionalities onto or with respect to the physical surface of the physical totem.

29. The method of claim 25, wherein the physical totem includes one or more physical structures, features, or demarcations that respectively correspond to one or more UI operations of the subset of UI operations, wherein the one or more UI operations are respectively rendered onto or with respect to the physical surface of the physical totem based at least in part upon the one or more physical structures, features, or demarcations of the physical totem.

30. The method of claim 25, wherein
the subset of UI operations is rendered onto or with respect to the physical surface of the physical totem to produce a petal-shaped virtual user interface having a plurality of petals that appears to emanate from the physical totem, and
each petal of the plurality of petals is respectively mapped to one or more UI operations that respectively correspond to one or more functions, one or more categories of functions, one or more categories of contents or media types, one or more tools, or one or more software applications.

31. The method of claim 25, wherein the physical totem comprises a physical element or feature, the physical element or feature replicates, when interacted upon by the user, a feel of a physical input element or feature but is not connected to physical or electrical switches or electronics for performing input functionalities, and at least one UI operation of the subset of UI operations is rendered onto or with respect to the physical element or feature as virtual content to provide an input functionality to the physical element or feature.

32. The method of claim 25, wherein the physical totem comprises a plurality of physical faces or surfaces, and each of the plurality of physical faces or surfaces respectively corresponds to one or more virtual UI operations, a function, a category or group of functions, a category of content types or media types, one or more tools, or one or more applications.

33. The method of claim 32, further comprising:
receiving the interaction by the user, wherein at least a portion of the subset of UI operations is rendered as an overlay on a first physical face or surface when the first physical face or surface is within a field of view of the user at a beginning of the interaction;
in response to the interaction, ceasing rendering the at least the portion of the subset of UI operations with respect to the first physical face or surface when the interaction by the user rotates the first physical face or surface out of the field of view of the user; and
in response to the interaction, rendering a new subset UI operations from the set of available UI operations onto or with respect to a second physical face or surface when the interaction by the user rotates the second physical face or surface into the field of view of the user.

34. The method of claim 25, wherein the physical totem comprises a shape of a handheld controller, the physical totem comprises a number of user input elements that includes at least one of a switch, a button, and a joy-or thumb-stick, the switch and the joy-or thumb-stick are not connected to any switches or electronics, and the switch and the joy-or thumb-stick, when at least some of the subset of UI operations are rendered onto or with respect to the switch and the joy-or thumb-stick and when interacted upon by the interaction, respectively perform a switch function and a control function.

35. The method of claim 25, wherein the physical totem comprises a shape of a handheld controller, the subset of UI operations comprises a number of virtual user input elements, and the physical totem comprises a corresponding number of physical features or elements that respectively corresponds to the number of virtual user input elements, and the number of physical features includes at least one of a depression, a texture, a protrusion, or a cavity that, when the number of virtual user input elements are rendered onto or with respect to the number of physical features, replicates a feel by the user of the number of virtual input elements.

36. The method of claim 25, wherein the physical totem comprises a shape of a ring having a first tubular portion for receiving a finger of the user and an interaction portion or a shape of a bracelet having a second tubular portion for receiving a wrist of the user and a touch surface, at least a first part of the subset of UI operations is rendered onto or with respect to the interaction portion or the touch portion of the physical totem, at least a second part of the subset of UI operations is rendered onto or with respect to the physical totem as emanating from the physical totem, and the physical totem has no physical input structures or physical electronics while providing input functions with the subset of UI operations in response to the interaction by the user.

37. The method of claim 25, wherein the physical totem comprises a shape of a glove or a partial glove that has an opening for receiving a wrist of the user and one or more glove fingers for receiving one or more respective fingers of a hand of the user, and the subset of UI operations is rendered onto or with respect to the glove or the partial glove.

38. The method of claim 37, further comprising:
tracking the glove or the partial glove, instead of hands and fingers of the user;

*mapping the first position, the first orientation, or the first movement pertaining to the glove or the partial glove to a set of user selections or inputs; and*

*mapping one or more other interactions by the user to one or more corresponding controls or functions, wherein the one or more other interactions by the user comprise a number of interactions by the user, a type of a plurality of interaction types, a duration of a respective interaction of a plurality of interactions.*

\* \* \* \* \*